US008637502B2

(12) United States Patent
Brown et al.

(10) Patent No.: US 8,637,502 B2
(45) Date of Patent: Jan. 28, 2014

(54) 2,3,4,5-TETRAHYDRO-BENZO{B}{1,4}DIAZEPINE-COMPRISING COMPOUNDS OF FORMULA(III) FOR TREATING PAIN

(75) Inventors: Kevin C. Brown, Philadelphia, PA (US); R. Richard Goehring, Pipersville, PA (US)

(73) Assignees: Purde Pharma L.P., Stamford, CT (US); Shionogi & Co., Ltd. (JP)

(*) Notice: Subject to any disclaimer, the term of this patent is extended or adjusted under 35 U.S.C. 154(b) by 0 days.

(21) Appl. No.: 13/349,522

(22) Filed: Jan. 12, 2012

(65) Prior Publication Data

US 2012/0108575 A1    May 3, 2012

Related U.S. Application Data

(60) Division of application No. 12/503,598, filed on Jul. 15, 2009, now Pat. No. 8,110,602, which is a continuation of application No. PCT/US2008/051096, filed on Jan. 15, 2008.

(60) Provisional application No. 60/880,955, filed on Jan. 16, 2007, provisional application No. 60/930,035, filed on May 11, 2007.

(51) Int. Cl.
*A61K 31/55* (2006.01)

(52) U.S. Cl.
USPC .................... 514/221; 540/593; 546/210

(58) Field of Classification Search
USPC .................... 514/221; 540/593; 546/210
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Grazie | |
| 5,073,543 A | 12/1991 | Marshall et al. | |
| 5,120,548 A | 6/1992 | McClelland et al. | |
| 5,283,244 A | 2/1994 | Sakamoto et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 5,739,129 A | 4/1998 | Aquino et al. | |
| 5,859,007 A | 1/1999 | Aquino et al. | |
| 5,922,717 A | 7/1999 | Pieper et al. | |
| 6,136,839 A | 10/2000 | Isakson et al. | |
| 6,172,067 B1 | 1/2001 | Ito et al. | |
| 6,262,066 B1 | 7/2001 | Tulshian et al. | |
| 6,423,716 B1 | 7/2002 | Matsuno et al. | |
| 6,455,527 B2 | 9/2002 | Tulshian et al. | |
| 6,576,644 B2 | 6/2003 | Bi et al. | |
| 6,635,653 B2 | 10/2003 | Goehring et al. | |
| 6,835,737 B2 | 12/2004 | Bi et al. | |
| 7,001,901 B2 | 2/2006 | Yang | |
| 7,459,556 B2 | 12/2008 | Mergelsberg et al. | |
| 2003/0134846 A1 | 7/2003 | Windsor et al. | |
| 2003/0149027 A1 | 8/2003 | Oi et al. | |
| 2003/0207886 A1 | 11/2003 | Plucker et al. | |
| 2004/0082784 A1 | 4/2004 | Sielecki-Dzurdz et al. | |
| 2004/0220177 A1 | 11/2004 | Kath et al. | |
| 2008/0214827 A1 | 9/2008 | Goehring et al. | |

FOREIGN PATENT DOCUMENTS

| | | |
|---|---|---|
| WO | WO 95/03299 A1 | 2/1995 |
| WO | WO 00/06545 A1 | 2/2000 |
| WO | WO 01/34571 A1 | 5/2001 |
| WO | WO 02/080895 A2 | 10/2002 |
| WO | WO 02/085361 A1 | 10/2002 |
| WO | WO 2008/089201 A2 | 7/2008 |

OTHER PUBLICATIONS

Jordan, V. C. Nature Reviews: Drug Discovery, 2, 2003, 205.*
Hackam, et al. JAMA, 296(14), 2006, 1731-1732.*
Bachmann et al., "Synthesis of 4,4-Methylenephenanthrene," *J.A.C.S.* vol. 63, pp. 204-206 (1941).
Barthó et al., "Involvement of capsaicin-sensitive neurons in hyperalgesia and enhanced opioid antinociception in inflammation-,"*Naunyn-Schmiedeberg's Arch. Pharmacol.* vol. 342, pp. 666-670 (1990).
Bignan et al., "Recent advances towards the discovery of ORL-1 receptor agonists and antagonists," *Exp. Opin. Ther. Patents* vol. 15, No. 4, pp. 357-388 (2005).
Bingham et al., "Over one hundred solvates of sulfathiazole," *ChemComm*, pp. 603-604 (2001).
Buchwald et al., "Long-term, continuous intravenous heparin administration by an implantable infusion pump in ambulatory patients with recurrent venous thrombosis," *Surgery* vol. 88, pp. 507-516 (1980).
Bundgaard, *Design of Prodrugs*, Elsevier (1985).
Bundgaard, "(C) Means to Enhance Penetration (1) Prodrugs as a means to improve the delivery of peptide drugs," *Advanced Drug Delivery Revs.* vol. 8, pp. 1-38 (1992).
Bundgaard, "Design and Application of Prodrugs,"*A Textbook of Drug Design and Development*, P. Krogsgaard-Larsen and H. Bundgaard, eds., Harwood Academic Publishers, Chapter 5, pp. 113-191 (1991).
Bundgaard et al., "Glycolamide Esters as Biolabile Prodrugs of Carboxylic Acid Agents: Synthesis, Stability, Bioconversion, and Physicochemical Properties," *J. Pharmaceut. Sci.* vol. 77, No. 4, pp. 285-298 (1988).
Caira et al., "Preparation and Crystal Characterization of a Polymorph, a Monohydrate, and an Ethyl Acetate Solvate of the Antifungal Fluconazole," *J. Pharmaceut. Sci.* vol. 93, No. 3, pp. 601-611 (2004).
Cramer et al., "Enantioselective Desymmetrization of Tropinone Derivatives by Hydroboration," *Synlett.* No. 14, pp. 2175-2177 (2003).

(Continued)

*Primary Examiner* — Douglas M Willis
(74) *Attorney, Agent, or Firm* — Dechert LLP

(57) ABSTRACT

The invention relates to Heterocyclic-Substituted Piperidine Compounds, compositions comprising an effective amount of a Heterocyclic-Substituted Piperidine Compound and methods to treat or prevent a condition, such as pain, comprising administering to an animal in need thereof an effective amount of a Heterocyclic-Substituted Piperidine Compound.

73 Claims, No Drawings

(56) References Cited

OTHER PUBLICATIONS

D'Amour et al., "A Method for Determining Loss of Pain Sensation," *J. Pharmacol. Exp. Ther.* vol. 72, pp. 74-79 (1941).

During et al., "Controlled Release of Dopamine from a Polymeric Brain Implant: In Vivo Characterization," *American Neurological Association Ann. Neurol.* vol. 25, pp. 351-356 (1989).

Filer, "The Preparation and Characterization of Tritiated Neurochemicals," *Isotopes in the Physical and Biomedical Sciences, vol. 1, Labeled Compounds (Part A)*, Chapter 6, pp. 155-192 (1987).

Goodson, "Dental Applications," in Medical Applications of Controlled Release, vol. 2, Applications and Evaluation, Langer and Wise, eds., CRC Press, Chapter 6, pp. 115-138 (1984).

Green et al., "Protective Groups in Organic Synthesis," John Wiley & Sons, Inc., 3$^{rd}$ Ed., New York, pp. 531-535 & 556-557 (1999).

Grupp et al., "Protection against Hypoxia-reoxygenation in the Absence of Poly (ADP-ribose) Synthetase in Isolated Working Hearts," *J. Mol. Cell Cardiol.* vol. 31, pp. 297-303 (1999).

*Handbook of Pharmaceutical Excipients*, American Pharmaceutical Association (1986).

Hanson, "Analgesic, Antipyretic and Anti-inflammatory Drugs," *Remington: The Science and Practice of Pharmacy, vol. II*, pp. 1196-1221 (1995).

Hargreaves et al., "A new and sensitive method for measuring thermal nociception in cutaneous hyperalgesia," *Pain* vol. 32, pp. 77-88 (1988).

Howard et al., "Intracerebral drug delivery in rats with lesion-induced memory deficits," *J. Neurosurg.* vol. 71, pp. 105-112 (1989).

Insel, "Analgesic-Antipyretic and Anti-inflammatory Agents and Drugs Employed in the Treatment of Gout," *Goodman & Gilman: The Pharmacological Basis of Therapeutics*, P.B. Molinhoff and R.W. Ruddon, eds., 9$^{th}$ Ed., pp. 617-657 (1996).

Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* vol. 32, No. 2, pp. 692-698 (1984).

Kim et al., "An experimental model for peripheral neuropathy produced by segmental spinal nerve ligation in the rat," *Pain* vol. 50, pp. 355-363 (1992).

Kolczewski et al., "Novel Hexahydrospiro[piperidine-4,1'-pyrrolo[3,4-c]pyrroles]: Highly Selective small-Molecule Nociceptin/Orphanin FQ Receptor Agonists," *J. Med. Chem.* vol. 46, pp. 255-264 (2003).

Langer et al., "Chemical and Physical Structure of Polymers as Carriers for Controlled Release of Bioactive Agents: A Review," *J. Macromol. Sci. Rev. Macromol. Chem.* vol. C23, No. 1, pp. 61-126 (1983).

Langer, "New Methods of Drug Delivery," *Science* vol. 249, pp. 1527-1533 (1990).

Lazareno, "Measurement of agonist-stimulated [$^{35}$S]GTPγS binding to cell membranes," *Methods in Molecular Biology* vol. 106, pp. 231-245 (1999).

Levy, "Inhibition of Calcification of Bioprosthetic Heart Valves by Local Controlled-Release Diphosphonate," *Science* vol. 228, pp. 190-192 (1985).

Lieberman et al., Pharmaceutical Dosage Forms: Tablets, 2$^{nd}$ Ed., Marcel Dekker, Inc., New York (1989 & 1990).

Lieberman et al., Pharmaceutical Dosage Forms: Disperse Systems, 2$^{nd}$ Ed., Marcel Dekker, Inc. (1996 & 1998).

Louie et al., "Palladium-Catalyzed Synthesis of Arylamines from Aryl Halides. Mechanistic Studies Lead to Coupling in the Absence of Tin Reagents," *Tetrahedron Lett.* vol. 36, No. 21, pp. 3609-3612 (1995).

*Medical Applications of Controlled Release*, Langer and Wise, eds. (1984).

Milligan, "Principles: Extending then utility of [$^{35}$S]GTPγS binding assays," *TIPS* vol. 14, pp. 87-90 (2003).

Narita et al., "Identification of the G-protein coupled ORLI receptor in the mouse spinal cord by [$^{35}$S]-GTPγS binding and immunohistochemistry," *Brit. J. Pharmacol.* vol. 128, pp. 1300-1306 (1999).

Perregaard et al., "Studies on Organophosphorus Compounds XVIII*. Oxidation of Tertiary Alicyclic Amines with Elemental Sulfur in Hexa-methylphosphoric Triamide (HMPA). Oxidative Rearrangements of Hexahy-Droazepines and Octahydroazocines to bis(3-Pyrroly1)Polysulfides.," *Bull. Soc. Chim. Belg.* vol. 86, pp. 679-691 (1977).

Poulain et al., "From Hit to Lead: Combining Two Complementary Methods for Focused Library Design. Application to μ Opiate Ligands," *J. Med. Chem.* vol. 44, pp. 3378-3390 (2001).

Poulain et al., "From Hit to Lead: Analyzing Structure-Profile Relationships," *J. Med. Chem.* vol. 44, pp. 3391-3401 (2001).

Radebough et al., "Preformulation," pp. 1447-1676 in Remington's Pharmaceutical Sciences vol. 2 (Gennaro, ed., 19$^{th}$ Ed., Mack Publishing, Easton, PA, 1995).

Robinson, "Coating of Pharmaceutical Dosage Forms," in Osol, ed., Remington's Pharmaceutical Sciences, 16$^{th}$ Ed., Mack Publishing, Easton, PA, Ch. 89, pp. 1553-1593 (1980).

Ronzoni et al., "Lead generation and lead optimization approaches in the discovery of selective, non-peptide ORL-1 receptor agonists and antagonists," *Exp. Opin. Ther. Patents* vol. 11, No. 4, pp. 525-546 (2001).

Sato et al., Psychotropic Agents. 3.$^{1}$ 4-(4-Substituted piperidiny1)-1-(4-fluorophenyl)-1-butanones with Potent Neuroleptic Activity, *J. Med. Chem.* vol. 21, No. 11, pp. 1116-1120 (1978).

Saudek et al., "A Preliminary Trial of the Programmable Implantable Medication System for Insulin Delivery," *New England J. Med.* vol. 321, pp. 574-579 (1989).

Sefton, "Implantable Pumps," *CRC Crit. Rev. Biomed. Eng.* vol. 14, No. 3, pp. 201-240 (1987).

Seltzer et al., "A novel behavioral model of neuropathic pain disorders produced in rats by partial sciatic nerve injury," *Pain* vol. 43, pp. 205-218 (1990).

Shimohigashi et al., "Sensitivity of opioid receptor-like receptor ORL1 for chemical modification on nociceptin, a naturally occurring nociceptive peptide," *J Biol. Chem.* vol. 271, No. 39, pp. 23642-23645 (1996).

Smolen et al., "Drug Product Design and Performance," Controlled Drug Bioavailability vol. 1, John Wiley & Sons, New York (Smolen and Ball, eds.) (1984).

Stein et al., "Unilateral Inflammation of the Hindpaw in Rats as a Model of Prolonged Noxious Stimulation: Alterations in Behavior and Nociceptive Thresholds," *Pharmacol. Biochem. & Behavior* vol. 31, pp. 445-451 (1988).

Tortolani et al., "A Convenient Synthesis to N-Aryl-Substituted 4-Piperidones," *Org Lett.* vol. 1, No. 8, pp. 1261-1262 (1999).

Treat et al., "Liposome Encapsulated Doxorubicin Preliminary Results of Phase I and Phase II Trials," *Liposomes in the Therapy of Infectious Disease and Cancer*, pp. 317-327 & 353-365 (1989).

van Tonder et al., "Preparation and Physicochemical Characterization of 5 Niclosamide Solvates and 1 Hemisolvate,"*AAPS Pharm. Sci. Tech.* vol. 5, No. 1, Article 12 (2004).

Widder et al., eds., "Drug and Enzyme Targeting, Part A," vol. 112 in Methods in Enzymology, Academic Press (1985).

Partial International Search Report for PCT application No. PCT/US2008/051096 mailed Jun. 18, 2008 (Form PCT/ISA/206).

International Search Report for PCT application No. PCT/US2008/051096 published Dec. 18, 2008 (WO 2008/089201 A3).

Communication pursuant to Article 94(3) EPC for EP application No. 08727696.0/2117 dated Aug. 21, 2009 (including Written Opinion of the International Searching Authority for PCT application No. PCT/US2008/051096).

* cited by examiner

US 8,637,502 B2

2,3,4,5-TETRAHYDRO-BENZO{B} {1,4}DIAZEPINE-COMPRISING COMPOUNDS OF FORMULA(III) FOR TREATING PAIN

This application is a divisional of application Ser. No. 12/503,598, filed Jul. 15, 2009, now U.S. Pat. No. 8,110,602, which is a continuation of PCT application no. PCT/US08/51096, filed Jan. 15, 2008, which claims the benefit under 35 U.S.C. §119(e) of provisional application no. 60/880,955, filed Jan. 16, 2007, and provisional application no. 60/930,035, filed May 11, 2007, the contents of all of which are incorporated herein by reference.

1. FIELD OF THE INVENTION

The invention relates to Heterocyclic-Substituted Piperidine Compounds, compositions comprising an effective amount of a Heterocyclic-Substituted Piperidine Compound and methods to treat or prevent a condition, such as pain, comprising administering to an animal in need thereof an effective amount of a Heterocyclic-Substituted Piperidine Compound.

2. BACKGROUND OF THE INVENTION

Chronic pain is a major contributor to disability and is the cause of much suffering. The successful treatment of severe and chronic pain is a primary goal of the physician, with opioid analgesics being preferred drugs for doing so.

Until recently, there was evidence of three major classes of opioid receptors in the central nervous system (CNS), with each class having subtype receptors. These receptor classes are known as $\mu$, $\delta$ and $\kappa$. As opiates have a high affinity for these receptors while not being endogenous to the body, research followed in order to identify and isolate the endogenous ligands to these receptors. These ligands were identified as enkephalins, endorphins and dynorphins.

Recent experimentation has led to the identification of a cDNA encoding an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for $\mu$, $\delta0$ and $\kappa$ receptors had low affinity for the ORL-1 receptor. This characteristic, along with the fact that an endogenous ligand had not yet been discovered, led to the term "orphan receptor".

Subsequent research led to the isolation and structure of the endogenous ligand of the ORL-1 receptor (i.e. nociceptin). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

The publications "From Hit to Lead: Combining Two Complementary Methods" and "From Hit to Lead: Analyzing Structure-Profile Relationships" of Poulain et al. (*J. Med. Chem.* 44:3378-3390 and 3391-3401, respectively (2001)) describe carbamates and carbamate analogs for use as opioid receptor ligands.

International PCT Publication No. WO 95/03299 describes benzodiazepine derivatives for use as CCK or gastrin antagonists.

International PCT Publication No. WO 00/06545 A1 describes piperidine derivatives as high affinity ligands for the nociceptin receptor ORL-1.

International PCT Publication No. WO 01/07050 A1 describes substituted piperidines as nociceptin receptor ORL-1 agonists for use to treat cough.

International PCT Publication No. WO 01/34571 describes $\beta$-amino acid compounds for use in inhibiting $\beta$-amyloid peptide release.

International PCT Publication No. WO 02/080895 A2 describes farnesyl protein transferase inhibitors comprising bicyclic groups for use in treating malaria.

U.S. published patent application No. US 2003/0134846 by Windsor et al. describes farnesyl protein transferase inhibitors, some of which comprise bicyclic groups, for use in treating *Trypanosoma Brucei* infection.

U.S. published patent application No. US 2003/0149027 by Oi et al. describes benzodiazepine compounds for use in regulating somatostatin receptors.

U.S. published patent application No. US 2003/0207886 by Plücker et al. describes quinoxaline derivatives for use in protecting human epidermis or hair against uv radiation.

U.S. published patent application No. US 2004/0082784 by Sielecki-Dzurdz et al. describes pyridino and pyrimidino pyrazinones for use as corticotropin releasing factor receptor antagonists to treat anxiety and depression.

U.S. published patent application No. US 2004/0220177 by Kath et al. describes pyrimidine derivatives for use in treating abnormal cell growth in cancer.

Japanese Application No. JP 08/291,071 A2 and U.S. Pat. No. 5,283,244 by Sakamoto et al. each describe fused pyrazine derivatives for use, respectively, as stable injection solutions and glutamate antagonists.

U.S. Pat. Nos. 5,739,129 and 5,859,007 by Aquino et al. describe benzodiazepine derivatives for use as CCK or gastrin modulators.

U.S. Pat. Nos. 6,576,644 and 6,835,737 by Bi et al. describe aminoquinolines for use as inhibitors of cGMP phosphodiesterase.

U.S. Pat. No. 7,001,901 by Yang describes tetrazolylpropionamides for use as inhibitors of Ar3 protein production.

Citation of any reference in Section 2 of this application is not to be construed as an admission that such reference is prior art to the present application.

3. SUMMARY OF THE INVENTION

It is an object of the invention to provide new compounds that exhibit affinity for the ORL-1 receptor.

In certain embodiments of the invention, such new compounds exhibit agonist activity at the ORL-1 receptor.

In certain other embodiments of the invention, such new compounds exhibit antagonist activity at the ORL-1 receptor.

In certain embodiments of the invention, such new compounds exhibit affinity for the ORL-1 receptor, and also for one or more of the $\mu$, $\delta$ or $\kappa$ receptors. In a particular embodiment, a new compound of the invention exhibits affinity for both the ORL-1 receptor and the $\mu$ receptor. In a more specific embodiment, a new compound of the invention acts as an ORL-1 receptor antagonist and as a $\mu$ receptor agonist.

Certain new compounds of the invention can be used to treat an animal suffering from chronic or acute pain.

It is a further object of the invention to provide methods of treating chronic or acute pain in an animal by administering one or more Heterocyclic-Substituted Piperidine Compounds of the invention to an animal in need of such treatment. In certain embodiments, such new Heterocyclic-Substituted Piperidine Compounds effectively treat chronic or acute pain in the animal, while producing fewer or reduced side effects compared to previously available compounds.

The invention encompasses compounds of formula (i):

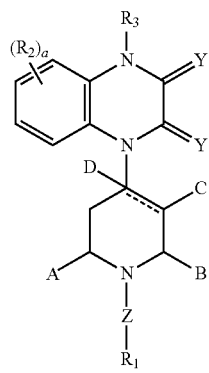

and pharmaceutically acceptable derivatives thereof wherein:
each $R_2$ is independently selected from:
(a) -halo, —CN, —NO$_2$, —OT$_3$, —C(O)T$_3$, —C(O)OT$_3$, —C(O)N(T$_1$)(T$_2$), —S(O)$_3$H, —S(O)T$_3$, —S(O)$_2$T$_3$, —S(O)$_2$N(T$_1$)(T$_2$), —N(T$_1$)(T$_2$), —N(T$_3$)C(O)T$_3$, —N(T$_3$)C(O)N(T$_1$)(T$_2$), —N(T$_3$)S(O)$_2$T$_3$, or —N(T$_3$)S(O)$_2$N(T$_1$)(T$_2$); or
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —(C$_{14}$)aryl, or -(5- or 6-membered)heteroaryl, each of which is unsubstituted or substituted with 1, 2 or 3 independently selected $R_7$ groups;
a is an integer selected from 0, 1 or 2;
$R_3$ is selected from:
(a) —H; or
(b) —(C$_1$-C$_6$)alkyl, —(C$_2$-C$_6$)alkenyl, —(C$_2$-C$_6$)alkynyl, —O(C$_1$-C$_6$)alkyl, —O(C$_2$-C$_6$)alkenyl, —O(C$_2$-C$_6$)alkynyl, —(C$_3$-C$_7$)cycloalkyl, —(C$_3$-C$_7$)cycloalkenyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —(C$_{14}$)aryl, or -(5- to 10-membered)heteroaryl, each of which is unsubstituted or substituted with 1, 2 or 3 independently selected $R_7$ groups; or
(d) —(C$_1$-C$_6$)alkyl(=O)W$_1$, —(C$_1$-C$_6$)alkyl(=NH)W$_1$, —C(O)OV$_1$, —C(O)N(V$_1$)$_2$, —S(O)$_2$N(V$_1$)$_2$, or —S(O)$_2$(C$_1$-C$_6$)alkyl; or
(e) —(C$_1$-C$_4$)alkyl substituted with 1, 2 or 3 substituents independently selected from —(C$_3$-C$_7$)cycloalkyl, —(C$_3$-C$_7$)cycloalkenyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkyl, -(3- to 7-membered)heterocycle, -(7- to 10-membered)bicycloheterocycle, -phenyl, -naphthalenyl, —(C$_{14}$)aryl, or -(5- to 10-membered)heteroaryl; or
(f) —(C$_1$-C$_3$)alkyl substituted with a substituent selected from —N(R$_6$)$_2$, —S(O)$_2$N(V$_1$)$_2$, —N(R$_9$)C(O)W$_1$, —N(R$_9$)S(O)$_2$W$_1$, and —C(O)N(V$_1$)$_2$;
each W$_1$ is independently selected from:
(a) —H, —(C$_1$-C$_6$)alkyl, —(C$_3$-C$_7$)cycloalkyl, —O(C$_1$-C$_6$)alkyl, —(C$_3$-C$_7$)cycloalkoxy, —CH$_2$CH$_2$OH, —N(R$_6$)$_2$; or
(b) -(5- or 6-membered)heteroaryl optionally substituted with 1, 2 or 3 independently selected —(C$_1$-C$_6$)alkyl;
each V$_1$ is independently selected from —H, —(C$_1$-C$_6$)alkyl, —(C$_3$-C$_7$)cycloalkyl, -phenyl, or -benzyl;
each Y is independently selected from O or S;
A and B are independently selected from:
(a) —H, —CN, —C(O)OT$_3$, —C(O)N(T)$_1$(T$_2$), —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl or —(C$_1$-C$_6$)alkoxy, each of which —(C$_3$-C$_{12}$)cycloalkyl, —(C$_3$-C$_{12}$)cycloalkoxy, —(C$_1$-C$_6$)alkyl, —(C$_2$-C$_6$)alkenyl or —(C$_2$-C$_6$)alkynyl is unsubstituted or substituted with 1 or 2 substituents independently selected from —OH, —S(O)$_2$NH$_2$, —N(R$_6$)$_2$, =NR$_6$, —C(O)OT$_3$, —C(O)N(R$_6$)$_2$, —N(R$_6$)C(O)R$_9$ and -(5- or 6-membered)heterocycle or 1, 2 or 3 independently selected -halo; or
(b) A-B together form a (C$_2$-C$_6$)bridge, which is unsubstituted or substituted with 1, 2 or 3 independently selected $R_8$ groups, and which bridge optionally contains —HC=CH— within the (C$_2$-C$_6$)bridge; wherein the piperazine ring that is fused to the phenyl group can be in the endo- or exo-conformation with respect to the A-B bridge; or
(c) A-B together form a —CH$_2$—N(R$_a$)—CH$_2$— bridge, a

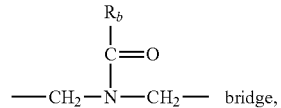

or a

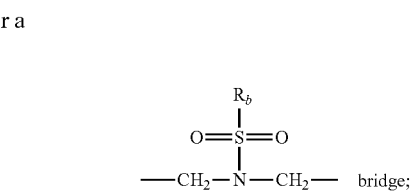

wherein the piperazine ring that is fused to the phenyl group can be in the endo- or exo-conformation with respect to the A-B bridge;
$R_a$ is selected from —H, —(C$_1$-C$_6$)alkyl, —(C$_3$-C$_7$)cycloalkyl, —CH$_2$—C(O)—R$_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$—N(R$_c$)$_2$, R$_c$, or —(CH$_2$)$_2$—N(R)S(O)$_2$—R$_c$;
$R_b$ is selected from:
(a) —H, —(C$_1$-C$_6$)alkyl, —(C$_3$-C$_7$)cycloalkyl, -(3- to 7-membered)heterocycle, —N(R$_c$)$_2$, —N(R$_c$)—(C$_3$-C$_7$)cycloalkyl, or —N(R$_c$)-(3- to 7-membered)heterocycle; or
(b) -phenyl, -naphthalenyl, or -(5- or 6-membered)heteroaryl, each of which is unsubstituted or substituted with 1, 2 or 3 independently selected $R_7$ groups; or
(c) —N(R$_c$)-phenyl, —N(R$_c$)-naphthalenyl, —N(R$_c$)—(C$_{14}$)aryl, or —N(R$_c$)-(5- to 10-membered)heteroaryl, each of which is unsubstituted or substituted with 1, 2 or 3 independently selected $R_7$ groups;

each $R_c$ is independently selected from —H or —($C_1$-$C_4$)alkyl;

C is selected from —H, -halo, —CN, —$OT_3$, —C(O)$OT_3$, —C(O)N($T$)$_1$($T_2$), —($C_3$-$C_{12}$)cycloalkyl, —($C_3$-$C_{12}$)cycloalkoxy, —N($R_6$)$_2$, —N($R_6$)C(O)$R_9$, —$NR_6SO_2N(R_6)_2$, —$NR_6$—C(=$NR_6$)N($R_6$)$_2$, —($C_1$-$C_6$)alkyl, —($C_2$-$C_6$)alkenyl, or —($C_2$-$C_6$)alkynyl, each of which —($C_1$-$C_6$)alkyl, —($C_2$-$C_6$)alkenyl or —($C_2$-$C_6$)alkynyl is unsubstituted or substituted with 1 or 2 substituents independently selected from —OH, —S(O)$_2NH_2$, —N($R_6$)$_2$, =$NR_6$, —C(O)$OT_3$, —C(O)N($R_6$)$_2$, —N($R_6$)C(O)$R_9$ and -(5- or 6-membered)heterocycle or from 1 to 3 independently selected -halo;

the dashed line in the piperidine or bridged piperidine central ring denotes the presence or absence of a bond, and when the dashed line denotes the presence of a bond then D is absent, otherwise D is:

(a) —H, —CN, —C(O)$OT_3$, or —C(O)N($T_1$)($T_2$); or (b) —($C_1$-$C_{10}$)alkyl which is unsubstituted or substituted with 1, 2 or 3 independently selected $R_8$ groups and, optionally, in which any D group carbon atom except the carbon atom bonded directly to the piperidine or bridged piperidine central ring, is independently replaced by O or S; or (c) -phenyl, -naphthalenyl, or -(5- or 6-membered)heteroaryl, each of which is unsubstituted or substituted with 1, 2 or 3 independently selected $R_7$ groups;

Z is a bond;

$R_1$ is selected from:

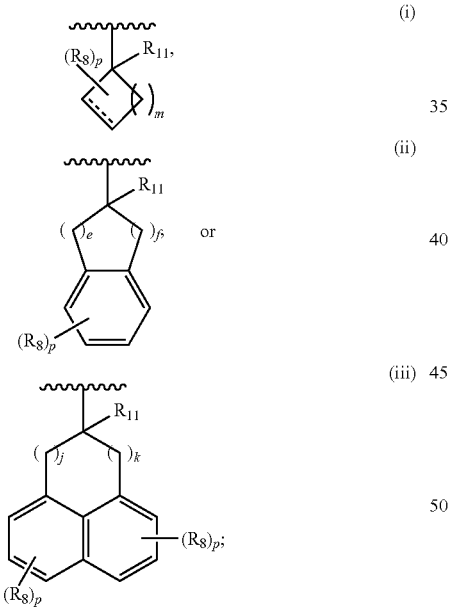

m is an integer selected from 0, 1, 2, 3, 4, 5, 6 or 7;

e and f are each an integer independently selected from 0, 1, 2, 3, 4 or 5 provided that $2 \leq (e+f) \leq 5$;

j and k are each an integer independently selected from 0, 1, 2, 3 or 4 provided that $1 \leq (j+k) \leq 4$;

each $T_1$, $T_2$, and $T_3$ is independently —H or —($C_1$-$C_{10}$)alkyl which is unsubstituted or substituted with 1, 2 or 3 independently selected $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O or S;

each $R_6$ is independently selected from —H, —($C_1$-$C_6$)alkyl, or —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_7$ is independently selected from —($C_1$-$C_4$)alkyl, —($C_2$-$C_6$)alkenyl, —($C_2$-$C_6$)alkynyl, —$OR_9$, —$SR_9$, —C(halo)$_3$, —CH(halo)$_2$, —$CH_2$(halo), —CN, -halo, —$N_3$, —$NO_2$, —CH=$NR_9$, —$NR_9$OH, —C(O)$OR_9$, —OC(O)$R_9$, —OC(O)$OR_9$, —S(O)$R_9$, or —S(O)$_2R_9$;

each $R_8$ is independently selected from —($C_1$-$C_4$)alkyl, —($C_2$-$C_6$)alkenyl, —($C_2$-$C_6$)alkynyl, —$OR_9$, —$SR_9$, —C(halo)$_3$, —CH(halo)$_2$, —$CH_2$(halo), —CN, oxo, =S, -phenyl, -halo, —$N_3$, —$NO_2$, —CH=$NR_9$, —$NR_9$OH, —C(O)$OR_9$, —OC(O)$R_9$, —OC(O)$OR_9$, —S(O)$R_9$, or —S(O)$_2R_9$;

each $R_9$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 7-membered)heterocycle, —C(halo)$_3$, —CH(halo)$_2$, or —$CH_2$(halo);

each p is an integer independently selected from 0 or 1;

$R_{11}$ is selected from —H, —C(O)$OR_9$, —C(O)N($R_6$)$_2$, or —($C_1$-$C_4$)alkyl which is unsubstituted or substituted with —OH, —($C_1$-$C_4$)alkoxy, —N($R_6$)$_2$, —C(O)$OR_9$, or —C(O)N($R_6$)$_2$; and each halo is independently selected from —F, —Cl, —Br, or —I.

The invention encompasses compounds of formula (II):

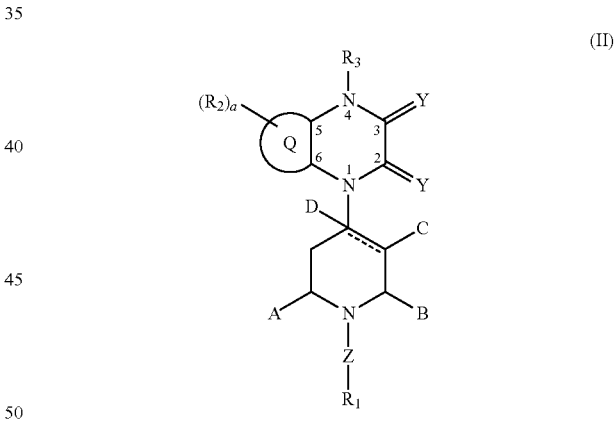

and pharmaceutically acceptable derivatives thereof wherein:

Q is selected from naphthalene or pyridino;

each $R_2$ is independently selected from:

(a) -halo, —CN, —$NO_2$, —$OT_3$, —C(O)$T_3$, —C(O)$OT_3$, —C(O)N($T_1$)($T_2$), —S(O)$_3$H, —S(O)$T_3$, —S(O)$_2T_3$, —S(O)$_2N(T_1)(T_2)$, —N($T_1$)($T_2$), —N($T_3$)C(O)$T_3$, —N($T_3$)C(O)N($T_1$)($T_2$), —N($T_3$)S(O)$_2T_3$, or —N($T_3$)S(O)$_2N(T_1)(T_2)$; or (b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or (c) -phenyl, -naphthalenyl, —($C_{14}$)aryl, or -(5- or 6-membered)heteroaryl, each of which is unsubstituted or substituted with 1, 2 or 3 independently selected $R_7$ groups;

a is an integer selected from 0, 1 or 2;

$R_3$ is selected from:

(a) —H; or (b) —($C_1$-$C_6$)alkyl, —($C_2$-$C_6$)alkenyl, —($C_2$-$C_6$)alkynyl, —O($C_1$-$C_6$)alkyl, —O($C_2$-$C_6$)alkenyl, —O($C_2$-$C_6$)alkynyl, —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, or -(7- to 10-membered)bicycloheterocycle, each of which is unsubstituted or substituted with 1, 2 or 3 independently selected $R_8$ groups; or (c) -phenyl, -naphthalenyl, —($C_{14}$)aryl, or -(5- to 10-membered)heteroaryl, each of which is unsubstituted or substituted with 1, 2 or 3 independently selected $R_7$ groups; or (d) —($C_1$-$C_6$)alkyl(=O)$W_1$, —($C_1$-$C_6$)alkyl(=NH)$W_1$, —C(O)O$V_1$, —C(O)N($V_1$)$_2$, —S(O)$_2$N($V_1$)$_2$, or —S(O)$_2$($C_1$-$C_6$)alkyl; or (e) —($C_1$-$C_4$)alkyl substituted with 1, 2 or 3 substituents independently selected from —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, -phenyl, -naphthalenyl, —($C_{14}$)aryl, or -(5- to 10-membered)heteroaryl; or (f) —($C_1$-$C_3$)alkyl substituted with a substituent selected from —N($R_6$)$_2$, —S(O)$_2$N($V_1$)$_2$, —N($R_9$)C(O)$W_1$, —N($R_9$)S(O)$_2$$W_1$, and —C(O)N($V_1$)$_2$;

each Y is independently selected from O or S;

A and B are independently selected from:

(a) —H, —CN, —C(O)O$T_3$, —C(O)N(T)$_1$(T$_2$), —($C_3$-$C_{12}$)cycloalkyl, —($C_3$-$C_{12}$)cycloalkoxy, —($C_1$-$C_6$)alkyl, —($C_2$-$C_6$)alkenyl, —($C_2$-$C_6$)alkynyl or —($C_1$-$C_6$)alkoxy, each of which —($C_3$-$C_{12}$)cycloalkyl, —($C_3$-$C_{12}$)cycloalkoxy, —($C_1$-$C_6$)alkyl, —($C_2$-$C_6$)alkenyl or —($C_2$-$C_6$)alkynyl is unsubstituted or substituted with 1 or 2 substituents independently selected from —OH, —S(O)$_2$NH$_2$, —N($R_6$)$_2$, —C(O)O$T_3$, —C(O)N($R_6$)$_2$, —N($R_6$)C(O)$R_9$ and -(5- or 6-membered)heterocycle or 1, 2 or 3 independently selected -halo; or (b) A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the piperazine ring that is fused to the Q group can be in the endo- or exo-conformation with respect to the A-B bridge; or (c) A-B together form a —CH$_2$—N($R_a$)—CH$_2$— bridge, a

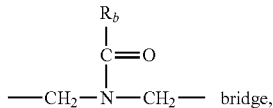

or a

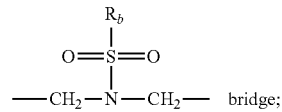

wherein the piperazine ring that is fused to the Q group can be in the endo- or exo-conformation with respect to the A-B bridge;

$R_a$ is selected from —H, —($C_1$-$C_6$)alkyl, —($C_3$-$C_7$)cycloalkyl, —CH$_2$—C(O)—$R_c$, —(CH$_2$)—C(O)—O$R_c$, —(CH$_2$)—C(O)—N($R_9$)$_2$, —(CH$_2$)$_2$—O—$R_c$, —(CH$_2$)$_2$—S(O)$_2$—N($R_9$)$_2$, $R_c$, or —(CH$_2$)$_2$—N(R)S(O)$_2$—$R_c$;

$R_b$ is selected from:

(a) —H, —($C_1$-$C_6$)alkyl, —($C_3$-$C_7$)cycloalkyl, -(3- to 7-membered)heterocycle, —N($R_c$)$_2$, —N($R_c$)—($C_3$-$C_7$)cycloalkyl, or —N($R_c$)-(3- to 7-membered)heterocycle; or (b) -phenyl, -naphthalenyl, or -(5- or 6-membered)heteroaryl, each of which is unsubstituted or substituted with 1, 2 or 3 independently selected $R_7$ groups; or (c) —N($R_c$)-phenyl, —N($R_c$)-naphthalenyl, —N($R_c$)—($C_{14}$)aryl, or —N($R_c$)-(5- to 10-membered)heteroaryl, each of which is unsubstituted or substituted with 1, 2 or 3 independently selected $R_7$ groups;

each $R_c$ is independently selected from —H or —($C_1$-$C_4$)alkyl;

C is selected from —H, -halo, —CN, —O$T_3$, —C(O)O$T_3$, —C(O)N(T)$_1$(T$_2$), —($C_3$-$C_{12}$)cycloalkyl, —($C_3$-$C_{12}$)cycloalkoxy, —N($R_6$)$_2$, —N($R_6$)C(O)$R_9$, —N$R_6$SO$_2$N($R_6$)$_2$, —N$R_6$—C(=N$R_6$)N($R_6$)$_2$, —($C_1$-$C_6$)alkyl, —($C_2$-$C_6$)alkenyl, or —($C_2$-$C_6$)alkynyl, each of which —($C_1$-$C_6$)alkyl, —($C_2$-$C_6$)alkenyl or —($C_2$-$C_6$)alkynyl is unsubstituted or substituted with 1 or 2 substituents independently selected from —OH, —S(O)$_2$NH$_2$, —N($R_6$)$_2$, =N$R_6$, —C(O)O$T_3$, —C(O)N($R_6$)$_2$, —N($R_6$)C(O)$R_9$ and -(5- or 6-membered)heterocycle or from 1 to 3 independently selected -halo;

the dashed line in the piperidine or bridged piperidine central ring denotes the presence or absence of a bond, and when the dashed line denotes the presence of a bond then D is absent, otherwise D is:

(a) —H, —CN, —C(O)O$T_3$, or —C(O)N(T$_1$)(T$_2$); or (b) -($C_1$-$C_{10}$)alkyl which is unsubstituted or substituted with 1, 2 or 3 independently selected $R_8$ groups and, optionally, in which any D group carbon atom except the carbon atom bonded directly to the piperidine or bridged piperidine central ring is independently replaced by O or S; or (c) -phenyl, -naphthalenyl, or -(5- or 6-membered)heteroaryl, each of which is unsubstituted or substituted with 1, 2 or 3 independently selected $R_7$ groups;

Z is —[($C_1$-$C_{10}$)alkyl optionally substituted by R]$_h$—, where h is 0 or 1; or —($C_1$-$C_{10}$)alkyl-N$R_6$C(=Y)—;

$R_1$ is selected from:

(a) —H, -halo, —CN, —OH, —CH$_2$OH, —CH$_2$CH$_2$OH, —NO$_2$, —N($R_6$)$_2$, —S(O)NH$_2$, —S(O)$_2$NH$_2$, —C(O)O$V_1$, or —C(O)CN; or (b) —($C_1$-$C_6$)alkyl, —($C_2$-$C_6$)alkenyl, —($C_2$-$C_6$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, each of which is unsubstituted or substituted with an $R_8$ group, or

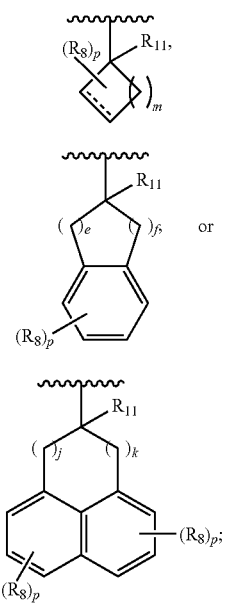

or (c) -phenyl, -naphthalenyl, —($C_{14}$)aryl, or -(5- to 10-membered)heteroaryl, each of which is unsubstituted or substituted with an $R_7$ group; or —Z—$R_1$ is 3,3-diphenylpropyl—optionally substituted at the 3 carbon of the propyl with —CN, —C(O)N($R_6$)$_2$, —C(O)O$V_1$, or -tetrazolyl; or —Z—$R_1$ is —($C_1$-$C_4$)alkyl substituted with tetrazolyl;

each $R_6$ is independently selected from —H, —($C_1$-$C_6$)alkyl, or —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_7$ is independently selected from —($C_1$-$C_4$)alkyl, —($C_2$-$C_6$)alkenyl, —($C_2$-$C_6$)alkynyl, —O$R_9$, —S$R_9$, —C(halo)$_3$, —CH(halo)$_2$, —CH$_2$(halo), —CN, -halo, —N$_3$, —NO$_2$, —CH=N$R_9$, —N$R_9$OH, —C(O)O$R_9$, —OC(O)$R_9$, —OC(O)O$R_9$, —S(O)$R_9$, or —S(O)$_2R_9$;

each $R_8$ is independently selected from —($C_1$-$C_4$)alkyl, —($C_2$-$C_6$)alkenyl, —($C_2$-$C_6$)alkynyl, —O$R_9$, —S$R_9$, —C(halo)$_3$, —CH(halo)$_2$, —CH$_2$(halo), —CN, oxo, =S, -phenyl, -halo, —N$_3$, —NO$_2$, —CH=N$R_9$, —N$R_9$OH, —C(O)O$R_9$, —OC(O)$R_9$, —OC(O)O$R_9$, —S(O)$R_9$, or —S(O)$_2R_9$;

each $R_9$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 7-membered)heterocycle, —C(halo)$_3$, —CH(halo)$_2$, or —CH$_2$(halo);

if h is 0, $R_{11}$ is selected from —H, —C(O)O$R_9$, —C(O)N($R_6$)$_2$, or —($C_1$-$C_4$)alkyl which is unsubstituted or substituted with —OH, —($C_1$-$C_4$)alkoxy, —N($R_6$)$_2$, —C(O)O$R_9$, or —C(O)N($R_6$)$_2$;

if h is 1, $R_{11}$ is selected from —H, —OH, -halo, —C(O)O$R_9$, —C(O)N($R_6$)$_2$, or —($C_1$-$C_4$)alkyl which is unsubstituted or substituted with —OH, —($C_1$-$C_4$)alkoxy, —N($R_6$)$_2$, —C(O)O$R_9$, or —C(O)N($R_6$)$_2$;

m is an integer selected from 0, 1, 2, 3, 4, 5, 6 or 7;

e and f are each an integer independently selected from 0, 1, 2, 3, 4 or 5 provided that $2 \leq (e+f) \leq 5$;

j and k are each an integer independently selected from 0, 1, 2, 3 or 4 provided that $1 \leq (j+k) \leq 4$;

each p is an integer independently selected from 0 or 1;

each $T_1$, $T_2$, and $T_3$ is independently —H or —($C_1$-$C_{10}$) alkyl which is unsubstituted or substituted with 1, 2 or 3 independently selected $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O or S;

each $V_1$ is independently selected from —H, —($C_1$-$C_6$) alkyl, —($C_3$-$C_7$)cycloalkyl, -phenyl, or -benzyl;

each $W_1$ is independently selected from:
(a) —H, —($C_1$-$C_6$)alkyl, —($C_3$-$C_7$)cycloalkyl, —O($C_1$-$C_6$)alkyl, —($C_3$-$C_7$)cycloalkoxy, —CH$_2$CH$_2$OH, —N($R_6$)$_2$; or
(b) -(5- or 6-membered)heteroaryl optionally substituted with 1, 2 or 3 independently selected —($C_1$-$C_6$)alkyl; and each halo is independently selected from —F, —Cl, —Br, or —I;

provided that when h is 0, then $R_1$ is not -halo or —NO$_2$;

provided that when Q is pyridino, then $R_2$ is not imidazolyl or triazolyl;

provided that when Q is pyridino and $R_2$ is -phenyl, -naphthalenyl, or -(5- or 6-membered)heteroaryl, then the $R_2$ group is not attached to a pyridino atom bonded to a 5- or 6-position carbon atom; and provided that $R_3$ does not include an imidazolyl group.

The invention encompasses compounds of formula (III):

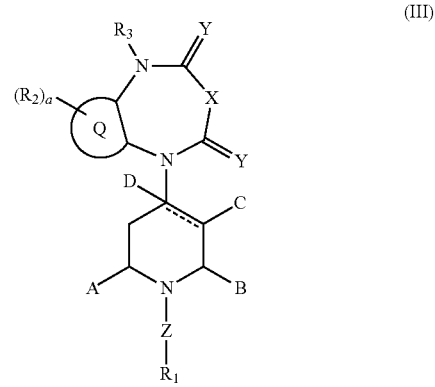

(III)

and pharmaceutically acceptable derivatives thereof wherein:

Q is selected from benzo, naphthaleno, ($C_{14}$)aryl, ($C_3$-$C_{12}$) cycloalkyl, ($C_6$-$C_{14}$)bicycloalkyl, ($C_5$-$C_{10}$)cycloalkenyl, ($C_7$-$C_{14}$)bicycloalkenyl, (3- to 7-membered)heterocycle, or (5- to 10-membered)heteroaryl;

each $R_2$ is independently selected from:
(a) -halo, —CN, —NO$_2$, —O$T_3$, —C(O)$T_3$, —C(O)O$T_3$, —C(O)N($T_1$)($T_2$), —S(O)$_3$H, —S(O)$T_3$, —S(O)$_2T_3$, —S(O)$_2$N($T_1$)($T_2$), —N($T_1$)($T_2$), —N($T_3$)C(O)$T_3$, —N($T_3$)C(O)N($T_1$)($T_2$), —N($T_3$)S(O)$_2T_3$, or —N($T_3$)S (O)$_2$N($T_1$)($T_2$); or
(b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, -($C_9$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or (c) -phenyl, -naphthalenyl, —$(C_{14})$aryl, or -(5- or 6-membered)heteroaryl, each of which is unsubstituted or substituted with 1, 2 or 3 independently selected $R_7$ groups;

a is an integer selected from 0, 1 or 2;

$R_3$ is selected from:

(a) —H; or (b) —$(C_1-C_6)$alkyl, —$(C_2-C_6)$alkenyl, —$(C_2-C_6)$alkynyl, —$O(C_1-C_6)$alkyl, —$O(C_2-C_6)$alkenyl, —$O(C_2-C_6)$alkynyl, —$(C_3-C_7)$cycloalkyl, —$(C_3-C_7)$cycloalkenyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, or -(7- to 10-membered)bicycloheterocycle, each of which is unsubstituted or substituted with 1, 2 or 3 independently selected $R_8$ groups; or (c) -phenyl, -naphthalenyl, —$(C_{14})$aryl, or -(5- to 10-membered)heteroaryl, each of which is unsubstituted or substituted with 1, 2 or 3 independently selected $R_7$ groups; or (d) —$(C_1-C_6)$alkyl(=O)$W_1$, —$(C_1-C_6)$alkyl(=NH)$W_1$, —C(O)O$V_1$, —C(O)N$(V_1)_2$, —S(O)$_2$N$(V_1)_2$, or —S(O)$_2$(C$_1$-C$_6$)alkyl; or (e) —$(C_1-C_4)$alkyl substituted with 1, 2 or 3 substituents independently selected from —$(C_3-C_7)$cycloalkyl, —$(C_3-C_7)$cycloalkenyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, -(7- to 10-membered)bicycloheterocycle, -phenyl, -naphthalenyl, —$(C_{14})$aryl, or -(5- to 10-membered)heteroaryl; or (f) —$(C_1-C_3)$alkyl substituted with a substituent selected from —N$(R_6)_2$, —S(O)$_2$N$(V_1)_2$, —N$(R_9)$C(O)$W_1$, —N$(R_9)$S(O)$_2$W , and —C(O)N$(V_1)_2$;

each Y is independently selected from O or S;

X is —C$(R_4)(R_5)$—, —N$(R_{13})$—, —C$(R_4)(R_5)$—C$(R_4')(R_5')$—, —C$(R_4)$=C$(R_4')$—, —C$(R_4)(R_5)$—N$(R_{13})$—, or —N$(R_{13})$—C$(R_4)(R_5)$—;

each $R_4$ and $R_4'$ is independently selected from —H, —OR$_6$, —$(C_1-C_6)$alkyl, or —$(C_3-C_7)$cycloalkyl; or, independently, any two of $R_4$ and $R_5$, or $R_4'$ and $R_5'$, together can form an oxo group; or any two of $R_4$ and $R_4'$ can form a 4- to 8-membered cycloalkyl ring, the number of atoms in the ring including the atoms to which the two of $R_4$ and $R_4'$ are attached and any intervening atoms, if present;

each $R_5$ and $R_5'$ is independently selected from —H, —$(C_1-C_6)$alkyl, or —$(C_3-C_7)$cycloalkyl;

$R_{13}$ is selected from:

(a) —H; or (b) —$(C_1-C_6)$alkyl, —$(C_2-C_6)$alkenyl, —$(C_2-C_6)$alkynyl, —$(C_3-C_7)$cycloalkyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, or -(7- to 10-membered)bicycloheterocycle, each of which is unsubstituted or substituted with 1, 2 or 3 independently selected $R_8$ groups; or (c) -phenyl, -naphthalenyl, —$(C_{14})$aryl, or -(5- to 10-membered)heteroaryl, each of which is unsubstituted or substituted with 1, 2 or 3 independently selected $R_7$ groups; or (d) —C(O)O(C$_3$-C$_8$)cycloalkyl, —CH$_2$CH$_2$OH, —$(C_1-C_6)$alkyl(=O)W$_2$, or —$(C_1-C_6)$alkyl-W$_2$; or (e) —$(C_1-C_4)$alkyl substituted with 1, 2 or 3 substituents independently selected from —N$(R_6)_2$; —C(O)OR$_9$; —C(O)N$(R_9)_2$; —OC(O)(C$_3$-C$_8$)cycloalkyl; —NHS(O)$_2$(C$_3$-C$_8$)cycloalkyl; —NHC(O)W$_2$; —NHS(O)$_2$W$_2$; —(C$_3$-C$_{12}$)cycloalkyl, —(C$_3$-C$_7$)cycloalkenyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle or -(7- to 10-membered)bicycloheterocycle, each of which is unsubstituted or further substituted with 1, 2 or 3 independently selected $R_8$ groups; or -phenyl, -naphthalenyl, —(C$_{14}$)aryl or -(5- to 10-membered)heteroaryl, each of which is unsubstituted or further substituted with 1, 2 or 3 independently selected $R_8$ groups;

each $W_2$ is independently selected from —(C$_3$-C$_7$)cycloalkyl, —O(C$_1$-C$_6$)alkyl, —(C$_3$-C$_7$)cycloalkoxy, (3- to 7-membered)heterocycle, —CH$_2$CH$_2$OH, and —N$(R_6)_2$;

A and B are independently selected from:

(a) —H, —CN, —C(O)OT$_3$, —C(O)N$(T)_1(T_2)$, —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl or —(C$_1$-C$_6$)alkoxy, each of which —(C$_3$-C$_{12}$)cycloalkyl, —(C$_3$-C$_{12}$)cycloalkoxy, —(C$_2$-C$_6$)alkenyl or —(C$_2$-C$_6$)alkynyl is unsubstituted or substituted with 1 or 2 substituents independently selected from —OH, —S(O)$_2$ NH$_2$, —N$(R_6)_2$, =NR$_6$, —C(O)OT$_3$, —C(O)N$(R_6)_2$, —N$(R_6)$C(O)R$_9$ and -(5- or 6-membered)heterocycle or 1, 2 or 3 independently selected -halo; or (b) A-B together form a (C$_2$-C$_6$)bridge, which is unsubstituted or substituted with 1, 2 or 3 independently selected $R_8$ groups, and which bridge optionally contains —HC=CH— within the (C$_2$-C$_6$)bridge; wherein the heterocyclic ring that is fused to the Q group can be in the endo- or exo-conformation with respect to the A-B bridge; or (c) A-B together form a —CH$_2$—N$(R_a)$—CH$_2$— bridge, a

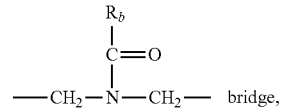

or a

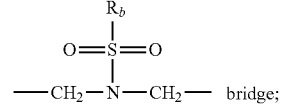

wherein the heterocyclic ring that is fused to the Q group can be in the endo- or exo-conformation with respect to the A-B bridge;

$R_a$ is selected from —H, —(C$_1$-C$_6$)alkyl, —(C$_3$-C$_7$)cycloalkyl, —CH$_2$—C(O)—R$_c$, —(CH$_2$)—C(O)—OR$_c$, —(CH$_2$)—C(O)—N$(R_c)_2$, —(CH$_2$)$_2$—O—R$_c$, —(CH$_2$)$_2$—S(O)$_2$—N$(R_c)_2$, R$_9$, or —(CH$_2$)$_2$—N$(R_c)$S(O)$_2$—R$_c$;

$R_b$ is selected from:

(a) —H, —(C$_1$-C$_6$)alkyl, —(C$_3$-C$_7$)cycloalkyl, -(3- to 7-membered)heterocycle, —N$(R_c)_2$, —N$(R_c)$—(C$_3$-C$_7$)cycloalkyl, or —N$(R_c)$-(3- to 7-membered)heterocycle; or (b) -phenyl, -naphthalenyl, or -(5- or 6-membered)heteroaryl, each of which is unsubstituted or substituted with 1, 2 or 3 independently selected $R_7$ groups; or (c) —N($R_c$)-phenyl, —N($R_c$)-naphthalenyl, —N($R_c$)—($C_{14}$)aryl, or —N($R_c$)-(5- to 10-membered)heteroaryl, each of which is unsubstituted or substituted with 1, 2 or 3 independently selected $R_7$ groups;

each $R_c$ is independently selected from —H or —($C_1$-$C_4$)alkyl;

C is selected from —H, -halo, —CN, —$OT_3$, —C(O)$OT_3$, —C(O)N(T)$_1$($T_2$), —($C_3$-$C_{12}$)cycloalkyl, —($C_3$-$C_{12}$)cycloalkoxy, —N($R_6$)$_2$, —N($R_6$)C(O)$R_9$, —N$R_6$SO$_2$N($R_6$)$_2$—N$R_6$—C(=N$R_6$)N($R_6$)$_2$, —($C_1$-$C_6$)alkyl, —($C_2$-$C_6$)alkenyl, or —($C_2$-$C_6$)alkynyl, each of which —($C_1$-$C_6$)alkyl, —($C_2$-$C_6$)alkenyl or —($C_2$-$C_6$)alkynyl is unsubstituted or substituted with 1 or 2 substituents independently selected from —OH, —S(O)$_2$NH$_2$, —N($R_6$)$_2$, =N$R_6$, —C(O)$OT_3$, —C(O)N($R_6$)$_2$, —N($R_6$)C(O)$R_9$ and -(5- or 6-membered)heterocycle or from 1 to 3 independently selected -halo;

the dashed line in the piperidine or bridged piperidine central ring denotes the presence or absence of a bond, and when the dashed line denotes the presence of a bond then D is absent, otherwise D is:

(a) —H, —CN, —C(O)$OT_3$, or —C(O)N($T_1$)($T_2$); or (b) —($C_1$-$C_{10}$)alkyl which is unsubstituted or substituted with 1, 2 or 3 independently selected $R_8$ groups and, optionally, in which any D group carbon atom except the carbon atom bonded directly to the piperidine or bridged piperidine central ring, is independently replaced by O or S; or (c) -phenyl, -naphthalenyl, or -(5- or 6-membered)heteroaryl, each of which is unsubstituted or substituted with 1, 2 or 3 independently selected $R_7$ groups;

Z is -[($C_1$-$C_{10}$)alkyl optionally substituted by $R_1$]$_h$—, where h is 0 or 1; or —($C_1$-$C_{10}$)alkyl-N$R_6$C(=Y)—;

$R_1$ is selected from:

(a) —H, -halo, —CN, —OH, —CH$_2$OH, —CH$_2$CH$_2$OH, —NO$_2$, —N($R_6$)$_2$, —S(O)NH$_2$, —S(O)$_2$NH$_2$, —C(O)$OV_1$, or —C(O)CN;

(b) —($C_1$-$C_6$)alkyl, —($C_2$-$C_6$)alkenyl, —($C_2$-$C_6$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, each of which is unsubstituted or substituted with an $R_8$ group, or

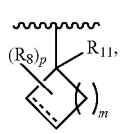
(i)

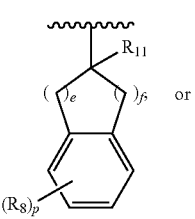
(ii)

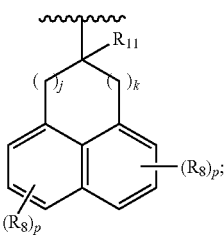
(iii)

or (c) -phenyl, -naphthalenyl, —($C_{14}$)aryl, or -(5- to 10-membered)heteroaryl, each of which is unsubstituted or substituted with an $R_7$ group; or —Z—$R_1$ is 3,3-diphenylpropyl—optionally substituted at the 3 carbon of the propyl with —CN, —C(O)N($R_6$)$_2$, —C(O)$OV_1$, or -tetrazolyl; or —Z—$R_1$ is —($C_1$-$C_4$)alkyl substituted with tetrazolyl;

each $R_6$ is independently selected from —H, —($C_1$-$C_6$)alkyl, or —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_7$ is independently selected from —($C_1$-$C_4$)alkyl, —($C_2$-$C_6$)alkenyl, —($C_2$-$C_6$)alkynyl, —O$R_9$, —S$R_9$, —C(halo)$_3$, —CH(halo)$_2$, —CH$_2$(halo), —CN, -halo, —N$_3$, —NO$_2$, —CH=N$R_9$, —N$R_9$OH, —C(O)O$R_9$, —OC(O)$R_9$, —OC(O)O$R_9$, —S(O)$R_9$, or —S(O)$_2$$R_9$;

each $R_8$ is independently selected from —($C_1$-$C_4$)alkyl, —($C_2$-$C_6$)alkenyl, —($C_2$-$C_6$)alkynyl, —O$R_9$, —S$R_9$, —C(halo)$_3$, —CH(halo)$_2$, —CH$_2$(halo), —CN, oxo, =S, -phenyl, -halo, —N$_3$, —NO$_2$, —CH=N$R_9$, —N$R_9$OH, —C(O)O$R_9$, —OC(O)$R_9$, —OC(O)O$R_9$, —S(O)$R_9$, or —S(O)$_2$$R_9$;

each $R_9$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 7-membered)heterocycle, —C(halo)$_3$, —CH(halo)$_2$, or —CH$_2$(halo);

if h is 0, $R_{11}$ is selected from —H, —C(O)O$R_9$, —C(O)N($R_6$)$_2$, or —($C_1$-$C_4$)alkyl which is unsubstituted or substituted with —OH, —($C_1$-$C_4$)alkoxy, —N($R_6$)$_2$, —C(O)O$R_9$, or —C(O)N($R_6$)$_2$;

if h is 1, $R_{11}$ is selected from —H, —OH, -halo, —C(O)O$R_9$, —C(O)N($R_6$)$_2$, or —($C_1$-$C_4$)alkyl which is unsubstituted or substituted with —OH, —($C_1$-$C_4$)alkoxy, —N($R_6$)$_2$, —C(O)O$R_9$, or —C(O)N($R_6$)$_2$;

m is an integer selected from 0, 1, 2, 3, 4, 5, 6 or 7;

e and f are each an integer independently selected from 0, 1, 2, 3, 4 or 5 provided that 2≤(e+f)≤5;

j and k are each an integer independently selected from 0, 1, 2, 3 or 4 provided that 1≤(j+k)≤4;

each p is an integer independently selected from 0 or 1;

each $T_1$, $T_2$, and $T_3$ is independently —H or —($C_1$-$C_{10}$)alkyl which is unsubstituted or substituted with 1, 2 or 3 independently selected $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O or S;

each $V_1$ is independently selected from —H, —($C_1$-$C_6$)alkyl, —($C_3$-$C_7$)cycloalkyl, -phenyl, or -benzyl;

each $W_1$ is independently selected from:
(a) —H, —($C_1$-$C_6$)alkyl, —($C_3$-$C_7$)cycloalkyl, —O($C_1$-$C_6$)alkyl, —($C_3$-$C_7$)cycloalkoxy, —CH$_2$CH$_2$OH, —N($R_6$)$_2$; or
(b) -(5- or 6-membered)heteroaryl optionally substituted with 1, 2 or 3 independently selected —($C_1$-$C_6$)alkyl; and each halo is independently selected from —F, —Cl, —Br, or —I;

provided that when h is 0, then $R_1$ is not -halo or —NO$_2$;
provided that when Q is benzo, then X is not —N($R_{13}$)—;
provided that when Q is benzo, then $R_3$ is not —($C_1$-$C_2$) alkyl substituted with —C(O)N($V_1$)$_2$; and
provided that $R_3$ does not include an imidazolyl group.

The invention encompasses compounds of formula (IV):

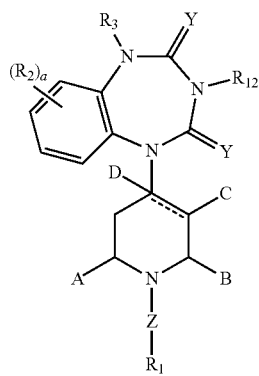

(IV)

and pharmaceutically acceptable derivatives thereof wherein:
each $R_2$ is independently selected from:
(a) -halo, —CN, —NO$_2$, —OT$_3$, —C(O)T$_3$, —C(O)OT$_3$, —C(O)N(T$_1$)(T$_2$), —S(O)$_3$H, —S(O)T$_3$, —S(O)$_2$T$_3$, —S(O)$_2$N(T$_1$)(T$_2$), —N(T$_1$)(T$_2$), —N(T$_3$)C(O)T$_3$, —N(T$_3$)C(O)N(T$_1$)(T$_2$), —N(T$_3$)S(O)$_2$T$_3$, or —N(T$_3$)S(O)$_2$N(T$_1$)(T$_2$); or
(b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —($C_{14}$)aryl, or -(5- or 6-membered)heteroaryl, each of which is unsubstituted or substituted with 1, 2 or 3 independently selected $R_7$ groups;
a is an integer selected from 0, 1 or 2;
$R_3$ is selected from:
(a) —H; or
(b) —($C_1$-$C_6$)alkyl, —($C_2$-$C_6$)alkenyl, —($C_2$-$C_6$)alkynyl, —O($C_1$-$C_6$)alkyl, —O($C_2$-$C_6$)alkenyl, —O($C_2$-$C_6$)alkynyl, —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —($C_{14}$)aryl, or -(5- to 10-membered)heteroaryl, each of which is unsubstituted or substituted with 1, 2 or 3 independently selected $R_7$ groups; or
(d) —($C_1$-$C_6$)alkyl(=NH)$W_1$, —C(O)OV$_1$, —C(O)N(V$_1$)$_2$, —S(O)$_2$N(V$_1$)$_2$, or —S(O)$_2$($C_1$-$C_6$)alkyl; or
(e) —($C_1$-$C_4$)alkyl substituted with 1, 2 or 3 substituents independently selected from —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, -phenyl, -naphthalenyl, —($C_{14}$)aryl, or -(5- to 10-membered)heteroaryl; or
(f) —($C_1$-$C_3$)alkyl substituted with a substituent selected from —N($R_6$)$_2$, —S(O)$_2$N(V$_1$)$_2$, —N($R_9$)C(O)$W_1$, —N($R_9$)S(O)$_2$$W_1$, and —C(O)N(V$_1$)$_2$;

each Y is independently selected from O or S;
$R_{12}$ is selected from:
(a) —($C_3$-$C_{12}$)cycloalkyl, —($C_3$-$C_{12}$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, each of which is unsubstituted or substituted with 1, 2 or 3 independently selected $R_8$ groups; or
(b) —($C_{14}$)aryl which is unsubstituted or substituted with 1, 2 or 3 independently selected $R_7$ groups; or
(c) —($C_1$-$C_4$)alkyl substituted with 1, 2 or 3 substituents independently selected from —C(O)OR$_9$, —C(O)N(R$_9$)$_2$, —($C_3$-$C_{12}$)cycloalkyl which is unsubstituted or further substituted with 1, 2 or 3 independently selected $R_8$ groups, —($C_3$-$C_{12}$)cycloalkoxy which is unsubstituted or further substituted with 1, 2 or 3 independently selected $R_8$ groups, -(3- to 7-membered)heterocycle which is unsubstituted or further substituted with 1, 2 or 3 independently selected $R_8$ groups, or —($C_{14}$)aryl which is unsubstituted or further substituted with 1, 2 or 3 independently selected $R_7$ groups; or
(d) —C(O)O($C_3$-$C_8$)cycloalkyl, —CH$_2$CH$_2$OH, —C(O)N(V$_1$)($C_3$-$C_8$)cycloalkyl, —($C_1$-$C_6$)alkyl(=O)$W_2$, or —($C_1$-$C_6$)alkyl-$W_2$; or
(e) —($C_1$-$C_4$)alkyl substituted with 1, 2 or 3 substituents independently selected from -OC(O)($C_3$-$C_8$)cycloalkyl, —NHS(O)$_2$($C_3$-$C_8$)cycloalkyl, —N(V$_1$)C(O)($C_3$-$C_8$)cycloalkyl, —NHC(O)$W_2$, and —NHS(O)$_2$$W_2$;

each $W_2$ is independently selected from —($C_3$-$C_7$)cycloalkyl, —O($C_1$-$C_6$)alkyl, —($C_3$-$C_7$)cycloalkoxy, (3- to 7-membered)heterocycle, —CH$_2$CH$_2$OH, and —N(R$_6$)$_2$;

A and B are independently selected from:
(a) —H, —CN, —C(O)OT$_3$, —C(O)N(T)$_1$(T$_2$), —($C_3$-$C_{12}$)cycloalkyl, —($C_3$-$C_{12}$)cycloalkoxy, —($C_1$-$C_6$)alkyl, —($C_2$-$C_6$)alkenyl, —($C_2$-$C_6$)alkynyl or —($C_1$-$C_6$)alkoxy, each of which —($C_3$-$C_{12}$)cycloalkyl, —($C_3$-$C_{12}$)cycloalkoxy, —($C_1$-$C_6$)alkyl, —($C_2$-$C_6$)alkenyl or —($C_2$-$C_6$)alkynyl is unsubstituted or substituted with 1 or 2 substituents independently selected from —OH, —S(O)$_2$NH$_2$, —N(R$_6$)$_2$, =NR$_6$, —C(O)OT$_3$, —C(O)N(R$_6$)$_2$, —N(R$_6$)C(O)R$_9$ and -(5- or 6-membered)heterocycle or 1, 2 or 3 independently selected -halo; or
(b) A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the heterocyclic ring that is fused to the phenyl group can be in the endo- or exo-conformation with respect to the A-B bridge; or (c) A-B together form a —CH$_2$—N(R$_a$)—CH$_2$— bridge, a

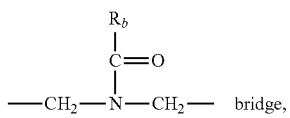 bridge, or a

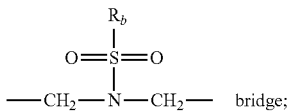 bridge;

wherein the heterocyclic ring that is fused to the phenyl group can be in the endo- or exo-conformation with respect to the A-B bridge;

R$_a$ is selected from —H, —(C$_1$-C$_6$)alkyl, —(C$_3$-C$_7$)cycloalkyl, —CH$_2$—C(O)—R$_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$—N(R$_c$)$_2$, R$_c$, or —(CH$_2$)$_2$—N(R$_c$)S(O)$_2$—R$_c$;

R$_b$ is selected from:
(a) —H, —(C$_1$-C$_6$)alkyl, —(C$_3$-C$_7$)cycloalkyl, -(3- to 7-membered)heterocycle, —N(R$_c$)$_2$, —N(R$_c$)—(C$_3$-C$_7$)cycloalkyl, or —N(R$_c$)-(3- to 7-membered)heterocycle; or
(b) -phenyl, -naphthalenyl, or -(5- or 6-membered)heteroaryl, each of which is unsubstituted or substituted with 1, 2 or 3 independently selected R$_7$ groups; or
(c) —N(R$_c$)-phenyl, —N(R$_c$)-naphthalenyl, —N(R$_c$)—(C$_{14}$)aryl, or —N(R$_c$)-(5- to 10-membered)heteroaryl, each of which is unsubstituted or substituted with 1, 2 or 3 independently selected R$_7$ groups;

each R$_c$ is independently selected from —H or —(C$_1$-C$_4$)alkyl;

C is selected from —H, -halo, —CN, —OT$_3$, —C(O)OT$_3$, —C(O)N(T)$_1$(T$_2$), —(C$_3$-C$_{12}$)cycloalkyl, —(C$_3$-C$_{12}$)cycloalkoxy, —N(R$_6$)$_2$, —N(R$_6$)C(O)R$_9$, —NR$_6$SO$_2$N(R$_6$)$_2$, —NR$_6$—C(=NR$_6$)N(R$_6$)$_2$, —(C$_1$-C$_6$)alkyl, —(C$_2$-C$_6$)alkenyl, or —(C$_2$-C$_6$)alkynyl, each of which —(C$_1$-C$_6$)alkyl, —(C$_2$-C$_6$)alkenyl or —(C$_2$-C$_6$)alkynyl is unsubstituted or substituted with 1 or 2 substituents independently selected from —OH, —S(O)$_2$NH$_2$, —N(R$_6$)$_2$, =NR$_6$, —C(O)OT$_3$, —C(O)N(R$_6$)$_2$, —N(R$_6$)C(O)R$_9$ and -(5- or 6-membered)heterocycle or from 1 to 3 independently selected -halo;

the dashed line in the piperidine or bridged piperidine central ring denotes the presence or absence of a bond, and when the dashed line denotes the presence of a bond then D is absent, otherwise D is:
(a) —H, —CN, —C(O)OT$_3$, or —C(O)N(T$_1$)(T$_2$); or
(b) —(C$_1$-C$_{10}$)alkyl which is unsubstituted or substituted with 1, 2 or 3 independently selected R$_8$ groups and, optionally, in which any D group carbon atom except the carbon atom bonded directly to the piperidine or bridged piperidine central ring, is independently replaced by O or S; or
(c) -phenyl, -naphthalenyl, or -(5- or 6-membered)heteroaryl, each of which is unsubstituted or substituted with 1, 2 or 3 independently selected R$_7$ groups;

Z is —[(C$_1$-C$_{10}$)alkyl optionally substituted by R$_1$]$_h$—, where h is 0 or 1; or —[(C$_1$-C$_{10}$)alkyl]NR$_6$C(=Y)—;

R$_1$ is selected from:
(a) —H, -halo, —CN, —OH, —CH$_2$OH, —CH$_2$CH$_2$OH, —NO$_2$, —N(R$_6$)$_2$, —S(O)NH$_2$, —S(O)$_2$NH$_2$, —C(O)OV$_1$, or —C(O)CN; or (b) —(C$_1$-C$_6$)alkyl, —(C$_2$-C$_6$)alkenyl, —(C$_2$-C$_6$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, -(7- to 10-membered)bicycloheterocycle, each of which is unsubstituted or substituted with an R$_8$ group, or

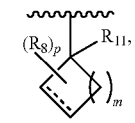

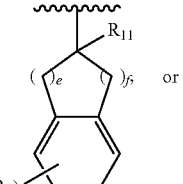

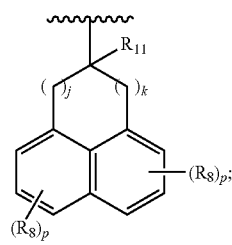

or (c) -phenyl, -naphthalenyl, —(C$_{14}$)aryl, or -(5- to 10-membered)heteroaryl, each of which is unsubstituted or substituted with an R$_7$ group; or —Z—R$_1$ is 3,3-diphenylpropyl—optionally substituted at the 3 carbon of the propyl with —CN, —C(O)N(R$_6$)$_2$, —C(O)OV$_1$, or -tetrazolyl; or —Z—R$_1$ is —(C$_1$-C$_4$)alkyl substituted with tetrazolyl;

each R$_6$ is independently selected from —H, —(C$_1$-C$_6$)alkyl, or —(C$_3$-C$_7$)cycloalkyl, or two R$_6$ groups attached to the same nitrogen atom can form a 5- to 8-membered ring, the number of atoms in the ring including the nitrogen atom, in which one of the ring carbon atoms is optionally replaced by O or S;

each R$_7$ is independently selected from —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, -halo, —N$_3$, —NO$_2$, —CH=NR$_9$, —NR$_9$OH, —C(O)OR$_9$, —OC(O)R$_9$, —OC(O)OR$_9$, —S(O)R$_9$, or —S(O)$_2$R$_9$;

each R$_8$ is independently selected from —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, oxo, =S, -phenyl, -halo, —N$_3$, —NO$_2$, —CH=NR$_9$, —NR$_9$OH, —C(O)OR$_9$, —OC(O)R$_9$, —OC(O)OR$_9$, —S(O)R$_9$, or —S(O)$_2$R$_9$;

each R$_9$ is independently selected from —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

if h is 0, R$_{11}$ is selected from —H, —C(O)OR$_9$, —C(O)N(R$_6$)$_2$, or —(C$_1$-C$_4$)alkyl which is unsubstituted or substituted with —OH, —(C$_1$-C$_4$)alkoxy, —N(R$_6$)$_2$, —C(O)OR$_9$, or —C(O)N(R$_6$)$_2$;

if h is 1, $R_{11}$ is selected from —H, —OH, -halo, —C(O)OR$_9$, —C(O)N(R$_6$)$_2$, or —(C$_1$-C$_4$)alkyl which is unsubstituted or substituted with —OH, —(C$_1$-C$_4$)alkoxy, —N(R$_6$)$_2$, —C(O)OR$_9$, or —C(O)N(R$_6$)$_2$;

m is an integer selected from 0, 1, 2, 3, 4, 5, 6 or 7;

e and f are each an integer independently selected from 0, 1, 2, 3, 4 or 5 provided that 2≤(e+f)≤5;

j and k are each an integer independently selected from 0, 1, 2, 3 or 4 provided that 1≤(j+k)≤4;

each p is an integer independently selected from 0 or 1;

each $T_1$, $T_2$, and $T_3$ is independently —H or —(C$_1$-C$_{10}$)alkyl which is unsubstituted or substituted with 1, 2 or 3 independently selected $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O or S;

each $V_1$ is independently selected from —H, —(C$_1$-C$_6$)alkyl, —(C$_3$-C$_7$)cycloalkyl, -phenyl, or -benzyl;

each $W_1$ is independently selected from:
(a) —H, —(C$_1$-C$_6$)alkyl, —(C$_3$-C$_7$)cycloalkyl, —O(C$_1$-C$_6$)alkyl, —(C$_3$-C$_7$)cycloalkoxy, —CH$_2$CH$_2$OH, —N(R$_6$)$_2$; or
(b) -(5- or 6-membered)heteroaryl optionally substituted with 1, 2 or 3 independently selected —(C$_1$-C$_6$)alkyl; and each halo is independently selected from —F, —Cl, —Br, or —I;

provided that when h is 0, $R_1$ is not -halo or —NO$_2$.

A compound of formula (i), (II), (III) or (IV) or a pharmaceutically acceptable derivative thereof (a "Heterocyclic-Substituted Piperidine Compound") is useful, e.g., as an analgesic, anti-inflammatory, diuretic, anesthetic agent, neuroprotective agent, anti-hypertensive, an anxiolytic agent, an agent for appetite control, hearing regulator, anti-tussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias, anti-epileptic, anti-convulsant, agent to treat withdrawal from alcohol, agent to treat withdrawal from drug(s) of addiction, agent to control water balance, agent to control sodium excretion, and/or agent to control arterial blood pressure disorder(s).

A Heterocyclic-Substituted Piperidine Compound is useful for treating and/or preventing pain, anxiety, cough, diarrhea, high blood pressure, epilepsy, anorexia/cachexia, urinary incontinence, drug abuse, a memory disorder, obesity, constipation, depression, dementia, or Parkinsonism (each being a "Condition") in an animal.

The invention also relates to compositions comprising an effective amount of a Heterocyclic-Substituted Piperidine Compound and a pharmaceutically acceptable carrier or excipient. The compositions are useful for treating or preventing a Condition in an animal.

The invention further relates to methods for treating a Condition, comprising administering to an animal in need thereof an effective amount of a Heterocyclic-Substituted Piperidine Compound.

The invention further relates to methods for preventing a Condition, comprising administering to an animal in need thereof an effective amount of a Heterocyclic-Substituted Piperidine Compound.

The invention further relates to a Heterocyclic-Substituted Piperidine Compound for use as a medicament.

The invention further relates to the use of a Heterocyclic-Substituted Piperidine Compound, e.g., of Formulas (I), (II), (III) and/or (IV), for the manufacture of a medicament useful for treating a Condition.

The invention further relates to the use of a Heterocyclic-Substituted Piperidine Compound, e.g., of Formulas (I), (II), (III) and/or (IV), for the manufacture of a medicament useful for preventing a Condition.

The invention still further relates to methods for inhibiting ORL-1 receptor function in a cell, comprising contacting a cell capable of expressing the ORL-1 receptor with an ORL-1 receptor function inhibiting amount of a Heterocyclic-Substituted Piperidine Compound.

The invention still further relates to methods for activating ORL-1 receptor function in a cell, comprising contacting a cell capable of expressing the ORL-1 receptor with an ORL-1 receptor function activating amount of a Heterocyclic-Substituted Piperidine Compound.

The invention still further relates to methods for preparing a composition, comprising the step of admixing a Heterocyclic-Substituted Piperidine Compound and a pharmaceutically acceptable carrier or excipient.

The invention still further relates to a kit comprising a container containing an effective amount of a Heterocyclic-Substituted Piperidine Compound.

The invention can be understood more fully by reference to the following detailed description and illustrative examples, which are intended to exemplify non-limiting embodiments of the invention. Other objects and advantages of the invention will become apparent from the following detailed description thereof.

4. DETAILED DESCRIPTION OF THE INVENTION

4.1 Heterocyclic-Substituted Piperidine Compounds of Formula (I)

As stated above, the invention encompasses Heterocyclic-Substituted Piperidine Compounds of Formula (I):

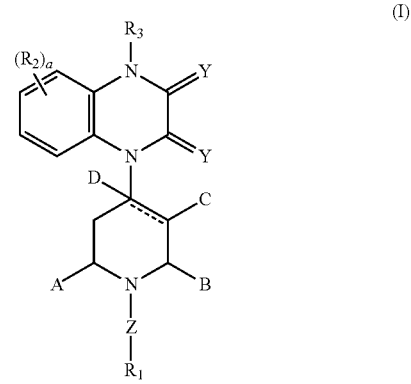

and pharmaceutically acceptable derivatives thereof where $R_1$, $R_2$, $R_3$, Y, Z, A, B, C, D, a and the dashed line are defined above for the Heterocyclic-Substituted Piperidine Compounds of Formula (I).

In one embodiment, each Y is O.

In another embodiment, each Y is S.

In another embodiment, A is H.

In another embodiment, B is H.

In another embodiment, A-B together form a $(C_2-C_6)$ bridge, which is unsubstituted or substituted with 1, 2 or 3 independently selected $R_8$ groups, and which bridge optionally contains —HC=CH— within the $(C_2-C_6)$bridge; wherein the piperazine ring that is fused to the phenyl group can be in the endo- or exo-conformation with respect to the A-B bridge.

In another embodiment, A-B together form a $(C_2-C_6)$ bridge, which is unsubstituted or substituted with an $R_8$ group, and which bridge optionally contains —HC=CH— within the $(C_2-C_6)$bridge; wherein the piperazine ring that is fused to the phenyl group can be in the endo- or exo-conformation with respect to the A-B bridge.

In another embodiment, A-B together form a $(C_2-C_3)$ bridge, which is unsubstituted or substituted with an $R_8$ group, and which bridge optionally contains —HC=CH— within the $(C_2-C_3)$bridge; wherein the piperazine ring that is fused to the phenyl group can be in the endo- or exo- conformation with respect to the A-B bridge.

In another embodiment, A-B together form a $(C_2-C_3)$ bridge, which is unsubstituted and which bridge optionally contains —HC=CH— within the $(C_2-C_3)$bridge; wherein the piperazine ring that is fused to the phenyl group can be in the endo- or exo-conformation with respect to the A-B bridge.

In another embodiment, A-B together form a $(C_2)$bridge, a —HC=CH— bridge, or a $(C_3)$bridge each of which is unsubstituted; wherein the piperazine ring that is fused to the phenyl group can be in the endo- or exo-conformation with respect to the A-B bridge.

In another embodiment, C is H.

In another embodiment, D is H.

In another embodiment, a is 0 or 1.

In another embodiment, a is 0.

In another embodiment, a is 1.

In another embodiment, a is 2.

In another embodiment, each Y is O, A, B, C and D are each H, and a is 0 or 1.

In another embodiment, each Y is S, A, B, C and D are each H, and a is 0 or 1.

In another embodiment, each Y is O, A, B, C and D are each H, and a is 0.

In another embodiment, each Y is S, A, B, C and D are each H, and a is 0.

In another embodiment, each Y is O, A, B, C and D are each H, and a is 1.

In another embodiment, each Y is S, A, B, C and D are each H, and a is 1.

In another embodiment, each Y is O, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with 1, 2 or 3 independently selected % groups, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0.

In another embodiment, each Y is S, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0.

In another embodiment, each Y is O, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 1.

In another embodiment, each Y is S, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 1.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 0.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 1.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the phenyl group can be in the endo- or exo-conformation with respect to the A-B bridge, C and D are each H, and a is 1.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0 or 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0 or 1.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0.

In another embodiment, each Y is O, A-B together form a $(C_2-C_3)$bridge, which is unsubstituted or substituted with an $R_8$ group, and which bridge optionally contains —HC=CH— within the $(C_2-C3)$bridge; wherein the piperazine ring that is fused to the phenyl group can be in the endo- or exo-conformation with respect to the A-B bridge, C and D are each H, and a is 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 1.

In another embodiment, each Y is O, A-B together form a $(C_2-C_3)$bridge, which is unsubstituted and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0 or 1.

In another embodiment, each Y is S, A-B together form a $(C_2-C_3)$bridge, which is unsubstituted and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0 or 1.

In another embodiment, each Y is O, A-B together form a $(C_2-C_3)$bridge, which is unsubstituted and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0.

In another embodiment, each Y is S, A-B together form a $(C_2-C_3)$bridge, which is unsubstituted and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 0.

In another embodiment, each Y is O, A-B together form a $(C_2-C_3)$bridge, which is unsubstituted and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 1.

In another embodiment, each Y is S, A-B together form a $(C_2-C_3)$bridge, which is unsubstituted and which bridge optionally contains —HC=CH— within the $(C_2-C_3)$bridge; wherein the piperazine ring that is fused to the phenyl group can be in the endo- or exo-conformation with respect to the A-B bridge, C and D are each H, and a is 1.

In another embodiment, $R_3$ is —H, —$(C_1-C_6)$alkyl, —$(C_1-C_6)$alkyl substituted by an $R_8$ group, —$(C_3-C_7)$cycloalkyl, or —$(C_3-C_7)$cycloalkyl substituted by an $R_8$ group.

In another embodiment, $R_3$ is —H, —C(O)OV$_1$, —C(O)N(V$_1$)$_2$, or —$(C_1-C_2)$alkyl substituted with a substituent selected from —NHS(O)$_2$W$_1$, —C(O)OV$_1$, and —C(O)N(V$_1$)$_2$.

In another embodiment, $R_3$ is —H.

In another embodiment, $R_3$ is —$(C_1-C_6)$alkyl.

In another embodiment, $R_3$ is methyl, ethyl, n-propyl or iso-propyl.

In another embodiment, $R_3$ is —$(C_1-C_6)$alkyl substituted by an $R_8$ group.

In another embodiment, $R_3$ is —$(C_1-C_6)$alkyl substituted by —CN.

In another embodiment, $R_3$ is methyl, ethyl, n-propyl or iso-propyl, each of which is substituted by an $R_8$ group.

In another embodiment, $R_3$ is methyl, ethyl, n-propyl or iso-propyl, each of which is substituted by —CN.

In another embodiment, $R_3$ is —$(C_3-C_7)$cycloalkyl.

In another embodiment, $R_3$ is cyclopentyl, cyclohexyl, or cycloheptyl.

In another embodiment, $R_3$ is —H or methyl substituted by —CN.

In another embodiment, each Y is O, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0 or 1.

In another embodiment, each Y is S, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0 or 1.

In another embodiment, each Y is O, A, B, C and D are each H, $R_3$ is —H or methyl substituted by —CN, and a is 0 or 1.

In another embodiment, each Y is S, A, B, C and D are each H, $R_3$ is —H or methyl substituted by —CN, and a is 0 or 1.

In another embodiment, each Y is O, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0.

In another embodiment, each Y is S, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0.

In another embodiment, each Y is O, A, B, C and D are each H, $R_3$ is —H or methyl substituted by —CN, and a is 0.

In another embodiment, each Y is S, A, B, C and D are each H, $R_3$ is —H or methyl substituted by —CN, and a is 0.

In another embodiment, each Y is O, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 1.

In another embodiment, each Y is S, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 1.

In another embodiment, each Y is O, A, B, C and D are each H, $R_3$ is —H or methyl substituted by —CN, and a is 1.

In another embodiment, each Y is S, A, B, C and D are each H, $R_3$ is —H or methyl substituted by —CN, and a is 1.

In another embodiment, each $R_2$ is independently -halo, —OH, —NH$_2$, —CN, —$(C_1-C_6)$alkyl, —$(C_3-C_7)$cycloalkyl, -(5- or 6-membered)heterocycle, -phenyl, -naphthalenyl or -(5- or 6-membered)heteroaryl.

In another embodiment, each $R_2$ is independently -halo.

In another embodiment, a is 2 and each $R_2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl or -(5- or 6-membered)heteroaryl.

In another embodiment, a is 2 and each $R_2$ is independently -halo, —OH, —NH$_2$, —CN, methyl, ethyl, n-propyl, iso-propyl, cyclopentyl, cyclohexyl, cycloheptyl, or phenyl.

In another embodiment, a is 2 and each $R_2$ is independently -halo.

In another embodiment, a is 1 and $R_2$ is -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl or -(5- or 6-membered)heteroaryl.

In another embodiment, a is 1 and $R_2$ is -halo, —OH, —NH$_2$, —CN, methyl, ethyl, n-propyl, iso-propyl, cyclopentyl, cyclohexyl, cycloheptyl, or phenyl.

In another embodiment, a is 1 and $R_2$ is -halo, optionally —F.

In another embodiment, each Y is O, A, B, C and D are each H, a is 1, and $R_2$ is -halo, optionally —F.

In another embodiment, each Y is O, A-B together form a (C$_2$-C$_6$)bridge, which is unsubstituted or substituted with 1, 2 or 3 independently selected $R_8$ groups, and which bridge optionally contains —HC=CH— within the (C$_2$-C$_6$)bridge; wherein the piperazine ring that is fused to the phenyl group can be in the endo- or exo-conformation with respect to the A-B bridge, C and D are each H, a is 1, and $R_2$ is -halo, optionally —F.

In another embodiment, each Y is O, A-B together form a (C$_2$-C$_6$)bridge, which is unsubstituted or substituted with an $R_8$ group, and which bridge optionally contains —HC=CH— within the (C$_2$-C$_6$)bridge; wherein the piperazine ring that is fused to the phenyl group can be in the endo- or exo-conformation with respect to the A-B bridge, C and D are each H, a is 1, and $R_2$ is -halo, optionally —F.

In another embodiment, each Y is O, A-B together form a (C$_2$-C$_3$)bridge, which is unsubstituted or substituted with an $R_8$ group, and which bridge optionally contains —HC=CH— within the (C$_2$-C$_3$)bridge; wherein the piperazine ring that is fused to the phenyl group can be in the endo- or exo-conformation with respect to the A-B bridge, C and D are each H, a is 1, and $R_2$ is -halo, optionally —F.

In another embodiment, each Y is O, A-B together form a (C$_2$-C$_3$)bridge, which is unsubstituted and which bridge optionally contains —HC=CH— within the (C$_2$-C$_3$)bridge; wherein the piperazine ring that is fused to the phenyl group can be in the endo- or exo-conformation with respect to the A-B bridge, C and D are each H, a is 1, and $R_2$ is -halo, optionally —F.

In another embodiment, each Y is O, A, B, C and D are each H, a is 0, and $R_3$ is methyl, ethyl, n-propyl or iso-propyl, each of which is substituted by an $R_8$ group, or —H.

In another embodiment, each Y is O, A-B together form a (C$_2$-C$_6$)bridge, which is unsubstituted or substituted with 1, 2 or 3 independently selected $R_8$ groups, and which bridge optionally contains —HC=CH— within the (C$_2$-C$_6$)bridge; wherein the piperazine ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a (C$_2$-C$_6$)bridge, which is unsubstituted or substituted with an $R_8$ group, and which bridge optionally contains —HC=CH— within the (C$_2$-C$_6$)bridge; wherein the piperazine ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a (C$_2$-C$_3$)bridge, which is unsubstituted or substituted with an $R_8$ group, and which bridge optionally contains —HC=CH— within the (C$_2$-C3)bridge; wherein the piperazine ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a (C$_2$-C$_3$)bridge, which is unsubstituted and which bridge optionally contains —HC=CH— within the (C$_2$-C$_3$)bridge; wherein the piperazine ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A, B, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a (C$_2$-C$_6$)bridge, which is unsubstituted or substituted with 1, 2 or 3 independently selected $R_8$ groups, and which bridge optionally contains —HC=CH— within the (C$_2$-C$_6$)bridge; wherein the piperazine ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a (C$_2$-C$_6$)bridge, which is unsubstituted or substituted with an $R_8$ group, and which bridge optionally contains —HC=CH— within the (C$_2$-C$_6$)bridge; wherein the piperazine ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a (C$_2$-C$_3$)bridge, which is unsubstituted or substituted with an $R_8$ group, and which bridge optionally contains —HC=CH— within the (C$_2$-C$_3$)bridge; wherein the piperazine ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a (C$_2$-C$_3$)bridge, which is unsubstituted and which bridge optionally contains —HC=CH— within the (C$_2$-C$_3$)bridge; wherein the piperazine ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, $R_1$ is selected from:

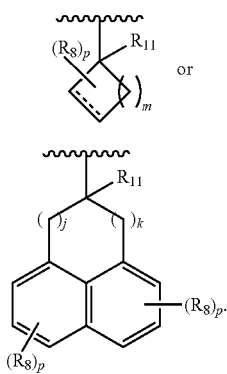

In another embodiment, $R_1$ is selected from formula (i) and m is 5.

In another embodiment, $R_1$ is selected from formula (i), m is 5, and p is 0.

In another embodiment, $R_1$ is selected from formula (i), m is 5, p is 0, and $R_{11}$ is —H.

In another embodiment, $R_1$ is selected from formula (i) and m is 3.

In another embodiment, $R_1$ is selected from formula (i), m is 3, and p is 1.

In another embodiment, $R_1$ is selected from formula (i), m is 3, p is 1, and $R_8$ is —($C_1$-$C_4$)alkyl, optionally iso-propyl.

In another embodiment, $R_1$ is selected from formula (i), m is 3, $R_{11}$ is —H, p is 1, and $R_8$ is —($C_1$-$C_4$)alkyl, optionally iso-propyl.

In another embodiment, $R_1$ is selected from formula (iii) and j+k=1.

In another embodiment, $R_1$ is selected from formula (iii), j+k=1, and p is 0.

In another embodiment, $R_1$ is selected from:

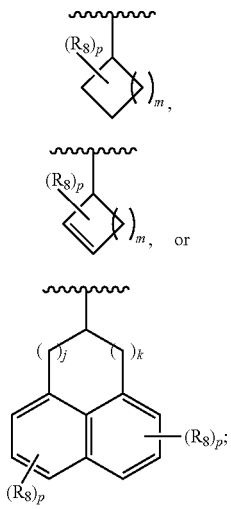

where m is an integer selected from 3, 4 or 5;
j is an integer selected from 1 or 2;
k is 0; and
each p is an integer independently selected from 0 or 1.

In another embodiment, each p is 0.

In another embodiment, in formulas (ia) and (ib) p is 1 and $R_8$ is selected from —($C_1$-$C_4$)alkyl, optionally iso-propyl.

In another embodiment, in formulas (ia) and (ib) m is 3, p is 1, and $R_8$ is selected from —($C_1$-$C_4$)alkyl, optionally iso-propyl.

In another embodiment, in formulas (ia) and (ib) m is 5, p is 1, and $R_8$ is selected from —($C_1$-$C_4$)alkyl, optionally iso-propyl.

In another embodiment, in formulas (ia) and (ib) m is 3 and p is 0.

In another embodiment, in formulas (ia) and (ib) m is 5 and p is 0.

In another embodiment, in formula (iii) one p is 0, the other p is 1, and $R_8$ is selected from —($C_1$-$C_4$)alkyl, optionally iso-propyl.

In another embodiment, in formula (iii) j is 1 and each p is 0.

In another embodiment, in formula (iii) j is 1, one p is 0, the other p is 1, and $R_8$ is selected from —($C_1$-$C_4$)alkyl, optionally iso-propyl.

In another embodiment, the Heterocyclic-Substituted Piperidine Compound of Formula (I) is

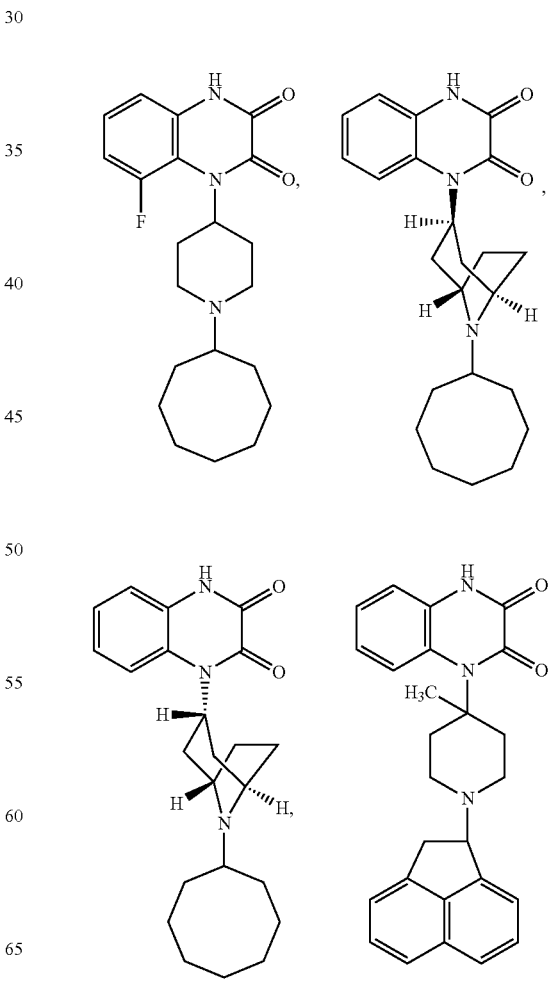

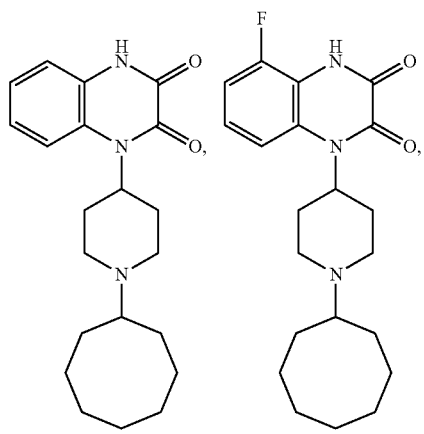
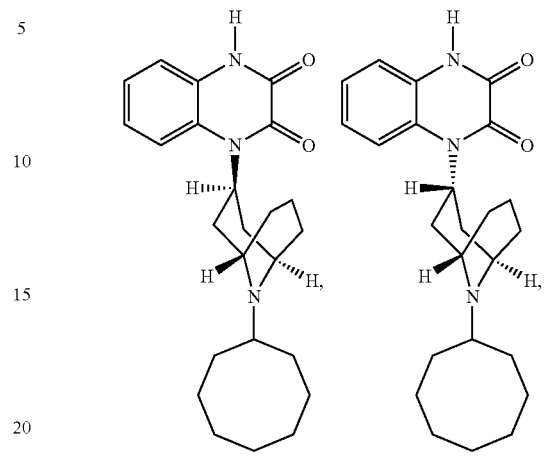
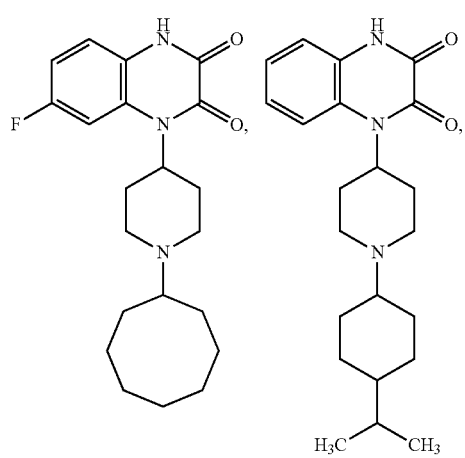
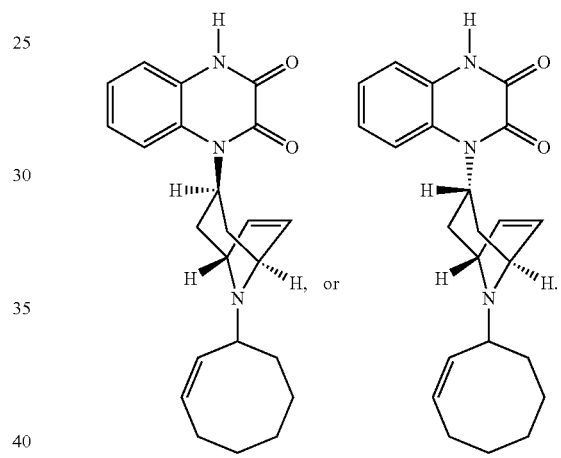
In another embodiment, the Heterocyclic-Substituted Piperidine Compound of Formula (I) is
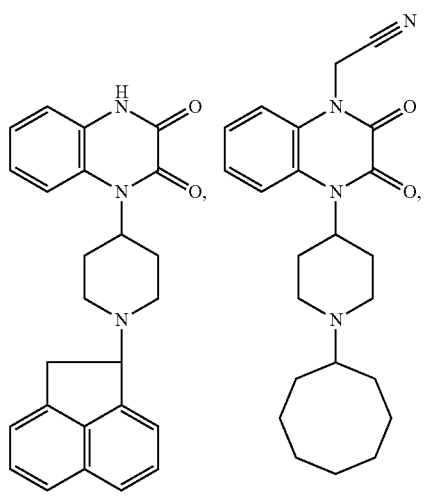
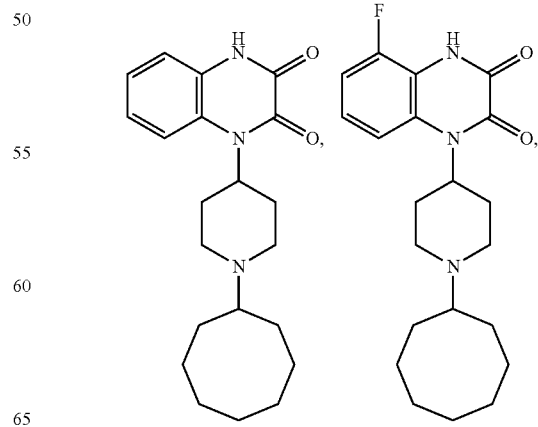

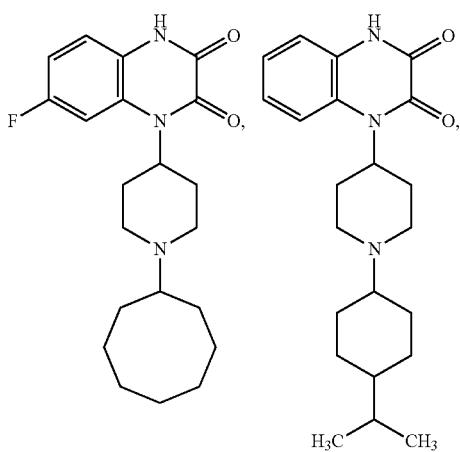
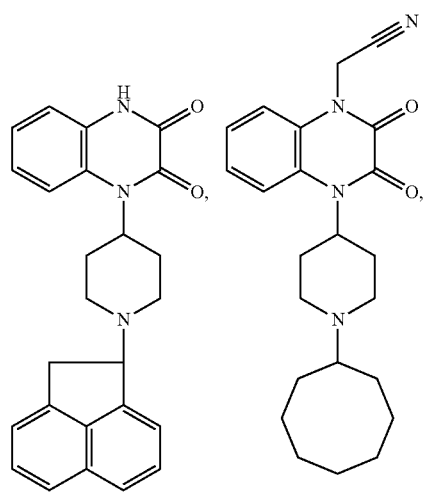
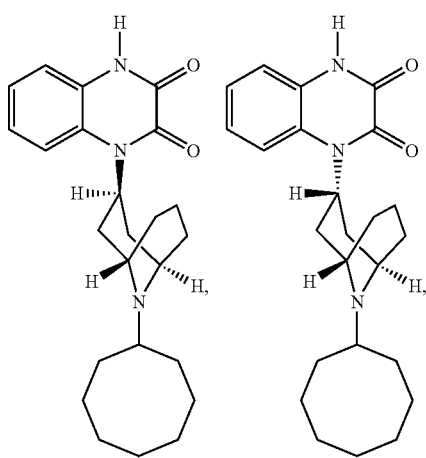

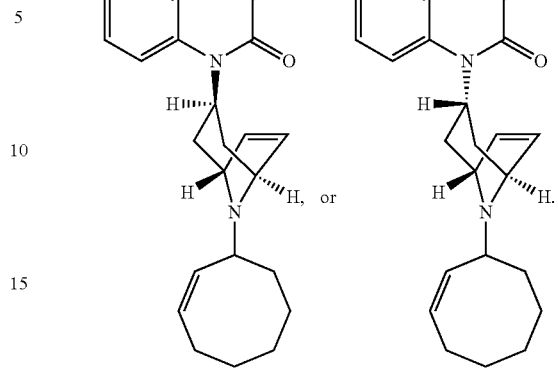

In another embodiment for the Heterocyclic-Substituted Piperidine Compounds of Formula (I):

each $R_2$ is independently selected from:
(a) -halo, —OH, —$NH_2$, —CN, or —$NO_2$; or
(b) —($C_1$-$C_6$)alkyl, —($C_2$-$C_6$)alkenyl, —($C_2$-$C_6$)alkynyl, —($C_3$-$C_7$)cycloalkyl, -(5- or 6-membered)heterocycle, -phenyl, -naphthyl (otherwise known as -naphthalenyl), or -(5- or 6-membered)heteroaryl, each of which is unsubstituted or substituted with 1, 2 or 3 $R_8$ groups;

a is an integer from 0 to 2;

$R_3$ is selected from:
(a) —H; or
(b) —($C_1$-$C_6$)alkyl, —($C_2$-$C_6$)alkenyl, —($C_2$-$C_6$)alkynyl, —O($C_1$-$C_6$)alkyl, —O($C_2$-$C_6$)alkenyl, —O($C_2$-$C_6$)alkynyl, —($C_3$-$C_7$)cycloalkyl, —($C_5$-$C_7$)cycloalkenyl, —($C_3$-$C_7$)cycloalkoxy, -(3- to 7-membered)heterocycle, -phenyl, -naphthyl, or -(5- to 10-membered)heteroaryl, each of which is unsubstituted or substituted with 1, 2 or 3 $R_8$ groups; or
(c) —$CH_2CH_2OH$, —($C_1$-$C_6$)alkyl(=O)$W_1$, —C(O)O$V_1$, —C(O)N($V_1$)$_2$, or —S(O)$_2$($C_1$-$C_6$)alkyl; or
(d) -($C_1$-$C_4$)alkyl substituted with 1, 2 or 3 substituents independently selected from —($C_3$-$C_7$)cycloalkyl, —($C_3$-$C_7$)cycloalkoxy, -(3- to 7-membered)heterocycle, -phenyl, -naphthyl, and -(5- to 10-membered) heteroaryl; or
(e) -($C_1$-$C_3$)alkyl substituted with a substituent selected from —N($R_6$)$_2$, —S(O)$_2NH_2$, —NHC(O)$W_1$, —NHS(O)$_2W_1$, —C(O)O$V_1$, and —C(O)N($V_1$)$_2$;

each $W_1$ is independently selected from:
(a) —H, —($C_1$-$C_6$)alkyl, —($C_3$-$C_7$)cycloalkyl, —O($C_1$-$C_6$)alkyl, —($C_3$-$C_7$)cycloalkoxy, —$CH_2CH_2OH$, —N($R_6$)$_2$; or
(b) -(5- or 6-membered)heteroaryl optionally substituted with 1, 2 or 3 independently selected —($C_1$-$C_6$)alkyl;

each $V_1$ is independently selected from —($C_1$-$C_6$)alkyl, —($C_3$-$C_7$)cycloalkyl, -phenyl, or -benzyl;

each Y is independently selected from O or S;

A and B are independently selected from —H, —N($R_6$)$_2$, —($C_3$-$C_{12}$)cycloalkyl, or —($C_1$-$C_6$)alkyl each of which —($C_1$-$C_6$)alkyl is unsubstituted or substituted with —OH, —S(O)$_2NH_2$, or from 1 to 3 independently selected -halo, or A-B together form a ($C_2$-$C_6$)bridge;

C is —H;
D is —H;
the dashed line in the piperidine or bridged piperidine central ring is absent;
Z is a bond;

$R_1$ is selected from:

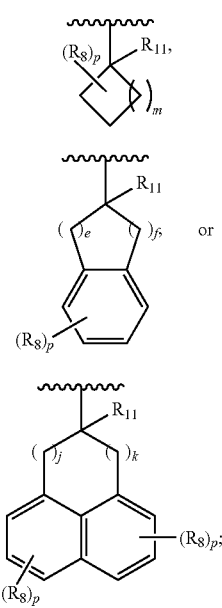

m is an integer from 1 to 7;

e and f are independently an integer from 0 to 5 provided that $2 \leq (e+f) \leq 5$;

j and k are independently an integer from 0 to 4 provided that $1 \leq (j+k) \leq 4$;

each $R_6$ is independently selected from —($C_1$-$C_6$)alkyl, or —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_8$ is independently selected from —($C_1$-$C_4$)alkyl, —O($C_1$-$C_4$)alkyl, —C(halo)$_3$, —CH(halo)$_2$, —CH$_2$(halo), —CN, —OH, -halo, or —C(O)O$R_9$;

each $R_9$ is independently selected from —H, —($C_1$-$C_6$)alkyl, -phenyl, or -benzyl;

each p is independently 0 or 1;

$R_{11}$ is selected from —H, —(O—$C_4$)alkyl, or -halo; and each halo is independently selected from —F, —Cl, —Br, or —I.

In another embodiment for the Heterocyclic-Substituted Piperidine Compounds of Formula (I):

each $R_2$ is independently selected from:
(a) -halo, —CN, —NO$_2$, —OT$_3$, —C(O)T$_3$, —C(O)OT$_3$, —C(O)N(T$_1$)(T$_2$), —S(O)$_3$H, —S(O)$_2$T$_3$, —S(O)$_2$N(T$_1$)(T$_2$), —N(T$_1$)(T$_2$), —N(T$_3$)C(O)T$_3$, —N(T$_3$)C(O)N(T$_1$)(T$_2$), —N(T$_3$)S(O)$_2$T$_3$, or —N(T$_3$)S(O)$_2$N(T$_1$)(T$_2$); or
(b) —($C_1$-$C_6$)alkyl, —($C_2$-$C_6$)alkenyl, —($C_2$-$C_6$)alkynyl, —($C_3$-$C_7$)cycloalkyl, —($C_6$—O$_4$)bicycloalkyl, —($C_8$-$C_{20}$)tricycloalkyl, —($C_{5-10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 $R_8$ groups; or
(c) -phenyl, -naphthyl, —($C_{14}$)aryl, or -(5- or 6-membered) heteroaryl, each of which is unsubstituted or substituted with 1, 2 or 3 $R_7$ groups;

a is an integer from 0 to 2;

$R_3$ is selected from:
(a) —H; or
(b) —($C_1$-$C_6$)alkyl, —($C_2$-$C_6$)alkenyl, —($C_2$-$C_6$)alkynyl, —O($C_1$-$C_6$)alkyl, —O($C_2$-$C_6$)alkenyl, —O($C_2$-$C_6$)alkynyl, —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, or -(7- to 10-membered)bicycloheterocycle, each of which is unsubstituted or substituted with 1, 2 or 3 $R_8$ groups; or
(c) -phenyl, -naphthyl, —($C_{14}$)aryl, or -(5- to 10-membered)heteroaryl, each of which is unsubstituted or substituted with 1, 2 or 3 $R_7$ groups; or
(d) —($C_1$-$C_6$)alkyl(=O)W$_1$, —($C_1$-$C_6$)alkyl(=NH)W$_1$ —C(O)OV$_1$, —C(O)N(V$_1$)$_2$, —S(O)$_2$N(V$_1$)$_2$, or —S(O)$_2$($C_1$-$C_6$)alkyl; or
(e) —($C_1$-$C_4$)alkyl substituted with 1, 2 or 3 substituents independently selected from —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, -phenyl, -naphthyl, —($C_{14}$)aryl, or -(5- to 10-membered)heteroaryl; or
(f) -($C_1$-$C_3$)alkyl substituted with a substituent selected from —N($R_6$)$_2$, —S(O)$_2$N(V$_1$)$_2$, —N($R_9$)C(O)W$_1$, —N($R_9$)S(O)$_2$W$_1$, and —C(O)N(V$_1$)$_2$;

each W$_1$ is independently selected from:
(a) —H, —($C_1$-$C_6$)alkyl, —($C_3$-$C_7$)cycloalkyl, —O($C_1$-$C_6$)alkyl, —($C_3$-$C_7$)cycloalkoxy, —CH$_2$CH$_2$OH, —N($R_6$)$_2$; or
(b) -(5- or 6-membered)heteroaryl optionally substituted with 1, 2 or 3 independently selected —($C_1$-$C_6$)alkyl;

each V$_1$ is independently selected from —H, —($C_1$-$C_6$)alkyl, —($C_3$-$C_7$)cycloalkyl, -phenyl, or -benzyl;

each Y is independently selected from O or S;

A and B are independently selected from:
(a) —H, —CN, —C(O)OT$_3$, —C(O)N(T)$_1$(T$_2$), —($C_3$-$C_{12}$)cycloalkyl, —($C_3$-$C_{12}$)cycloalkoxy, —($C_1$-$C_6$)alkyl, —($C_2$-$C_6$)alkenyl, or —($C_2$-$C_6$)alkynyl, each of which —($C_1$-$C_6$)alkyl, —($C_2$-$C_6$)alkenyl or —($C_2$-$C_6$)alkynyl is unsubstituted or substituted with 1 or 2 substituents selected from —OH, —S(O)$_2$NH$_2$, —N($R_6$)$_2$, =N$R_6$, —C(O)OT$_3$, —C(O)N($R_6$)$_2$, —N($R_6$)C(O)$R_9$ and -(5- or 6-membered)heterocycle or from 1 to 3 independently selected -halo, or
(b) A-B together form a ($C_2$-$C_6$)bridge, which is unsubstituted or optionally substituted with from 1 to 3-OH or optionally contains —HC=CH— within the ($C_2$-$C_6$) bridge, or
(c) A-B together form a —CH$_2$—N($R_a$)—CH$_2$— bridge, a

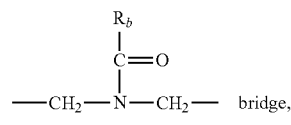
bridge, or a

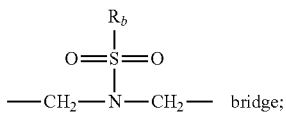 bridge;

$R_a$ is selected from —H, —$(C_1-C_6)$alkyl, —$(C_3-C_7)$cycloalkyl, —$CH_2$—$C(O)$—$R_c$, —$(CH_2)$—$C(O)$—$OR_c$, —$(CH_2)$—$C(O)$—$N(R_c)_2$, —$(CH_2)_2$—$OR_c$, —$(CH_2)_2$—$S(O)_2$—$N(R_c)_2$, $R_c$, or —$(CH_2)_2$—$N(R_c)S(O)_2$—$R_c$;

$R_b$ is selected from:
(a) —H, —$(C_3-C_7)$cycloalkyl, -(3- to 7-membered)heterocycle, —$N(R_9)_2$, —$N(R_c)$—$(C_3-C_7)$cycloalkyl, or —$N(R_c)$-(3- to 7-membered)heterocycle,
(b) -phenyl, -naphthyl, or -(5- or 6-membered)heteroaryl, each of which is unsubstituted or substituted with 1, 2 or 3 $R_7$ groups, or
(c) —$N(R_c)$-phenyl, —$N(R_c)$-naphthyl, —$N(R_c)$—$(C_{14})$aryl, or —$N(R_c)$-(5- to 10-membered)heteroaryl, each of which is unsubstituted or substituted with 1, 2 or 3 $R_7$ groups;

each $R_c$ is independently selected from —H or —$(C_1-C_4)$alkyl;

C is selected from —H, -halo, —CN, —$OT_3$, —$C(O)OT_3$, —$C(O)N(T)_1(T_2)$, —$(C_3-C_{12})$cycloalkyl, —$(C_3-C_{12})$cycloalkoxy, —$N(R_6)_2$, —$N(R_6)C(O)R_9$, —$NR_6SO_2N(R_6)_2$, —$NR_6$—$C(=NR_6)N(R_6)_2$, —$(C_1-C_6)$alkyl, —$(C_2-C_6)$alkenyl, or —$(C_2-C_6)$alkynyl, each of which —$(C_1-C_6)$alkyl, —$(C_2-C_6)$alkenyl or —$(C_2-C_6)$alkynyl is unsubstituted or substituted with 1 or 2 substituents selected from —OH, —$S(O)_2NH_2$, —$N(R_6)_2$, =$NR_6$, —$C(O)OT_3$, —$C(O)N(R_6)_2$, —$N(R_6)C(O)R_9$ and -(5- or 6-membered)heterocycle or from 1 to 3 independently selected -halo;

the dashed line in the piperidine or bridged piperidine central ring denotes the presence or absence of a bond, and when the dashed line denotes the presence of a bond then D is absent, otherwise D is:
(a) —H, —CN, —$C(O)OT_3$, or —$C(O)N(T_1)(T_2)$; or
(b) —$(C_1-C_{10})$alkyl which is unsubstituted or substituted with 1, 2 or 3 $R_8$ groups and, optionally, in which any D group carbon atom except the carbon atom bonded directly to the piperidine or bridged piperidine central ring, is independently replaced by O or S; or
(c) -phenyl, -naphthyl, or -(5- or 6-membered)heteroaryl, each of which is unsubstituted or substituted with 1, 2 or 3 $R_7$ groups;

Z is a bond;

$R_1$ is selected from:

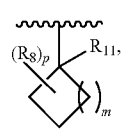

(i)

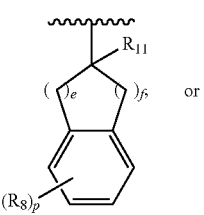

(ii)

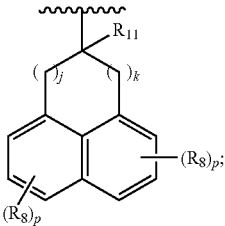

(iii)

m is an integer from 1 to 7;

e and f are independently an integer from 0 to 5 provided that $2 \leq (e+f) \leq 5$;

j and k are independently an integer from 0 to 4 provided that $1 \leq (j+k) \leq 4$;

each $T_1$, $T_2$, and $T_3$ is independently —H or —$(C_1-C_{10})$alkyl which is unsubstituted or substituted with 1, 2 or 3 $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2 or 3 $R_8$ groups and, optionally, any carbon atom in said 5- to 8-membered ring is independently replaced by O or S;

each $R_6$ is independently selected from —H, —$(C_1-C_6)$alkyl, or —$(C_3-C_7)$cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_7$ is independently selected from —$(C_1-C_4)$alkyl, —$(C_2-C_6)$alkenyl, —$(C_2-C_6)$alkynyl, —$OR_9$, —$SR_9$, —$C(halo)_3$, —$CH(halo)_2$, —$CH_2(halo)$, —CN, -halo, —$N_3$, —$NO_2$, —CH=$NR_9$, —$NR_9OH$, —$C(O)OR_9$, —$OC(O)R_9$, —$OC(O)OR_9$, —$S(O)R_9$, or —$S(O)_2R_9$;

each $R_8$ is independently selected from —$(C_1-C_4)$alkyl, —$(C_2-C_6)$alkenyl, —$(C_2-C_6)$alkynyl, —$OR_9$, —$SR_9$, —$C(halo)_3$, —$CH(halo)_2$, —$CH_2(halo)$, —CN, oxo, =S, -halo, —$N_3$, —$NO_2$, —CH=$NR_9$, —$NR_9OH$, —$C(O)OR_9$, —$OC(O)R_9$, —$OC(O)OR_9$, —$S(O)R_9$, or —$S(O)_2R_9$;

each $R_9$ is independently selected from —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, -(3- to 6-membered)heterocycle, —$C(halo)_3$, —$CH(halo)_2$, or —$CH_2(halo)$;

each p is independently 0 or 1;

$R_{11}$ is selected from —H or —$(C_1-C_4)$alkyl which is unsubstituted or substituted with —OH, —$(C_1-C_4)$alkoxy, —$N(R_6)_2$, —$C(O)OR_9$, or —$C(O)N(R_6)_2$; and each halo is independently selected from —F, —Cl, —Br, or —I.

4.2 Heterocyclic-Substituted Piperidine Compounds of Formula (II)

As stated above, the invention encompasses Heterocyclic-Substituted Piperidine Compounds of Formula (II):

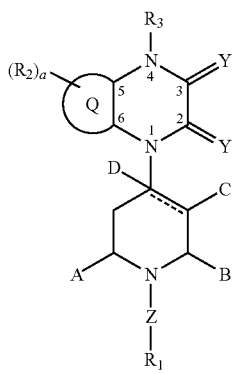

(II)

and pharmaceutically acceptable derivatives thereof where $R_1$, $R_2$, $R_3$, Q, Y, Z, A, B, C, D, a and the dashed line are defined above for the Heterocyclic-Substituted Piperidine Compounds of Formula (II).

In one embodiment, each Y is O.
In another embodiment, each Y is S.
In another embodiment, A is H.
In another embodiment, B is H.
In another embodiment, A-B together form a $(C_2-C_6)$ bridge, which is unsubstituted or substituted with 1, 2 or 3 independently selected $R_8$ groups, and which bridge optionally contains —HC═CH— within the $(C_2-C_6)$bridge; wherein the piperazine ring that is fused to the Q group can be in the endo- or exo-conformation with respect to the A-B bridge.

In another embodiment, A-B together form a $(C_2-C_6)$ bridge, which is unsubstituted or substituted with an $R_8$ group, and which bridge optionally contains —HC═CH— within the $(C_2-C_6)$bridge; wherein the piperazine ring that is fused to the Q group can be in the endo- or exo-conformation with respect to the A-B bridge.

In another embodiment, A-B together form a $(C_2-C_3)$ bridge, which is unsubstituted or substituted with an $R_8$ group, and which bridge optionally contains —HC═CH— within the $(C_2-C_3)$bridge; wherein the piperazine ring that is fused to the Q group can be in the endo- or exo-conformation with respect to the A-B bridge.

In another embodiment, A-B together form a $(C_2-C_3)$ bridge, which is unsubstituted and which bridge optionally contains —HC═CH— within the $(C_2-C_3)$bridge; wherein the piperazine ring that is fused to the Q group can be in the endo- or exo-conformation with respect to the A-B bridge.

In another embodiment, A-B together form a $(C_2)$ bridge, a —HC═CH— bridge, or a $(C_3)$ bridge each of which is unsubstituted; wherein the piperazine ring that is fused to the Q group can be in the endo- or exo-conformation with respect to the A-B bridge.

In another embodiment, C is H.
In another embodiment, D is H.
In another embodiment, a is 0 or 1.
In another embodiment, a is 0.
In another embodiment, a is 1.
In another embodiment, a is 2.
In another embodiment, each Y is O, A, B, C and D are each H, and a is 0 or 1.
In another embodiment, each Y is S, A, B, C and D are each H, and a is 0 or 1.
In another embodiment, each Y is O, A, B, C and D are each H, and a is 0.
In another embodiment, each Y is S, A, B, C and D are each H, and a is 0.
In another embodiment, each Y is O, A, B, C and D are each H, and a is 1.
In another embodiment, each Y is S, A, B, C and D are each H, and a is 1.

In another embodiment, each Y is O, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 0.

In another embodiment, each Y is S, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 0.

In another embodiment, each Y is O, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 1.

In another embodiment, each Y is S, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 1.

In another embodiment, each Y is O, A-B together form a $(C_2-C_6)$bridge, which is unsubstituted or substituted with an $R_8$ group, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with an $R_8$ group, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with an $R_8$ group, and which bridge optionally contains —HC═CH— within the $(C_2-C_6)$bridge; wherein the piperazine ring that is fused to the Q group can be in the endo- or exo-conformation with respect to the A-B bridge, C and D are each H, and a is 0.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the Q group can be in the endo- or exo-conformation with respect to the A-B bridge, C and D are each H, and a is 0.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the Q group can be in the endo- or exo-conformation with respect to the A-B bridge, C and D are each H, and a is 1.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the piperazine ring that is fused to the Q group can be in the endo- or exo-conformation with respect to the A-B bridge, C and D are each H, and a is 1.

In another embodiment, each Y is O, A-B together form a $(C_2-C_3)$bridge, which is unsubstituted or substituted with an $R_8$ group, and which bridge optionally contains —HC=CH— within the $(C_2-C3)$bridge; wherein the piperazine ring that is fused to the Q group can be in the endo- or exo-conformation with respect to the A-B bridge, C and D are each H, and a is 0 or 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge;wherein the piperazine ring that is fused to the Q group can be in the endo- or exo-conformation with respect to the A-B bridge, C and D are each H, and a is 0 or 1.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 0.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 0.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 1.

In another embodiment, each Y is O, A-B together form a $(C_2-C_3)$bridge, which is unsubstituted and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 0 or 1.

In another embodiment, each Y is S, A-B together form a $(C_2-C_3)$bridge, which is unsubstituted and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 0 or 1.

In another embodiment, each Y is O, A-B together form a $(C_2-C_3)$bridge, which is unsubstituted and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 0.

In another embodiment, each Y is S, A-B together form a $(C_2-C_3)$bridge, which is unsubstituted and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 0.

In another embodiment, each Y is O, A-B together form a $(C_2-C_3)$bridge, which is unsubstituted and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 1.

In another embodiment, each Y is S, A-B together form a $(C_2-C_3)$bridge, which is unsubstituted and which bridge optionally contains —HC=CH— within the $(C_2-C_3)$bridge; wherein the piperazine ring that is fused to the Q group can be in the endo- or exo-conformation with respect to the A-B bridge, C and D are each H, and a is 1.

In another embodiment, $R_3$ is —H, —$(C_1-C_6)$alkyl, —$(C_1-C_6)$alkyl substituted by an $R_8$ group, —$(C_3-C_7)$cycloalkyl, or —$(C_3-C_7)$cycloalkyl substituted by an $R_8$ group.

In another embodiment, $R_3$ is —H, —C(O)O$V_1$, —C(O)N$(V_1)_2$, or —$(C_1-C_2)$alkyl substituted with a substituent selected from —NHS(O)$_2W_1$, —C(O)O$V_1$, and —C(O)N$(V_1)_2$.

In another embodiment, $R_3$ is —H.

In another embodiment, $R_3$ is —$(C_1-C_6)$alkyl.

In another embodiment, $R_3$ is methyl, ethyl, n-propyl or iso-propyl.

In another embodiment, $R_3$ is —$(C_1-C_6)$alkyl substituted by an $R_8$ group.

In another embodiment, $R_3$ is —$(C_1-C_6)$alkyl substituted by —CN.

In another embodiment, $R_3$ is methyl, ethyl, n-propyl or iso-propyl, each of which is substituted by an $R_8$ group.

In another embodiment, $R_3$ is methyl, ethyl, n-propyl or iso-propyl, each of which is substituted by —CN.

In another embodiment, $R_3$ is —$(C_3-C_7)$cycloalkyl.

In another embodiment, $R_3$ is cyclopentyl, cyclohexyl, or cycloheptyl.

In another embodiment, $R_3$ is —H or methyl substituted by —CN.

In another embodiment, each Y is O, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0 or 1.

In another embodiment, each Y is S, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0 or 1.

In another embodiment, each Y is O, A, B, C and D are each H, $R_3$ is —H or methyl substituted by —CN, and a is 0 or 1.

In another embodiment, each Y is S, A, B, C and D are each H, $R_3$ is —H or methyl substituted by —CN, and a is 0 or 1.

In another embodiment, each Y is O, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 0.

In another embodiment, each Y is S, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 0.

In another embodiment, each Y is O, A, B, C and D are each H, $R_3$ is —H or methyl substituted by —CN, and a is 0.

In another embodiment, each Y is S, A, B, C and D are each H, $R_3$ is —H or methyl substituted by —CN, and a is 0.

In another embodiment, each Y is O, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 1.

In another embodiment, each Y is S, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 1.

In another embodiment, each Y is O, A, B, C and D are each H, $R_3$ is —H or methyl substituted by —CN, and a is 1.

In another embodiment, each Y is S, A, B, C and D are each H, $R_3$ is —H or methyl substituted by —CN, and a is 1.

In another embodiment, each $R_2$ is independently -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, each $R_2$ is independently -halo.

In another embodiment, a is 2 and each $R_2$ is independently -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 2 and each $R_2$ is independently -halo, —OH, —$NH_2$, —CN, methyl, ethyl, n-propyl, iso-propyl, cyclopentyl, cyclohexyl, cycloheptyl, or phenyl.

In another embodiment, a is 2 and each $R_2$ is independently -halo.

In another embodiment, a is 1 and $R_2$ is -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 1 and $R_2$ is -halo, —OH, —$NH_2$, —CN, methyl, ethyl, n-propyl, iso-propyl, cyclopentyl, cyclohexyl, cycloheptyl, or phenyl.

In another embodiment, a is 1 and $R_2$ is -halo, optionally —F.

In another embodiment, each Y is O, A, B, C and D are each H, a is 1, and $R_2$ is -halo, optionally —F.

In another embodiment, each Y is O, A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the piperazine ring that is fused to the Q group can be in the endo- or exo-conformation with respect to the A-B bridge, C and D are each H, a is 1, and $R_2$ is -halo, optionally —F.

In another embodiment, each Y is O, A-B together form a ($C_2$-$C_6$)bridge, which is unsubstituted or substituted with an $R_8$ group, and which bridge optionally contains —HC=CH— within the ($C_2$-$C_6$)bridge; wherein the piperazine ring that is fused to the Q group can be in the endo- or exo-conformation with respect to the A-B bridge, C and D are each H, a is 1, and $R_2$ is -halo, optionally —F.

In another embodiment, each Y is O, A-B together form a ($C_2$-$C_3$)bridge, which is unsubstituted or substituted with an $R_8$ group, and which bridge optionally contains —HC=CH— within the ($C_2$-$C_3$)bridge; wherein the piperazine ring that is fused to the Q group can be in the endo- or exo-conformation with respect to the A-B bridge, C and D are each H, a is 1, and $R_2$ is -halo, optionally —F.

In another embodiment, each Y is O, A-B together form a ($C_2$-$C_3$)bridge, which is unsubstituted and which bridge optionally contains —HC=CH— within the ($C_2$-$C_3$)bridge; wherein the piperazine ring that is fused to the Q group can be in the endo- or exo-conformation with respect to the A-B bridge, C and D are each H, a is 1, and $R_2$ is -halo, optionally —F.

In another embodiment, each Y is O, A, B, C and D are each H, a is 0, and $R_3$ is methyl, ethyl, n-propyl or iso-propyl, each of which is substituted by an $R_8$ group, or —H.

In another embodiment, each Y is O, A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the piperazine ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a ($C_2$-$C_6$)bridge, which is unsubstituted or substituted with an $R_8$ group, and which bridge optionally contains —HC=CH— within the ($C_2$-$C_6$)bridge; wherein the piperazine ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a ($C_2$-$C_3$)bridge, which is unsubstituted or substituted with an $R_8$ group, and which bridge optionally contains —HC=CH— within the ($C_2$-$C_3$)bridge; wherein the piperazine ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a ($C_2$-$C_3$)bridge, which is unsubstituted and which bridge optionally contains —HC=CH— within the ($C_2$-$C_3$)bridge; wherein the piperazine ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A, B, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the piperazine ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a ($C_2$-$C_6$)bridge, which is unsubstituted or substituted with an $R_8$ group, and which bridge optionally contains —HC=CH— within the ($C_2$-$C_6$)bridge; wherein the piperazine ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a ($C_2$-$C_3$)bridge, which is unsubstituted or substituted with an $R_8$ group, and which bridge optionally contains —HC=CH— within the ($C_2$-$C_3$)bridge; wherein the piperazine ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a ($C_2$-$C_3$)bridge, which is unsubstituted and which bridge optionally contains —HC=CH— within the ($C_2$-$C_3$)bridge; wherein the piperazine ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, Q is naphthaleno.

In another embodiment, Q is pyridino.

In another embodiment, Z is a bond.

In another embodiment, Z is a bond and $R_1$ is selected from:

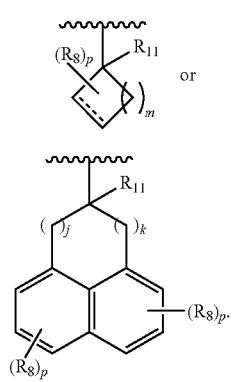

In another embodiment, Z is a bond, $R_1$ is selected from formula (i), and m is 5.

In another embodiment, Z is a bond, $R_1$ is selected from formula (i), m is 5, and p is 0.

In another embodiment, Z is a bond, $R_1$ is selected from formula (i), m is 5, p is O, and $R_{11}$ is —H.

In another embodiment, Z is a bond, $R_1$ is selected from formula (i), and m is 3.

In another embodiment, Z is a bond, $R_1$ is selected from formula (i), m is 3, and p is 1.

In another embodiment, Z is a bond, $R_1$ is selected from formula (i), m is 3, p is 1, and $R_8$ is —($C_1$-$C_4$)alkyl, optionally iso-propyl.

In another embodiment, Z is a bond, $R_1$ is selected from formula (i), m is 3, $R_{11}$ is —H, p is 1, and $R_8$ is —($C_1$-$C_4$) alkyl, optionally iso-propyl.

In another embodiment, Z is a bond, $R_1$ is selected from formula (iii), and j+k=1.

In another embodiment, 2 is a bond, $R_1$ is selected from formula (iii), j+k=1, and p is 0.

In another embodiment, Q is pyridino, Z is a bond, and $R_1$ is selected from:

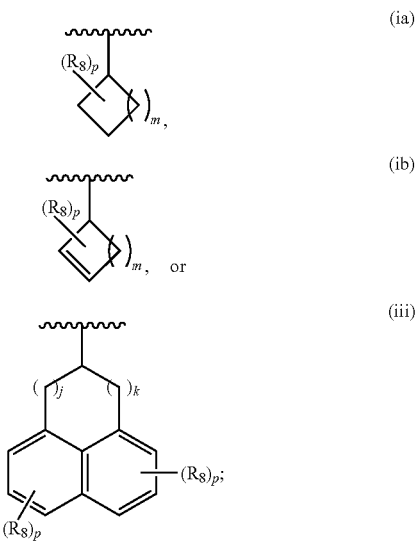

where m is an integer selected from 3, 4 or 5;

j is an integer selected from 1 or 2;

k is 0; and each p is an integer independently selected from 0 or 1.

In another embodiment, each p is 0.

In another embodiment, in formulas (ia) and (ib) p is 1 and $R_8$ is selected from —($C_1$-$C_4$)alkyl, optionally iso-propyl.

In another embodiment, in formulas (ia) and (ib) m is 3, p is 1, and $R_8$ is selected from —($C_1$-$C_4$)alkyl, optionally iso-propyl.

In another embodiment, in formulas (ia) and (ib) m is 5, p is 1, and $R_8$ is selected from —($C_1$-$C_4$)alkyl, optionally iso-propyl.

In another embodiment, in formulas (ia) and (ib) m is 3 and p is 0.

In another embodiment, in formulas (ia) and (ib) m is 5 and p is 0.

In another embodiment, in formula (iii) one p is O, the other p is 1, and $R_8$ is selected from —($C_1$-$C_4$)alkyl, optionally iso-propyl.

In another embodiment, in formula (iii) j is 1 and each p is 0.

In another embodiment, in formula (iii) j is 1, one p is O, the other p is 1, and $R_8$ is selected from —($C_1$-$C_4$)alkyl, optionally iso-propyl.

In another embodiment, the Heterocyclic-Substituted Piperidine Compound of Formula (II) is

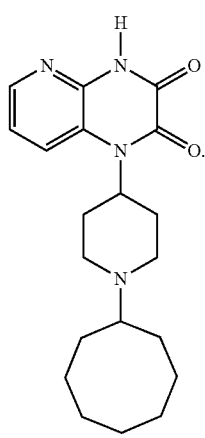 [SMILES: O=c1[nH]c2ncccc2n(C2CCN(C3CCCCCCC3)CC2)c1=O]

In another embodiment for the Heterocyclic-Substituted Piperidine Compounds of Formula (II):

Q is selected from naphtho (otherwise known as naphthaleno) or pyridino;

each $R_2$ is independently selected from:
(a) -halo, —OH, —$NH_2$, —CN, or —$NO_2$; or
(b) —($C_1$-$C_6$)alkyl, —($C_2$-$C_6$)alkenyl, —($C_2$-$C_6$)alkynyl, —($C_3$-$C_7$)cycloalkyl, -(5- or 6-membered)heterocycle, -phenyl, -naphthyl, or -(5- or 6-membered)heteroaryl, each of which is unsubstituted or substituted with 1, 2 or 3 $R_8$ groups;

a is an integer from 0 to 2;

$R_3$ is selected from:
(a) —H; or
(b) —($C_1$-$C_6$)alkyl, —($C_2$-$C_6$)alkenyl, —($C_2$-$C_6$)alkynyl, —O($C_1$-$C_6$)alkyl, —O($C_2$-$C_6$)alkenyl, —O($C_2$-$C_6$)alkynyl, —($C_3$-$C_7$)cycloalkyl, —($C_5$-$C_7$)cycloalkenyl, —($C_3$-$C_7$)cycloalkoxy, -(3- to 7-membered)heterocycle, -phenyl, -naphthyl, or -(5- to 10-membered)heteroaryl, each of which is unsubstituted or substituted with 1, 2 or 3 $R_8$ groups; or
(c) —$CH_2CH_2OH$, —($C_1$-$C_6$)alkyl(=O)$W_1$, —C(O)O$V_1$, —C(O)N($V_1$)$_2$, or —S(O)$_2$($C_1$-$C_6$)alkyl; or
(d) -($C_1$-$C_4$)alkyl substituted with 1, 2 or 3 substituents independently selected from —($C_3$-$C_7$)cycloalkyl, —($C_3$-$C_7$)cycloalkoxy, -(3- to 7-membered)heterocycle, -phenyl, -naphthyl, and -(5- to 10-membered) heteroaryl; or
(e) —($C_1$-$C_3$)alkyl substituted with a substituent selected from —N($R_6$)$_2$, —S(O)$_2NH_2$, —NHC(O)$W_1$, —NHS(O)$_2W_1$, —C(O)O$V_1$, and —C(O)N($V_1$)$_2$;

each Y is independently selected from O or S;

A and B are independently selected from —H, —N($R_6$)$_2$, —($C_3$-$C_{12}$)cycloalkyl, or —($C_1$-$C_6$)alkyl each of which —($C_1$-$C_6$)alkyl is unsubstituted or substituted with —OH, —S(O)$_2NH_2$, or from 1 to 3 independently selected -halo, or A-B together form a ($C_2$-$C_6$)bridge;

C is —H;

D is —H;

the dashed line in the piperidine or bridged piperidine central ring is absent;

Z is —[($C_1$-$C_{10}$)alkyl]$_h$-, wherein h is 0 or 1; or —($C_1$-$C_{10}$)alkyl-N$R_6$C(=Y)—;

$R_1$ is selected from:
(a) —H, -halo, —CN, —OH, —$CH_2OH$, —$CH_2CH_2OH$, —$NO_2$, —N($R_6$)$_2$, —S(O)$NH_2$, —S(O)$_2NH_2$, —C(O)O$V_1$, or —C(O)CN; or
(b) —($C_1$-$C_6$)alkyl, —($C_2$-$C_6$)alkenyl, —($C_2$-$C_6$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, each of which is unsubstituted or substituted with an $R_8$ group, or

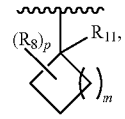

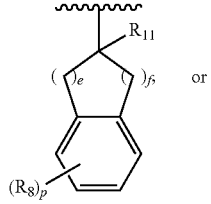

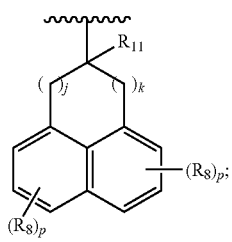

(c) -phenyl, -naphthyl, —($C_{14}$)aryl, or -(5- to 10-membered)heteroaryl, each of which is unsubstituted or substituted with an $R_8$ group; or —Z—$R_1$ is 3,3-diphenylpropyl—optionally substituted at the 3 carbon of the propyl with —CN, —C(O)N($R_6$)$_2$, —C(O)O$V_1$, or -tetrazolyl; or —Z—$R_1$ is —($C_1$-$C_4$)alkyl substituted with tetrazolyl;

each $R_6$ is independently selected from —H, —($C_1$-$C_6$) alkyl, or —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_8$ is independently selected from —($C_1$-$C_4$)alkyl, —O($C_1$-$C_4$)alkyl, —C(halo)$_3$, —CH(halo)$_2$, —$CH_2$(halo), —CN, —OH, -halo, or —C(O)O$R_9$;

each $R_9$ is independently selected from —H, —($C_1$-$C_6$) alkyl, -phenyl, or -benzyl;

$R_{11}$ is selected from —H, —($C_1$-$C_4$)alkyl, or -halo;

m is an integer from 1 to 7;

e and f are independently an integer from 0 to 5 provided that 2≤(e+f)≤5;

j and k are independently an integer from 0 to 4 provided that 1≤(j+k)≤4;

each p is independently 0 or 1;

each $V_1$ is independently selected from —H, —($C_1$-$C_6$) alkyl, —($C_3$-$C_7$)cycloalkyl, -phenyl, or -benzyl;

each $W_1$ is independently selected from:
(a) —H, —($C_1$-$C_6$)alkyl, —($C_3$-$C_7$)cycloalkyl, —O($C_1$-$C_6$)alkyl, —($C_3$-$C_7$)cycloalkoxy, —$CH_2CH_2OH$, —N($R_6$)$_2$; or
(b) -(5- or 6-membered)heteroaryl optionally substituted with 1, 2 or 3 independently selected —($C_1$-$C_6$)alkyl; and each halo is independently selected from —F, —Cl, —Br, or —I;

provided that when h is 0, then $R_1$ is not -halo or —$NO_2$;

provided that when Q is pyridino, then $R_2$ is not imidazolyl or triazolyl;

provided that when Q is pyridino and $R_2$ is -phenyl, -naphthyl, or -(5- or 6-membered)heteroaryl, then the $R_2$ group is not attached to a pyridino atom bonded to a 5- or 6-position carbon atom; and provided that $R_3$ does not include an imidazolyl group.

In another embodiment for the Heterocyclic-Substituted Piperidine Compounds of Formula (II):

Q is selected from naphthalene or pyridino;

each $R_2$ is independently selected from:
- (a) -halo, —CN, —$NO_2$, —$OT_3$, —$C(O)T_3$, —$C(O)OT_3$, —$C(O)N(T_1)(T_2)$, —$S(O)_3H$, —$S(O)_2T_3$, —$S(O)_2N(T_1)(T_2)$, —$N(T_1)(T_2)$, —$N(T_3)C(O)T_3$, —$N(T_3)C(O)N(T_1)(T_2)$, —$N(T_3)S(O)_2T_3$, or —$N(T_3)S(O)_2N(T_1)(T_2)$; or
- (b) —$(C_1-C_6)$alkyl, —$(C_2-C_6)$alkenyl, —$(C_2-C_6)$alkynyl, —$(C_3-C_7)$cycloalkyl, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(5- or 6-membered)heterocycle, or -(7- to 10-membered)bicycloheterocycle, each of which is unsubstituted or substituted with 1, 2 or 3 $R_8$ groups; or
- (c) -phenyl, -naphthyl, —$(C_{14})$aryl, or -(5- or 6-membered)heteroaryl, each of which is unsubstituted or substituted with 1, 2 or 3 $R_7$ groups;

a is an integer from 0 to 2;

$R_3$ is selected from:
- (a) —H; or
- (b) —$(C_1-C_6)$alkyl, —$(C_2-C_6)$alkenyl, —$(C_2-C_6)$alkynyl, —$O(C_1-C_6)$alkyl, —$O(C_2-C_6)$alkenyl, —$O(C_2-C_6)$alkynyl, —$(C_3-C_7)$cycloalkyl, —$(C_3-C_7)$cycloalkenyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, or -(7- to 10-membered)bicycloheterocycle, each of which is unsubstituted or substituted with 1, 2 or 3 $R_8$ groups; or
- (c) -phenyl, -naphthyl, —$(C_{14})$aryl, or -(5- to 10-membered)heteroaryl, each of which is unsubstituted or substituted with 1, 2 or 3 $R_7$ groups; or
- (d) —$(C_1-C_6)$alkyl$(=O)W_1$, —$C(O)OV_1$, —$C(O)N(V_1)_2$, —$S(O)_2N(V_1)_2$, or —$S(O)_2(C_1-C_6)$alkyl; or
- (e) —$(C_1-C_4)$alkyl substituted with 1, 2 or 3 substituents independently selected from —$(C_3-C_7)$cycloalkyl, —$(C_3-C_7)$cycloalkenyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, -(7- to 10-membered)bicycloheterocycle, -phenyl, -naphthyl, —$(C_{14})$aryl, or -(5- to 10-membered)heteroaryl; or
- (f) -$(C_1-C_3)$alkyl substituted with a substituent selected from —$N(R_6)_2$, —$S(O)_2N(V_1)_2$, —$N(R_9)C(O)W_1$, —$N(R_9)S(O)_2W_1$, and —$C(O)N(V_1)_2$;

each Y is independently selected from O or S;

A and B are independently selected from:
- (a) —H, —CN, —$C(O)OT_3$, —$C(O)N(T_1)(T_2)$, —$(C_3-C_{12})$cycloalkyl, —$(C_3-C_{12})$cycloalkoxy, —$(C_1-C_6)$alkyl, —$(C_2-C_6)$alkenyl, or —$(C_2-C_6)$alkynyl, each of which —$(C_1-C_6)$alkyl, —$(C_2-C_6)$alkenyl or —$(C_2-C_6)$alkynyl is unsubstituted or substituted with 1 or 2 substituents selected from —OH, —$S(O)_2NH_2$, —$N(R_6)_2$, =$NR_6$, —$C(O)OT_3$, —$C(O)N(R_6)_2$, —$N(R_6)C(O)R_9$ and -(5- or 6-membered)heterocycle or from 1 to 3 independently selected -halo, or
- (b) A-B together form a $(C_2-C_6)$bridge, which is unsubstituted or optionally substituted with from 1 to 3 -OH or optionally contains —HC=CH— within the $(C_2-C_6)$ bridge, or
- (c) A-B together form a —$CH_2$—N($R_a$)—$CH_2$— bridge, a

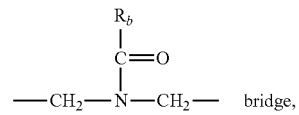

bridge, or a

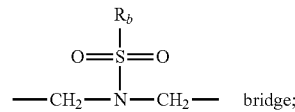

bridge;

$R_a$ is selected from —H, —$(C_1-C_6)$alkyl, —$(C_3-C_7)$cycloalkyl, —$CH_2$—C(O)—$R_c$, —$(CH_2)$—C(O)—$OR_c$, —$(CH_2)$—C(O)—N($R_c)_2$, —$(CH_2)_2$—O—$R_c$, —$(CH_2)_2$—$S(O)_2$—N($R_9)_2$, $R_c$, or —$(CH_2)_2$—N($R_c$)$S(O)_2$—$R_9$;

$R_b$ is selected from:
- (a) —H, —$(C_1-C_6)$alkyl, —$(C_3-C_7)$cycloalkyl, -(3- to 7-membered)heterocycle, —N($R_c)_2$, —N($R_c$)—$(C_3-C_7)$cycloalkyl, or —N($R_c$)-(3- to 7-membered)heterocycle,
- (b) -phenyl, -naphthyl, or -(5- or 6-membered)heteroaryl, each of which is unsubstituted or substituted with 1, 2 or 3 $R_7$ groups, or
- (c) —N($R_c$)-phenyl, —N($R_c$)-naphthyl, —N($R_c$)—$(C_{14})$aryl, or —N($R_c$)-(5- to 10-membered)heteroaryl, each of which is unsubstituted or substituted with 1, 2 or 3 $R_7$ groups;

each $R_c$ is independently selected from —H or —$(C_1-C_4)$alkyl;

C is selected from —H, -halo, —CN, —$OT_3$, —$C(O)OT_3$, —$C(O)N(T)_1(T_2)$, —$(C_3-C_{12})$cycloalkyl, —$(C_3-C_{12})$cycloalkoxy, —$N(R_6)_2$, —$N(R_6)C(O)R_9$, —$NR_6SO_2N(R_6)_2$, —$NR_6$—$C(=NR_6)N(R_6)_2$, —$(C_1-C_6)$alkyl, —$(C_2-C_6)$alkenyl, or —$(C_2-C_6)$alkynyl, each of which —$(C_1-C_6)$alkyl, —$(C_2-C_6)$alkenyl or —$(C_2-C_6)$alkynyl is unsubstituted or substituted with 1 or 2 substituents selected from —OH, —$S(O)_2NH_2$, —$N(R_6)_2$, =$NR_6$, —$C(O)OT_3$, —$C(O)N(R_6)_2$, —$N(R_6)C(O)R_9$ and -(5- or 6-membered)heterocycle or from 1 to 3 independently selected -halo;

the dashed line in the piperidine or bridged piperidine central ring denotes the presence or absence of a bond, and when the dashed line denotes the presence of a bond then D is absent, otherwise D is:
- (a) —H, —CN, —$C(O)OT_3$, or —$C(O)N(T_1)(T_2)$; or
- (b) —$(C_1-C_{10})$alkyl which is unsubstituted or substituted with 1, 2 or 3 $R_8$ groups and, optionally, in which any D group carbon atom except the carbon atom bonded directly to the piperidine or bridged piperidine central ring, is independently replaced by O or S; or (c) -phenyl, -naphthyl, or -(5- or 6-membered)heteroaryl, each of which is unsubstituted or substituted with 1, 2 or 3 $R_7$ groups;

Z is —$[(C_1-C_{10})alkyl]_h$-, wherein h is 0 or 1; or —$(C_1-C_{10})$alkyl-$NR_6C(=Y)$—;

$R_1$ is selected from:
(a) —H, -halo, —CN, —OH, —$CH_2OH$, —$CH_2CH_2OH$, —$NO_2$, —$N(R_6)_2$, —$S(O)NH_2$, —$S(O)_2NH_2$, —$C(O)OV_1$, or —$C(O)CN$; or
(b) —$(C_1-C_6)$alkyl, —$(C_2-C_6)$alkenyl, —$(C_2-C_6)$alkynyl, —$O(C_1-C_6)$alkyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, -(7- to 10-membered)bicycloheterocycle, each of which is unsubstituted or substituted with an $R_8$ group, or

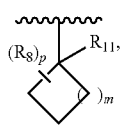
(i)

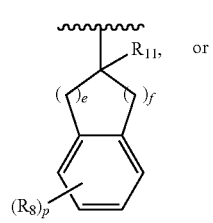
(ii) or

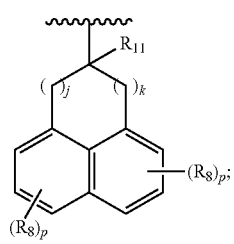
(iii)

or
(c) -phenyl, -naphthyl, —$(C_{14})$aryl, or -(5- to 10-membered)heteroaryl, each of which is unsubstituted or substituted with an $R_7$ group; or —Z—$R_1$ is 3,3-diphenylpropyl—optionally substituted at the 3 carbon of the propyl with —CN, —$C(O)N(R_6)_2$, —$C(O)OV_1$, or -tetrazolyl; or —Z—$R_1$ is —$(C_1-C_4)$alkyl substituted with tetrazolyl;

each $R_6$ is independently selected from —H, —$(C_1-C_6)$alkyl, or —$(C_3-C_7)$cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_7$ is independently selected from —$(C_1-C_4)$alkyl, —$(C_2-C_6)$alkenyl, —$(C_2-C_6)$alkynyl, —$OR_9$, —$SR_9$, —$C(halo)_3$, —$CH(halo)_2$, —$CH_2(halo)$, —CN, -halo, —$N_3$, —$NO_2$, —$CH=NR_9$, —$NR_9OH$, —$C(O)OR_9$, —$OC(O)R_9$, —$OC(O)OR_9$, —$S(O)R_9$, or —$S(O)_2R_9$;

each $R_8$ is independently selected from —$(C_1-C_4)$alkyl, —$(C_2-C_6)$alkenyl, —$(C_2-C_6)$alkynyl, —$OR_9$, —$SR_9$, —$C(halo)_3$, —$CH(halo)_2$, —$CH_2(halo)$, —CN, oxo, =S, -halo, —$N_3$, —$NO_2$, —$CH=NR_9$, —$NR_9OH$, —$C(O)OR_9$, —$OC(O)R_9$, —$OC(O)OR_9$, —$S(O)R_9$, or —$S(O)_2R_9$;

each $R_9$ is independently selected from —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, -(3- to 6-membered)heterocycle, —$C(halo)_3$, —$CH(halo)_2$, or —$CH_2(halo)$;

if h is O, $R_{11}$ is selected from —H or —$(C_1-C_4)$alkyl which is unsubstituted or substituted with —OH, —$(C_1-C_4)$alkoxy, —$N(R_6)_2$, —$C(O)OR_9$, or —$C(O)N(R_6)_2$;

if h is 1, $R_{11}$ is selected from —H, —OH, -halo, or —$(C_1-C_4)$alkyl which is unsubstituted or substituted with —OH, —$(C_1-C_4)$alkoxy, —$N(R_6)_2$, —$C(O)OR_9$, or —$C(O)N(R_6)_2$;

m is an integer from 1 to 7;

e and f are independently an integer from 0 to 5 provided that $2 \le (e+f) \le 5$;

j and k are independently an integer from 0 to 4 provided that $1 \le (j+k) \le 4$;

each p is independently 0 or 1;

each $T_1$, $T_2$, and $T_3$ is independently —H or —$(C_1-C_{10})$alkyl which is unsubstituted or substituted with 1, 2 or 3 $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2 or 3 $R_8$ groups and, optionally, any carbon atom in said 5- to 8-membered ring is independently replaced by O or S;

each $V_1$ is independently selected from —H, —$(C_1-C_6)$alkyl, —$(C_3-C_7)$cycloalkyl, -phenyl, or -benzyl;

each $W_1$ is independently selected from:
(a) —H, —$(C_1-C_6)$alkyl, —$(C_3-C_7)$cycloalkyl, —$O(C_1-C_6)$alkyl, —$(C_3-C_7)$cycloalkoxy, —$CH_2CH_2OH$, —$N(R_6)_2$; or
(b) -(5- or 6-membered)heteroaryl optionally substituted with 1, 2 or 3 independently selected —$(C_1-C_6)$alkyl; and each halo is independently selected from —F, —Cl, —Br, or —I;

provided that when h is O, then $R_1$ is not -halo or —$NO_2$;

provided that when Q is pyridino, then $R_2$ is not imidazolyl or triazolyl;

provided that when Q is pyridino and $R_2$ is -phenyl, -naphthyl, or -(5- or 6-membered)heteroaryl, then the $R_2$ group is not attached to a pyridino atom bonded to a 5- or 6-position carbon atom; and provided that $R_3$ does not include an imidazolyl group.

4.3 Heterocyclic-Substituted Piperidine Compounds of Formula (III)

As stated above, the invention encompasses Heterocyclic-Substituted Piperidine Compounds of Formula (III):

(III)

and pharmaceutically acceptable derivatives thereof where $R_1$, $R_2$, $R_3$, Q, X, Y, Z, A, B, C, D, a and the dashed line are defined above for the Heterocyclic-Substituted Piperidine Compounds of Formula (III).

In one embodiment, each Y is O.
In another embodiment, each Y is S.
In another embodiment, A is H.
In another embodiment, B is H.
In another embodiment, A-B together form a $(C_2-C_6)$ bridge, which is unsubstituted or substituted with 1, 2 or 3 independently selected $R_8$ groups, and which bridge optionally contains —HC=CH— within the $(C_2-C_6)$bridge; wherein the heterocyclic ring that is fused to the Q group can be in the endo- or exo-conformation with respect to the A-B bridge.

In another embodiment, A-B together form a $(C_2-C_6)$ bridge, which is unsubstituted or substituted with an $R_8$ group, and which bridge optionally contains —HC=CH— within the $(C_2-C_6)$bridge; wherein the heterocyclic ring that is fused to the Q group can be in the endo- or exo-conformation with respect to the A-B bridge.

In another embodiment, A-B together form a $(C_2-C_3)$ bridge, which is unsubstituted or substituted with an $R_8$ group, and which bridge optionally contains —HC=CH— within the $(C_2-C_3)$bridge; wherein the heterocyclic ring that is fused to the Q group can be in the endo- or exo- conformation with respect to the A-B bridge.

In another embodiment, A-B together form a $(C_2-C_3)$ bridge, which is unsubstituted and which bridge optionally contains —HC=CH— within the $(C_2-C_3)$bridge; wherein the heterocyclic ring that is fused to the Q group can be in the endo- or exo-conformation with respect to the A-B bridge.

In another embodiment, A-B together form a $(C_2)$bridge, a —HC=CH— bridge, or a $(C_3)$bridge each of which is unsubstituted; wherein the heterocyclic ring that is fused to the Q group can be in the endo- or exo-conformation with respect to the A-B bridge.

In another embodiment, C is H.
In another embodiment, D is H.
In another embodiment, a is 0 or 1.
In another embodiment, a is 0.
In another embodiment, a is 1.
In another embodiment, a is 2.
In another embodiment, each Y is O, A, B, C and D are each H, and a is 0 or 1.
In another embodiment, each Y is S, A, B, C and D are each H, and a is 0 or 1.
In another embodiment, each Y is O, A, B, C and D are each H, and a is 0.
In another embodiment, each Y is S, A, B, C and D are each H, and a is 0.
In another embodiment, each Y is O, A, B, C and D are each H, and a is 1.
In another embodiment, each Y is S, A, B, C and D are each H, and a is 1.
In another embodiment, each Y is O, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with 1, 2 or 3 independently selected $R_s$ groups, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0.

In another embodiment, each Y is S, A-B together form a $(C_2-C_6)$bridge, which is unsubstituted or substituted with 1, 2 or 3 independently selected $R_s$ groups, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0.

In another embodiment, each Y is O, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 1.

In another embodiment, each Y is S, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 1.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 0.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 1.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the Q group can be in the endo- or exo-conformation with respect to the A-B bridge, C and D are each H, and a is 1.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0 or 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0 or 1.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 1.

In another embodiment, each Y is O, A-B together form a $(C_2-C_3)$bridge, which is unsubstituted and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0 or 1.

In another embodiment, each Y is S, A-B together form a $(C_2-C_3)$bridge, which is unsubstituted and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0 or 1.

In another embodiment, each Y is O, A-B together form a $(C_2-C_3)$bridge, which is unsubstituted and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0.

In another embodiment, each Y is S, A-B together form a $(C_2-C_3)$bridge, which is unsubstituted and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 0.

In another embodiment, each Y is O, A-B together form a $(C_2-C_3)$bridge, which is unsubstituted and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 1.

In another embodiment, each Y is S, A-B together form a $(C_2-C_3)$bridge, which is unsubstituted and which bridge optionally contains —HC=CH— within the $(C_2-C_3)$bridge; wherein the heterocyclic ring that is fused to the Q group can be in the endo- or exo-conformation with respect to the A-B bridge, C and D are each H, and a is 1.

In another embodiment, $R_3$ is —H, —$(C_1-C_6)$alkyl, —$(C_1-C_6)$alkyl substituted by an $R_8$ group, —$(C_3-C_7)$cycloalkyl, or —$(C_3-C_7)$cycloalkyl substituted by an $R_8$ group.

In another embodiment, $R_3$ is —H, —C(O)OV$_1$, —C(O)N(V$_1$)$_2$, or —$(C_1-C_2)$alkyl substituted with a substituent selected from —NHS(O)$_2$W$_1$, —C(O)OV$_1$, and —C(O)N(V$_1$)$_2$.

In another embodiment, $R_3$ is —H.

In another embodiment, $R_3$ is —$(C_1-C_6)$alkyl.

In another embodiment, $R_3$ is methyl, ethyl, n-propyl or iso-propyl.

In another embodiment, $R_3$ is —$(C_1-C_6)$alkyl substituted by an $R_8$ group.

In another embodiment, $R_3$ is —$(C_1-C_6)$alkyl substituted by —CN.

In another embodiment, $R_3$ is methyl, ethyl, n-propyl or iso-propyl, each of which is substituted by an $R_8$ group.

In another embodiment, $R_3$ is methyl, ethyl, n-propyl or iso-propyl, each of which is substituted by —CN.

In another embodiment, $R_3$ is —$(C_3-C_7)$cycloalkyl.

In another embodiment, $R_3$ is cyclopentyl, cyclohexyl, or cycloheptyl.

In another embodiment, $R_3$ is —H or methyl substituted by —CN.

In another embodiment, each Y is O, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0 or 1.

In another embodiment, each Y is S, A, B, C and D are each H, $R_3$ is —H, —$(C_1-C_6)$alkyl, —$(C_1-C_6)$alkyl substituted by an $R_8$ group, or —$(C_3-C_7)$cycloalkyl, and a is 0 or 1.

In another embodiment, each Y is O, A, B, C and D are each H, $R_3$ is —H or methyl substituted by —CN, and a is 0 or 1.

In another embodiment, each Y is S, A, B, C and D are each H, $R_3$ is —H or methyl substituted by —CN, and a is 0 or 1.

In another embodiment, each Y is O, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 0.

In another embodiment, each Y is S, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 0.

In another embodiment, each Y is O, A, B, C and D are each H, $R_3$ is —H or methyl substituted by —CN, and a is 0.

In another embodiment, each Y is S, A, B, C and D are each H, $R_3$ is —H or methyl substituted by —CN, and a is 0.

In another embodiment, each Y is O, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 1.

In another embodiment, each Y is S, A, B, C and D are each H, $R_3$ is —H, —($C_1$-$C_6$)alkyl, —($C_1$-$C_6$)alkyl substituted by an $R_8$ group, or —($C_3$-$C_7$)cycloalkyl, and a is 1.

In another embodiment, each Y is O, A, B, C and D are each H, $R_3$ is —H or methyl substituted by —CN, and a is 1.

In another embodiment, each Y is S, A, B, C and D are each H, $R_3$ is —H or methyl substituted by —CN, and a is 1.

In another embodiment, each $R_2$ is independently -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, each $R_2$ is independently -halo.

In another embodiment, a is 2 and each $R_2$ is independently -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 2 and each $R_2$ is independently -halo, —OH, —$NH_2$, —CN, methyl, ethyl, n-propyl, iso-propyl, cyclopentyl, cyclohexyl, cycloheptyl, or phenyl.

In another embodiment, a is 2 and each $R_2$ is independently -halo.

In another embodiment, a is 1 and $R_2$ is -halo, —OH, —$NH_2$, —CN, —($C_1$-$C_6$)alkyl, —($C_3$-$C_2$)cycloalkyl, -(5- or 6-membered)heterocycle, -phenyl, -naphthalenyl or -(5- or 6-membered)heteroaryl.

In another embodiment, a is 1 and $R_2$ is -halo, —OH, —$NH_2$, —CN, methyl, ethyl, n-propyl, iso-propyl, cyclopentyl, cyclohexyl, cycloheptyl, or phenyl.

In another embodiment, a is 1 and $R_2$ is -halo, optionally —F.

In another embodiment, each Y is O, A, B, C and D are each H, a is 1, and $R_2$ is -halo, optionally —F.

In another embodiment, each Y is O, A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the heterocyclic ring that is fused to the Q group can be in the endo- or exo-conformation with respect to the A-B bridge, C and D are each H, a is 1, and $R_2$ is -halo, optionally —F.

In another embodiment, each Y is O, A-B together form a ($C_2$-$C_6$)bridge, which is unsubstituted or substituted with an $R_8$ group, and which bridge optionally contains —HC=CH— within the ($C_2$-$C_6$)bridge; wherein the heterocyclic ring that is fused to the Q group can be in the endo- or exo-conformation with respect to the A-B bridge, C and D are each H, a is 1, and $R_2$ is -halo, optionally —F.

In another embodiment, each Y is O, A-B together form a ($C_2$-$C_3$)bridge, which is unsubstituted or substituted with an $R_8$ group, and which bridge optionally contains —HC=CH— within the ($C_2$-$C_3$)bridge; wherein the heterocyclic ring that is fused to the Q group can be in the endo- or exo-conformation with respect to the A-B bridge, C and D are each H, a is 1, and $R_2$ is -halo, optionally —F.

In another embodiment, each Y is O, A-B together form a ($C_2$-$C_3$)bridge, which is unsubstituted and which bridge optionally contains —HC=CH— within the ($C_2$-$C_3$)bridge; wherein the heterocyclic ring that is fused to the Q group can be in the endo- or exo-conformation with respect to the A-B bridge, C and D are each H, a is 1, and $R_2$ is -halo, optionally —F.

In another embodiment, each Y is O, A, B, C and D are each H, a is 0, and $R_3$ is methyl, ethyl, n-propyl or iso-propyl, each of which is substituted by an $R_8$ group, or —H.

In another embodiment, each Y is O, A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the heterocyclic ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_9$ group, or —H.

In another embodiment, each Y is O, A-B together form a ($C_2$-$C_6$)bridge, which is unsubstituted or substituted with an $R_8$ group, and which bridge optionally contains —HC=CH— within the ($C_2$-$C_6$)bridge; wherein the heterocyclic ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a ($C_2$-$C_3$)bridge, which is unsubstituted or substituted with an $R_8$ group, and which bridge optionally contains —HC=CH— within the ($C_2$-$C_3$)bridge; wherein the heterocyclic ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A-B together form a ($C_2$-$C_3$)bridge, which is unsubstituted and which bridge optionally contains —HC=CH— within the ($C_2$-$C_3$)bridge; wherein the heterocyclic ring that is fused to the Q group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A, B, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a ($C_2$-$C_6$)bridge, which is unsubstituted or substituted with 1, 2 or 3 independently selected $R_8$ groups, and which bridge optionally contains —HC=CH— within the ($C_2$-$C_6$)bridge; wherein the heterocyclic ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a ($C_2$-$C_6$)bridge, which is unsubstituted or substituted with an $R_8$ group, and which bridge optionally contains —HC=CH— within the ($C_2$-$C_6$)bridge; wherein the heterocyclic ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a $(C_2-C_3)$bridge, which is unsubstituted or substituted with an $R_8$ group, and which bridge optionally contains —HC═CH— within the $(C_2-C_3)$bridge; wherein the heterocyclic ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a $(C_2-C_3)$bridge, which is unsubstituted and which bridge optionally contains —HC═CH— within the $(C_2-C_3)$bridge; wherein the heterocyclic ring that is fused to the Q group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, Q is benzo, naphthaleno, or (5- to 10-membered)heteroaryl.

In another embodiment, Q is benzo.

In another embodiment, Q is naphthaleno.

In another embodiment, Q is pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino.

In another embodiment, Q is pyridino.

In another embodiment, Q is benzo, naphthaleno, or pyridino.

In another embodiment, Q is benzo or pyridino.

In another embodiment, Z is a bond.

In another embodiment, Z is a bond and $R_1$ is selected from:

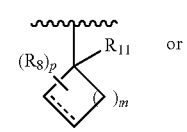
(i)

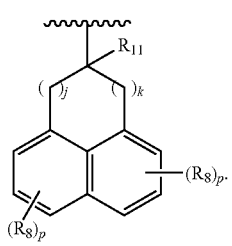
(iii)

In another embodiment, Z is a bond, $R_1$ is selected from formula (i), and m is 5.

In another embodiment, Z is a bond, $R_1$ is selected from formula (i), m is 5, and p is 0.

In another embodiment, Z is a bond, $R_1$ is selected from formula (i), m is 5, p is 0, and $R_{11}$ is —H.

In another embodiment, Z is a bond, $R_1$ is selected from formula (i), and m is 3.

In another embodiment, Z is a bond, $R_1$ is selected from formula (i), m is 3, and p is 1.

In another embodiment, Z is a bond, $R_1$ is selected from formula (i), m is 3, p is 1, and $R_8$ is —$(C_1-C_4)$alkyl, optionally iso-propyl.

In another embodiment, Z is a bond, $R_1$ is selected from formula (i), m is 3, $R_{11}$ is —H, p is 1, and $R_8$ is —$(C_1-C_4)$alkyl, optionally iso-propyl.

In another embodiment, Z is a bond, $R_1$ is selected from formula (iii), and j+k=1.

In another embodiment, Z is a bond, $R_1$ is selected from formula j+k=1, and p is 0.

In another embodiment, Q is benzo, Z is a bond, and $R_1$ is selected from:

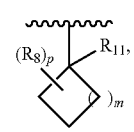
(ia)

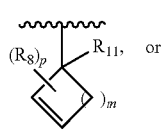
(ib) or

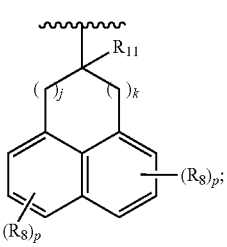
(iii)

where m is an integer selected from 3, 4 or 5;
j is an integer selected from 1 or 2;
k is 0;
each p is an integer independently selected from 0 or 1; and and $R_{11}$ is —H, —C(O)O$R_9$, —C(O)N$(R_6)_2$, or —$(C_1-C_4)$alkyl which is unsubstituted or substituted with —C(O)O$R_9$ or —C(O)N$(R_6)_2$.

In another embodiment, Q is pyridino, Z is a bond, and $R_1$ is selected from:

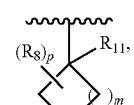
(ia)

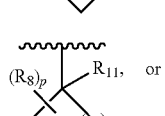
(ib) or

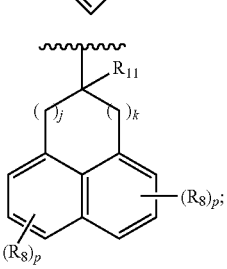
(iii)

where m is an integer selected from 3, 4 or 5;
j is an integer selected from 1 or 2;
k is 0;

each p is an integer independently selected from 0 or 1; and and $R_{11}$ is —H, —C(O)O$R_9$, —C(O)N($R_6$)$_2$, or —($C_1$-$C_4$)alkyl which is unsubstituted or substituted with —C(O)O$R_9$ or —C(O)N($R_6$)$_2$.

In another embodiment, $R_{11}$ is —H, —C(O)O$R_9$ or —C(O)N($R_6$)$_2$.

In another embodiment, $R_{11}$ is —H or —C(O)O$R_9$.

In another embodiment, $R_{11}$ is —H.

In another embodiment, $R_{11}$ is —C(O)O$R_9$.

In another embodiment, $R_{11}$ is —C(O)OH or —C(O)O($C_1$-$C_6$)alkyl.

In another embodiment, $R_{11}$ is —H or —C(O)O($C_1$-$C_6$)alkyl.

In another embodiment, $R_{11}$ is —C(O)OH or —C(O)OCH$_3$.

In another embodiment, $R_{11}$ is —H or —C(O)OCH$_3$.

In another embodiment, each p is 0.

In another embodiment, in formulas (ia) and (ib) p is 1 and $R_8$ is selected from —($C_1$-$C_4$)alkyl, optionally iso-propyl.

In another embodiment, in formulas (ia) and (ib) m is 3, p is 1, and $R_8$ is selected from —($C_1$-$C_4$)alkyl, optionally iso-propyl.

In another embodiment, in formulas (ia) and (ib) m is 5, p is 1, and $R_8$ is selected from —($C_1$-$C_4$)alkyl, optionally iso-propyl.

In another embodiment, in formulas (ia) and (ib) m is 3 and p is 0.

In another embodiment, in formulas (ia) and (ib) m is 5 and p is 0.

In another embodiment, in formula (iii) one p is 0, the other p is 1, and $R_8$ is selected from —($C_1$-$C_4$)alkyl, optionally iso-propyl.

In another embodiment, in formula (iii) j is 1 and each p is 0.

In another embodiment, in formula (iii) j is 1, one p is 0, the other p is 1, and $R_8$ is selected from —($C_1$-$C_4$)alkyl, optionally iso-propyl.

In another embodiment, $R_{11}$ is —H or —C(O)O($C_1$-$C_6$)alkyl and each p is 0.

In another embodiment, in formulas (ia) and (ib) $R_{11}$ is —H or —C(O)O($C_1$-$C_6$)alkyl, p is 1, and $R_8$ is selected from —($C_1$-$C_4$)alkyl, optionally iso-propyl.

In another embodiment, in formulas (ia) and (ib) $R_{11}$ is —H or —C(O)O($C_1$-$C_6$)alkyl, m is 3, p is 1, and $R_8$ is selected from —($C_1$-$C_4$)alkyl, optionally iso-propyl.

In another embodiment, in formulas (ia) and (ib) $R_{11}$ is —H or —C(O)O($C_1$-$C_6$)alkyl, m is 5, p is 1, and $R_8$ is selected from —($C_1$-$C_4$)alkyl, optionally iso-propyl.

In another embodiment, in formulas (ia) and (ib) $R_{11}$ is —H or —C(O)O($C_1$-$C_6$)alkyl, m is 3, and p is 0.

In another embodiment, in formulas (ia) and (ib) $R_{11}$ is —H or —C(O)O($C_1$-$C_6$)alkyl, m is 5, and p is 0.

In another embodiment, in formula (iii) $R_{11}$ is —H or —C(O)O($C_1$-$C_6$)alkyl, one p is 0, the other p is 1, and $R_8$ is selected from —($C_1$-$C_4$)alkyl, optionally iso-propyl.

In another embodiment, in formula (iii) $R_{11}$ is —H or —C(O)O($C_1$-$C_6$)alkyl, j is 1, and each p is 0.

In another embodiment, in formula (iii) $R_{11}$ is —H or —C(O)O($C_1$-$C_6$)alkyl, j is 1, one p is 0, the other p is 1, and $R_8$ is selected from —($C_1$-$C_4$)alkyl, optionally iso-propyl.

In another embodiment, X is —C($R_4$)($R_5$)— or —N($R_{13}$)—.

In another embodiment, X is —C($R_4$)($R_5$)—.

In another embodiment, X is —CH$_2$—.

In another embodiment, X is —C($R_4$)($R_5$)—, $R_4$ is —($C_1$-$C_6$)alkyl, and $R_5$ is —($C_1$-$C_6$)alkyl.

In another embodiment, X is —C[($C_1$-$C_6$)alkyl]$_2$-.

In another embodiment, X is —C($C_2$H$_5$)$_2$—.

In another embodiment, X is —N($R_{13}$)—.

In another embodiment, $R_{13}$ is ($C_1$-$C_4$)alkyl substituted with 1, 2 or 3 substituents independently selected from —($C_3$-$C_{12}$)cycloalkyl which is unsubstituted or further substituted with 1, 2 or 3 independently selected $R_8$ groups, or -(3- to 7-membered)heterocycle which is unsubstituted or further substituted with 1, 2 or 3 independently selected $R_8$ groups.

In another embodiment, $R_{13}$ is —($C_1$-$C_4$)alkyl substituted with 1, 2 or 3 substituents independently selected from —OC(O)($C_3$-$C_8$)cycloalkyl, —NHS(O)$_2$($C_3$-$C_8$)cycloalkyl, —NHC(O)W$_2$, and —NHS(O)$_2$W$_2$.

In another embodiment, $R_{13}$ is —($C_1$-$C_6$)alkyl(=O)W$_2$ or —($C_1$-$C_6$)alkyl-W$_2$.

In another embodiment, $R_{13}$ is —($C_1$-$C_6$)alkyl(=O)W$_2$.

In another embodiment, $R_{13}$ is —($C_1$-$C_6$)alkyl(=O)N($R_6$)$_2$.

In another embodiment, $R_{13}$ is —($C_1$-$C_6$)alkyl(=O)NH($R_6$).

In another embodiment, $R_{13}$ is —($C_1$-$C_6$)alkyl(=O)NH($C_1$-$C_6$)alkyl).

In another embodiment, $R_{13}$ is —($C_1$-$C_6$)alkyl(=O)N[($C_1$-$C_6$)alkyl]$_2$.

In another embodiment, $R_{13}$ is —($C_1$-$C_6$)alkyl(=O)N(CH$_3$)$_2$.

In another embodiment, $R_{13}$ is —($C_1$-$C_6$)alkyl-W$_2$.

In another embodiment, $R_{13}$ is —($C_1$-$C_6$)alkyl-N($R_6$)$_2$.

In another embodiment, $R_{13}$ is —($C_1$-$C_6$)alkyl-NH($R_6$).

In another embodiment, $R_{13}$ is —($C_1$-$C_6$)alkyl-NH($C_1$-$C_6$)alkyl).

In another embodiment, $R_{13}$ is —($C_1$-$C_6$)alkyl-N[($C_1$-$C_6$)alkyl]$_2$.

In another embodiment, $R_{13}$ is —($C_1$-$C_6$)alkyl-N($C_2$H$_5$)$_2$.

In another embodiment, X is —NH—.

In another embodiment, X is —N($C_1$-$C_6$)alkyl where the ($C_1$-$C_6$)alkyl is optionally substituted with 1, 2 or 3 independently selected $R_8$ groups.

In another embodiment, X is —N($C_1$-$C_4$)alkyl where the ($C_1$-$C_4$)alkyl is substituted with —N($R_6$)$_2$.

In another embodiment, X is —N($C_2$-)alkyl where the ($C_2$) alkyl is substituted with —N($R_6$)$_2$.

In another embodiment, X is —N($C_1$-$C_4$)alkyl where the ($C_1$-$C_4$)alkyl is substituted with —C(O)N($R_9$)$_2$.

In another embodiment, X is —N($C_1$)alkyl where the ($C_1$) alkyl is substituted with —C(O)N($R_9$)$_2$.

In another embodiment, X is —N($C_1$-$C_4$)alkyl where the ($C_1$-$C_4$)alkyl is substituted with —C(O)O$R_9$.

In another embodiment, X is —N($C_1$)alkyl where the ($C_1$) alkyl is substituted with —C(O)O$R_9$.

In another embodiment, the Heterocyclic-Substituted Piperidine Compound of Formula (III) is

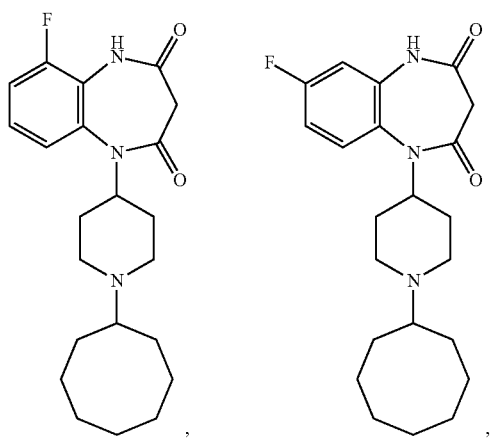
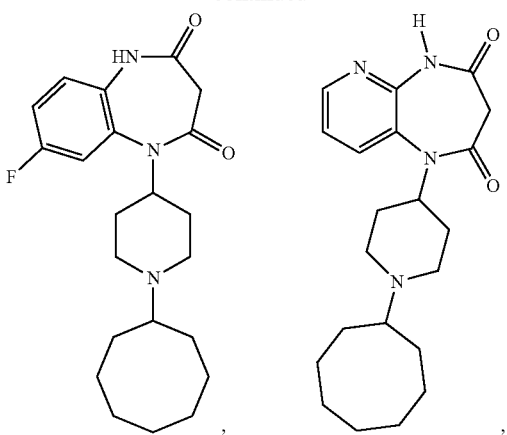
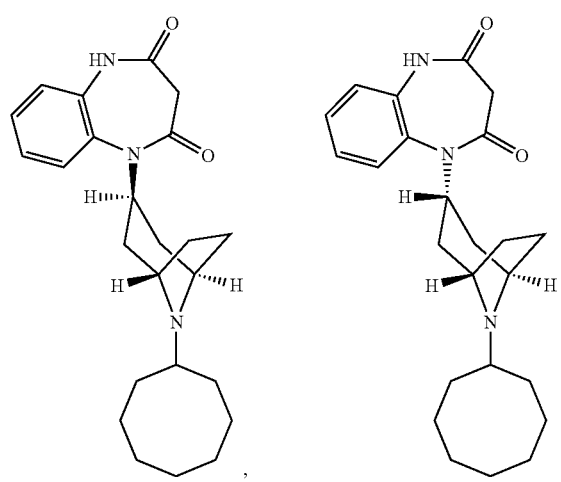
In another embodiment, the Heterocyclic-Substituted Piperidine Compound of Formula (III) is
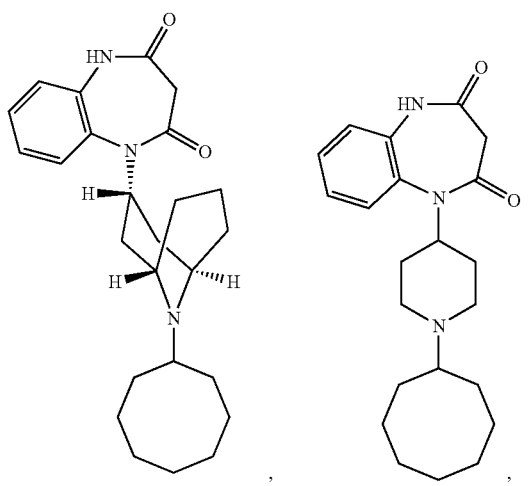
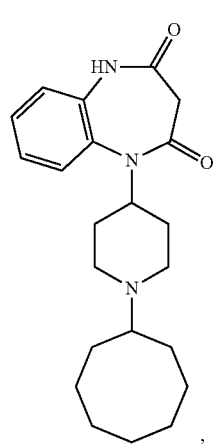

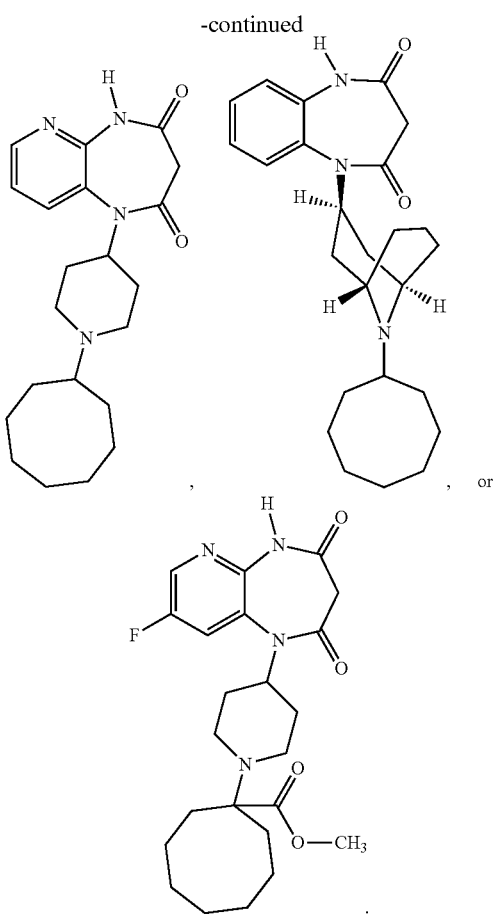

, or

In another embodiment for the Heterocyclic-Substituted Piperidine Compounds of Formula (III):

Q is selected from benzo, naphtho, $(C_{14})$aryl, $(C_3$-$C_{12})$cycloalkyl, $(C_6$-$C_{14})$bicycloalkyl, $(C_5$-$C_{10})$cycloalkenyl, $(C_7$-$C_{14})$bicycloalkenyl, (3- to 7-membered)heterocycle, or (5- to 10-membered)heteroaryl;

each $R_2$ is independently selected from:
(a) -halo, —OH, —$NH_2$, —CN, or —$NO_2$; or
(b) —$(C_1$-$C_6)$alkyl, —$(C_2$-$C_6)$alkenyl, —$(C_2$-$C_6)$alkynyl, —$(C_3$-$C_7)$cycloalkyl, -(5- or 6-membered)heterocycle, -phenyl, -naphthyl, or -(5- or 6-membered)heteroaryl, each of which is unsubstituted or substituted with 1, 2 or 3 $R_8$ groups;

a is an integer from 0 to 2;

$R_3$ is selected from:
(a) —H; or
(b) —$(C_1$-$C_6)$alkyl, —$(C_2$-$C_6)$alkenyl, —$(C_2$-$C_6)$alkynyl, —$O(C_1$-$C_6)$alkyl, —$O(C_2$-$C_6)$alkenyl, —$O(C_2$-$C_6)$alkynyl, —$(C_3$-$C_7)$cycloalkyl, —$(C_5$-$C_7)$cycloalkenyl, —$(C_3$-$C_7)$cycloalkoxy, -(3- to 7-membered)heterocycle, -phenyl, -naphthyl, or -(5- to 10-membered)heteroaryl, each of which is unsubstituted or substituted with 1, 2 or 3 $R_8$ groups; or
(c) —$CH_2CH_2OH$, —$(C_1$-$C_6)$alkyl(=O)$W_1$, —C(O)O$V_1$, —C(O)N($V_1$)$_2$, or —S(O)$_2(C_1$-$C_6)$alkyl; or
(d) —$(C_1$-$C_4)$alkyl substituted with 1, 2 or 3 substituents independently selected from —$(C_3$-$C_7)$cycloalkyl, —$(C_3$-$C_7)$cycloalkoxy, -(3- to 7-membered)heterocycle, -phenyl, -naphthyl, and -(5- to 10-membered)heteroaryl; or
(e) —$(C_1$-$C_3)$alkyl substituted with a substituent selected from —N($R_6$)$_2$, —S(O)$_2NH_2$, —NHC(O)$W_1$, —NHS(O)$_2W_1$, —C(O)O$V_1$, and —C(O)N($V_1$)$_2$;

each Y is independently selected from O or S;

X is —C($R_4$)($R_5$)—, —N($R_6$)—, —C($R_4$)($R_5$)—C($R_4'$)($R_5'$)-, —C($R_4$)($R_5$)—N($R_6$)—, or —N($R_6$)—C($R_4$)($R_5$)—;

each $R_4$ and $R_4'$ is independently selected from —H, —O$R_6$, —$(C_1$-$C_6)$alkyl, or —$(C_3$-$C_7)$cycloalkyl; or, independently, any two of $R_4$ and $R_5$, or $R_4'$ and $R_5'$, together can form an oxo group; or any two of $R_4$ and $R_4'$ can form a 4- to 8-membered cycloalkyl ring, the number of atoms in the ring including the atoms to which the two of $R_4$ and $R_4'$ are attached and any intervening atoms, if present;

each $R_5$ and $R_5'$ is independently selected from —H, —$(C_1$-$C_6)$alkyl, or —$(C_3$-$C_7)$cycloalkyl;

A and B are independently selected from —H, —N($R_6$)$_2$, —$(C_3$-$C_{12})$cycloalkyl, or —$(C_1$-$C_6)$alkyl each of which —$(C_1$-$C_6)$alkyl is unsubstituted or substituted with —OH, —S(O)$_2NH_2$, or from 1 to 3 independently selected -halo, or A-B together form a $(C_2$-$C_6)$bridge;

C is —H;

D is —H;

the dashed line in the piperidine or bridged piperidine central ring is absent;

Z is —[$(C_1$-$C_{10})$alkyl]$_h$-, wherein h is 0 or 1; or —$(C_1$-$C_{10})$alkyl-N$R_6$C(=Y)—;

$R_1$ is selected from:
(a) —H, -halo, —CN, —OH, —$CH_2OH$, —$CH_2CH_2OH$, —$NO_2$, —N($R_6$)$_2$, —S(O)$NH_2$, —S(O)$_2NH_2$, —C(O)O$V_1$, or —C(O)CN;
(b) —$(C_1$-$C_6)$alkyl, —$(C_2$-$C_6)$alkenyl, —$(C_2$-$C_6)$alkynyl, —$O(C_1$-$C_6)$alkyl, —$(C_3$-$C_7)$cycloalkoxy, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(3- to 7-membered)heterocycle, -(7- to 10-membered)bicycloheterocycle, each of which is unsubstituted or substituted with an $R_8$ group, or

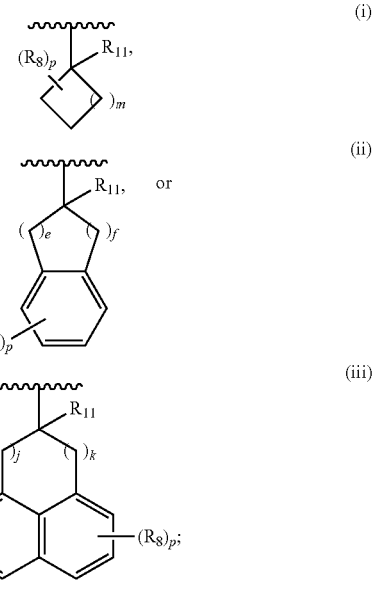

or (c) -phenyl, -naphthyl, —$(C_{14})$aryl, or -(5- to 10-membered)heteroaryl, each of which is unsubstituted or substituted with an $R_8$ group;

—Z—$R_1$ is 3,3-diphenylpropyl—optionally substituted at the 3 carbon of the propyl with —CN, —C(O)N($R_6$)$_2$, —C(O)O$V_1$, or -tetrazolyl; or —Z—$R_1$ is —($C_1$-$C_4$)alkyl substituted with tetrazolyl;

each $R_6$ is independently selected from —H, —($C_1$-$C_6$)alkyl, or —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_8$ is independently selected from —($C_1$-$C_4$)alkyl, —O($C_1$-$C_4$)alkyl, —C(halo)$_3$, —CH(halo)$_2$, —CH$_2$(halo), —CN, —OH, -halo, or —C(O)O$R_9$;

each $R_9$ is independently selected from —H, —($C_1$-$C_6$)alkyl, -phenyl, or -benzyl;

$R_{11}$ is selected from —H, —($C_1$-$C_4$)alkyl, or -halo;

m is an integer from 1 to 7;

e and f are independently an integer from 0 to 5 provided that $2 \leq (e+f) \leq 5$;

j and k are independently an integer from 0 to 4 provided that $1 \leq (j+k) \leq 4$;

each p is independently 0 or 1;

each $V_1$ is independently selected from —H, —($C_1$-$C_6$)alkyl, —($C_3$-$C_7$)cycloalkyl, -phenyl, or -benzyl;

each $W_1$ is independently selected from:
(a) —H, —($C_1$-$C_6$)alkyl, —($C_3$-$C_7$)cycloalkyl, —O($C_1$-$C_6$)alkyl, —($C_3$-$C_7$)cycloalkoxy, —CH$_2$CH$_2$OH, —N($R_6$)$_2$; or
(b) -(5- or 6-membered)heteroaryl optionally substituted with 1, 2 or 3 independently selected —($C_1$-$C_6$)alkyl; and each halo is independently selected from —F, —Cl, —Br, or —I;

provided that when h is 0, then $R_1$ is not -halo or —NO$_2$;

provided that when Q is benzo, then X is not —N($R_6$)—;

provided that when Q is benzo, then $R_3$ is not —($C_1$-$C_2$)alkyl substituted with —C(O)N($V_1$)$_2$; and provided that $R_3$ does not include an imidazolyl group.

In another embodiment for the Heterocyclic-Substituted Piperidine Compounds of Formula (III):

Q is selected from benzo, naphthaleno, ($C_{14}$)aryl, ($C_3$-$C_{12}$)cycloalkyl, ($C_6$-$C_{14}$)bicycloalkyl, ($C_5$-$C_{10}$)cycloalkenyl, ($C_7$-$C_{14}$)bicycloalkenyl, (3- to 7-membered)heterocycle, or (5- to 10-membered)heteroaryl;

each $R_2$ is independently selected from:
(a) -halo, —CN, —NO$_2$, —O$T_3$, —C(O)$T_3$, —C(O)O$T_3$, —C(O)N($T_1$)($T_2$), —S(O)$_3$H, —S(O)$_2$$T_3$, —S(O)$_2$N($T_1$)($T_2$), —N($T_1$)($T_2$), —N($T_3$)C(O)$T_3$, —N($T_3$)C(O)N($T_1$)($T_2$), —N($T_3$)S(O)$_2$$T_3$, or —N($T_3$)S(O)$_2$N($T_1$)($T_2$); or
(b) —($C_1$-$C_6$)alkyl, —($C_2$-$C_6$)alkenyl, —($C_2$-$C_6$)alkynyl, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 $R_8$ groups; or
(c) -phenyl, -naphthyl, —($C_{14}$)aryl, or -(5- or 6-membered)heteroaryl, each of which is unsubstituted or substituted with 1, 2 or 3 $R_7$ groups;

a is an integer from 0 to 2;

$R_3$ is selected from:
(a) —H; or
(b) —($C_1$-$C_6$)alkyl, —($C_2$-$C_6$)alkenyl, —($C_2$-$C_6$)alkynyl, —O($C_1$-$C_6$)alkyl, —O($C_2$-$C_6$)alkenyl, —O($C_2$-$C_6$)alkynyl, —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, or -(7- to 10-membered)bicycloheterocycle, each of which is unsubstituted or substituted with 1, 2 or 3 $R_8$ groups; or
(c) -phenyl, -naphthyl, —($C_{14}$)aryl, or -(5- to 10-membered)heteroaryl, each of which is unsubstituted or substituted with 1, 2 or 3 $R_7$ groups; or
(d) —($C_1$-$C_6$)alkyl(=O)$W_1$, —($C_1$-$C_6$)alkyl(=NH)$W_1$, —C(O)O$V_1$, —C(O)N($V_1$)$_2$, —S(O)$_2$N($V_1$)$_2$, or —S(O)$_2$($C_1$-$C_6$)alkyl; or
(e) —($C_1$-$C_4$)alkyl substituted with 1, 2 or 3 substituents independently selected from —($C_3$-$C_7$)cycloalkyl, —($C_3$-$C_7$)cycloalkenyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, -phenyl, -naphthyl, —($C_{14}$)aryl, or -(5- to 10-membered)heteroaryl; or
(f) —($C_1$-$C_3$)alkyl substituted with a substituent selected from —N($R_6$)$_2$, —S(O)$_2$N($V_1$)$_2$, —N($R_9$)C(O)$W_1$, —N($R_9$)S(O)$_2$$W_1$, and —C(O)N($V_1$)$_2$;

each Y is independently selected from O or S;

X is —C($R_4$)($R_5$)—, —N($R_6$)—, —C($R_4$)($R_5$)—C($R_4$')($R_5$')—, —C($R_4$)=C($R_4$')—, —C($R_4$)($R_5$)—N($R_6$)—, or —N($R_6$)—C($R_4$)($R_5$)—;

each $R_4$ and $R_4$' is independently selected from —H, —O$R_6$, —($C_1$-$C_6$)alkyl, or —($C_3$-$C_7$)cycloalkyl; or, independently, any two of $R_4$ and $R_5$, or $R_4$' and $R_5$', together can form an oxo group; or any two of $R_4$ and $R_4$' can form a 4- to 8-membered cycloalkyl ring, the number of atoms in the ring including the atoms to which the two of $R_4$ and $R_4$' attached and any intervening atoms, if present;

each $R_5$ and $R_5$' is independently selected from —H, —($C_1$-$C_6$)alkyl, or —($C_3$-$C_7$)cycloalkyl;

A and B are independently selected from:
(a) —H, —CN, —C(O)O$T_3$, —C(O)N(T)$_1$(T$_2$), —($C_3$-$C_{12}$)cycloalkyl, —($C_3$-$C_{12}$)cycloalkoxy, —($C_1$-$C_6$)alkyl, —($C_2$-$C_6$)alkenyl, or —($C_2$-$C_6$)alkynyl, each of which —($C_1$-$C_6$)alkyl, —($C_2$-$C_6$)alkenyl or —($C_2$-$C_6$)alkynyl is unsubstituted or substituted with 1 or 2 substituents selected from —OH, —S(O)$_2$NH$_2$, —N($R_6$)$_2$, =N$R_6$, —C(O)O$T_3$, —C(O)N($R_6$)$_2$, —N($R_6$)C(O)$R_9$ and -(5- or 6-membered)heterocycle or from 1 to 3 independently selected -halo, or
(b) A-B together form a ($C_2$-$C_6$)bridge, which is unsubstituted or optionally substituted with from 1 to 3-OH or optionally contains —HC=CH— within the ($C_2$-$C_6$) bridge, or
(c) A-B together form a —CH$_2$—N($R_a$)—CH$_2$— bridge, a

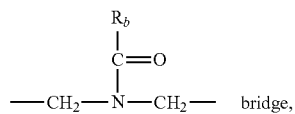

or a

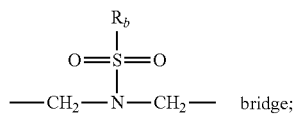

$R_a$ is selected from —H, —$(C_1-C_6)$alkyl, —$(C_3-C_7)$cycloalkyl, —$CH_2$—C(O)—$R_c$, —$(CH_2)$—C(O)—$OR_c$, —$(CH_2)$—C(O)—$N(R_c)_2$, —$(CH_2)_2$—O—$R_c$, —$(CH_2)_2$—$S(O)_2$—$N(R_c)_2$, $R_c$, or —$(CH_2)_2$—N(R)$S(O)_2$—$R_c$;

$R_b$ is selected from:

(a) —H, —$(C_1-C_6)$alkyl, —$(C_3-C_7)$cycloalkyl, -(3- to 7-membered)heterocycle, —$N(R_c)_2$, —$N(R_c)$—$(C_3-C_7)$cycloalkyl, or —$N(R_c)$-(3- to 7-membered)heterocycle, (b) -phenyl, -naphthyl, or -(5- or 6-membered)heteroaryl, each of which is unsubstituted or substituted with 1, 2 or 3 $R_7$ groups, or (c) $_7$N($R_c$)-phenyl, —N($R_c$-naphthyl, —N($R_c$)—$(C_{14})$aryl, or —N($R_c$)-(5- to 10-membered)heteroaryl, each of which is unsubstituted or substituted with 1, 2 or 3 $R_7$ groups;

each $R_c$ is independently selected from —H or —$(C_1-C_4)$alkyl;

C is selected from —H, -halo, —CN, —$OT_3$, —$C(O)OT_3$, —$C(O)N(T)_1(T_2)$, —$(C_3-C_{12})$cycloalkyl, —$(C_3-C_{12})$cycloalkoxy, —$N(R_6)_2$, —$N(R_6)C(O)R_9$, —$NR_6SO_2N(R_6)_2$, —$NR_6$—C(=$NR_6$)$N(R_6)_2$, —$(C_1-C_6)$alkyl, —$(C_2-C_6)$alkenyl, or —$(C_2-C_6)$alkynyl, each of which —$(C_1-C_6)$alkyl, —$(C_2-C_6)$alkenyl or —$(C_2-C_6)$alkynyl is unsubstituted or substituted with 1 or 2 substituents selected from —OH, —$S(O)_2NH_2$, —$N(R_6)_2$, =$NR_6$, —$C(O)OT_3$, —$C(O)N(R_6)_2$, —$N(R_6)C(O)R_9$ and -(5- or 6-membered) heterocycle or from 1 to 3 independently selected -halo;

the dashed line in the piperidine or bridged piperidine central ring denotes the presence or absence of a bond, and when the dashed line denotes the presence of a bond then D is absent, otherwise D is:

(a) —H, —CN, —$C(O)OT_3$, or —$C(O)N(T_1)(T_2)$; or (b) —$(C_1-C_{10})$alkyl which is unsubstituted or substituted with 1, 2 or 3 $R_8$ groups and, optionally, in which any D group carbon atom except the carbon atom bonded directly to the piperidine or bridged piperidine central ring, is independently replaced by O or S; or (c) -phenyl, -naphthyl, or -(5- or 6-membered)heteroaryl, each of which is unsubstituted or substituted with 1, 2 or 3 $R_7$ groups;

Z is -[$(C_1-C_{10})$alkyl]$_h$-, wherein h is 0 or 1; or —$(C_1-C_{10})$alkyl-$NR_6$C(=Y)—;

$R_1$ is selected from:

(a) —H, -halo, —CN, —OH, —$CH_2OH$, —$CH_2CH_2OH$, —$NO_2$, —$N(R_6)_2$, —$S(O)NH_2$, —$S(O)_2NH_2$, —$C(O)OV_1$, or —C(O)CN;

(b) —$(C_1-C_6)$alkyl, —$(C_2-C_6)$alkenyl, —$(C_2-C_6)$alkynyl, —O$(C_1-C_6)$alkyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, -(7- to 10-membered)bicycloheterocycle, each of which is unsubstituted or substituted with an $R_8$ group, or

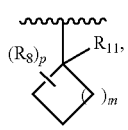

(i)

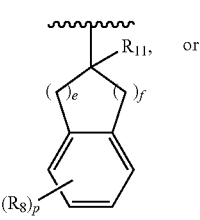

(ii)

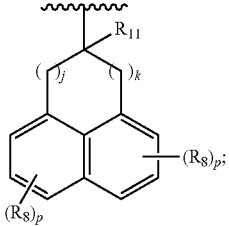

(iii)

or (c) -phenyl, -naphthyl, —$(C_{14})$aryl, or -(5- to 10-membered)heteroaryl, each of which is unsubstituted or substituted with an $R_7$ group;

—Z—$R_1$ is 3,3-diphenylpropyl—optionally substituted at the 3 carbon of the propyl with —CN, —$C(O)N(R_6)_2$, —$C(O)OV_1$, or -tetrazolyl; or —Z—$R_1$ is —$(C_1-C_4)$alkyl substituted with tetrazolyl;

each $R_6$ is independently selected from —H, —$(C_1-C_6)$alkyl, or —$(C_3-C_7)$cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_7$ is independently selected from —$(C_1-C_4)$alkyl, —$(C_2-C_6)$alkenyl, —$(C_2-C_6)$alkynyl, —$OR_9$, —$SR_9$, —C(halo)$_3$, —CH(halo)$_2$, —$CH_2$(halo), —CN, -halo, —$N_3$, —$NO_2$, —CH=$NR_9$, —$NR_9OH$, —$C(O)OR_9$, —$OC(O)R_9$, —$OC(O)OR_9$, —$S(O)R_9$, or —$S(O)_2R_9$;

each $R_8$ is independently selected from —$(C_1-C_4)$alkyl, —$(C_2-C_6)$alkenyl, —$(C_2-C_6)$alkynyl, —$OR_9$, —$SR_9$, —C(halo)$_3$, —CH(halo)$_2$, —$CH_2$(halo), —CN, oxo, =S, -halo, —$N_3$, —$NO_2$, —CH=$NR_9$, —$NR_9OH$, —$C(O)OR_9$, —$OC(O)R_9$, —$OC(O)OR_9$, —$S(O)R_9$, or —$S(O)_2R_9$;

each $R_9$ is independently selected from —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, -(3- to 6-membered)heterocycle, —C(halo)$_3$, —CH(halo)$_2$, or —$CH_2$(halo);

if h is 0, $R_{11}$ is selected from —H or —$(C_1-C_4)$alkyl which is unsubstituted or substituted with —OH, —$(C_1-C_4)$alkoxy, —$N(R_6)_2$, —$C(O)OR_9$, or —$C(O)N(R_6)_2$;

if h is 1, $R_{11}$ is selected from —H, —OH, -halo, or —$(C_1-C_4)$alkyl which is unsubstituted or substituted with —OH, —$(C_1-C_4)$alkoxy, —$N(R_6)_2$, —$C(O)OR_9$, or —$C(O)N(R_6)_2$;

m is an integer from 1 to 7;

e and f are independently an integer from 0 to 5 provided that 2≤(e+f)≤5;

j and k are independently an integer from 0 to 4 provided that 1≤(j+k)≤4;

each p is independently 0 or 1;

each $T_1$, $T_2$, and $T_3$ is independently —H or —$(C_1-C_{10})$alkyl which is unsubstituted or substituted with 1, 2 or 3 $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2 or 3 $R_8$ groups and, optionally, any carbon atom in said 5- to 8-membered ring is independently replaced by O or S;

each $V_1$ is independently selected from —H, —$(C_1-C_6)$ alkyl, —$(C_3-C_7)$cycloalkyl, -phenyl, or -benzyl;

each $W_1$ is independently selected from:
- (a) —H, —$(C_1-C_6)$alkyl, —$(C_3-C_7)$cycloalkyl, —O$(C_1-C_6)$alkyl, —$(C_3-C_7)$cycloalkoxy, —$CH_2CH_2OH$, —$N(R_6)_2$; or
- (b) -(5- or 6-membered)heteroaryl optionally substituted with 1, 2 or 3 independently selected —$(C_1-C_6)$alkyl; and each halo is independently selected from —F, —Cl, —Br, or —I;

provided that when h is 0, then $R_1$ is not -halo or —$NO_2$;
provided that when Q is benzo, then X is not —$N(R_6)$—;
provided that when Q is benzo, then $R_3$ is not —$(C_1-C_2)$ alkyl substituted with —$C(O)N(V_1)_2$; and
provided that $R_3$ does not include an imidazolyl group.

4.4 Heterocyclic-Substituted Piperidine Compounds of Formula (IV)

As stated above, the invention encompasses Heterocyclic-Substituted Piperidine Compounds of Formula (IV):

or a pharmaceutically acceptable derivative thereof where $R_1$, $R_2$, $R_3$, $R_{12}$, Y, Z, A, B, C, D, a and the dashed line are defined above for the Heterocyclic-Substituted Piperidine Compounds of Formula (IV).

In one embodiment, each Y is O.
In another embodiment, each Y is S.
In another embodiment, A is H.
In another embodiment, B is H.
In another embodiment, A-B together form a $(C_2-C_6)$ bridge, which is unsubstituted or substituted with 1, 2 or 3 independently selected $R_8$ groups, and which bridge optionally contains —HC═CH— within the $(C_2-C_6)$bridge; wherein the heterocyclic ring that is fused to the phenyl group can be in the endo- or exo-conformation with respect to the A-B bridge.

In another embodiment, A-B together form a $(C_2-C_6)$ bridge, which is unsubstituted or substituted with an $R_8$ group, and which bridge optionally contains —HC═CH— within the $(C_2-C_6)$bridge; wherein the heterocyclic ring that is fused to the phenyl group can be in the endo- or exo-conformation with respect to the A-B bridge.

In another embodiment, A-B together form a $(C_2-C_3)$ bridge, which is unsubstituted or substituted with an $R_8$ group, and which bridge optionally contains —HC═CH— within the $(C_2-C_3)$bridge; wherein the heterocyclic ring that is fused to the phenyl group can be in the endo- or exo-conformation with respect to the A-B bridge.

In another embodiment, A-B together form a $(C_2-C_3)$ bridge, which is unsubstituted and which bridge optionally contains —HC═CH— within the $(C_2-C_3)$bridge; wherein the heterocyclic ring that is fused to the phenyl group can be in the endo- or exo-conformation with respect to the A-B bridge.

In another embodiment, A-B together form a $(C_2)$bridge, a —HC═CH— bridge, or a $(C_3)$bridge each of which is unsubstituted; wherein the heterocyclic ring that is fused to the phenyl group can be in the endo- or exo-conformation with respect to the A-B bridge.

In another embodiment, C is H.
In another embodiment, D is H.
In another embodiment, a is 0 or 1.
In another embodiment, a is 0.
In another embodiment, a is 1.
In another embodiment, a is 2.
In another embodiment, each Y is O, A, B, C and D are each H, and a is 0 or 1.
In another embodiment, each Y is S, A, B, C and D are each H, and a is 0 or 1.
In another embodiment, each Y is O, A, B, C and D are each H, and a is 0.
In another embodiment, each Y is S, A, B, C and D are each H, and a is 0.
In another embodiment, each Y is O, A, B, C and D are each H, and a is 1.
In another embodiment, each Y is S, A, B, C and D are each H, and a is 1.

In another embodiment, each Y is O, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the heterocyclic ring that is fused to the phenyl group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the heterocyclic ring that is fused to the phenyl group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the heterocyclic ring that is fused to the phenyl group can be in the endo- or exo-conformation with respect to the A-B bridge, C and D are each H, and a is 0.

In another embodiment, each Y is S, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the heterocyclic ring that is fused to the phenyl group can be in the endo- or exo-conformation with respect to the A-B bridge, C and D are each H, and a is 0.

In another embodiment, each Y is O, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge;

wherein the heterocyclic ring that is fused to the phenyl group can be in the endo- or exo-conformation with respect to the A-B bridge, C and D are each H, and a is 1.

In another embodiment, each Y is S, A-B together form a $(C_2-C_6)$bridge, which is unsubstituted or substituted with 1, 2 or 3 independently selected $R_8$ groups, and which bridge optionally contains —HC=CH— within the $(C_2-C_6)$bridge; wherein the heterocyclic ring that is fused to the phenyl group can be in the endo- or exo-conformation with respect to the A-B bridge, C and D are each H, and a is 1.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the phenyl group can be in the endo- or exo-conformation with respect to the A-B bridge, C and D are each H, and a is 0 or 1.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the phenyl group can be in the endo- or exo-conformation with respect to the A-B bridge, C and D are each H, and a is 0 or 1.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the phenyl group can be in the endo- or exo-conformation with respect to the A-B bridge, C and D are each H, and a is 0.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the phenyl group can be in the endo- or exo-conformation with respect to the A-B bridge, C and D are each H, and a is 0.

In another embodiment, each Y is O, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the phenyl group can be in the endo- or exo-conformation with respect to the A-B bridge, C and D are each H, and a is 1.

In another embodiment, each Y is S, A-B together form a $(C_2-C_6)$bridge, which is unsubstituted or substituted with an $R_8$ group, and which bridge optionally contains —HC=CH— within the $(C_2-C_6)$bridge; wherein the heterocyclic ring that is fused to the phenyl group can be in the endo- or exo-conformation with respect to the A-B bridge, C and D are each H, and a is 1.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0 or 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0 or 1.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0.

In another embodiment, each Y is O, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 1.

In another embodiment, each Y is S, A-B together form a $(C_2-C_3)$bridge, which is unsubstituted or substituted with an $R_8$ group, and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 1.

In another embodiment, each Y is O, A-B together form a $(C_2-C_3)$bridge, which is unsubstituted and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0 or 1.

In another embodiment, each Y is S, A-B together form a $(C_2-C_3)$bridge, which is unsubstituted and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0 or 1.

In another embodiment, each Y is O, A-B together form a $(C_2-C_3)$bridge, which is unsubstituted and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0.

In another embodiment, each Y is S, A-B together form a $(C_2-C_3)$bridge, which is unsubstituted and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 0.

In another embodiment, each Y is O, A-B together form a $(C_2-C_3)$bridge, which is unsubstituted and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 1.

In another embodiment, each Y is S, A-B together form a $(C_2-C_3)$bridge, which is unsubstituted and which bridge optionally contains —HC=CH— within the $(C_2-C_3)$bridge; wherein the heterocyclic ring that is fused to the phenyl group can be in the endo- or exo-conformation with respect to the A-B bridge, C and D are each H, and a is 1.

In another embodiment, $R_3$ is —H, —$(C_1-C_6)$alkyl, —$(C_1-C_6)$alkyl substituted by an $R_8$ group, —$(C_3-C_7)$cycloalkyl, or —$(C_3-C_7)$cycloalkyl substituted by an $R_8$ group.

In another embodiment, $R_3$ is —H, —C(O)OV$_1$, —C(O)N(V$_1$)$_2$, or —(C$_1$-C$_2$)alkyl substituted with a substituent selected from —NHS(O)$_2$W$_1$, —C(O)OV$_1$, and —C(O)N(V$_1$)$_2$.

In another embodiment, $R_3$ is —H.

In another embodiment, $R_3$ is —(C$_1$-C$_6$)alkyl.

In another embodiment, $R_3$ is methyl, ethyl, n-propyl or iso-propyl.

In another embodiment, $R_3$ is —(C$_1$-C$_6$)alkyl substituted by an R$_8$ group.

In another embodiment, $R_3$ is —(C$_1$-C$_6$)alkyl substituted by —CN.

In another embodiment, $R_3$ is methyl, ethyl, n-propyl or iso-propyl, each of which is substituted by an R$_8$ group.

In another embodiment, $R_3$ is methyl, ethyl, n-propyl or iso-propyl, each of which is substituted by —CN.

In another embodiment, $R_3$ is —(C$_3$-C$_7$)cycloalkyl.

In another embodiment, $R_3$ is cyclopentyl, cyclohexyl, or cycloheptyl.

In another embodiment, $R_3$ is —H or methyl substituted by —CN.

In another embodiment, each Y is O, A, B, C and D are each H, $R_3$ is —H, —(C$_1$-C$_6$)alkyl, —(C$_1$-C$_6$)alkyl substituted by an R$_8$ group, or —(C$_3$-C$_7$)cycloalkyl, and a is 0 or 1.

In another embodiment, each Y is S, A, B, C and D are each H, $R_3$ is —H, —(C$_1$-C$_6$)alkyl, —(C$_1$-C$_6$)alkyl substituted by an R$_8$ group, or —(C$_3$-C$_7$)cycloalkyl, and a is 0 or 1.

In another embodiment, each Y is O, A, B, C and D are each H, $R_3$ is —H or methyl substituted by —CN, and a is 0 or 1.

In another embodiment, each Y is S, A, B, C and D are each H, $R_3$ is —H or methyl substituted by —CN, and a is 0 or 1.

In another embodiment, each Y is O, A, B, C and D are each H, $R_3$ is —H, —(C$_1$-C$_6$)alkyl, —(C$_1$-C$_6$)alkyl substituted by an R$_8$ group, or —(C$_3$-C$_7$)cycloalkyl, and a is 0.

In another embodiment, each Y is S, A, B, C and D are each H, $R_3$ is —H, —(C$_1$-C$_6$)alkyl, —(C$_1$-C$_6$)alkyl substituted by an R$_8$ group, or —(C$_3$-C$_7$)cycloalkyl, and a is 0.

In another embodiment, each Y is O, A, B, C and D are each H, $R_3$ is —H or methyl substituted by —CN, and a is 0.

In another embodiment, each Y is S, A, B, C and D are each H, $R_3$ is —H or methyl substituted by —CN, and a is 0.

In another embodiment, each Y is O, A, B, C and D are each H, $R_3$ is —H, —(C$_1$-C$_6$)alkyl, —(C$_1$-C$_6$)alkyl substituted by an R$_8$ group, or —(C$_3$-C$_7$)cycloalkyl, and a is 1.

In another embodiment, each Y is S, A, B, C and D are each H, $R_3$ is —H, —(C$_1$-C$_6$)alkyl substituted by an R$_8$ group, or —(C$_3$-C$_7$)cycloalkyl, and a is 1.

In another embodiment, each Y is O, A, B, C and D are each H, $R_3$ is —H or methyl substituted by —CN, and a is 1.

In another embodiment, each Y is S, A, B, C and D are each H, $R_3$ is —H or methyl substituted by —CN, and a is 1.

In another embodiment, each $R_2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl or -(5- or 6-membered)heteroaryl.

In another embodiment, each $R_2$ is independently -halo.

In another embodiment, a is 2 and each $R_2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl or -(5- or 6-membered)heteroaryl.

In another embodiment, a is 2 and each $R_2$ is independently -halo, —OH, —NH$_2$, —CN, methyl, ethyl, n-propyl, iso-propyl, cyclopentyl, cyclohexyl, cycloheptyl, or phenyl.

In another embodiment, a is 2 and each $R_2$ is independently -halo.

In another embodiment, a is 1 and $R_2$ is -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl or -(5- or 6-membered)heteroaryl.

In another embodiment, a is 1 and $R_2$ is -halo, —OH, —NH$_2$, —CN, methyl, ethyl, n-propyl, iso-propyl, cyclopentyl, cyclohexyl, cycloheptyl, or phenyl.

In another embodiment, a is 1 and $R_2$ is -halo, optionally —F.

In another embodiment, each Y is O, A, B, C and D are each H, a is 1, and $R_2$ is -halo, optionally —F.

In another embodiment, each Y is O, A-B together form a (C$_2$-C$_6$)bridge, which is unsubstituted or substituted with 1, 2 or 3 independently selected R$_8$ groups, and which bridge optionally contains —HC=CH— within the (C$_2$-C$_6$)bridge; wherein the heterocyclic ring that is fused to the phenyl group can be in the endo- or exo-conformation with respect to the A-B bridge, C and D are each H, a is 1, and $R_2$ is -halo, optionally —F.

In another embodiment, each Y is O, A-B together form a (C$_2$-C$_6$)bridge, which is unsubstituted or substituted with an R$_8$ group, and which bridge optionally contains —HC=CH— within the (C$_2$-C$_6$)bridge; wherein the heterocyclic ring that is fused to the phenyl group can be in the endo- or exo-conformation with respect to the A-B bridge, C and D are each H, a is 1, and $R_2$ is -halo, optionally —F.

In another embodiment, each Y is O, A-B together form a (C$_2$-C$_3$)bridge, which is unsubstituted or substituted with an R$_8$ group, and which bridge optionally contains —HC=CH— within the (C$_2$-C$_3$)bridge; wherein the heterocyclic ring that is fused to the phenyl group can be in the endo- or exo-conformation with respect to the A-B bridge, C and D are each H, a is 1, and $R_2$ is -halo, optionally —F.

In another embodiment, each Y is O, A-B together form a (C$_2$-C$_3$)bridge, which is unsubstituted and which bridge optionally contains —HC=CH— within the (C$_2$-C$_3$)bridge; wherein the heterocyclic ring that is fused to the phenyl group can be in the endo- or exo-conformation with respect to the A-B bridge, C and D are each H, a is 1, and $R_2$ is -halo, optionally —F.

In another embodiment, each Y is O, A, B, C and D are each H, a is 0, and $R_3$ is methyl, ethyl, n-propyl or iso-propyl, each of which is substituted by an R$_8$ group, or —H.

In another embodiment, each Y is O, A-B together form a (C$_2$-C$_6$)bridge, which is unsubstituted or substituted with 1, 2 or 3 independently selected R$_8$ groups, and which bridge optionally contains —HC=CH— within the (C$_2$-C$_6$)bridge; wherein the heterocyclic ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an R$_8$ group, or —H.

In another embodiment, each Y is O, A-B together form a (C$_2$-C$_6$)bridge, which is unsubstituted or substituted with an R$_8$ group, and which bridge optionally contains —HC=CH— within the (C$_2$-C$_6$)bridge; wherein the heterocyclic ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an R$_8$ group, or —H.

In another embodiment, each Y is O, A-B together form a (C$_2$-C$_3$)bridge, which is unsubstituted or substituted with an R$_g$ group, and which bridge optionally contains —HC=CH— within the (C$_2$-C$_3$)bridge; wherein the heterocyclic ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an Rg group, or —H.

In another embodiment, each Y is O, A-B together form a $(C_2-C_3)$bridge, which is unsubstituted and which bridge optionally contains —HC═CH— within the $(C_2-C_3)$bridge; wherein the heterocyclic ring that is fused to the phenyl group can be in the endo- or exo-conformation with respect to the A-B bridge, C and D are each H, a is 0, and $R_3$ is methyl, ethyl, n-propyl or iso-propyl, each of which is substituted by an $R_8$ group, or —H.

In another embodiment, each Y is O, A, B, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a $(C_2-C_6)$bridge, which is unsubstituted or substituted with 1, 2 or 3 independently selected $R_8$ groups, and which bridge optionally contains —HC═CH— within the $(C_2-C_6)$bridge; wherein the heterocyclic ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a $(C_2-C_6)$bridge, which is unsubstituted or substituted with an $R_8$ group, and which bridge optionally contains —HC═CH— within the $(C_2-C_6)$bridge; wherein the heterocyclic ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a $(C_2-C_3)$bridge, which is unsubstituted or substituted with an $R_8$ group, and which bridge optionally contains —HC═CH— within the $(C_2-C_3)$bridge; wherein the heterocyclic ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, each Y is O, A-B together form a $(C_2-C_3)$bridge, which is unsubstituted and which bridge optionally contains —HC═CH— within the $(C_2-C_3)$bridge; wherein the heterocyclic ring that is fused to the phenyl group can be in the endo- or exo-conformation with respect to the A-B bridge, C and D are each H, a is 1, $R_2$ is -halo, optionally —F, and $R_3$ is methyl, ethyl, n-propyl or iso-propyl, each of which is substituted by an $R_8$ group, or —H.

In another embodiment, $R_{12}$ is $(C_1-C_4)$alkyl substituted with 1, 2 or 3 substituents independently selected from —$(C_3-C_{12})$cycloalkyl which is unsubstituted or further substituted with 1, 2 or 3 independently selected $R_8$ groups, —$(C_3-C_{12})$cycloalkoxy which is unsubstituted or further substituted with 1, 2 or 3 independently selected $R_8$ groups, or -(3- to 7-membered)heterocycle which is unsubstituted or further substituted with 1, 2 or 3 independently selected $R_8$ groups.

In another embodiment, $R_{12}$ is —$(C_1-C_4)$alkyl substituted with 1, 2 or 3 substituents independently selected from —OC(O)$(C_3-C_8)$cycloalkyl, —NHS(O)$_2(C_3-C_8)$cycloalkyl, —N($V_1$)C(O)$(C_3-C_8)$cycloalkyl, —NHC(O)$W_2$, and —NHS(O)$_2W_2$.

In another embodiment, $R_{12}$ is —$(C_1-C_6)$alkyl(═O)$W_2$ or —$(C_1-C_6)$alkyl-$W_2$.

In another embodiment, $R_{12}$ is —$(C_1-C_6)$alkyl(═O)$W_2$.

In another embodiment, $R_{12}$ is —$(C_1-C_6)$alkyl(═O)N($R_6$)$_2$.

In another embodiment, $R_{12}$ is —$(C_1-C_6)$alkyl(═O)NH($R_6$).

In another embodiment, $R_{12}$ is —$(C_1-C_6)$alkyl(═O)NH($C_1-C_6$)alkyl).

In another embodiment, $R_{12}$ is —$(C_1-C_6)$alkyl(═O)NH[(3- to 7-membered)heterocycle].

In another embodiment, $R_{12}$ is —$(C_1-C_6)$alkyl(═O)N[$(C_1-C_6)$alkyl]$_2$.

In another embodiment, $R_{12}$ is —$(C_1-C_6)$alkyl(═O)N(CH$_3$)$_2$.

In another embodiment, $R_{12}$ is —$(C_1-C_6)$alkyl-$W_2$.

In another embodiment, $R_{12}$ is —$(C_1-C_6)$alkyl-N($R_6$)$_2$.

In another embodiment, $R_{12}$ is —$(C_1-C_6)$alkyl-NH($R_6$).

In another embodiment, $R_{12}$ is —$(C_1-C_6)$alkyl-NH($C_1-C_6$)alkyl).

In another embodiment, $R_{12}$ is —$(C_1-C_6)$alkyl-N[$(C_1-C_6)$alkyl]$_2$.

In another embodiment, $R_{12}$ is —$(C_1-C_6)$alkyl-N(C$_2$H$_5$)$_2$.

In another embodiment, Z is a bond.

In another embodiment, Z is a bond and $R_1$ is selected from:

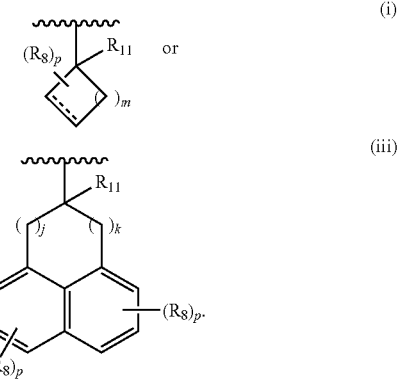

In another embodiment, Z is a bond, $R_1$ is selected from formula (i), and m is 5.

In another embodiment, Z is a bond, $R_1$ is selected from formula (i), m is 5, and p is 0.

In another embodiment, Z is a bond, $R_1$ is selected from formula (i), m is 5, p is 0, and $R_{11}$ is —H.

In another embodiment, Z is a bond, $R_1$ is selected from formula (i), and m is 3.

In another embodiment, Z is a bond, $R_1$ is selected from formula (i), m is 3, and p is 1.

In another embodiment, Z is a bond, $R_1$ is selected from formula (i), m is 3, p is 1, and $R_8$ is —$(C_1-C_4)$alkyl, optionally iso-propyl.

In another embodiment, Z is a bond, $R_1$ is selected from formula (i), m is 3, $R_{11}$ is —H, p is 1, and $R_8$ is —$(C_1-C_4)$alkyl, optionally iso-propyl.

In another embodiment, Z is a bond, $R_1$ is selected from formula and j+k=1.

In another embodiment, Z is a bond, $R_1$ is selected from formula (iii), j+k=1, and p is 0.

In another embodiment, Z is a bond and $R_1$ is selected from:

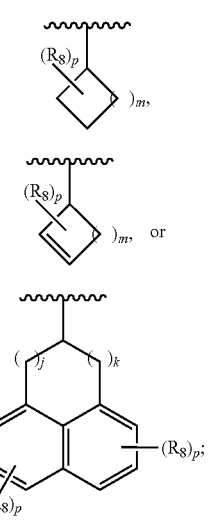

(ia)

(ib)

(iii)

where m is an integer selected from 3, 4 or 5;
j is an integer selected from 1 or 2;
k is 0; and
each p is an integer independently selected from 0 or 1.

In another embodiment, each p is 0.

In another embodiment, in formulas (ia) and (ib) p is 1 and $R_8$ is selected from —$(C_1$-$C_4)$alkyl, optionally iso-propyl.

In another embodiment, in formulas (ia) and (ib) m is 3, p is 1, and $R_8$ is selected from —$(C_1$-$C_4)$alkyl, optionally iso-propyl.

In another embodiment, in formulas (ia) and (ib) m is 5, p is 1, and $R_8$ is selected from —$(C_1$-$C_4)$alkyl, optionally iso-propyl.

In another embodiment, in formulas (ia) and (ib) m is 3 and p is 0.

In another embodiment, in formulas (ia) and (ib) m is 5 and p is 0.

In another embodiment, in formula (iii) one p is 0, the other p is 1, and $R_8$ is selected from —$(C_1$-$C_4)$alkyl, optionally iso-propyl.

In another embodiment, in formula (iii) j is 1 and each p is 0.

In another embodiment, in formula (iii) j is 1, one p is 0, the other p is 1, and $R_8$ is selected from —$(C_1$-$C_4)$alkyl, optionally iso-propyl.

In another embodiment for the Heterocyclic-Substituted Piperidine Compounds of Formula (IV):

each $R_2$ is independently selected from:
(a) -halo, —OH, —$NH_2$, —CN, or —$NO_2$; or
(b) —$(C_1$-$C_6)$alkyl, —$(C_2$-$C_6)$alkenyl, —$(C_2$-$C_6)$alkynyl, —$(C_3$-$C_7)$cycloalkyl, -(5- or 6-membered)heterocycle, -phenyl, -naphthyl, or -(5- or 6-membered)heteroaryl, each of which is unsubstituted or substituted with 1, 2 or 3 $R_8$ groups;

a is an integer from 0 to 2;

$R_3$ is selected from:
(a) —H; or
(b) —$(C_1$-$C_6)$alkyl, —$(C_2$-$C_6)$alkenyl, —$(C_2$-$C_6)$alkynyl, —O$(C_1$-$C_6)$alkyl, —O$(C_2$-$C_6)$alkenyl, —O$(C_2$-$C_6)$alkynyl, —$(C_3$-$C_7)$cycloalkyl, —$(C_5$-$C_7)$cycloalkenyl, —$(C_3$-$C_7)$cycloalkoxy, -(3- to 7-membered)heterocycle, -phenyl, -naphthyl, or -(5- to 10-membered)heteroaryl, each of which is unsubstituted or substituted with 1, 2 or 3 $R_8$ groups; or (c) —$CH_2CH_2OH$, —$(C_1$-$C_6)$alkyl(=O)$W_1$, —C(O)O$V_1$, —C(O)N($V_1)_2$, or —S(O)$_2$($C_1$-$C_6)$alkyl; or (d) -$(C_1$-$C_4)$alkyl substituted with 1, 2 or 3 substituents independently selected from —$(C_3$-$C_7)$cycloalkyl, —$(C_3$-$C_7)$cycloalkoxy, -(3- to 7-membered)heterocycle, -phenyl, -naphthyl, and -(5- to 10-membered) heteroaryl; or (e) -$(C_1$-$C_3)$alkyl substituted with a substituent selected from —N($R_6)_2$, —S(C)$_2M^1_2$, —NHC(O)$W_1$, —NHS(O)$_2W_1$, —C(O)O$V_1$, and —C(O)N($V_1)_2$;

each Y is independently selected from O or S;

$R_{12}$ is selected from:
(a) -$(C_3$-$C_{12})$cycloalkyl, —$(C_3$-$C_{12})$cycloalkoxy, —$(C_6$-$C_{14})$bicycloalkyl, —$(C_8$-$C_{20})$tricycloalkyl, —$(C_5$-$C_{20})$cycloalkenyl, —$(C_7$-$C_{14})$bicycloalkenyl, —$(C_8$-$C_{20})$tricycloalkenyl, —$(C_{14})$aryl, -(3- to 7-membered)heterocycle, each of which is unsubstituted or substituted with 1, 2 or 3 $R_8$ groups; or (b) -$(C_1$-$C_4)$alkyl substituted with 1, 2 or 3 substituents independently selected from —$(C_3$-$C_{12})$cycloalkyl, —$(C_3$-$C_{12})$cycloalkoxy, -(3- to 7-membered)heterocycle, and —$(C_{14})$aryl, each of which is unsubstituted or further substituted with 1, 2 or 3 $R_8$ groups; or (c) —C(O)O($C_3$-$C_8)$cycloalkyl, —$CH_2CH_2OH$, —C(O)N($V_1)(C_3$-$C_8)$cycloalkyl, or —$(C_1$-$C_6)$alkyl(=O)$W_2$; or (d) -$(C_1$-$C_4)$alkyl substituted with 1, 2 or 3 substituents independently selected from —OC(O)($C_3$-$C_8)$cycloalkyl, —NHS(O)$_2$($C_3$-$C_8)$cycloalkyl, —N($V_1)$C(O)($C_3$-$C_8)$cycloalkyl, —NHC(O)$W_2$, and —NHS(O)$_2W_2$;

each $W_2$ is independently selected from —$(C_3$-$C_7)$cycloalkyl, —O($C_1$-$C_6)$alkyl, —$(C_3$-$C_7)$cycloalkoxy, —$CH_2CH_2OH$, and —N($R_6)_2$;

A and B are independently selected from —H, —N($R_6)_2$, —$(C_3$-$C_{12})$cycloalkyl, or —$(C_1$-$C_6)$alkyl each of which —$(C_1$-$C_6)$alkyl is unsubstituted or substituted with —OH, —S(O)$_2NH_2$, or from 1 to 3 independently selected -halo, or A-B together form a ($C_2$-$C_6$)bridge;

C is —H;

D is —H;

the dashed line in the piperidine or bridged piperidine central ring is absent;

Z is -[($C_1$-$C_{10}$)alkyl]$_h$-, wherein h is 0 or 1; or -[($C_1$-$C_{10}$)alkyl]N$R_6$C(=Y)—;

$R_1$ is selected from:
(a) —H, -halo, —CN, —OH, —$CH_2OH$, —$CH_2CH_2OH$, —$NO_2$, —N($R_6)_2$, —S(O)$NH_2$, —S(O)$_2NH_2$, —C(O)O$V_1$, or —C(O)CN; or (b) —$(C_1$-$C_6)$alkyl, —$(C_2$-$C_6)$alkenyl, —$(C_2$-$C_6)$alkynyl, —O$(C_1$-$C_6)$alkyl, —$(C_3$-$C_7)$cycloalkoxy, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(3- to 7-membered)heterocycle, -(7- to 10-membered)bicycloheterocycle, each of which is unsubstituted or substituted with an $R_8$ group, or

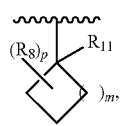

(i)

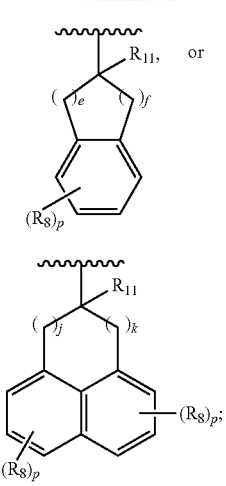

or (c) -phenyl, -naphthyl, —(C$_{14}$)aryl, or -(5- to 10-membered)heteroaryl, each of which is unsubstituted or substituted with an R$_8$ group;

—Z—R$_1$ is 3,3-diphenylpropyl—optionally substituted at the 3 carbon of the propyl with —CN, —C(O)N(R$_6$)$_2$, —C(O)OV$_1$, or -tetrazolyl; or —Z—R$_1$ is —(C$_1$-C$_4$)alkyl substituted with tetrazolyl;

each R$_6$ is independently selected from —H, —(C$_1$-C$_6$)alkyl, or —(C$_3$-C$_7$)cycloalkyl, or two R$_6$ groups attached to the same nitrogen atom can form a 5- to 8-membered ring, the number of atoms in the ring including the nitrogen atom, in which one of the ring carbon atoms is optionally replaced by O or S;

each R$_8$ is independently selected from —(C$_1$-C$_4$)alkyl, —O(C$_1$-C$_4$)alkyl, —C(halo)$_3$, —CH(halo)$_2$, —CH$_2$(halo), —CN, —OH, -halo, or —C(O)OR$_9$;

each R$_9$ is independently selected from —H, —(C$_1$-C$_6$)alkyl, -phenyl, or -benzyl;

R$_{11}$ is selected from —H, —(C$_1$-C$_4$)alkyl, or -halo;

m is an integer from 1 to 7;

e and f are independently an integer from 0 to 5 provided that 2≤(e+f)≤5;

j and k are independently an integer from 0 to 4 provided that 1≤(j+k)≤4;

each p is independently 0 or 1;

each V$_1$ is independently selected from —H, —(C$_1$-C$_6$)alkyl, —(C$_3$-C$_7$)cycloalkyl, -phenyl, or -benzyl;

each W$_1$ is independently selected from:

(a) —H, —(C$_1$-C$_6$)alkyl, —(C$_3$-C$_7$)cycloalkyl, —O(C$_1$-C$_6$)alkyl, —(C$_3$-C$_7$)cycloalkoxy, —CH$_2$CH$_2$OH, —N(R$_6$)$_2$; or (b) -(5- or 6-membered)heteroaryl optionally substituted with 1, 2 or 3 independently selected —(C$_1$-C$_6$)alkyl; and each halo is independently selected from —F, —Br, or —I;

provided that when h is 0, R$_1$ is not -halo or —NO$_2$.

In another embodiment for the Heterocyclic-Substituted Piperidine Compounds of Formula (IV):

each R$_2$ is independently selected from:

(a) -halo, —CN, —NO$_2$, —OT$_3$, —C(O)T$_3$, —C(O)OT$_3$, —C(O)N(T$_1$)(T$_2$), —S(O)$_3$H, —S(O)$_2$T$_3$, —S(O)$_2$N(T$_1$)(T$_2$), —N(T$_1$)(T$_2$), —N(T$_3$)C(O)T$_3$, —N(T$_3$)C(O)N(T$_1$)(T$_2$), —N(T$_3$)S(O)$_2$T$_3$, or —N(T$_3$)S(O)$_2$N(T$_1$)(T$_2$); or (b) —(C$_1$-C$_6$)alkyl, —(C$_2$-C$_6$)alkenyl, —(C$_2$-C$_6$)alkynyl, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 R$_8$ groups; or (c) -phenyl, -naphthyl, —(C$_{14}$)aryl, or -(5- or 6-embered)heteroaryl, each of which is unsubstituted or substituted with 1, 2 or 3 R$_7$ groups;

a is an integer from 0 to 2;

R$_3$ is selected from:

(a) —H; or (b) —(C$_1$-C$_6$)alkyl, —(C$_2$-C$_6$)alkenyl, —(C$_2$-C$_6$)alkynyl, —O(C$_1$-C$_6$)alkyl, —O(C$_2$-C$_6$)alkenyl, —O(C$_2$-C$_6$)alkynyl, —(C$_3$-C$_7$)cycloalkyl, —(C$_3$-C$_7$)cycloalkenyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, or -(7- to 10-membered)bicycloheterocycle, each of which is unsubstituted or substituted with 1, 2 or 3 R$_8$ groups; or (c) -phenyl, -naphthyl, —(C$_{14}$)aryl, or -(5- to 10-membered)heteroaryl, each of which is unsubstituted or substituted with 1, 2 or 3 R$_7$ groups; or (d) —(C$_1$-C$_6$)alkyl(=O)W$_1$, —(C$_1$-C$_6$)alkyl(=NH)W$_1$, —C(O)OV$_1$, —C(O)N(V1)$_2$, —S(O)$_2$N(V$_1$)$_2$, or —S(O)$_2$(C$_1$-C$_6$)alkyl; or (e) —(C$_1$-C$_4$)alkyl substituted with 1, 2 or 3 substituents independently selected from —(C$_3$-C$_7$)cycloalkyl, —(C$_3$-C$_7$)cycloalkenyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkyl, —(C$_8$-C$_{20}$)tricycloalkenyl, -(3- to 7-membered)heterocycle, -(7- to 10-membered)bicycloheterocycle, -phenyl, -naphthyl, —(C$_{14}$)aryl, or -(5- to 10-membered)heteroaryl; or (f) —(C$_1$-C$_3$)alkyl substituted with a substituent selected from —N(R$_6$)$_2$, —S(O)$_2$N(V$_1$)$_2$, —N(R$_9$)C(O)W$_1$, —N(R$_9$)S(O)$_2$W$_1$, and —C(O)N(V$_1$)$_2$;

each Y is independently selected from O or S;

R$_{12}$ is selected from:

(a) —(C$_3$-C$_{12}$)cycloalkyl, —(C$_3$-C$_{12}$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, each of which is unsubstituted or substituted with 1, 2 or 3 R$_8$ groups; or (b) —(C$_{14}$)aryl which is unsubstituted or substituted with 1, 2 or 3 R$_7$ groups; or (c) -(C$_1$-C$_4$)alkyl substituted with 1, 2 or 3 substituents independently selected from —(C$_3$-C$_{12}$)cycloalkyl which is unsubstituted or further substituted with 1, 2 or 3 R$_8$ groups, —(C$_3$-C$_{12}$)cycloalkoxy which is unsubstituted or further substituted with 1, 2 or 3 R$_8$ groups, -(3- to 7-membered)heterocycle which is unsubstituted or further substituted with 1, 2 or 3 R$_8$ groups, or —(C$_{14}$) aryl which is unsubstituted or further substituted with 1, 2 or 3 R$_7$ groups; or (d) —C(O)O(C$_3$-C$_8$)cycloalkyl, —CH$_2$CH$_2$OH, —C(O)N(V$_1$)(C$_3$-C$_8$)cycloalkyl, or —(C$_1$-C$_6$)alkyl(=O)W$_2$; or (e) —(C$_1$-C$_4$)alkyl substituted with 1, 2 or 3 substituents independently selected from —OC(O)(C$_3$-C$_8$)cycloalkyl, —NHS(O)$_2$(C$_3$-C$_8$)cycloalkyl, —N(V$_1$)C(O)(C$_3$-C$_8$)cycloalkyl, —NHC(O)W$_2$, and —NHS(O)$_2$W$_2$;

each W$_2$ is independently selected from —(C$_3$-C$_7$)cycloalkyl, —O(C$_1$-C$_6$)alkyl, —(C$_3$-C$_7$)cycloalkoxy, —CH$_2$CH$_2$OH, and —N(R$_6$)$_2$;

A and B are independently selected from:
(a) —H, —CN, —C(O)OT$_3$, —C(O)N(T)$_1$(T$_2$), —(C$_3$-C$_{12}$)cycloalkyl, —(C$_3$-C$_{12}$)cycloalkoxy, —(C$_1$-C$_6$)alkyl, —(C$_2$-C$_6$)alkenyl, or —(C$_2$-C$_6$)alkynyl, each of which —(C$_1$-C$_6$)alkyl, —(C$_2$-C$_6$)alkenyl or —(C$_2$-C$_6$)alkynyl is unsubstituted or substituted with 1 or 2 substituents selected from —OH, —S(O)$_2$NH$_2$, —N(R$_6$)$_2$, =NR$_6$, —C(O)OT$_3$, —C(O)N(R$_6$)$_2$, —N(R$_6$)C(O)R$_9$ and -(5- or 6-membered)heterocycle or from 1 to 3 independently selected -halo, or
(b) A-B together form a (C$_2$-C$_6$)bridge, which is unsubstituted or optionally substituted with from 1 to 3-OH or optionally contains —HC=CH— within the (C$_2$-C$_6$) bridge, or
(c) A-B together form a —CH$_2$—N(R$_a$)—CH$_2$— bridge, a

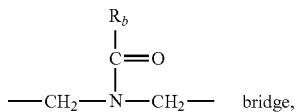 bridge, or a

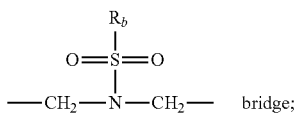 bridge;

R$_a$ is selected from —H, —(C$_1$-C$_6$)alkyl, —(C$_3$-C$_7$)cycloalkyl, —CH$_2$—C(O)—R$_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$—N(R$_c$)$_2$, R$_c$, or —(CH$_2$)$_2$—N(R)S(O)$_2$—R$_c$;

R$_b$ is selected from:
(a) —H, —(C$_3$-C$_7$)cycloalkyl, -(3- to 7-membered)heterocycle, —N(R$_c$)$_2$, —N(R$_c$)—(C$_3$-C$_7$)cycloalkyl, or —N(R$_c$)-(3- to 7-membered)heterocycle,
(b) -phenyl, -naphthyl, or -(5- or 6-membered)heteroaryl, each of which is unsubstituted or substituted with 1, 2 or 3 R$_7$ groups, or
(c) —N(R$_c$)-phenyl, —N(R$_c$)-naphthyl, —N(R$_c$)—(C$_{14}$)aryl, or —N(R$_c$)-(5- to 10-membered)heteroaryl, each of which is unsubstituted or substituted with 1, 2 or 3 R$_7$ groups;

each R$_c$ is independently selected from —H or —(C$_1$-C$_4$)alkyl;

C is selected from —H, -halo, —CN, —OT$_3$, —C(O)OT$_3$, —C(O)N(T)$_1$(T$_2$), —(C$_3$-C$_{12}$)cycloalkyl, —(C$_3$-C$_{12}$)cycloalkoxy, —N(R$_6$)$_2$, —N(R$_6$)C(O)R$_9$, —NR$_6$SO$_2$N(R$_6$)$_2$, —NR$_6$—C(=NR$_6$)N(R$_6$)$_2$, —(C$_1$-C$_6$)alkyl, —(C$_2$-C$_6$)alkenyl, or —(C$_2$-C$_6$)alkynyl, each of which —(C$_1$-C$_6$)alkyl, —(C$_2$-C$_6$)alkenyl or —(C$_2$-C$_6$)alkynyl is unsubstituted or substituted with 1 or 2 substituents selected from —OH, —S(O)$_2$NH$_2$, —N(R$_6$)$_2$, —C(O)OT$_3$, —C(O)N(R$_6$)$_2$, —N(R$_6$)C(O)R$_9$ and -(5- or 6-membered)heterocycle or from 1 to 3 independently selected -halo;

the dashed line in the piperidine or bridged piperidine central ring denotes the presence or absence of a bond, and when the dashed line denotes the presence of a bond then D is absent, otherwise D is:
(a) —H, —CN, —C(O)OT$_3$, or —C(O)N(T$_1$)(T$_2$); or
(b) -(C$_1$-C$_{10}$)alkyl which is unsubstituted or substituted with 1, 2 or 3 R$_8$ groups and, optionally, in which any D group carbon atom except the carbon atom bonded directly to the piperidine or bridged piperidine central ring is independently replaced by O or S; or
(c) -phenyl, -naphthyl, or -(5- or 6-membered)heteroaryl, each of which is unsubstituted or substituted with 1, 2 or 3 R$_7$ groups;

Z is -[(C$_1$-C$_{10}$)alkyl]$_h$-, wherein h is 0 or 1; or -[(C$_1$-C$_{10}$)alkyl]NR$_6$C(=Y)—;

R$_1$ is selected from:
(a) —H, -halo, —CN, —OH, —CH$_2$OH, —CH$_2$CH$_2$OH, —NO$_2$, —N(R$_6$)$_2$, —S(O)NH$_2$, —S(O)$_2$NH$_2$, —C(O)OV$_1$, or —C(O)CN; or
(b) -(C$_2$-C$_6$)alkenyl, —(C$_2$-C$_6$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, -(7- to 10-membered)bicycloheterocycle, each of which is unsubstituted or substituted with an R$_8$ group, or

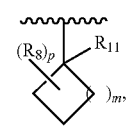 (i)

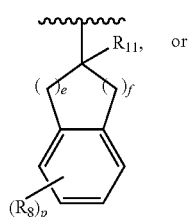 (ii)

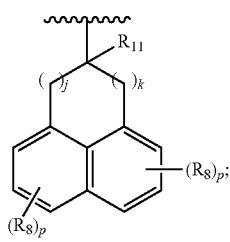 (iii)

or
(c) -phenyl, -naphthyl, —(C$_{14}$)aryl, or -(5- to 10-membered)heteroaryl, each of which is unsubstituted or substituted with an R$_7$ group;

—Z—R$_1$ is 3,3-diphenylpropyl—optionally substituted at the 3 carbon of the propyl with —CN, —C(O)N(R$_6$)$_2$, —C(O)OV$_1$, or -tetrazolyl; or —Z—R$_1$ is —(C$_1$-C$_4$)alkyl substituted with tetrazolyl;

each R$_6$ is independently selected from —H, —(C$_1$-C$_6$)alkyl, or —(C$_3$-C$_7$)cycloalkyl, or two R$_6$ groups attached to the same nitrogen atom can form a 5- to 8-membered ring, the number of atoms in the ring including the nitrogen atom, in which one of the ring carbon atoms is optionally replaced by O or S;

each R$_7$ is independently selected from —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, -halo, —N$_3$, —NO$_2$, —CH=NR$_9$, —NR$_9$OH, —C(O)OR$_9$, —OC(O)R$_9$, —OC(O)OR$_9$, —S(O)R$_9$, or —S(O)$_2$R$_9$;

each R$_8$ is independently selected from —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, oxo, =S, -halo, —N$_3$, —NO$_2$, —CH=NR$_9$, —NR$_9$OH, —C(O)OR$_9$, —OC(O)R$_9$, —OC(O)OR$_9$, —S(O)R$_9$, or —S(O)$_2$R$_9$;

each R$_9$ is independently selected from —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 6-membered)heterocycle, —C(halo)$_3$, —CH(halo)$_2$, or —CH$_2$(halo);

if h is 0, R$_{11}$ is selected from —H or —(C$_1$-C$_4$)alkyl which is unsubstituted or substituted with —OH, —(C$_1$-C$_4$)alkoxy, —N(R$_6$)$_2$, —C(O)OR$_9$, or —C(O)N(R$_6$)$_2$;

if h is 1, R$_{11}$ is selected from —H, —OH, -halo, or —(C$_1$-C$_4$)alkyl which is unsubstituted or substituted with —OH, —(C$_1$-C$_4$)alkoxy, —N(R$_6$)$_2$, —C(O)OR$_9$, or —C(O)N(R$_6$)$_2$;

m is an integer from 1 to 7;

e and f are independently an integer from 0 to 5 provided that 2≤(e+f)≤5;

j and k are independently an integer from 0 to 4 provided that 1≤(j+k)≤4;

each p is independently 0 or 1;

each T$_1$, T$_2$, and T$_3$ is independently —H or —(C$_1$-C$_{10}$)alkyl which is unsubstituted or substituted with 1, 2 or 3 R$_8$ groups and, optionally, in which any carbon atom is independently replaced by O or S, or T$_1$ and T$_2$ together can form a 5- to 8-membered ring where the number of atoms in the ring includes the nitrogen atom to which T$_1$ and T$_2$ are bonded, said 5- to 8-membered ring is unsubstituted or substituted with 1, 2 or 3 R$_8$ groups and, optionally, any carbon atom in said 5- to 8-membered ring is independently replaced by O or S;

each V$_1$ is independently selected from —H, —(C$_1$-C$_6$)alkyl, —(C$_3$-C$_7$)cycloalkyl, -phenyl, or -benzyl;

each W$_1$ is independently selected from:
(a) —H, —(C$_1$-C$_6$)alkyl, —(C$_3$-C$_7$)cycloalkyl, —O(C$_1$-C$_6$)alkyl, —(C$_3$-C$_7$)cycloalkoxy, —CH$_2$CH$_2$OH, —N(R$_6$)$_2$; or
(b) -(5- or 6-membered)heteroaryl optionally substituted with 1, 2 or 3 independently selected —(C$_1$-C$_6$)alkyl; and each halo is independently selected from —F, —Cl, —Br, or —I;

provided that when h is 0, R$_1$ is not -halo or —NO$_2$.

4.5 Definitions

As used in connection with the Heterocyclic-Substituted Piperidine Compounds herein, the terms used herein having following meaning:

"—(C$_1$-C$_{10}$)alkyl" means a straight chain or branched non-cyclic hydrocarbon having from 1 to 10 carbon atoms. Representative straight chain —(C$_1$-C$_{10}$)alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —(C$_1$-C$_8$)alkyl groups, such as methyl, ethyl or propyl, replace one or both hydrogens in a —CH$_2$— group of a straight chain alkyl. A branched non-cyclic hydrocarbon means that one or more straight chain —(C$_1$-C$_{10}$)alkyl groups, such as methyl, ethyl or propyl, replace one or both hydrogens in a —CH$_2$— group of a straight chain non-cyclic hydrocarbon. Representative branched —(C$_1$-C$_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—(C$_1$-C$_6$)alkyl" means a straight chain or branched non-cyclic hydrocarbon having from 1 to 6 carbon atoms. Representative straight chain —(C$_1$-C$_6$)alkyls include -methyl, -ethyl, -n-propyl, -n-butyl, -n-pentyl, and -n-hexyl. Representative branched —(C$_1$-C$_6$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—(C$_1$-C$_4$)alkyl" means a straight chain or branched non-cyclic hydrocarbon having from 1 to 4 carbon atoms. Representative straight chain —(C$_1$-C$_4$)alkyls include -methyl, -ethyl, -n-propyl, and -n-butyl. Representative branched —(C$_1$-C$_4$)alkyls include -iso-propyl, -sec-butyl, -iso-butyl, and -tert-butyl.

"—(C$_1$-C$_3$)alkyl" means a straight chain or branched non-cyclic hydrocarbon having from 1 to 3 carbon atoms. Representative straight chain —(C$_1$-C$_3$)alkyls include -methyl, -ethyl, and -n-propyl. Representative branched —(C$_1$-C$_3$) alkyls include -iso-propyl.

"—(C$_1$-C$_2$)alkyl" means a straight chain non-cyclic hydrocarbon having 1 or 2 carbon atoms. Representative straight chain —(C$_1$-C$_2$)alkyls include -methyl and -ethyl.

"—(C$_2$-C$_{10}$)alkenyl" means a straight chain or branched non-cyclic hydrocarbon having from 2 to 10 carbon atoms and including at least one carbon-carbon double bond. A branched alkenyl means that one or more straight chain —(C$_1$-C$_8$)alkyl groups, such as methyl, ethyl or propyl, replace one or both hydrogens in a —CH$_2$— or —CH=group of a straight chain alkenyl. Representative straight chain and branched (C$_2$-C$_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

"—(C$_2$-C$_6$)alkenyl" means a straight chain or branched non-cyclic hydrocarbon having from 2 to 6 carbon atoms and including at least one carbon-carbon double bond. Representative straight chain and branched (C$_2$-C$_6$)alkenyls include -vinyl, -allyl, -1-butenyl, -2-butenyl, -iso-butylenyl, -1-pentenyl, -pentenyl, -3-methyl-1-butenyl, -2-methyl-2-butenyl, -2,3-dimethyl-2-butenyl, -1-hexenyl, 2-hexenyl, 3-hexenyl, and the like.

"—(C$_2$-C$_{10}$)alkynyl" means a straight chain or branched non-cyclic hydrocarbon having from 2 to 10 carbon atoms and including at least one carbon-carbon triple bond. A branched alkynyl means that one or more straight chain —(C$_1$-C$_8$)alkyl groups, such as methyl, ethyl or propyl, replace one or both hydrogens in a —CH$_2$— group of a straight chain alkynyl. Representative straight chain and branched —(C$_2$-C$_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—(C$_2$-C$_6$)alkynyl" means a straight chain or branched non-cyclic hydrocarbon having from 2 to 6 carbon atoms and including at least one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_1-C_6)$alkoxy" means a straight chain or branched non cyclic hydrocarbon having one or more ether groups and from 1 to 6 carbon atoms. Representative straight chain and branched —$(C_1-C_6)$alkoxys include methoxy, ethoxy, methoxymethyl, 2-methoxyethyl, 5-methoxypentyl, 3-ethoxybutyl, and the like.

"—$(C_3-C_{12})$cycloalkyl" means a saturated monocyclic hydrocarbon having from 3 to 12 carbon atoms. Representative $(C_3-C_{12})$cycloalkyls are -cyclopropyl, -cyclobutyl, -cyclopentyl, -cyclohexyl, -cycloheptyl, -cyclooctyl, -cyclononyl, -cyclodecyl, and -cyclododecyl.

"—$(C_4-C_8)$cycloalkyl" or "4- to 8-member cycloalkyl ring" means a saturated monocyclic hydrocarbon having from 4 to 8 carbon atoms unless, if X is —$C(R_4)(R_5)$—N$(R_6)$—$C(R_4')(R_5')$- and $R_4$ and $R_4'$ form a 4- to 8-member cycloalkyl ring, the 4- to 8-member cycloalkyl ring includes the intervening nitrogen atom (to which $R_6$ is attached) and the number of atoms in the ring includes the intervening nitrogen atom. Representative —$(C_4-C_8)$ cycloalkyls are -cyclobutyl, cyclopentyl, cyclohexyl, -cycloheptyl, and -cyclooctyl.

"—$(C_3-C_8)$cycloalkyl" means a saturated monocyclic hydrocarbon having from 3 to 8 carbon atoms. Representative $(C_3-C_8)$cycloalkyls include -cyclopropyl, -cyclobutyl, -cyclopentyl, -cyclohexyl, -cycloheptyl, and -cyclooctyl.

"—$(C_3-C_7)$cycloalkyl" means a saturated monocyclic hydrocarbon having from 3 to 7 carbon atoms. Representative $(C_3-C_7)$cycloalkyls include cyclopropyl, -cyclobutyl, -cyclopentyl, -cyclohexyl, and -cycloheptyl.

"—$(C_6-C_{14})$bicycloalkyl" means a bi-cyclic hydrocarbon ring system having from 6 to 14 carbon atoms and at least one saturated cyclic alkyl ring. Representative —$(C_6-C_{14})$bicycloalkyls include -indanyl, -norbornyl, -1,2,3,4-tetrahydronaphthalenyl, -5,6,7,8-tetrahydronaphthalenyl, -perhydronaphthalenyl, and the like.

"—$(C_8-C_{20})$tricycloalkyl" means a tri-cyclic hydrocarbon ring system having from 8 to 20 carbon atoms and at least one saturated cyclic alkyl ring. Representative —$(C_8-C_{20})$tricycloalkyls include -pyrenyl, -adamantyl, -1,2,3,4-tetrahydroanthracenyl, -perhydroanthracenyl -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

"—$(C_5-C_{12})$cycloalkenyl" means a cyclic non-aromatic hydrocarbon having at least one carbon-carbon double bond in the cyclic system and from 5 to 12 carbon atoms. Representative $(C_5-C_{12})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclododecadienyl, -norbornenyl, and the like.

"—$(C_5-C_{10})$cycloalkenyl" means a cyclic non-aromatic hydrocarbon having at least one carbon-carbon double bond in the cyclic system and from 5 to 10 carbon atoms. Representative $(C_5-C_{10})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl -norbornenyl, and the like.

"—$(C_5-C_8)$cycloalkenyl" means a cyclic non-aromatic hydrocarbon having at least one carbon-carbon double bond in the cyclic system and from 5 to 8 carbon atoms. Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -norbornenyl, and the like.

"—$(C_5-C_7)$cycloalkenyl" means a cyclic non-aromatic hydrocarbon having at least one carbon-carbon double bond in the cyclic system and from 5 to 7 carbon atoms. Representative $(C_5-C_7)$cycloalkenyls include -cyclopentenyl, -cyclopentadienyl, -cyclohexenyl, -cyclohexadienyl, -cycloheptenyl, -cycloheptadienyl, -cycloheptatrienyl, and the like.

"—$(C_7-C_{14})$bicycloalkenyl" means a bi-cyclic hydrocarbon ring system having at least one carbon-carbon double bond in each ring and from 7 to 14 carbon atoms. Representative —$(C_7-C_{14})$bicycloalkenyls include -bicyclo[3.2.0]hept-2-eneyl, -indenyl, -pentalenyl, -naphthalenyl, -azulenyl, -heptalenyl, -1,2,7,8-tetrahydronaphthalenyl, and the like.

"—$(C_8-C_{20})$tricycloalkenyl" means a tri-cyclic hydrocarbon ring system having at least one carbon-carbon double bond in each ring and from 8 to 20 carbon atoms. Representative —$(C_8-C_{20})$tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a, c]cyclooctenyl, 2,3,4,5,6,7,8,9,10,11,12,13-dodecahydro-1H-dibenzo[a,d]cyclononenyl, and the like.

"-(3- to 7-membered)heterocycle" or "-(3- to 7-membered)heterocyclo" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered) heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(3- to 6-membered)heterocycle" or "-(3- to 6-membered)heterocyclo" means a 3- to 6-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, and a 6-membered heterocycle can contain up to 4 heteroatoms. Each heteroatom is independently selected from nitrogen, which can be quaternized; oxygen; and sulfur, including sulfoxide and sulfone. The -(3- to 6-membered) heterocycle can be attached via a nitrogen or carbon atom. Representative -(3- to 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring which is either saturated, unsaturated non-aromatic, or aromatic. A 5-membered heterocycle can contain up to 4 heteroatoms and a 6-membered heterocycle can contain up to 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(3- to 5-membered)heterocycle" or "-(3- to 5-membered) heterocyclo" means a 3- to 5-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, and a 5-membered heterocycle can contain up to 4 heteroatoms. Each heteroatom is independently selected from nitrogen, which can be quaternized; oxygen; and sulfur, including sulfoxide and sulfone. The -(3- to 5-membered) heterocycle can be attached via a nitrogen or carbon atom. Representative -(3- to 5-membered)heterocycles include furyl, thiophenyl, pyrrolyl, oxazolyl, imidazolyl, thiazolidinyl, thiadiazolyl, thiazolyl, isoxazolyl, pyrazolyl, isothiazolyl, triazinyl, pyrrolidinonyl, pyrrolidinyl, 2,3-dihydrofuranyl, hydantoinyl, oxiranyl, oxetanyl, tetrahydrofuranyl, tetrahydrothiophenyl, pyrazolidinyl, and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, -isoindolinyl, -1,2,3,4-tetrahydroquinolinyl, -1,2,3,4-tetrahydroisoquinolinyl, pyrrolopyrrolyl, and the like.

"—($C_3$-$C_{12}$)cycloalkoxy" means a saturated monocyclic hydrocarbon having from 3 to 12 carbon atoms where at least one of the carbon atoms is replaced by an oxygen atom. Representative ($C_3$-$C_{12}$)cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—($C_3$-$C_7$)cycloalkoxy" means a saturated monocyclic hydrocarbon having from 3 to 7 carbon atoms where at least one of the carbon atoms is replaced by an oxygen atom. Representative ($C_3$-$C_7$)cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—($C_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,2,5-thiadiazolyl, 1,3,5-triazinyl, and thiophenyl.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CH_{12}$.

"—C(halo)$_3$" means a methyl group where each of the hydrogens of the methyl group has been replaced with a halogen. Representative —C(halo)$_3$ groups include —$CF_3$, —$CCl_3$, —$CBr_3$, and —$Cl_3$.

"-Halogen" or "-halo" means —F, —Cl, —Br, or —I.

"($C_2$-$C_6$)bridge" as used herein means a hydrocarbon chain containing 2 to 6 carbon atoms joining two atoms of the piperidine ring of Formula (I), Formula (II), Formula (III), or Formula (IV) to form a fused bicyclic ring system. For example, compounds of the invention can comprise a ($C_2$-$C_6$) bridge joining positions 2 and 6 of the piperidine ring (A-B can together form a ($C_2$-$C_6$)bridge). Examples of compounds where A-B can together form a ($C_2$-$C_6$)bridge include compounds comprising the following ring systems: 8-aza-bicyclo

[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane.

"Oxo", "=O", and the like as used herein mean an oxygen atom doubly bonded to carbon or another element. "(=O)" when used in combination with a hydrocarbyl group having a variable number of atoms, such as —(C$_1$-C$_6$)alkyl(=O)W$_1$, means that two of the hydrogens of any methylene group are replaced by an oxo group.

"Thiooxo", "thioxo", "=S", and the like as used herein mean a sulfur atom doubly bonded to carbon or another element.

"(=NH)" when used in combination with a hydrocarbyl group having a variable number of atoms, such as —(C$_1$-C$_6$) alkyl(=NH)W$_1$, means that two of the hydrogens of any methylene group are replaced by an imino group.

As used herein in connection with Formula (I), when the dashed line in the piperidine or bridged piperidine central ring is absent, then Formula (I) is understood to appear as follows

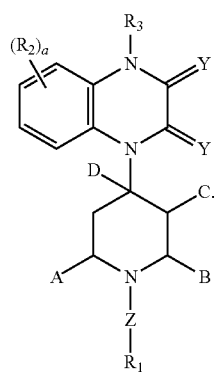

(I)

As used herein in connection with Formula (I), when the dashed line in the piperidine or bridged piperidine central ring indicates the presence of a bond, then Formula (I) is understood to appear as follows

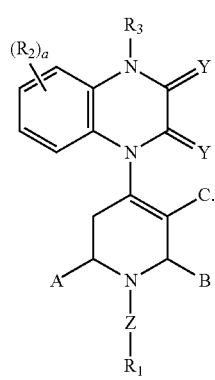

(I)

As used herein in connection with Formula (II), when the dashed line in the piperidine or bridged piperidine central ring is absent, then Formula (II) is understood to appear as follows

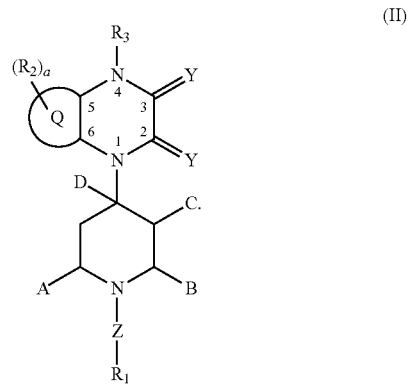

(II)

As used herein in connection with Formula (II), when the dashed line in the piperidine or bridged piperidine central ring indicates the presence of a bond, then Formula (II) is understood to appear as follows

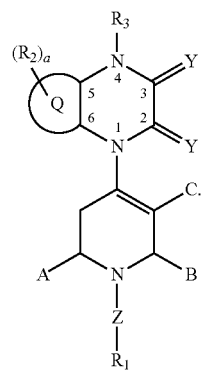

(II)

As used herein in connection with Formula (III), when the dashed line in the piperidine or bridged piperidine central ring is absent, then Formula (III) is understood to appear as follows

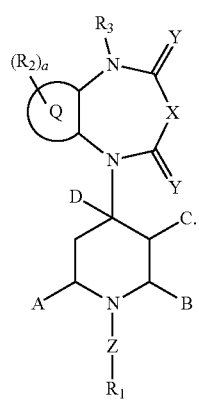

(III)

As used herein in connection with Formula (III), when the dashed line in the piperidine or bridged piperidine central ring indicates the presence of a bond, then Formula (III) is understood to appear as follows

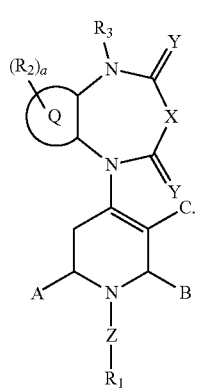
(III)

As used herein in connection with Formula (IV), when the dashed line in the piperidine or bridged piperidine central ring is absent, then Formula (IV) is understood to appear as follows

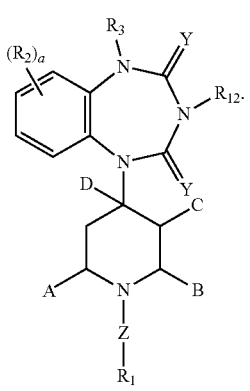
(IV)

As used herein in connection with Formula (IV), when the dashed line in the piperidine or bridged piperidine central ring indicates the presence of a bond, then Formula (IV) is understood to appear as follows

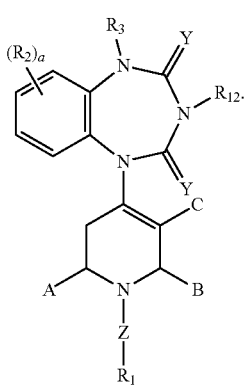
(IV)

"—[(C$_1$-C$_{10}$)alkyl optionally substituted by R$_1$]$_h$—" as used herein in connection with Z means that, when h is 0, Z is a bond. When h is 1, Z—R$_1$, as attached to the piperidine ring bearing A and B substituents, is

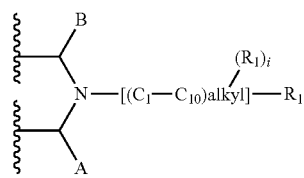

where; when i is 0, the (C$_1$-C$_{10}$)alkyl is unsubstituted by an R$_1$ group at any position other than at the carbon atom furthest removed from the piperidine ring bearing A and B substituents; and, when i is 1, (i.e., the (C$_1$-C$_{10}$)alkyl is optionally substituted by R$_1$) the (C$_1$-C$_{10}$)alkyl is substituted by an R$_1$ group at the carbon atom furthest removed from the piperidine ring bearing A and B substituents and substituted by another independently selected R$_1$ group at any carbon atom of the (C$_1$-C$_{10}$)alkyl including at the carbon atom furthest removed from the piperidine ring bearing A and B substituents.

As used herein in connection with formula (i) of R$_1$, when the dashed line indicates the presence of a bond, then formula (i) is understood to appear as follows

(i)

As used herein in connection with formula (i) of R$_1$, when the dashed line is absent, then formula (i) is understood to appear as follows

(i)

The phrase "3,3-diphenylpropyl-" and the like, when used in connection with the —Z—R$_1$ group, means

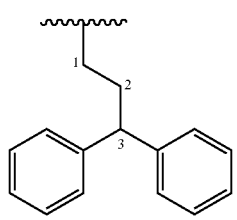 [SMILES: *CCC(c1ccccc1)c1ccccc1]

where the 3 carbon of the propyl is indicated by the number 3 in the structure above.

The phrase "tetrazolyl group" means

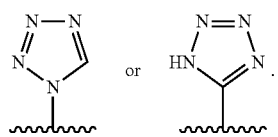 [SMILES: *n1cnnn1 ; *c1nnn[nH]1]

In one embodiment, the tetrazolyl group is

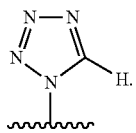

In another embodiment, the tetrazolyl group is

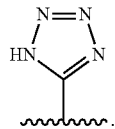

The phrase "quinolinyl," "quinolinyl group" and the like means

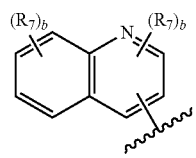

where R$_7$ is defined above for the Heterocyclic-Substituted Piperidine Compounds of Formulas (I), (II) and (III) and b is zero or a positive integer.

The phrase "imidazolyl," "imidazolyl group" and the like means

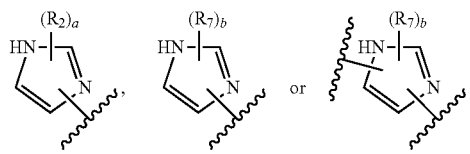

where R$_2$ and a are defined above for the Heterocyclic-Substituted Piperidine Compounds of Formula (II), R$_7$ is defined above for the Heterocyclic-Substituted Piperidine Compounds of Formulas (II) and (III), and b is zero or a positive integer. The bond(s) between an imidazolyl substituent and the atom(s) of the group to which the imidazolyl substituent is attached can be effected through the removal of any hydrogen atom(s) of the imidazolyl substituent, including the hydrogen atom bonded to an imidazolyl nitrogen atom.

The phrase "triazolyl," "triazolyl group" and the like means

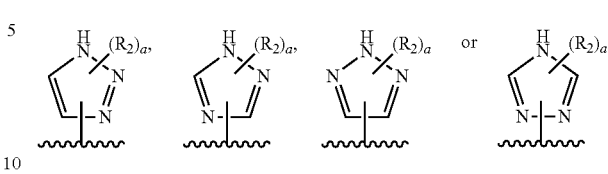

where R$_2$ and a are defined above for the Heterocyclic-Substituted Piperidine Compounds of Formula (II). The bond(s) between a triazolyl substituent and the atom(s) of the group to which the triazolyl substituent is attached can be effected through the removal of any hydrogen atom(s) of the triazolyl substituent, including the hydrogen atom bonded to a triazolyl nitrogen atom.

The phrase "benzo," "benzo group" and the like, when used in connection with the Q group, means

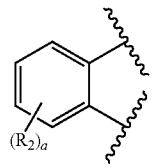

where R$_2$, and a are defined above for the Heterocyclic-Substituted Piperidine Compounds of Formula (III).

The phrase "pyridino," "pyridino group" and the like, when used in connection with the Q group, means

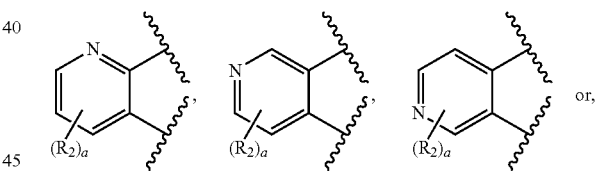

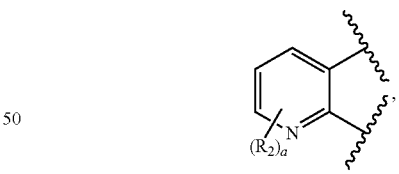

where R$_2$, and a are defined above for the Heterocyclic-Substituted Piperidine Compounds of Formulas (II) and (III). In one embodiment, the optionally-substituted pyridino Q group is

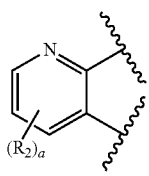

In another embodiment, the optionally-substituted pyridino Q group is

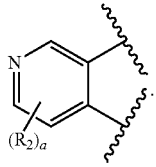

In another embodiment, the optionally-substituted pyridino Q group is

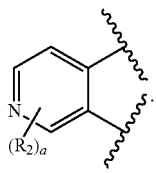

In another embodiment, the optionally-substituted pyridino Q group is

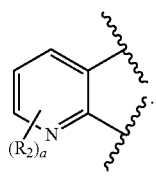

The phrase "naphthaleno," "naphthaleno group" and the like, when used in connection with the Q group, means

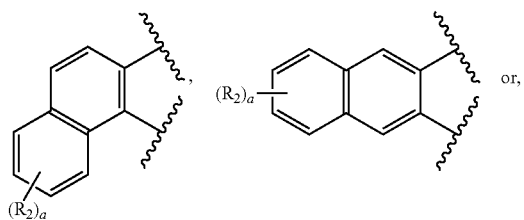

where $R_2$, and a are defined above for the Heterocyclic-Substituted Piperidine Compounds of Formulas (II) and (III) and where an $R_2$ group can be attached to any substitutable ring carbon atom of either, or both rings, of the naphthaleno group. In one embodiment, the optionally-substituted naphthaleno Q group is

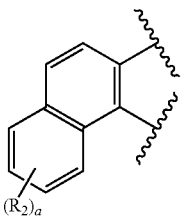

where an $R_2$ group can be attached to any substitutable ring carbon atom of either, or both rings, of the naphthaleno group. In another embodiment, the optionally-substituted naphthaleno Q group is

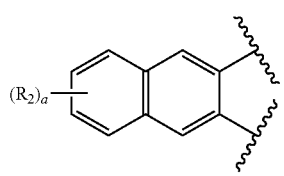

where an $R_2$ group can be attached to any substitutable ring carbon atom of either, or both rings, of the naphthaleno group. In another embodiment, the optionally-substituted naphthaleno Q group is

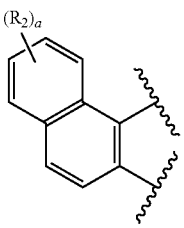

where an $R_2$ group can be attached to any substitutable ring carbon atom of either, or both rings, of the naphthaleno group.

The phrase "pyrimidino", "pyrimidino group" and the like, when used in connection with the optionally-substituted Q group, means

where $R_2$ and a are defined above for the Heterocyclic-Substituted Piperidine Compounds of Formula (III). In one embodiment, the optionally-substituted pyrimidino Q group is In another embodiment, the optionally-substituted pyrimidino Q group is

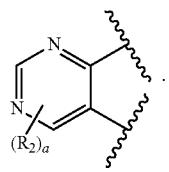

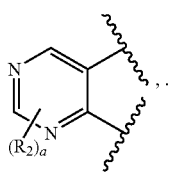

The phrase "pyrazino", "pyrazino group" and the like, when used in connection with the optionally-substituted Q group, means

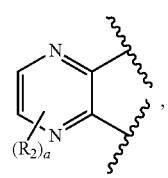

where $R_2$ and a are defined above for the Heterocyclic-Substituted Piperidine Compounds of Formula (III).

The phrase "pyridazino", "pyridazino group" and the like, when used in connection with the optionally-substituted Q group, means

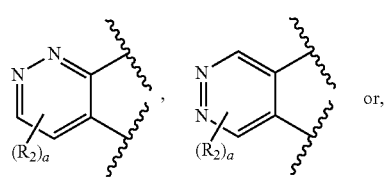

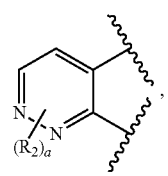

where $R_2$ and a are defined above for the Heterocyclic-Substituted Piperidine Compounds of Formula (III). In one embodiment, the optionally-substituted pyridazino Q group is In another embodiment, the optionally-substituted pyridazino Q group is

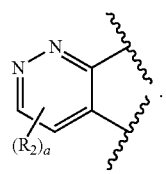

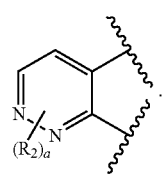

In another embodiment, the optionally-substituted pyridazino Q group is

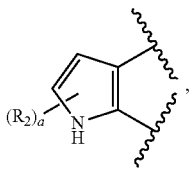

The phrase "pyrrolino", "pyrrolino group" and the like, when used in connection with the optionally-substituted Q group, means

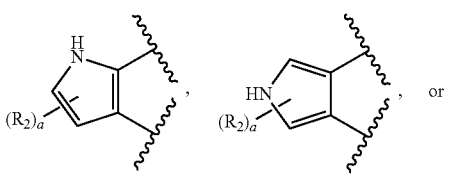

where $R_2$ and a are defined above for the Heterocyclic-Substituted Piperidine Compounds of Formula (III). In one embodiment, the optionally-substituted pyrrolino Q group is

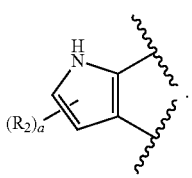

In another embodiment, the optionally-substituted pyrrolino Q group is

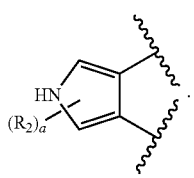

In another embodiment, the optionally-substituted pyrrolino Q group is

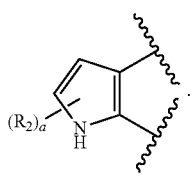

The phrase "imidazolino", "imidazolino group" and the like, when used in connection with the optionally-substituted Q group, means

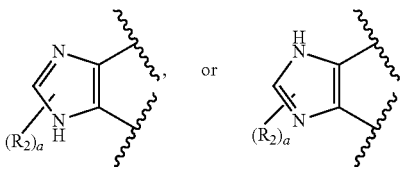

where R₂ and a are defined above for the Heterocyclic-Substituted Piperidine Compounds of Formula (III). In one embodiment, the optionally-substituted imidazolino Q group is

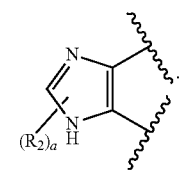

In another embodiment, the optionally-substituted imidazolino Q group is

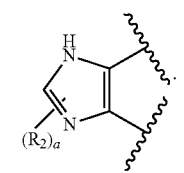

The phrase "pyrazolino", "pyrazolino group" and the like, when used in connection with the optionally-substituted Q group, means

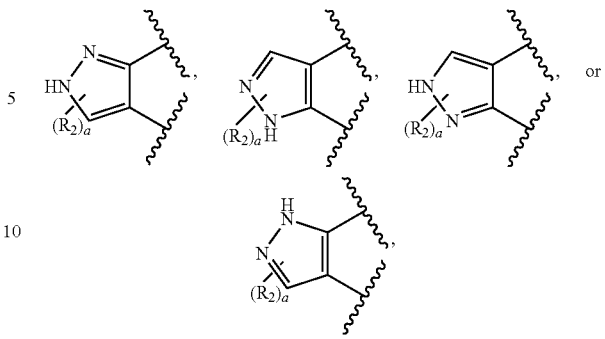

where R₂ and a are defined above for the Heterocyclic-Substituted Piperidine Compounds of Formula (III). In one embodiment, the optionally-substituted pyrazolino Q group is

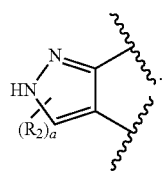

In another embodiment, the optionally-substituted pyrazolino Q group is

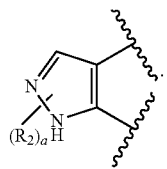

In another embodiment, the optionally-substituted pyrazolino Q group is

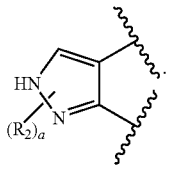

In another embodiment, the optionally-substituted pyrazolino Q group is

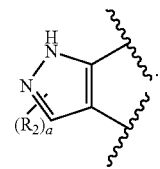

The phrase "triazolino", "triazolino group" and the like, when used in connection with the optionally-substituted Q group, means

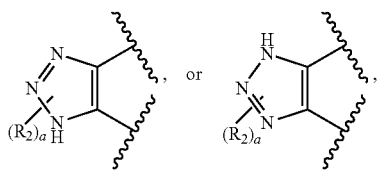, or 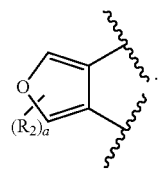, where R₂ and a are defined above for the Heterocyclic-Substituted Piperidine Compounds of Formula (III). In one embodiment, the optionally-substituted triazolino Q group is

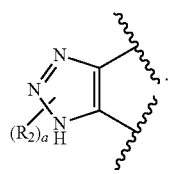.

In another embodiment, the optionally-substituted triazolino Q group is

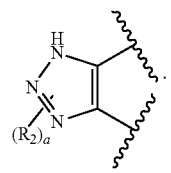.

The phrase "furano", "furano group" and the like, when used in connection with the optionally-substituted Q group, means

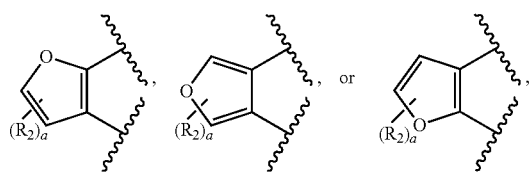

where R₂ and a are defined above for the Heterocyclic-Substituted Piperidine Compounds of Formula (III). In one embodiment, the optionally-substituted furano Q group is

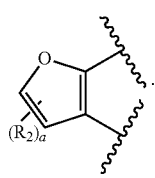.

In another embodiment, the optionally-substituted furano Q group is

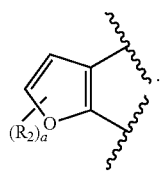.

The phrase "oxazolino", "oxazolino group" and the like, when used in connection with the optionally-substituted Q group, means

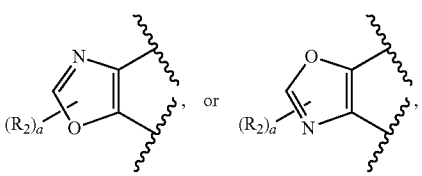

where R₂ and a are defined above for the Heterocyclic-Substituted Piperidine Compounds of Formula (III). In one embodiment, the optionally-substituted oxazolino Q group is

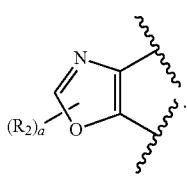.

In another embodiment, the optionally-substituted oxazolino Q group is

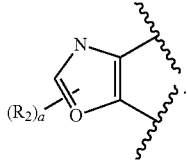.

The phrase "isoxazolino", "isoxazolino group" and the like, when used in connection with the optionally-substituted Q group, means

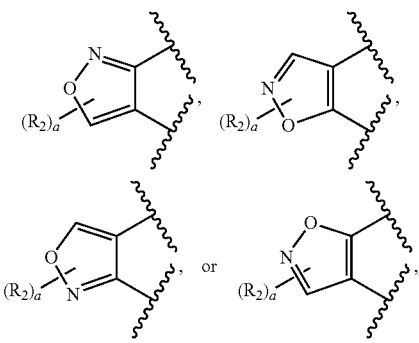

where $R_2$ and a are defined above for the Heterocyclic-Substituted Piperidine Compounds of Formula (III). In one embodiment, the optionally-substituted isoxazolino Q group is

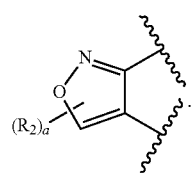

In another embodiment, the optionally-substituted isoxazolino Q group is

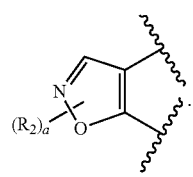

In another embodiment, the optionally-substituted isoxazolino Q group is

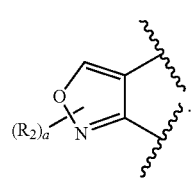

In another embodiment, the optionally-substituted isoxazolino Q group is

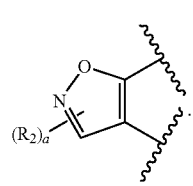

The phrase "oxadiazolino", "oxadiazolino group" and the like, when used in connection with the optionally-substituted Q group, means

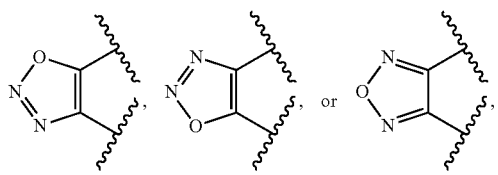

where $R_2$ and a are defined above for the Heterocyclic-Substituted Piperidine Compounds of Formula (III). In one embodiment, the optionally-substituted oxadiazolino Q group is

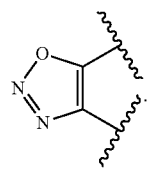

In another embodiment, the optionally-substituted oxadiazolino Q group is

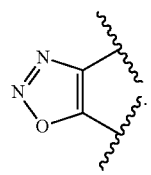

In another embodiment, the optionally-substituted oxadiazolino Q group is

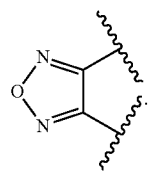

The phrase "thiopheno", "thiopheno group" and the like, when used in connection with the optionally-substituted Q group, means

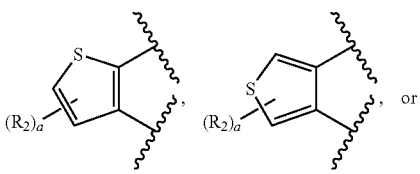

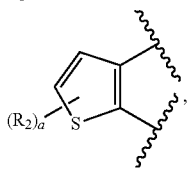

where R₂ and a are defined above for the Heterocyclic-Substituted Piperidine Compounds of Formula (III). In one embodiment, the optionally-substituted thiopheno Q group is

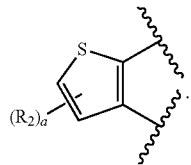

In another embodiment, the optionally-substituted thiopheno Q group is

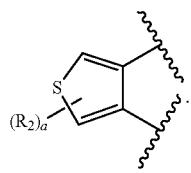

In another embodiment, the optionally-substituted thiopheno Q group is

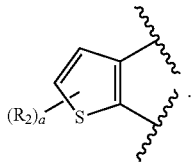

The phrase "thiazolino", "thiazolino group" and the like, when used in connection with the optionally-substituted Q group, means

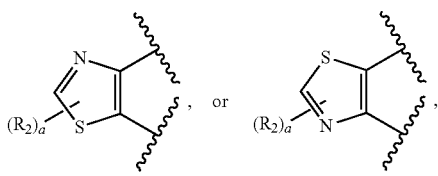

where R₂ and a are defined above for the Heterocyclic-Substituted Piperidine Compounds of Formula (III). In one embodiment, the optionally-substituted thiazolino Q group is

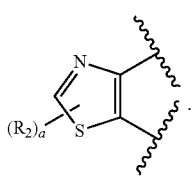

In another embodiment, the optionally-substituted thiazolino Q group is

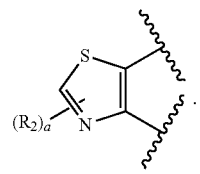

The phrase "isothiazolino", "isothiazolino group" and the like, when used in connection with the optionally-substituted Q group, means

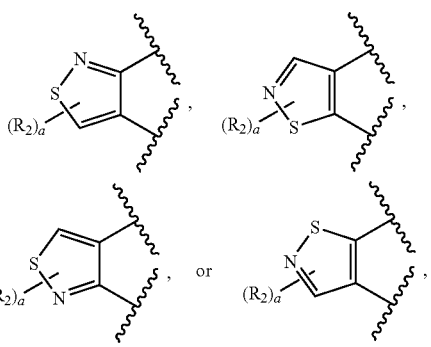

where R₂ and a are defined above for the Heterocyclic-Substituted Piperidine Compounds of Formula (III). In one embodiment, the optionally-substituted isothiazolino Q group is

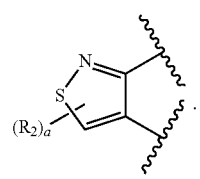

In another embodiment, the optionally-substituted isothiazolino Q group is

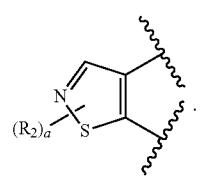

In another embodiment, the optionally-substituted isothiazolino Q group is

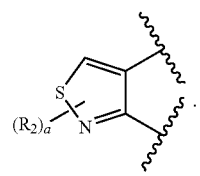

In another embodiment, the optionally-substituted isothiazolino Q group is

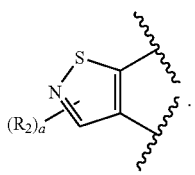

The phrase "thiadiazolino", "thiadiazolino group" and the like, when used in connection with the optionally-substituted Q group, means

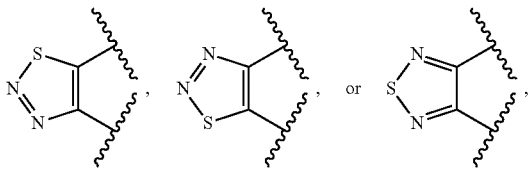

where $R_2$ and a are defined above for the Heterocyclic-Substituted Piperidine Compounds of Formula (III). In one embodiment, the optionally-substituted thiadiazolino Q group is

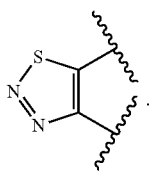

In another embodiment, the optionally-substituted thiadiazolino Q group is

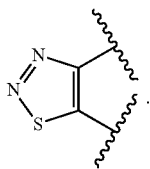

In another embodiment, the optionally-substituted thiadiazolino Q group is

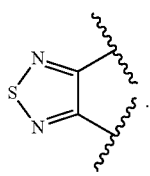

When a first group is "substituted with one or more" second groups, one or more hydrogen atoms of the first group is replaced with a corresponding number of second groups. When the number of second groups is two or greater, each second group can be the same or different.

In one embodiment, a first group is substituted with up to three second groups.

In another embodiment, a first group is substituted with one or two second groups.

In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

The phrase "pharmaceutically acceptable derivative," as used herein, includes any pharmaceutically acceptable salt, solvate, prodrug, radiolabeled, stereoisomer, enantiomer, diastereomer, other stereoisomeric form, racemic mixture, geometric isomer, and/or tautomer, e.g., of a Heterocyclic-Substituted Piperidine Compound of the invention. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a Heterocyclic-Substituted Piperidine Compound of the invention. In another embodiment, the pharmaceutically acceptable derivative is a pharmaceutically acceptable salt, e.g., of a Heterocyclic-Substituted Piperidine Compound of the invention.

The phrase "pharmaceutically acceptable salt," as used herein, is any pharmaceutically acceptable salt that can be prepared from a Heterocyclic-Substituted Piperidine Compound including a salt formed from an acid and a basic functional group, such as a nitrogen group, of a Heterocyclic-Substituted Piperidine Compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Heterocyclic-Substituted Piperidine Compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl, N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a Heterocyclic-Substituted Piperidine Compound can be prepared by reaction of the compounds with the appropriate acid via a variety of known methods.

The invention disclosed herein is also meant to encompass all solvates of the Heterocyclic-Substituted Piperidine Compounds. "Solvates" are known in the art and are considered to be a combination, physical association and/or solvation of a Heterocyclic-Substituted Piperidine Compound with a solvent molecule, e.g., a disolvate, monosolvate or hemisolvate when the solvent molecule:Heterocyclic-Substituted Piperidine Compound molecule ratio is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate," as used herein, encompasses both solution-phase and isolatable solvates. A Heterocyclic-Substituted Piperidine Compound of the invention can be present as a solvated form with a pharmaceutically acceptable solvent, such as water, methanol, ethanol, and the like, and it is intended that the invention include both solvated and unsolvated Heterocyclic-Substituted Piperidine Compound forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.*, 93(3):601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.*, 5(1):Article 12 (2004), and A. L. Bingham et al., *Chem. Commun.*, 603-604 (2001). A typical, non-limiting, process involves dissolving the Heterocyclic-Substituted Piperidine Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The invention disclosed herein is also meant to encompass all prodrugs of the Heterocyclic-Substituted Piperidine Compounds. "Prodrugs" are known in the art and, while not necessarily possessing any pharmaceutical activity as such, are considered to be any covalently bonded carrier(s) that releases the active parent drug in vivo. In general, such prodrugs will be a functional derivative of a Heterocyclic-Substituted Piperidine Compound of Formulas (I), (II), (III) and/or (IV) which is readily convertible in vivo, e.g., by being metabolized, into the required Heterocyclic-Substituted Piperidine Compound of Formulas (I), (II), (III) and/or (IV). Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984).

In addition, one or more hydrogen, carbon or other atoms of a Heterocyclic-Substituted Piperidine Compound can be replaced by an isotope of the hydrogen, carbon or other atoms. Such a "radiolabeled," "radiolabeled form", and the like of a Heterocyclic-Substituted Piperidine Compound, each of which is encompassed by the invention, is useful as a research and/or diagnostic tool in metabolism pharmacokinetic studies and in binding assays. Examples of isotopes that can be incorporated into a Heterocyclic-Substituted Piperidine Compound of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Radiolabeled compounds of the invention can be prepared by methods known in the art. For example, tritiated compounds of Formula (I) can be prepared by introducing tritium into the particular compound of Formula (I), for example, by catalytic dehalogenation with tritium. This method can include reacting a suitably halogen-substituted precursor of a compound of Formula (I) with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

A Heterocyclic-Substituted Piperidine Compound can contain one or more asymmetric centers and may thus give rise to enantiomers, diastereomers, and other stereoisomeric forms. The invention is also meant to encompass all such possible forms as well as their racemic and resolved forms or any mixture thereof. When a Heterocyclic-Substituted Piperidine Compound contains an olefinic double bond or other center of geometric asymmetry, and unless specified otherwise, it is intended to include all "geometric isomers," e.g., both E and Z geometric isomers. All "tautomers," e.g., ketone-enol, amide-imidic acid, lactam-lactim, enamine-imine, amine-imine, and enamine-enimine tautomers, are intended to be encompassed by the invention as well.

As used herein, the terms "stereoisomer," "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Optical isomers of a Heterocyclic-Substituted Piperidine Compound can be obtained by known techniques such as chiral chromatography or formation of diastereomeric salts from an optically active acid or base.

The phrase "effective amount," when used in connection with a Heterocyclic-Substituted Piperidine Compound, means an amount effective for: (a) treating or preventing a Condition; (b) detectably inhibiting ORL-1 receptor function in a cell; or (c) detectably activating ORL-1 receptor function in a cell.

The phrase "effective amount," when used in connection with a second therapeutic agent means an amount for providing the therapeutic effect of the second therapeutic agent.

The terms "modulate," "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, antagonists, mixed agonists/antagonists and compounds which directly or indirectly affect regulation of the receptor activity.

The term "MeOH" means methanol, i.e., methyl alcohol.

The term "EtOH" means ethanol, i.e., ethyl alcohol.

The term "THF" means tetrahydrofuran.
The term "DMF" means N,N-dimethylformamide.
The term "DCM" means methylene chloride, i.e., dichloromethane.
The term "DCE" means dichloroethane.
The term "EtOAc" means ethyl acetate.
The term "NH₄OH" means ammonium hydroxide.
The term "TEA" means triethylamine.
The term "MeCN" means acetonitrile.
The term "NaH" means sodium hydride.
The term "AcOH" means acetic acid.
The term "DIEA" means N,N-diisopropylethylamine or N-ethyl-N-isopropylpropan-2-amine.
The term "TFFA" means trifluoroacetic anhydride or 2,2,2-trifluoroacetic anhydride.
The term "DMSO" means dimethylsulfoxide, i.e., methylsulfinylmethane.
The term "Bn" means benzyl or

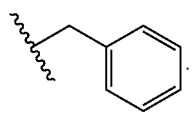

The term "BOC" means tert-butyloxycarbonyl or

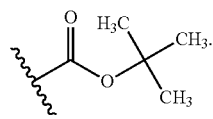

The term "CBZ" means benzyloxycarbonyl or

The term "IBD" means inflammatory-bowel disease.
The term "IBS" means irritable-bowel syndrome.
The term "ALS" means amyotrophic lateral sclerosis.

The phrases "treatment of," "treating", and the like include the amelioration or cessation of a Condition or a symptom thereof. In one embodiment, treating includes inhibiting, for example, decreasing the overall frequency of episodes of a Condition or a symptom thereof.

The phrases "prevention of," "preventing", and the like include the avoidance of the onset of a Condition or a symptom thereof.

4.6 Methods for Making the Heterocyclic-Substituted Piperidine Compounds

The Heterocyclic-Substituted Piperidine Compounds can be made using conventional organic synthesis, in view of the present disclosure, and including the following illustrative methods shown in the schemes below where A, B, Y, Z, $R_1$, $R_2$, $R_3$, $R_{12}$ and a are defined above, L is a halogen leaving group such as Br or I, L' is F or Cl, each R is independently, e.g., a —($C_1$-$C_4$)alkyl group, and q is the integer 0, 1, or 2.

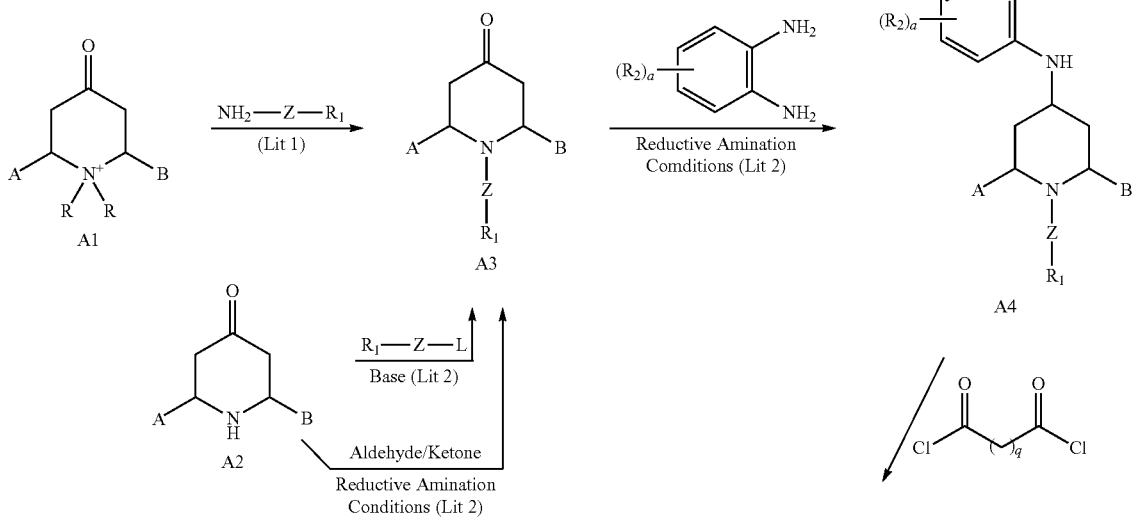

Scheme A

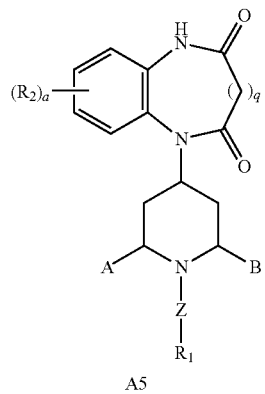

A5

In Scheme A and in the other schemes, "Lit 1" refers to the procedures described in the publications D. A. Tortolani and M. A. Poss, *Org. Lett.* 1:1261 (1999) and/or International PCT Publication No. WO 2005/075459 A1 of Euro-Celtique S. A. and "Lit 2" refers to the procedures described in U.S. Pat. No. 6,635,653 by Goehring et al.

Compounds of formula A1 and A2 are commercially available or can be prepared by methods known to the art.

A piperidinium salt of structure A1 can be reacted with a primary amine in a suitable solvent such as ethanol under reflux conditions in the presence of a base such as potassium carbonate as described in reference "Lit 1" to provide the 1-(substituted)piperidine-4-one compound A3. As described in reference "Lit 2," compound A3 can also be prepared by alkylation of a piperidine-4-one of structure A2 with, e.g., an alkyl bromide or alkyl iodide, in a suitable solvent such as dimethyl formamide, acetonitrile or dimethyl sulfoxide in the presence of an inorganic base such as potassium carbonate or an organic base such as diisopropylethylamine. As described in reference "Lit 2," compound A3 can also be prepared by reductive amination of compound A2 with an aldehyde or ketone using an acid such as acetic acid and either sodium triacetoxyborohydride or sodium cyanoborohydride in a suitable solvent such as dichloromethane or methanol, respectively. Compound A3 can then be reductively aminated with a substituted or unsubstituted 1,2-phenylenediamine using an acid such as acetic acid and either sodium triacetoxyborohydride or sodium cyanoborohydride in a suitable solvent such as dichloromethane or methanol, respectively, to provide compound A4, as described in reference "Lit 2." Compound A4 can be dissolved in a suitable solvent such as dichloromethane and cyclized with a cyclizing reagent, such as a di-acid chloride, e.g., oxalyl dichloride or malonyl dichloride (q=0 and q=1, respectively), to provide compound A5.

Scheme B

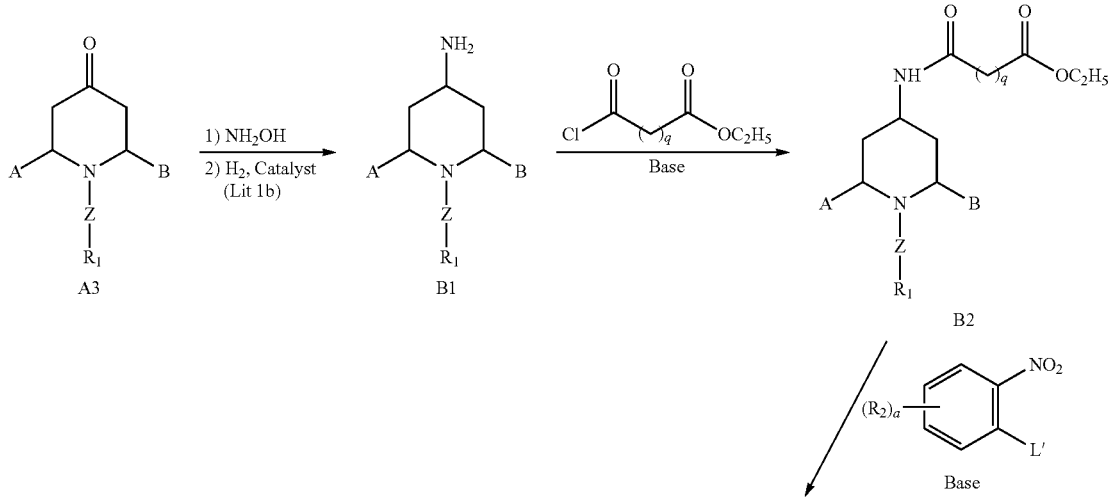

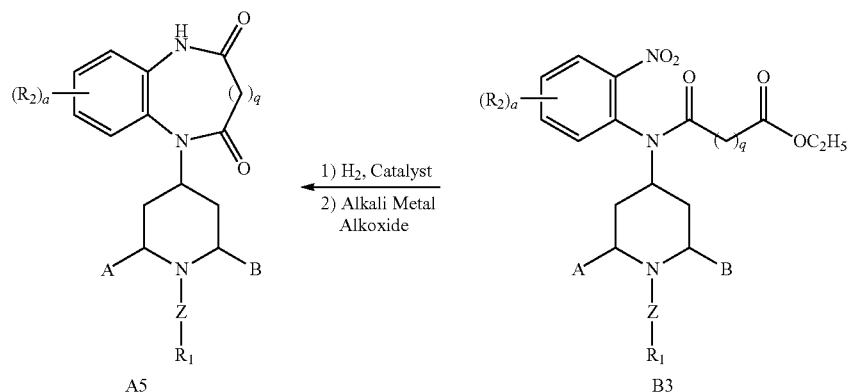

In Scheme B, "Lit 1b" refers to the procedures described in International PCT Publication No. WO 2005/075459 A1 of Euro-Celtique S. A.

As described in reference "Lit 1b," compound A3 can be reacted with 50% aqueous hydroxylamine in a suitable solvent such as hexanes to provide an intermediate hydroxylamine which can be converted to an oxime by dehydration in a suitable solvent such as toluene under reflux conditions using a Dean-Stark apparatus. The oxime intermediate can be reduced to the primary amine compound B1 by catalytic hydrogenation using a catalyst such as 5% rhodium on alumina in a suitable solvent such as ethanol under a hydrogen atmosphere at a pressure of 1 atm or greater in a suitable apparatus such as a Parr Hydrogenator according to reference "Lit 1b." Compound B1 can be reacted with a cyclizing reagent, such as ethyl 2-chloro-2-oxoacetate or or ethyl 3-chloro-3-oxopropanoate, in the presence of a base such as triethylamine to provide compound B2. Compound B2 can be reacted with a substituted or unsubstituted 2-halo-1-nitrobenzene, such as 2-fluoro-1-nitrobenzene, in the presence of a base such as potassium carbonate in a suitable solvent such as acetonitrile under reflux conditions to provide compound B3. Compound B3 can be treated with a hydrogenation catalyst such as Raney nickel in a suitable solvent such as ethanol under a hydrogen atmosphere, and the product immediately treated with an alkali metal alkoxide such as sodium ethoxide in a suitable solvent such as methanol or ethanol to provide compound A5.

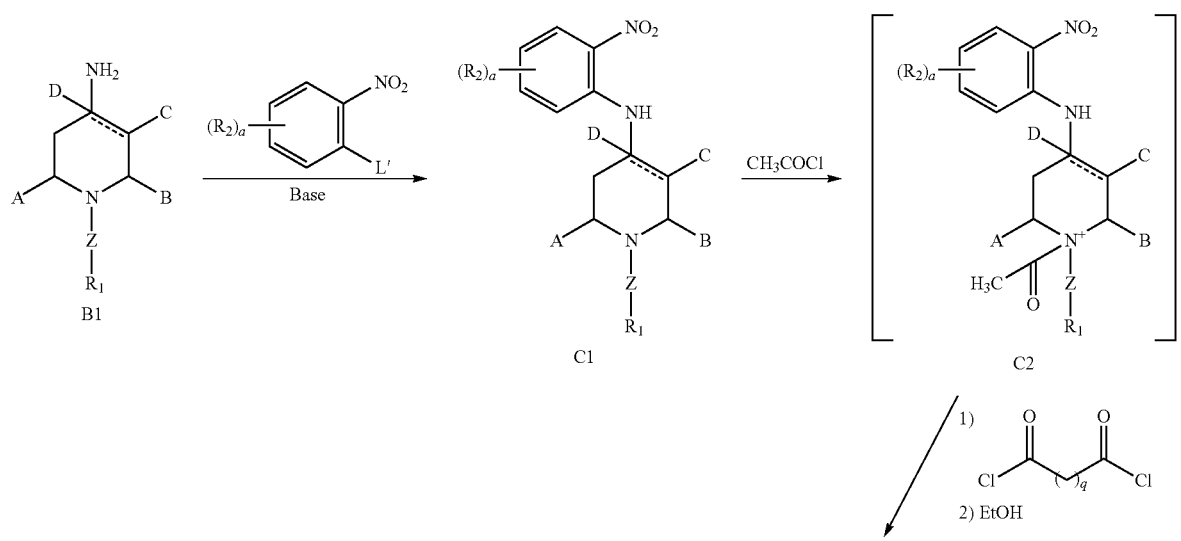

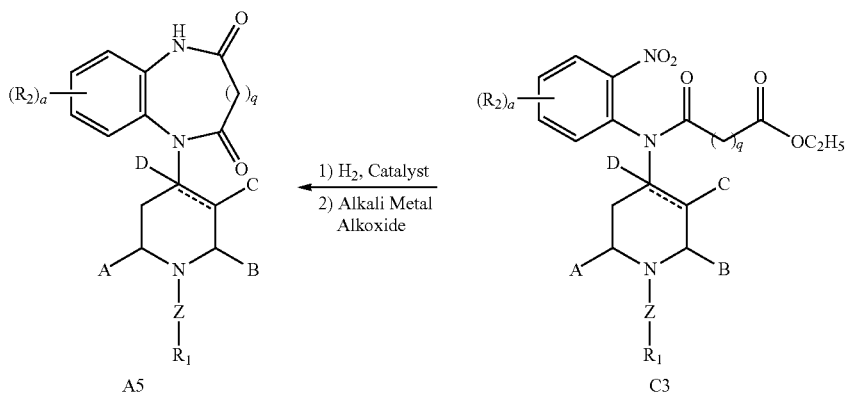

Compound B1 can be reacted with a substituted or unsubstituted 2-halo-1-nitrobenzene, such as substituted or unsubstituted 2-fluoro-1-nitrobenzene, in the presence of a base as described in Scheme B to provide compound C1. The reactivity of the piperidine nitrogen is then masked by reaction with a sacrificial acylating agent acetyl chloride to provide the acetyl-piperidinium salt C2. Compound C2 can then be reacted with a cyclizing reagent, such as a di-acid chloride, e.g., oxalyl dichloride or malonyl dichloride, in a suitable solvent such as dichloromethane, followed by treatment of the mixture with ethanol to provide compound C3. As described in Scheme B, compound C3 can then be treated with a catalyst, such as Raney nickel, under a hydrogen atmosphere to provide an intermediate which is immediately cyclized to provide compound A5.

Compound A4 can be treated with ethoxycarbonyl isocyanate in a suitable solvent, such as 1,2-dichloroethane, in a microwave reactor (Ethos MicroSYNTH, Milestone Inc., Shelton, Conn.) to provide compound D1.

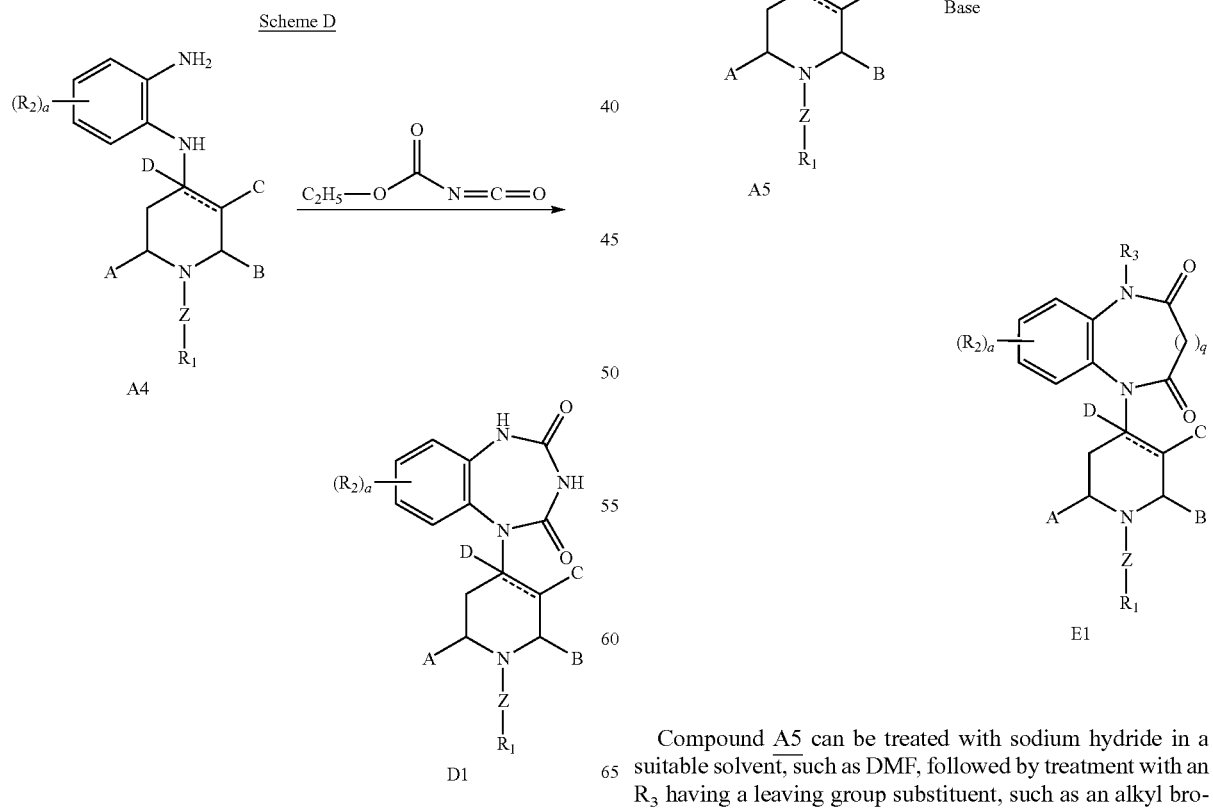

Compound A5 can be treated with sodium hydride in a suitable solvent, such as DMF, followed by treatment with an R₃ having a leaving group substituent, such as an alkyl bromide, to provide compound E1.

Scheme F

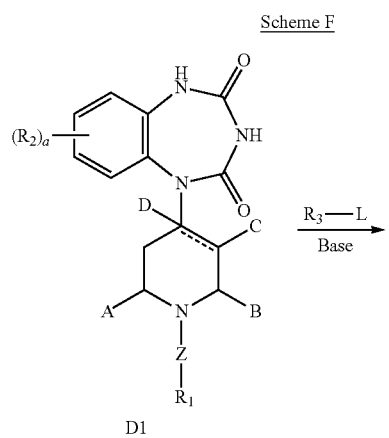

D1

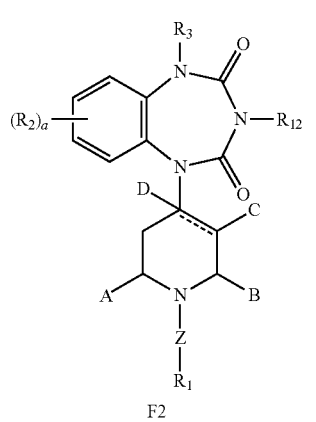

F1

F2

Scheme G

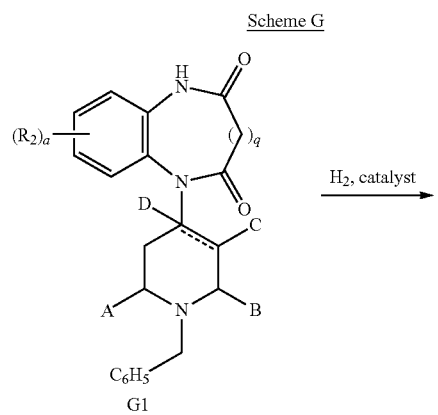

G1

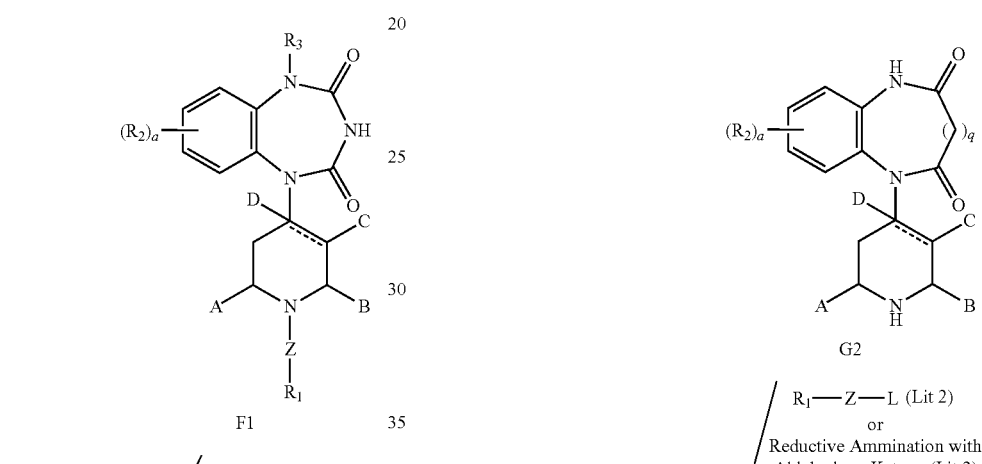

G2

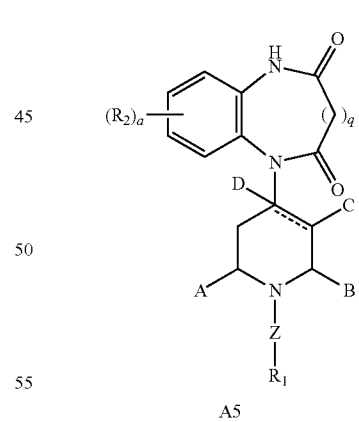

A5

Compound D1 can be alkylated with an $R_3$ group having a leaving group substituent, such as an alkyl bromide, using a suitable base to provide compound F1. Compound F1 can be further alkylated with an $R_{12}$ group having a leaving group substituent, such as an alkyl bromide, using a suitable base to provide compound F2.

Compound G1 can be hydrogenolyzed using a catalyst, such as palladium on charcoal, in a suitable solvent, such as methanol, under a hydrogen atmosphere to provide compound G2. The —Z—$R_1$ group can be attached to compound G2 as described in Scheme A, e.g., using either alkylation or reductive amination conditions, to provide compound A5.

Scheme H

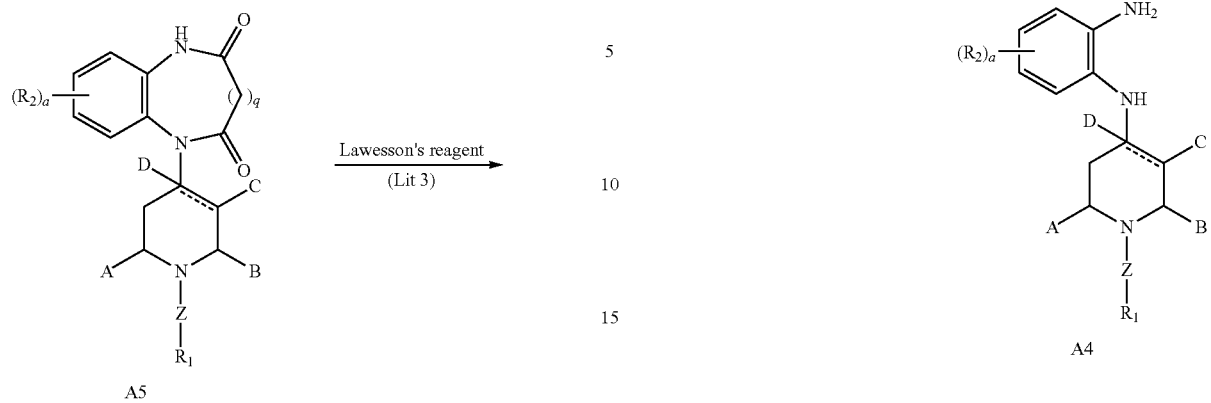

The Compound of Formula H1 where each Y is S can be made by, e.g., reacting a Compound of Formula A5 (i.e., where each Y is O) with Lawesson's reagent (i.e., 2,4-bis(4-methoxyphenyl)-1,3-dithia-2,4-diphosphetane-2,4-disulfide) according to the procedure described in "Lit 3," which refers the publication Perregaard et al., *Bull. Soc. Chim. Belg.* 86:679-691 (1977). In one embodiment, the Compound of Formula H1 can be made by reacting a Compound of Formula A5 with Lawesson's reagent in a nonpolar solvent such as THF or toluene at a temperature of about 100° C. for about 2-3 hours, as shown above.

Scheme I

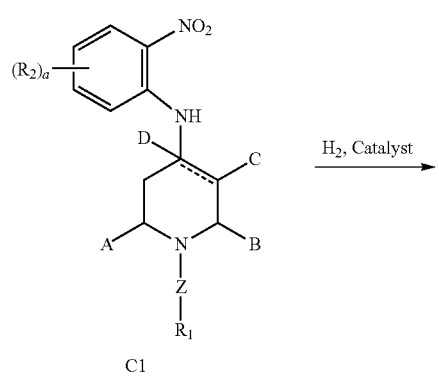

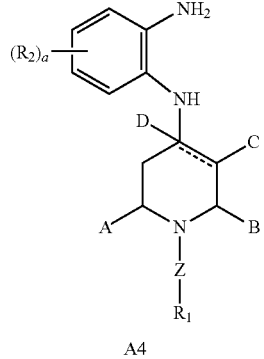

Compound C1 can be converted to compound A4 using a catalyst, such as Raney nickel, in a suitable solvent, such as ethanol, under a hydrogen atmosphere.

Scheme J

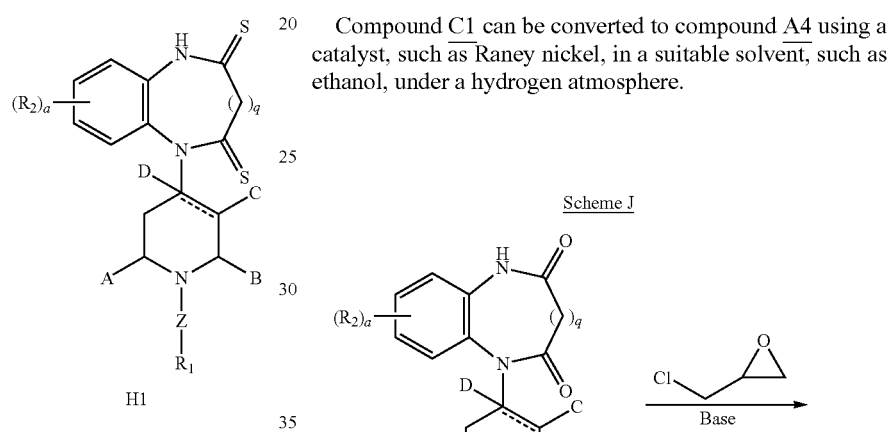

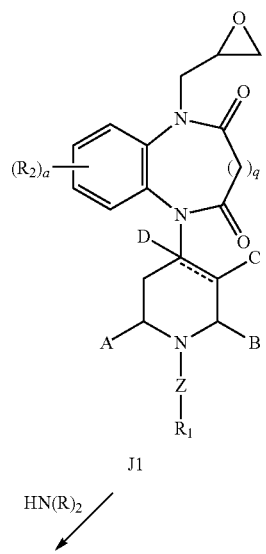

HN(R)$_2$

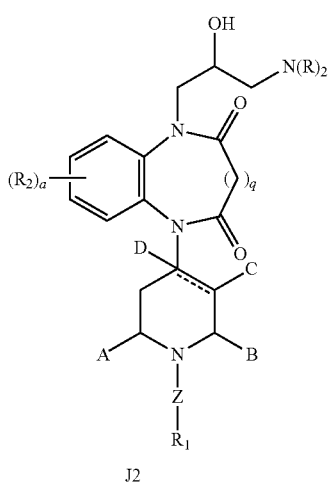

J2

Compound A5 can be reacted with epichlorohydrin in the presence of a suitable base to provide compound J1. Compound J1 can be reacted with a suitable amine, such as NH(R)$_2$, in a suitable solvent to provide compound J2.

The piperidine nitrogen of compound A2 can be protected as, e.g., the trifluoroacetamide or carbobenzyloxy carbamate using trifluoroacetic anhydride or benzychloroformate, respectively, in a suitable solvent such as dichloromethane in the presence of an organic base such as triethylamine to provide compound K1. Compound K1 can be reductively aminated with a substituted or unsubstituted 1,2-phenylenediamine using sodium triacetoxyborohydride in a solvent such as dichloromethane in the presence of acetic acid to provide compound K1. Compound K2 can be cyclized with a cyclizing reagent, such as a di-acid chloride, e.g., oxalyl dichloride or malonyl dichloride, to provide compound K3. The protecting group (such as —C(O)R illustrated above) can be removed under standard conditions (see, e.g., "Protective Groups in Organic Synthesis," T. W. Greene and P. G. M. Wuts, John Wiley & Sons, Inc., 3$^{rd}$ Ed., New York (1999), pp. 531-535, 556-557) to provide compound K4. The —Z—R$_1$ group can be attached to compound K4 as described in Scheme A, e.g., using either alkylation or reductive amination conditions, to provide compound A5.

Scheme K

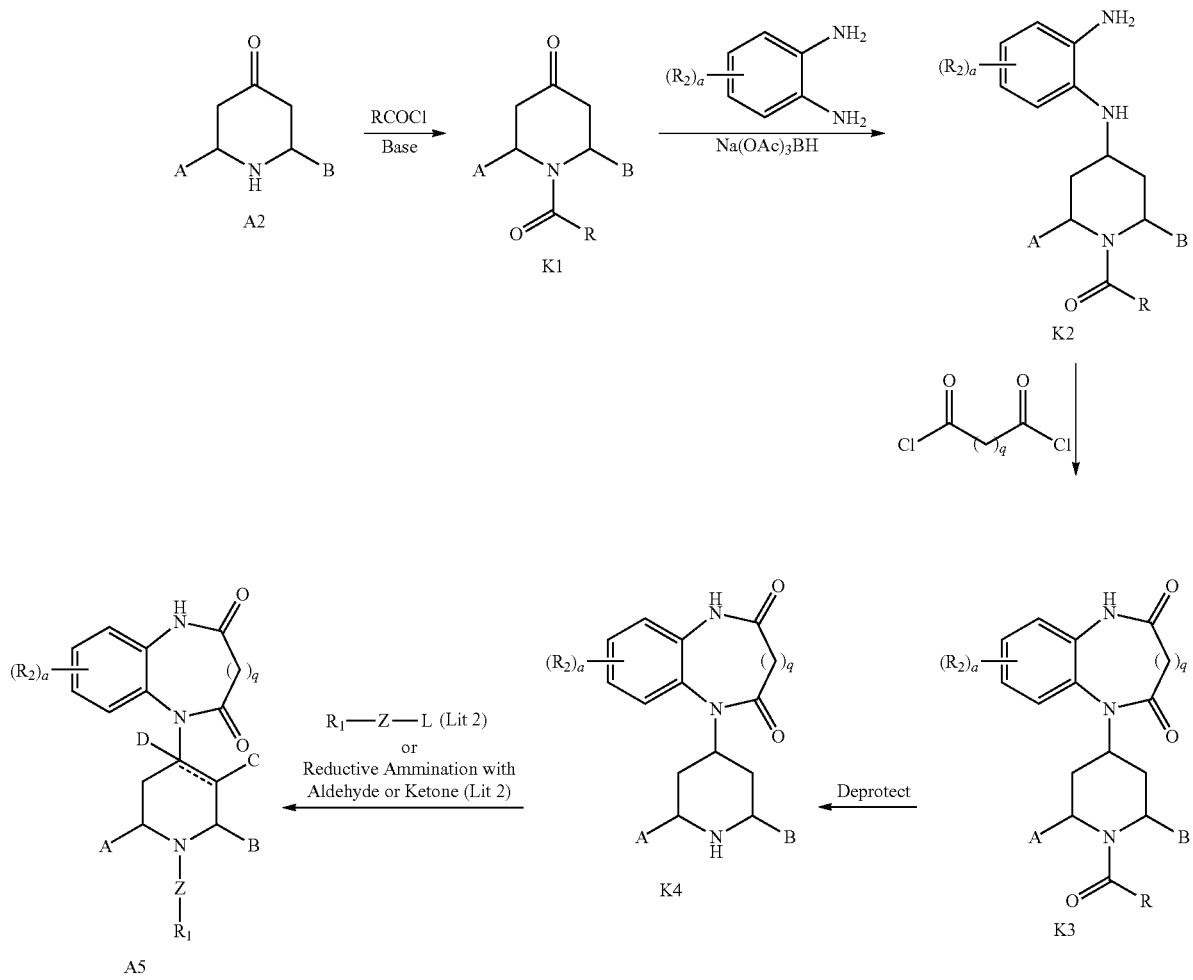

Scheme L

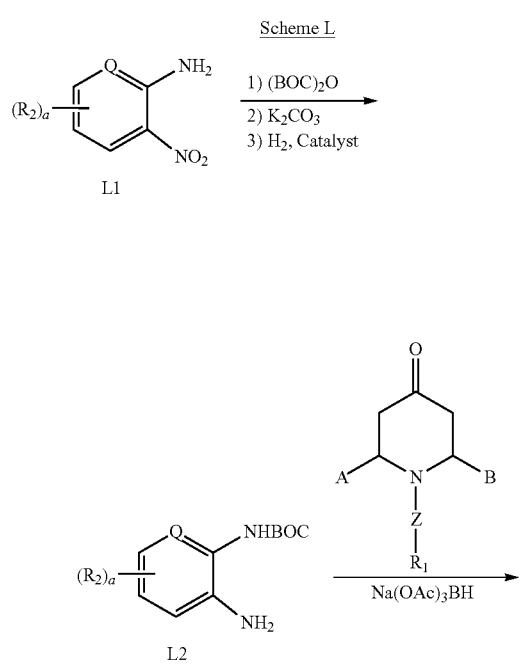

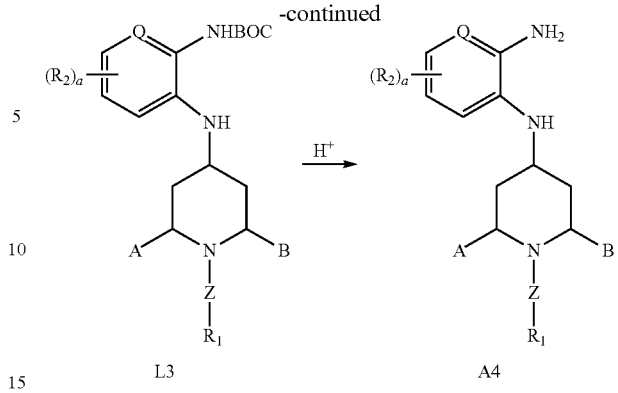

Compound L1 can be converted to compound L2 in a three step procedure as follows. Substituted pyridine compound L1 can be treated with di-tert-butyl-dicarbonate and 4-dimethylamino pyridine in a suitable solvent to provide a di-BOC protected intermediate. The intermediate can be treated with potassium carbonate to provide the mono-BOC protected intermediate which can be converted to compound L2 by hydrogenating using Raney nickel or other standard conditions (using palladium on carbon or the like). Compound L2 can be reductively aminated with a suitably functionalized 4-piperidone (containing a Z—$R_1$ group on the piperidine nitrogen and substituents A and B) using sodium triacetoxyborohydride and an acid such as acetic acid in a suitable solvent such as dichloromethane to provide compound L3. The BOC protecting group can be removed under acid conditions (for example, using hydrogen chloride in ethyl acetate) to provide compound A4.

Scheme M

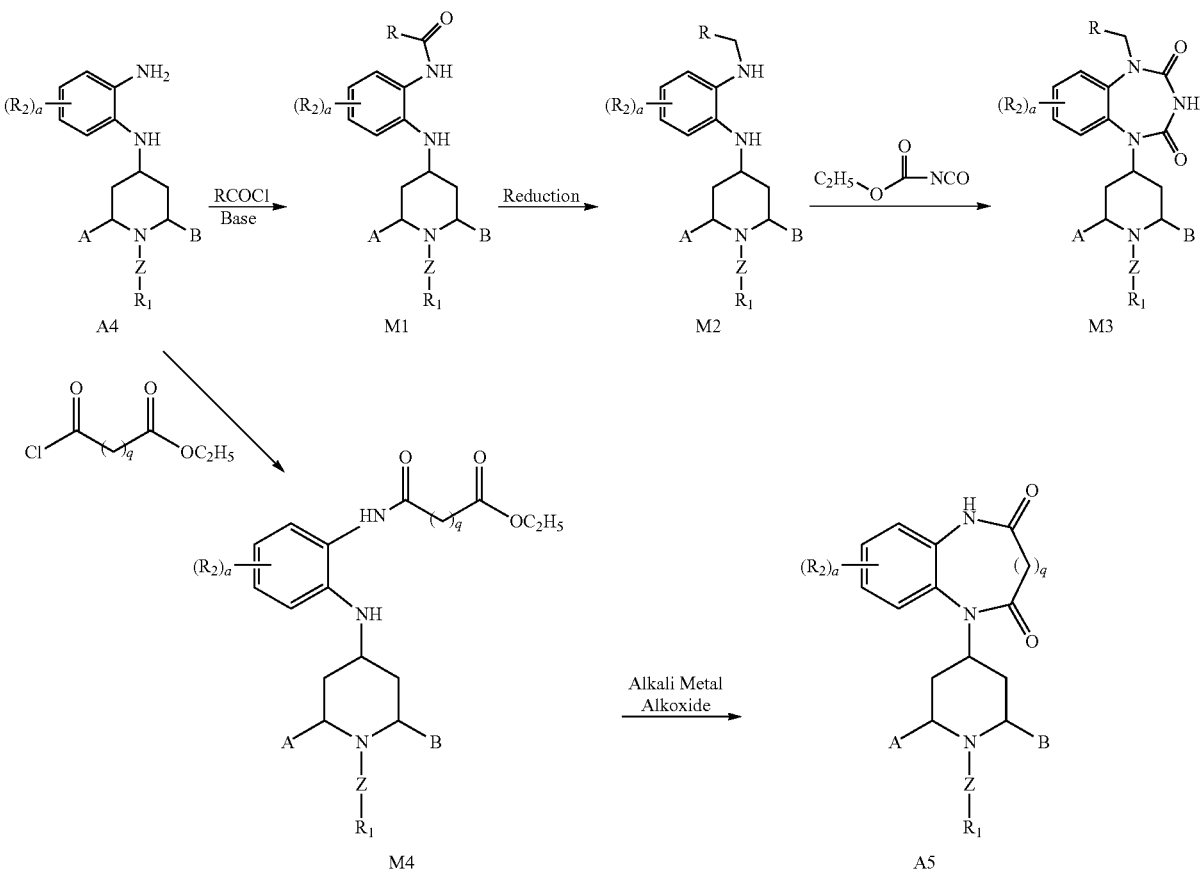

Compound A4 can be converted to the 4-methoxybenzoyl derivative compound M1 using 4-methoxy-benzoylchloride in a suitable solvent in the presence of an organic or inorganic base. Compound M1 can be reduced to compound M2, e.g., using lithium aluminum hydride. As described in Scheme D, compound M2 can be converted to compound M3 using ethoxycarbonyl isocyanate in a microwave reactor. Alternatively, compound A4 can be reacted with a cyclizing reagent, such as ethyl 2-chloro-2-oxoacetate or ethyl 3-chloro-3-oxo-propanoate, and a base such as triethylamine in a suitable solvent such as dichloromethane to provide compound M4. Compound M4 can be converted to compound A5 using an alkali metal alkoxide such as sodium ethoxide in a suitable solvent such as ethanol.

Scheme N
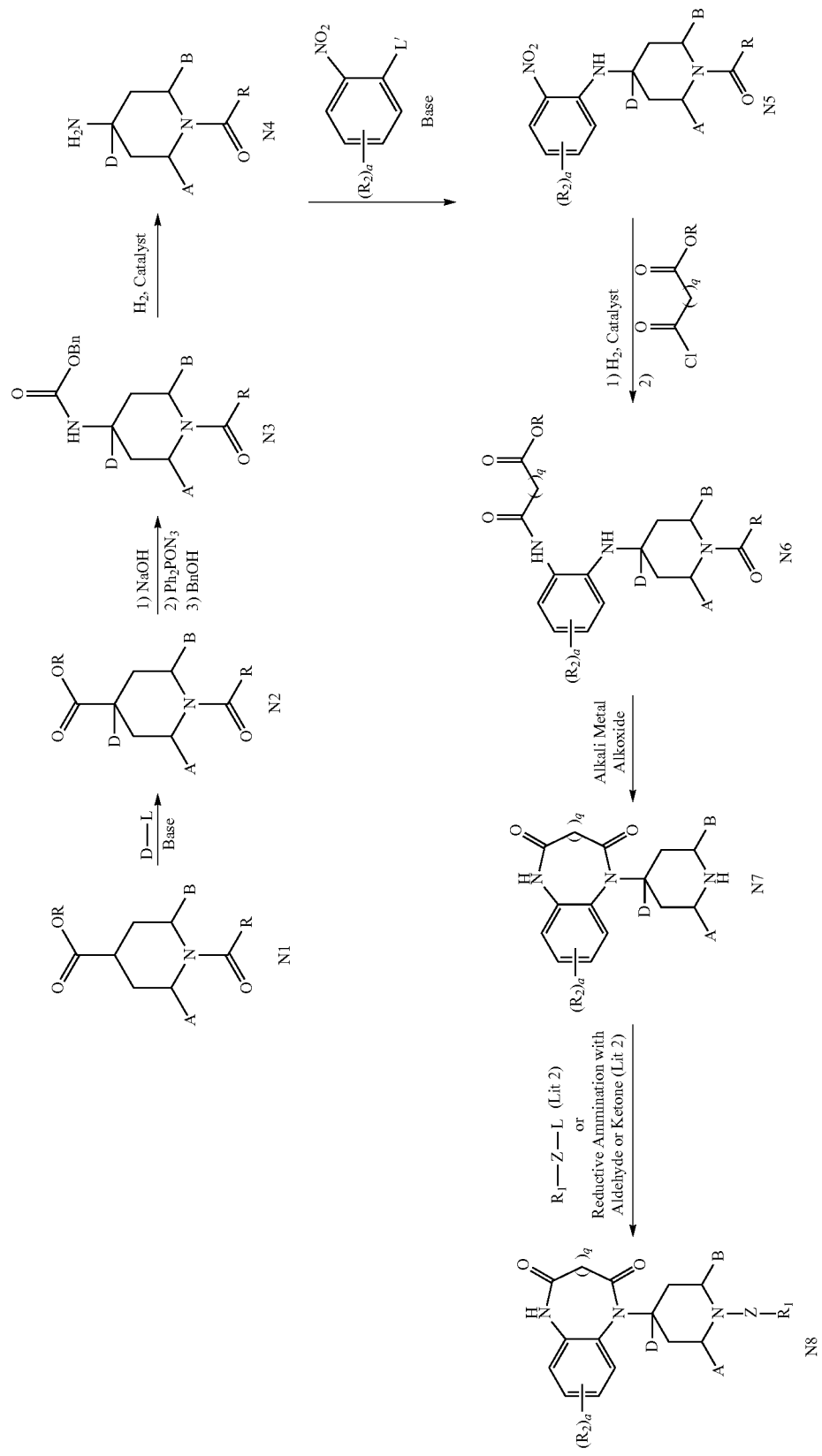

Compound N1 can be converted to compound N2 using lithium diisopropylamide in a suitable solvent such as tetrahydrofuran followed by treatment with a D having a leaving group substituent, e.g., iodomethane. Compound N2 can be converted to compound N3 in a two step procedure. First, the ester can be hydrolyzed to the carboxylic acid using an aqueous base such as sodium hydroxide. This can be followed by treatment with diphenylphosphoryl azide and benzyl alcohol under Curtius rearrangement conditions. The benzyloxycarbonyl group of compound N3 can be removed under hydrogenolysis conditions, e.g., using palladium on charcoal, to provide compound N4. Compound N4 can be converted to compound N5 by reaction with a substituted or unsubstituted 2-halo-1-nitrobenzene, such substituted or unsubstituted as 2-fluoro-1-nitrobenzene, in the presence of a base such as potassium carbonate in a suitable solvent such as acetonitrile. Compound N5 can be converted to compound N6 in a two step procedure. First, reduction of the nitro group can be carried out by hydrogenation using a metal catalyst such as Raney nickel in a suitable solvent such as ethanol. This can be followed by reaction with a cyclizing reagent, such as ethyl 2-chloro-2-oxoacetate or ethyl 3-chloro-3-oxopropanoate, and a base such as triethylamine and a suitable solvent such as dichloromethane. Compound N6 can be converted to compound N7 using an alkali metal alkoxide, such as sodium ethoxide, in a suitable solvent, such as ethanol, followed by removal of the protecting group R under standard conditions. The —Z—$R_1$ group can be attached to compound N7 as described in Scheme A, e.g., using either alkylation or reductive amination conditions, to provide compound N8.

Scheme O

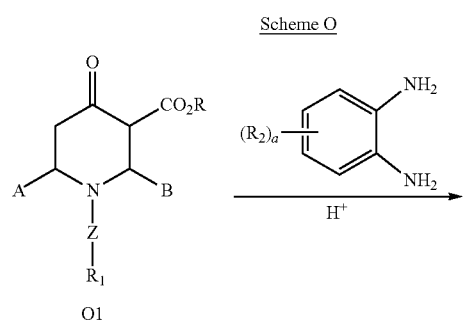

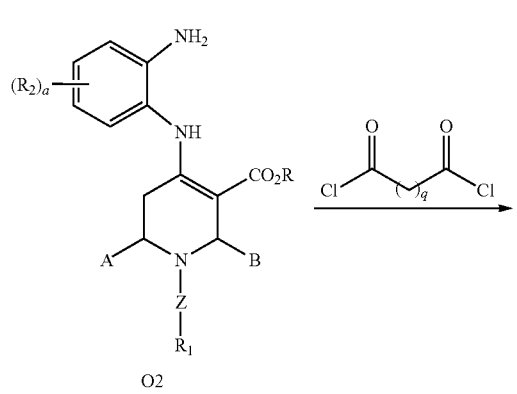

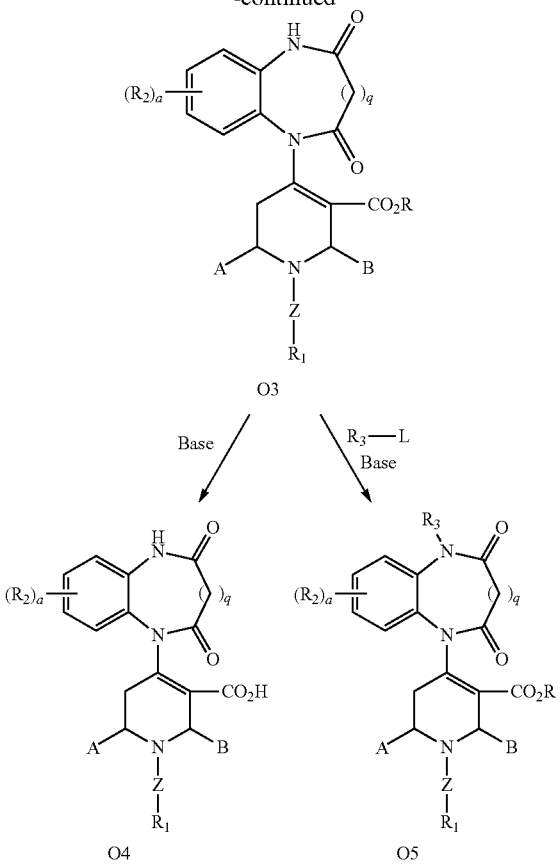

Compound O1 can be reacted with a substituted or unsubstituted 1,2-phenylenediamine and a catalytic amount of an acid such as acetic acid in a suitable solvent such as toluene with azeotropic water removal in a Dean-Stark apparatus to provide compound O2. Compound O2 can be cyclized to compound O3 by reaction with cyclizing reagent, such as a di-acid chloride, e.g., oxalyl dichloride or malonyl dichloride, in a suitable solvent such as dichloromethane under high dilution conditions. Compound O3 can be converted to compound O4 under basic conditions in a suitable solvent, e.g., by reaction with aqueous sodium hydroxide in ethanol. Alternatively, compound O3 can be alkylated with an $R_3$ group having a leaving group substituent, such as an alkyl bromide or alkyl chloride, using a suitable base such as sodium hydride in a suitable solvent such as DMF to provide compound O5.

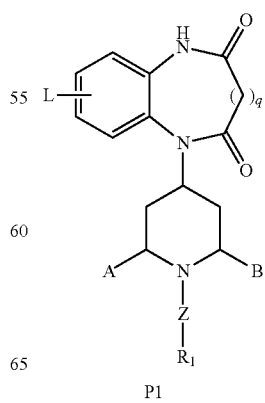

-continued

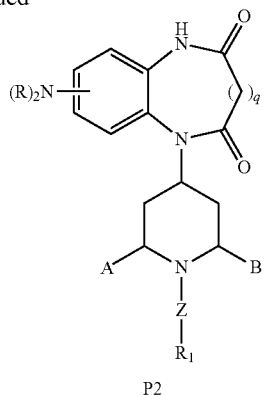

P2

Compound P1 can be converted to compound P2 using the desired amine under Buchwald-Hartwig palladium-catalyzed amination conditions, e.g., by adapting the procedure described in the publication J. Louie and J. F. Hartwig, *Tetrahedron Lett.* 36(21):3609-3612 (1995).

4.7 Therapeutic Uses of the Heterocyclic-Substituted Piperidine Compounds

In accordance with the invention, the Heterocyclic-Substituted Piperidine Compounds are administered to an animal in need of treatment or prevention of a Condition.

In one embodiment, an effective amount of a Heterocyclic-Substituted Piperidine Compound can be used to treat or prevent any condition treatable or preventable by inhibiting the activity of the ORL-1 receptor. Examples of conditions that are treatable or preventable by inhibiting the activity of the ORL-1 receptor include, but are not limited to, pain (CNS effect), memory disorders, obesity, constipation, depression, dementia, and Parkinsonism.

In another embodiment, an effective amount of a Heterocyclic-Substituted Piperidine Compound can be used to treat or prevent any condition treatable or preventable by activating the ORL-1 receptor. Examples of conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, and drug abuse.

The Heterocyclic-Substituted Piperidine Compounds can be used to treat or prevent acute or chronic pain. Examples of pain that can be treated or prevented using a Heterocyclic-Substituted Piperidine Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Heterocyclic-Substituted Piperidine Compounds can also be used to treat or prevent pain associated with inflammation or with an inflammatory disease in an animal. Such pain can arise where there is an inflammation of the body tissue which can be a local inflammatory response or a systemic inflammation. For example, a Heterocyclic-Substituted Piperidine Compound can be used to treat or prevent pain associated with inflammatory diseases including, but not limited to, organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalu-minuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. A Heterocyclic-Substituted Piperidine Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Heterocyclic-Substituted Piperidine Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Heterocyclic-Substituted Piperidine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

According to the invention, some of the Heterocyclic-Substituted Piperidine Compounds are agonists at the ORL-1 receptor, and some of the Heterocyclic-Substituted Piperidine Compounds are antagonists at the ORL-1 receptor. In another embodiment, a Heterocyclic-Substituted Piperidine Compound is an agonist at the ORL-1 receptor and an agonist at a μ, κ and/or δ opioid receptor, particularly at a μ opioid receptor. In another embodiment, a Heterocyclic-Substituted Piperidine Compound is an antagonist at the ORL-1 receptor and an agonist at a μ, κ and/or δ opioid receptor, particularly at a μ opioid receptor. In another embodiment, a Heterocyclic-Substituted Piperidine Compound is an agonist at the ORL-1 receptor and an antagonist at a μ, κ and/or δ opioid receptor, particularly at a μ opioid receptor. In another embodiment, a Heterocyclic-Substituted Piperidine Compound is an antagonist at the ORL-1 receptor and an antagonist at a μ, κ and/or δ opioid receptor, particularly at a μ opioid receptor.

The invention also provides methods for inhibiting ORL-1 receptor function in a cell, comprising contacting a cell capable of expressing the ORL-1 receptor with an amount of a Heterocyclic-Substituted Piperidine Compound effective to inhibit ORL-1 receptor function in the cell. This method can be adapted for use in vitro as part of an assay to select compounds that may be useful for treating or preventing a Condition in an animal. Alternatively, this method can be adapted for use in vivo, (i.e., in an animal such as a human) by contacting a cell in the animal with an effective amount of a Heterocyclic-Substituted Piperidine Compound. In one embodiment, the method is useful for treating or preventing pain in an animal in need of such treatment or prevention. In another embodiment, the method is useful for treating or preventing a memory disorder, obesity, constipation, depression, dementia, or Parkinsonism in an animal in need of such treatment or prevention.

The invention also relates to methods for activating ORL-1 receptor function in a cell, comprising contacting a cell capable of expressing the ORL-1 receptor with an amount of a Heterocyclic-Substituted Piperidine Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of a Heterocyclic-Substituted Piperidine compound. In one embodiment the method is useful for treating or preventing pain in an animal in need of such treatment or prevention. In another embodiment, the method is useful for treating or preventing anxiety, cough, diarrhea, high blood pressure, epilepsy, anorexia/cachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Y Shimohigashi et al., "Sensitivity of opioid receptor-like receptor ORL1 for chemical modification on nociceptin, a naturally occurring nociceptive peptide," *J Biol. Chem.* 271(39):23642-23645 (1996); M. Narita et al., "Identification of the G-protein coupled ORL1 receptor in the mouse spinal cord by [$^{35}$S]-GTPγS binding and immunohistochemistry," *Brit. J. Pharmacol.* 128:1300-1306 (1999); G. Milligan, "Principles: Extending then utility of [$^{35}$S]GTPγS binding assays," *TIPS* 14:87-90 (2003); and S. Lazareno, "Measurement of agonist-stimulated [$^{35}$S]GTPγS binding to cell membranes," *Methods in Molecular Biology* 106:231-245 (1999).

4.8 Therapeutic/Prophylactic Administration and Compositions of the Invention

Due to their activity, the Heterocyclic-Substituted Piperidine Compounds are advantageously useful in human and veterinary medicine. As described above, the Heterocyclic-Substituted Piperidine Compounds are useful for treating or preventing a Condition in an animal in need thereof. The Heterocyclic-Substituted Piperidine Compounds of the invention can be administered to any animal requiring modulation of the opioid and/or ORL-1 receptors.

When administered to an animal, a Heterocyclic-Substituted Piperidine Compound can be administered as a component of a composition that comprises a pharmaceutically acceptable carrier or excipient. The invention compositions, which comprise a Heterocyclic-Substituted Piperidine Compound, can be administered orally. A Heterocyclic-Substituted Piperidine Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Heterocyclic-Substituted Piperidine Compound.

Methods of administration include, but are not limited to, intradermal, intramuscular, intraperitoneal, parenteral, intravenous, subcutaneous, intranasal, epidural, oral, sublingual, intracerebral, intravaginal, transdermal, rectal, by inhalation, or topical, particularly to the ears, nose, eyes, or skin. The method of administration is left to the discretion of the practitioner. In most instances, administration will result in the release of a Heterocyclic-Substituted Piperidine Compound into the bloodstream.

In specific embodiments, it can be desirable to administer a Heterocyclic-Substituted Piperidine Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Heterocyclic-Substituted Piperidine Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Heterocyclic-Substituted Piperidine Compound can be formulated as a suppository, with traditional binders and excipients such as triglycerides.

When a Heterocyclic-Substituted Piperidine Compound of the invention is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A Heterocyclic-Substituted Piperidine Compound of the invention can also be in the form of a powder for reconstitution as an injectable formulation.

In another embodiment, a Heterocyclic-Substituted Piperidine Compound can be delivered in a vesicle, in particular a liposome (see Langer, Science 249:1527-1533 (1990); and Treat et al., *Liposomes in the Therapy of Infectious Disease and Cancer* 317-327 and 353-365 (1989)).

In yet another embodiment, a Heterocyclic-Substituted Piperidine Compound can be delivered in a controlled-release system or sustained-release system (see, e.g., Goodson, "Dental Applications" (pp. 115-138) in *Medical Applications of Controlled Release, Vol. 2, Applications and Evaluation*, R. S. Langer and D. L. Wise eds., CRC Press (1984)). Other controlled- or sustained-release systems discussed in the review by Langer, Science 249:1527-1533 (1990) can be used. In one embodiment, a pump can be used (Langer, Science 249:1527-1533 (1990); Sefton, CRC *Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Langer and Peppas, *J. Macromol Sci. Rev. MacromoL Chem.* C23:61 (1983); Levy et al., Science 228:190 (1985); During et al., *Ann. Neurol* 25:351 (1989); and Howard et al., *J. Neurosurg.* 71:105 (1989)). In yet another embodiment, a controlled- or sustained-release system can be placed in proximity of a target of a Heterocyclic-Substituted Piperidine Compound, e.g., the spinal column, brain, or gastrointestinal tract, thus requiring only a fraction of the systemic dose.

The invention compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Heterocyclic-Substituted Piperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

The invention compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Heterocyclic-Substituted Piperidine Compounds are formulated in accordance with routine procedures as a composition adapted for oral administration to human beings. A Heterocyclic-Substituted Piperidine Compound to be orally delivered can be in the form of tablets, capsules, gelcaps, caplets, lozenges, aqueous or oily solutions, suspensions, granules, powders, emulsions, syrups, or elixirs, for example. When a Heterocyclic-Substituted Piperidine Compound is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems*, (Lieberman, Rieger and Banker, eds.) published by Marcel Dekker, Inc.

When a Heterocyclic-Substituted Piperidine Compound is to be injected parenterally, it can be, e.g., in the form of an isotonic sterile solution. Alternatively, when a Heterocyclic-Substituted Piperidine Compound is to be inhaled, it can be formulated into a dry aerosol or can be formulated into an aqueous or partially aqueous solution.

An orally administered Heterocyclic-Substituted Piperidine Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Heterocyclic-Substituted Piperidine Compounds can be formulated for intravenous administration. Typically, compositions for intravenous administration comprise sterile isotonic aqueous buffer. Where necessary, the compositions can also include a solubilizing agent. A Heterocyclic-Substituted Piperidine Compound for intravenous administration can optionally include a local anesthetic such as benzocaine or prilocalne to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Heterocyclic-Substituted Piperidine Compound is to be administered by infusion, it can be dispensed, for example, with an infusion bottle containing sterile pharmaceutical grade water or saline. Where a Heterocyclic-Substituted Piperidine Compound is administered by injection, an ampule of sterile water for injection or saline can be provided so that the ingredients can be mixed prior to administration.

A Heterocyclic-Substituted Piperidine Compound can be administered by controlled-release or sustained-release means or by delivery devices that are known to those in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Heterocyclic-Substituted Piperidine Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Heterocyclic-Substituted Piperidine Compound, and can thus reduce the occurrence of adverse side effects.

Controlled- or sustained-release compositions can initially release an amount of a Heterocyclic-Substituted Piperidine Compound that promptly produces the desired therapeutic or prophylactic effect, and gradually and continually release other amounts of the Heterocyclic-Substituted Piperidine Compound to maintain this level of therapeutic or prophylactic effect over an extended period of time. To maintain a constant level of the Heterocyclic-Substituted Piperidine Compound in the body, the Heterocyclic-Substituted Piperidine Compound can be released from the dosage form at a rate that will replace the amount of Heterocyclic-Substituted Piperidine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Heterocyclic-Substituted Piperidine Compound that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Heterocyclic-Substituted Piperidine Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Heterocyclic-Substituted Piperidine Compound is administered, the effective dosage amounts correspond to the total amount administered.

Where a cell capable of expressing the ORL-1 receptor is contacted with a Heterocyclic-Substituted Piperidine Compound in vitro, the amount effective for inhibiting or activating the ORL-1 receptor function in a cell will typically range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Heterocyclic-Substituted Piperidine Compound will be from about 0.01 μL to about 1 mL. In another embodiment, the volume of solution or suspension will be about 200 μL.

The Heterocyclic-Substituted Piperidine Compounds will have a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

Typically, the Heterocyclic-Substituted Piperidine Compounds will have a $K_i$ (nM) of from about 300 to about 0.1 for binding to ORL-1 receptors. In one embodiment, the Heterocyclic-Substituted Piperidine Compounds will have a $K_i$ (nM) of from about 300 to about 100. In another embodiment, the Heterocyclic-Substituted Piperidine Compounds of the invention will have a $K_i$ (nM) of from about 100 to about 35. In another embodiment, the Heterocyclic-Substituted Piperidine Compounds of the invention will have a $K_i$ (nM) of from about 35 to about 20. In another embodiment, the Heterocyclic-Substituted Piperidine Compounds of the invention will have a $K_i$ (nM) of from about 20 to about 15. In another embodiment, the Heterocyclic-Substituted Piperidine Compounds of the invention will have a $K_i$ (nM) of from about 15 to about 10. In another embodiment, the Heterocyclic-Substituted Piperidine Compounds of the invention will have a $K_i$ (nM) of from about 10 to about 4. In another embodiment, the Heterocyclic-Substituted Piperidine Compounds of the invention will have a $K_i$ (nM) of from about 4 to about 1. In another embodiment, the Heterocyclic-Substituted Piperidine Compounds of the invention will have a $K_i$ (nM) of from about 1 to about 0.4. In another embodiment, the Heterocyclic-Substituted Piperidine Compounds of the invention will have a $K_i$ (nM) of from about 0.4 to about 0.1 or less.

ORL-1 GTP $EC_{50}$ is the concentration of a compound providing 50% of the maximal response for the compound at an ORL-1 receptor. Heterocyclic-Substituted Piperidine Compounds typically will have an ORL-1 GTP $EC_{50}$ (nM) of from about 5000 to about 0.1 to stimulate ORL-1 receptor function. In one embodiment, the Heterocyclic-Substituted Piperidine Compounds of the invention will have an ORL-1 GTP $EC_{50}$ (nM) of from about 5000 to about 1000. In another embodiment, the Heterocyclic-Substituted Piperidine Compounds of the invention will have an ORL-1 GTP $EC_{50}$ (nM) of from about 1000 to about 100. In another embodiment, the Heterocyclic-Substituted Piperidine Compounds of the invention will have an ORL-1 GTP $EC_{50}$ (nM) of from about 100 to about 80. In another embodiment, the Heterocyclic-Substituted Piperidine Compounds of the invention will have an ORL-1 GTP $EC_{50}$ (nM) of from about 80 to about 50. In another embodiment, the Heterocyclic-Substituted Piperidine Compounds of the invention will have an ORL-1 GTP $EC_{50}$ (nM) of from about 50 to about 35. In another embodiment, the Heterocyclic-Substituted Piperidine Compounds of the invention will have an ORL-1 GTP $EC_{50}$ (nM) of from about 35 to about 15. In another embodiment, the Heterocyclic-Substituted Piperidine Compounds of the invention will have an ORL-1 GTP $EC_{50}$ (nM) of from about 15 to about 10. In another embodiment, the Heterocyclic-Substituted Piperidine Compounds will have an ORL-1 GTP $EC_{50}$ (nM) of from about 10 to about 4. In another embodiment, the Heterocyclic-Substituted Piperidine Compounds will have an ORL-1 GTP $EC_{50}$ (nM) of from about 4 to about 1. In another embodiment, the Heterocyclic-Substituted Piperidine Compounds will have an ORL-1 GTP $EC_{50}$ (nM) of from about 1 to about 0.4. In another embodiment, the Heterocyclic-Substituted Piperidine Compounds will have an ORL-1 GTP $EC_{50}$ (nM) of from about 0.4 to about 0.1 or less.

ORL-1 GTP Emax (%) is the maximal effect elicited by a compound relative to the effect elicited by nociceptin, a standard ORL-1 agonist. Typically, the Heterocyclic-Substituted Piperidine Compounds of the invention will have an ORL-1 GTP Emax (%) of from about 50% to about 110%. In one embodiment, the Heterocyclic-Substituted Piperidine Compound Heterocyclic-Substituted Piperidine Compounds will have an ORL-1 GTP Emax (%) of from about 50% to about 75%. In another embodiment, the Heterocyclic-Substituted Piperidine Compounds will have an ORL-1 GTP Emax (%) of from about 75% to about 85%. In another embodiment, the Heterocyclic-Substituted Piperidine Compounds will have an ORL-1 GTP Emax (%) of from about 85% to about 95%. In another embodiment, the Heterocyclic-Substituted Piperidine Compounds will have an ORL-1 GTP Emax (%) of from about 95% to about 100%. In another embodiment, the Heterocyclic-Substituted Piperidine Compounds will have an ORL-1 GTP Emax (%) of from about 100 to about 110% or greater.

Where a cell capable of expressing the μ-opioid receptors is contacted with a Heterocyclic-Substituted Piperidine Compound in vitro, the amount effective for inhibiting or activating the α-opioid receptors function in a cell will typically range from about 10-12 mol/L to about 10-4 mol/L, in one embodiment, from about 10-12 mol/L to about 10-5 mol/L, in another embodiment, from about 10-12 mol/L to about 10-6 mol/L, and in another embodiment, from about 10-12 mol/L to about 10-9 mol/L of a solution or suspension of a pharmaceutically acceptable carrier or excipient. In one embodiment, the volume of solution or suspension comprising the Heterocyclic-Substituted Piperidine Compound will be from about 0.01 μL to about 1 mL. In another embodiment, the volume of solution or suspension will be about 200 μL.

The Heterocyclic-Substituted Piperidine Compounds will have a binding affinity ($K_i$) for the human μ-opioid receptors of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

Generally, the lower the $K_i$ value, the more effective the Heterocyclic-Substituted Piperidine Compounds will be at treating a Condition such as pain or diarrhea. Typically, the Heterocyclic-Substituted Piperidine Compounds will have a $K_i$ (nM) of from about 3000 to about 0.1 for binding to μ-opioid receptors. In one embodiment, the Heterocyclic-Substituted Piperidine Compounds will have a $K_i$ (nM) of from about 3000 to about 1000. In another embodiment, the Heterocyclic-Substituted Piperidine Compounds of the invention will have a $K_i$ (nM) of from about 1000 to about 650. In another embodiment, the Heterocyclic-Substituted Piperidine Compounds of the invention will have a $K_i$ (nM) of from about 650 to about 525. In another embodiment, the Heterocyclic-Substituted Piperidine Compounds of the invention will have a $K_i$ (nM) of from about 525 to about 250. In another embodiment, the Heterocyclic-Substituted Piperidine Compounds of the invention will have a $K_i$ (nM) of from about 250 to about 100. In another embodiment, the Heterocyclic-Substituted Piperidine Compounds of the invention will have a $K_i$ (nM) of from about 100 to about 10. In another embodiment, the Heterocyclic-Substituted Piperidine Compounds of the invention will have a $K_i$ (nM) of from about 10 to about 1. In another embodiment, the Heterocyclic-Substituted Piperidine Compounds of the invention will have a $K_i$ (nM) of from about 1 to about 0.1 or less.

μ GTP $EC_{50}$ is the concentration of a compound providing 50% of the maximal response for the compound at a μ-opioid receptor. Heterocyclic-Substituted Piperidine Compounds typically will have a μ GTP $EC_{50}$ (nM) of from about 5000 to about 0.1 to stimulate μ-opioid receptor function. In one embodiment, the Heterocyclic-Substituted Piperidine Compounds of the invention will have a μ GTP $EC_{50}$ (nM) of from about 5000 to about 4100. In another embodiment, the Heterocyclic-Substituted Piperidine Compounds of the invention will have a μ GTP $EC_{50}$ (nM) of from about 4100 to about 3100. In another embodiment, the Heterocyclic-Substituted Piperidine Compounds of the invention will have a μ GTP $EC_{50}$ (nM) of from about 3100 to about 2000. In another embodiment, the Heterocyclic-Substituted Piperidine Compounds of the invention will have a μ GTP $EC_{50}$ (nM) of from about 2000 to about 1000. In another embodiment, the Heterocyclic-Substituted Piperidine Compounds of the invention will have a μ GTP $EC_{50}$ (nM) of from about 1000 to about 100. In another embodiment, the Heterocyclic-Substituted Piperidine Compounds of the invention will have a μ GTP $EC_{50}$ (nM) of from about 100 to about 10. In another embodiment, the Heterocyclic-Substituted Piperidine Compounds will have a μ GTP $EC_{50}$ (nM) of from about 10 to about 1. In another embodiment, the Heterocyclic-Substituted Piperidine Compounds will have a μ GTP $EC_{50}$ (nM) of from about 1 to about 0.4. In another embodiment, the Heterocyclic-Substituted Piperidine Compounds will have a μ GTP $EC_{50}$ (nM) of from about 0.4 to about 0.1 or less.

μ GTP Emax (%) is the maximal effect elicited by a compound relative to the effect elicited by DAMGO, a standard agonist. Generally, the μ GTP Emax (%) value measures the efficacy of a compound to treat or prevent a Condition such as pain or diarrhea. Typically, the Heterocyclic-Substituted Piperidine Compounds of the invention will have a μ GTP Emax (%) of from about 10% to about 100%. In one embodiment, the Heterocyclic-Substituted Piperidine Compounds will have a μ GTP Emax (%) of from about 10% to about 20%. In another embodiment, the Heterocyclic-Substituted Piperidine Compounds will have a μ GTP Emax (%) of from about 20 to about 50%. In another embodiment, the Heterocyclic-Substituted Piperidine Compounds will have a μ GTP Emax (%) of from about 50 to about 65%. In another embodiment, the Heterocyclic-Substituted Piperidine Compounds will have a μ GTP Emax (%) of from about 65% to about 75%. In another embodiment, the Heterocyclic-Substituted Piperidine Compounds will have a μ GTP Emax (%) of from about 75% to about 88%. In another embodiment, the Heterocyclic-Substituted Piperidine Compounds will have a μ GTP Emax (%) of from about 88% to about 100% or greater.

Typically, the Heterocyclic-Substituted Piperidine Compounds will have a $K_i$ (nM) of from about 10,000 to about 10 for κ receptors. In one embodiment, the Heterocyclic-Substituted Piperidine Compounds will have no activity. In another embodiment, the Heterocyclic-Substituted Piperidine Compounds will have a $K_i$ (nM) of from about 10,000 to about 5000. In another embodiment, the Heterocyclic-Substituted Piperidine Compounds will have a $K_i$ (nM) of from about 5000 to about 1000. In another embodiment, the Heterocyclic-Substituted Piperidine Compounds will have a $K_i$ (nM) of from about 1000 to about 500. In another embodiment, the Heterocyclic-Substituted Piperidine Compounds will have a $K_i$ (nM) of from about 500 to about 300. In another embodiment, the Heterocyclic-Substituted Piperidine Compounds will have a $K_i$ (nM) of from about 300 to about 100. In another embodiment, the Heterocyclic-Substituted Piperidine Compounds will have a $K_i$ (nM) of from about 100 to about 50. In another embodiment, the Heterocyclic-Substituted Piperidine Compounds will have a $K_i$ (nM) of from about 50 to about 20. In another embodiment, the Heterocyclic-Substituted Piperidine Compounds will have a $K_i$ (nM) of from about 20 to about 15. In another embodiment, the Heterocyclic-Substituted Piperidine Compounds will have a $K_i$ (nM) of from about 15 to about 10 or less.

κ GTP $EC_{50}$ is the concentration of a compound providing 50% of the maximal response for the compound at a κ receptor. Heterocyclic-Substituted Piperidine Compounds typically will have a κ GTP $EC_{50}$ (nM) of from about 10,000 to about 10 to stimulate κ opioid receptor function. In one embodiment, the Heterocyclic-Substituted Piperidine Compounds will have a κ GTP $EC_{50}$ (nM) of from about 10,000 to about 5000. In another embodiment, the Heterocyclic-Substituted Piperidine Compounds will have a κ GTP $EC_{50}$ (nM) of from about 5000 to about 2000. In another embodiment, the Heterocyclic-Substituted Piperidine Compounds will have a κ GTP $EC_{50}$ (nM) of from about 2000 to about 1500. In another embodiment, the Heterocyclic-Substituted Piperidine Compounds will have a κ GTP $EC_{50}$ (nM) of from about 1500 to about 800. In another embodiment, the Heterocyclic-Substituted Piperidine Compounds will have a κ GTP $EC_{50}$ (nM) of from about 800 to about 500. In another embodiment, the Heterocyclic-Substituted Piperidine Compounds will have a κ GTP $EC_{50}$ (nM) of from about 500 to about 300. In another embodiment, the Heterocyclic-Substituted Piperidine Compounds will have a κ GTP $EC_{50}$ (nM) of from about 300 to about 100. In another embodiment, the Heterocyclic-Substituted Piperidine Compounds will have a κ GTP $EC_{50}$ (nM) of from about 100 to about 50. In another embodiment, the Heterocyclic-Substituted Piperidine Compounds will have a κ GTP $EC_{50}$ (nM) of from about 50 to about 25. In another embodiment, the Heterocyclic-Substituted Piperidine Compounds will have a κ GTP $EC_{50}$ (nM) of from about 25 to about 10 or less.

κ GTP Emax (%) is the maximal effect elicited by a compound relative to the effect elicited by U.S. Pat. No. 69,593. Typically, the Heterocyclic-Substituted Piperidine Compounds of the invention will have a κ GTP Emax (%) of from about 15% to about 100%. In one embodiment, the Heterocyclic-Substituted Piperidine Compounds will have a κ GTP Emax (%) of from about 15% to about 30%. In another embodiment, the Heterocyclic-Substituted Piperidine Compounds will have a κ GTP Emax (%) of from about 30 to about 40%. In another embodiment, the Heterocyclic-Substituted Piperidine Compounds will have a κ GTP Emax (%) of from about 40 to about 45%. In another embodiment, the Heterocyclic-Substituted Piperidine Compounds will have a κ GTP Emax (%) of from about 45% to about 75%. In another embodiment, the Heterocyclic-Substituted Piperidine Compounds will have a κ GTP Emax (%) of from about 75% to about 90%. In another embodiment, the Heterocyclic-Substituted Piperidine Compounds will have a κ GTP Emax (%) of from about 90% to about 100% or greater.

Typically, the Heterocyclic-Substituted Piperidine Compounds will have a $K_i$ (nM) of from about 10,000 to about 10 for δ receptors. In one embodiment, the Heterocyclic-Substituted Piperidine Compounds will have no activity. In another embodiment, the Heterocyclic-Substituted Piperidine Compounds will have a $K_i$ (nM) of from about 10,000 to about 9000. In another embodiment, the Heterocyclic-Substituted Piperidine Compounds will have a $K_i$ (nM) of from about 9000 to about 7500. In another embodiment, the Heterocyclic-Substituted Piperidine Compounds will have a $K_i$ (nM) of from about 7500 to about 6500. In another embodiment, the Heterocyclic-Substituted Piperidine Compounds will have a $K_i$ (nM) of from about 6500 to about 5000. In another embodiment, the Heterocyclic-Substituted Piperidine Compounds will have a $K_i$ (nM) of from about 5000 to about 3000. In another embodiment, the Heterocyclic-Substituted Piperidine Compounds will have a $K_i$ (nM) of from about 3000 to about 2500. In another embodiment, the Heterocyclic-Substituted Piperidine Compounds will have a $K_i$ (nM) of from about 2500 to about 1000. In another embodiment, the Heterocyclic-Substituted Piperidine Compounds will have a $K_i$ (nM) of from about 1000 to about 500. In another embodiment, the Heterocyclic-Substituted Piperidine Compounds will have a $K_i$ (nM) of from about 500 to about 350. In another embodiment, the Heterocyclic-Substituted Piperidine Compounds will have a $K_i$ (nM) of from about 350 to about 250. In another embodiment, the Heterocyclic-Substituted Piperidine Compounds will have a $K_i$ (nM) of from about 250 to about 100. In another embodiment, the Heterocyclic-Substituted Piperidine Compounds will have a $K_i$ (nM) of from about 100 to about 10 or less.

δ GTP $EC_{50}$ is the concentration of a compound providing 50% of the maximal response for the compound at a δ receptor. Heterocyclic-Substituted Piperidine Compounds typically will have a δ GTP $EC_{50}$ (nM) of from about 10,000 to about 10 to stimulate δ opioid receptor function. In one embodiment, the Heterocyclic-Substituted Piperidine Compounds will have a δ GTP $EC_{50}$ (nM) of from about 10,000 to about 1000. In another embodiment, the Heterocyclic-Substituted Piperidine Compounds will have a δ GTP $EC_{50}$ (nM) of from about 1000 to about 100. In another embodiment, the Heterocyclic-Substituted Piperidine Compounds will have a δ GTP $EC_{50}$ (nM) of from about 100 to about 90. In another embodiment, the Heterocyclic-Substituted Piperidine Compounds will have a GTP $EC_{50}$ (nM) of from about 90 to about 50. In another embodiment, the Heterocyclic-Substituted Piperidine Compounds will have a δ GTP $EC_{50}$ (nM) of from about 50 to about 25. In another embodiment, the Heterocyclic-Substituted Piperidine Compounds will have a δ GTP $EC_{50}$ (nM) of from about 25 to about 10 or less.

δ GTP Emax (%) is the maximal effect elicited by a compound relative to the effect elicited by met-enkephalin. Typically, the Heterocyclic-Substituted Piperidine Compounds of the invention will have a δ GTP Emax (%) of from about 10% to about 110%. In one embodiment, the Heterocyclic-Substituted Piperidine Compounds will have a δ GTP Emax (%) of from about 10% to about 30%. In another embodiment, the Heterocyclic-Substituted Piperidine Compounds will have a δ GTP Emax (%) of from about 30% to about 50%. In another embodiment, the Heterocyclic-Substituted Piperidine Compounds will have a δ GTP Emax (%) of from about 50% to about 75%. In another embodiment, the Heterocyclic-Substituted Piperidine Compounds will have a δ GTP Emax (%) of from about 75% to about 90%. In another embodiment, the Heterocyclic-Substituted Piperidine Compounds will have a δ GTP Emax (%) of from about 90% to about 100%. In another embodiment, the Heterocyclic-Substituted Piperidine Compounds will have a δ GTP Emax (%) of from about 100% to about 110% or greater.

The Heterocyclic-Substituted Piperidine Compounds can be assayed in vitro or in vivo for the desired therapeutic or prophylactic activity prior to use in humans. Animal model systems can be used to demonstrate safety and efficacy.

The invention methods for treating or preventing a Condition in an animal in need thereof can further comprise co-administering to the animal being administered a Heterocyclic-Substituted Piperidine Compound (i.e., a first therapeutic agent) a second therapeutic agent. In one embodiment, the second therapeutic agent is administered in an effective amount.

An effective amount of the second therapeutic agent will be known to the art depending on the agent. However, it is well within the skilled artisan's purview to determine the second therapeutic agent's optimal effective-amount range. In one embodiment of the invention, where a second therapeutic agent is administered to an animal for treatment of a Condition (e.g., pain), the minimal effective amount of the Heterocyclic-Substituted Piperidine Compound will be less than its minimal effective amount would be where the second therapeutic agent is not administered. In this embodiment, the Heterocyclic-Substituted Piperidine Compound and the second therapeutic agent can act synergistically to treat or prevent a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a Ca2+-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout, in Goodman & Gilman's The Pharmacological Basis of Therapeutics* 617-57 (Perry B. Molinhoff and Raymond W. Ruddon eds., 9$^{th}$ ed 1996); and Glen R. Hanson, *Analgesic, Antipyretic and Anti-Inflammatory Drugs in Remington: The Science and Practice of Pharmacy Vol II* 1196-1221 (A. R. Gennaro ed. 19$^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A Heterocyclic-Substituted Piperidine Compound and the second therapeutic agent combined can act either additively or synergistically to treat the same condition, or they may act independently of each other such that the Heterocyclic-Substituted Piperidine Compound treats or prevents a first Condition and the second therapeutic agent treats or prevents a second Condition. In one embodiment, a Heterocyclic-Substituted Piperidine Compound is administered concurrently with a second therapeutic agent as a single composition comprising an effective amount of a Heterocyclic-Substituted Piperidine Compound and an effective amount of the second therapeutic agent. Alternatively, a composition comprising an effective amount of a Heterocyclic-Substituted Piperidine Compound and a second composition comprising an effective amount of the second therapeutic agent are concurrently administered. In another embodiment, an effective amount of a Heterocyclic-Substituted Piperidine Compound is administered prior or subsequent to administration of an effective amount of the second therapeutic agent. In this embodiment, the Heterocyclic-Substituted Piperidine Compound is administered while the second therapeutic agent exerts its therapeutic effect, or the second therapeutic agent is administered while the Heterocyclic-Substituted Piperidine Compound exerts its therapeutic effect for treating or preventing a Condition.

A composition of the invention is prepared by a method comprising admixing a Heterocyclic-Substituted Piperidine Compound or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the Heterocyclic-Substituted Piperidine Compound is present in the composition in an effective amount.

4.9 Kits

The invention further provides kits that can simplify the handling and administration of a Heterocyclic-Substituted Piperidine Compound to an animal.

A typical kit of the invention comprises a unit dosage form of a Heterocyclic-Substituted Piperidine Compound. In one embodiment, the unit dosage form comprises a first container, which can be sterile, containing an effective amount of a Heterocyclic-Substituted Piperidine Compound and a pharmaceutically acceptable carrier or excipient. The kit can further comprise a label or printed instructions instructing the use of the Heterocyclic-Substituted Piperidine Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Heterocyclic-Substituted Piperidine Compound, an effective amount of a second therapeutic agent and a pharmaceutically acceptable carrier or excipient. Examples of second therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

The following examples illustrate various aspects of the invention, and are not to be construed to limit the claims in any manner whatsoever.

5.1 Example 1

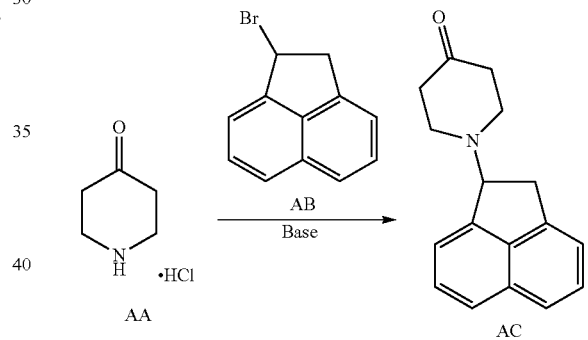

7-Bromo-acenaphthalene (AB) was prepared according to a literature method known to those in the art (Bachmann et al., "Synthesis of 4,4-Methylenephenanthrene," J.A.C.S. 63:204-206 (1941)). The compound of formula AB was added to 20 mL of acetonitrile. Thereafter, the mixture was added, in one portion, to a 100 mL solution of the compound of formula AA, piperidine-4-one (1.20 g, 7.8 mmol, Sigma-Aldrich, St. Louis, Mo.), and DIEA (4.1 mL, 23.4 mmol, Sigma-Aldrich). This mixture was heated to reflux for 48 h, cooled to about 25° C., and adsorbed onto silica gel to provide residues that were chromatographed with a silica gel column eluted with a gradient of from 100%:0% EtOAc:MeOH to 0%:100% EtOAc:MeOH(COMBIFLASH, Teledyne Isco, Inc., Lincoln, Nebr.). The product fractions were combined and concentrated to dryness under reduced pressure to provide 1.31 g of the compound of formula AC, determined to be about 90% pure by liquid chromatography/mass spectrometry ("LC/MS") (yield 44.3%).

The identity of the compound of formula AC, 1-(1,2-dihydroacenaphthylen-1-yl)piperidin-4-one, was confirmed using $^1$H NMR and LC/MS.

Compound AC: $^1$H NMR: $\delta_H$ (400 MHz, MeOD): 7.68 (2H, m), 7.47 (4H, m), 5.04 (1H, m), 3.39 (2H, m), 2.86 (2H, m), 2.70 (2H, m), 2.45 (4H, m); LC/MS (90.1%, $t_r$=2.434 min), m/z=252.2 [M+H]$^+$ (Calc: 251.3).

Example 2

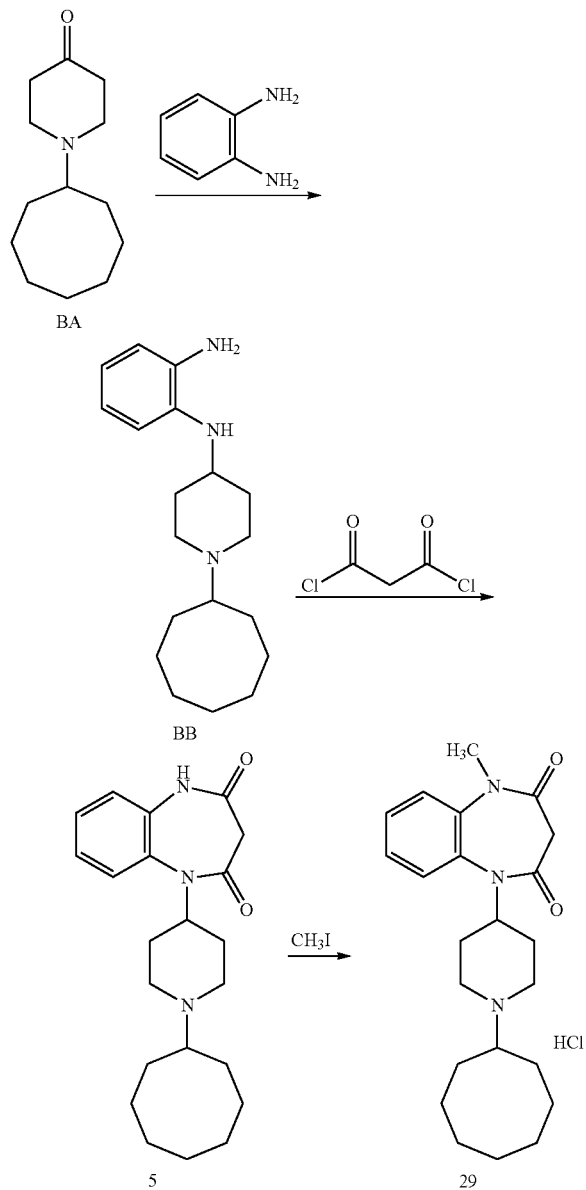

1-Cyclooctylpiperidin-4-one (compound of formula BA) was purchased from Vasudha Pharma Chem LTD (Hyderabad, Andhra Pradesh, India).

The compound of formula BA (10.00 g, 48.0 mmol) and o-phenylenediamine (10.38 g, 96.0 mmol, Sigma-Aldrich) were suspended in 200 mL of methylene chloride. To this mixture, sodium triacetoxyborohydride (NaBH(OAc)$_3$, 30.42 g, 144.0 mmol, Acros Organics, Geel, Belgium) and acetic acid (10 mL) were added. These ingredients were stirred at a temperature of about 25° C. for 24 h after which the reaction mixture was extracted 10 times with about 200 mL of water each time. The organic layer was dried (MgSO$_4$), filtered, and concentrated to dryness under reduced pressure to provide 9.48 g of a compound of formula BB as a light orange oil (yield 65.6%).

The identity of the compound of formula BB, N$^1$-(1-cyclooctylpiperidin-4-yl)benzene-1,2-diamine, was confirmed using LC/MS.

Compound BB: LC/MS (95%, $t_r$=1.832 min), m/z=301.1 [M+H]$^+$ (Calc: 302.2).

The compound of formula BB (14.40 g, 47.84 mmol) was added to 100 mL of dry DCE. This mixture was added dropwise to a solution of malonyl dichloride (10.1 g, 71.77 mmol, Sigma-Aldrich) in 200 mL of dry DCE. The resulting mixture was magnetically stirred under an argon atmosphere at a temperature of about 25° C. for 1 h. The mixture was then warmed to 60° C. for 10 h. The mixture was then cooled to a temperature of about 25° C. and the solvent was removed under reduced pressure. The remaining material was added to 300 mL of methanol and adsorbed onto silica gel to provide residues that were chromatographed with a silica gel column eluted with a gradient of from 100%:0% EtOAc:MeOH to 0%:100% EtOAc:MeOH. The product fractions were combined and concentrated to dryness under reduced pressure to provide 10.0 g of Heterocyclic-Substituted Piperidine Compound 5 as a light orange solid (yield 58%).

The identity of Heterocyclic-Substituted Piperidine Compound 5, 1-(1-cyclooctylpiperidin-4-yl)-1H-benzo[b][1,4]diazepine-2,4(3H,5H)-dione, was confirmed using $^1$H NMR and LC/MS.

Heterocyclic-Substituted Piperidine Compound 5: $^1$H NMR: $\delta_H$ (400 MHz, MeOD): 7.43 (1H, m), 7.26 (2H, m), 7.14 (1H, m), 4.17 (1H, m), 3.37 (4H, m), 3.10-2.99 (3H, m), 2.69 (2H, m), 2.02 (2H, m), 1.87-1.46 (14H, m); LC/MS (100%, $t_r$=4.944 m/z=370.4 [M+H]$^+$ (Calc: 369.5).

Heterocyclic-Substituted Piperidine Compound 5 (1 g) was added to 20 mL of methanol. To this was added 1 eg of 4M HCl in 1,4-dioxane. The solvent was removed under reduced pressure and the resulting solid was triturated, washed with methanol, and filtered. This material was dried under reduced pressure to provide 0.55 g of the hydrochloride of Heterocyclic-Substituted Piperidine Compound 5 (yield 50%).

Heterocyclic-Substituted Piperidine Compound 5 (60 mg, 0.163 mmol) and K$_2$CO$_3$ (45 mg, 0.036 mmol) were added to 2 mL DMF at a temperature of about 25° C. To this was added methyl iodide (20 µL, 0.32 mmol, TCI America, Portland, Oreg.) and the mixture was stirred for 16 h at a temperature of about 25° C. Thereafter, water was added to the mixture which was then extracted with EtOAc. The organic layer was washed with water, dried (Na$_2$SO$_4$), filtered, and concentrated to dryness under reduced pressure. The residue was chromatographed with a silica gel column eluted with a gradient of from 100%:0% chloroform:MeOH to 10%:90% chloroform:MeOH and the product fractions were combined and concentrated to dryness under reduced pressure. The residue was added to 1 mL of EtOAc. To this was added 0.5 mL of 4M HCl in EtOAc. The mixture was concentrated to dryness under reduced pressure and the resulting solid triturated with 10:1 EtOAc:MeOH and filtered. The residue was concentrated to dryness under reduced pressure to provide 9.8 mg of the hydrochloride of Heterocyclic-Substituted Piperidine Compound 29 (yield 14.3%).

The identity of Heterocyclic-Substituted Piperidine Compound 29, 1-(1-cyclooctylpiperidin-4-yl)-5-methyl-1H-benzo[b][1,4]diazepine-2,4(3H,5H)-dione, was confirmed using $^1$H NMR and LC/MS.

Heterocyclic-Substituted Piperidine Compound 29: $^1$H NMR: $\delta_H$ (400 MHz, DMSO-d$_6$): 9.74 (1H, brs), 7.55 (2H, m), 7.41 (1H, m), 7.35 (1H, m), 4.32 (1H, m), 3.41 (2H, d, J=8.0 Hz), 3.31 (3H, s), 3.15 (2H, m), 2.98 (2H, d, 0.1=8.0 Hz), 2.63 (1H, m), 2.45 (1H, m), 2.09 (1H, m), 1.94 (2H, m), 1.31-1.70 (15H, cm); LC/MS (100%, $t_r$=1.89 min), m/z=384.0 [M+H]$^+$ (Calc: 383).

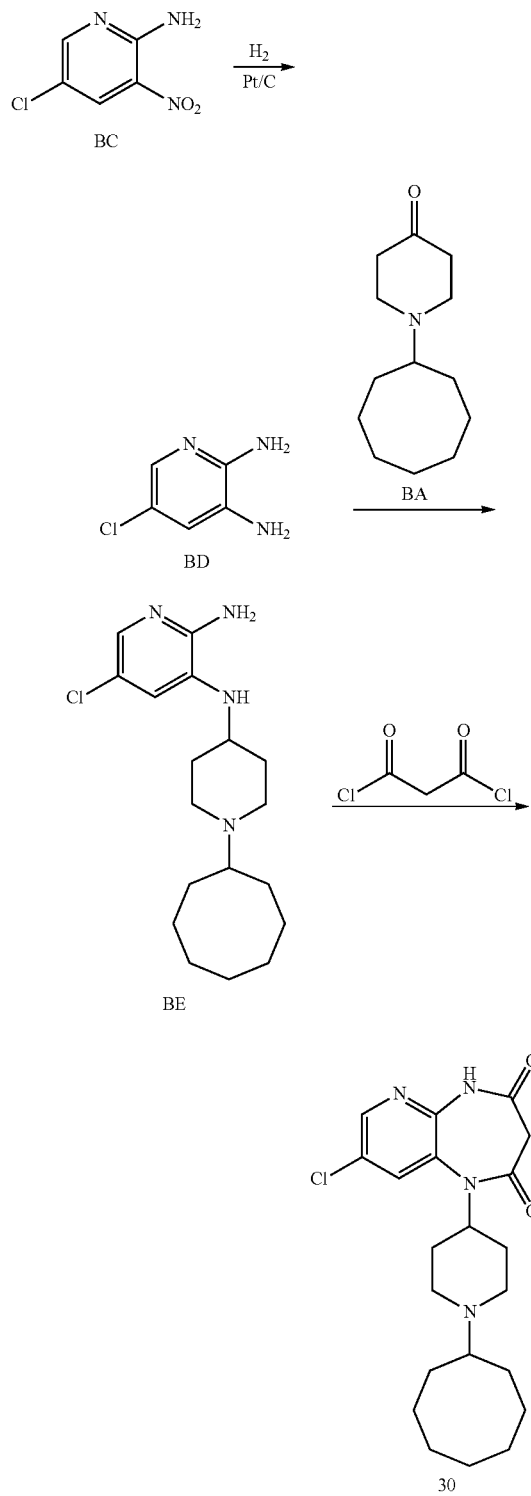

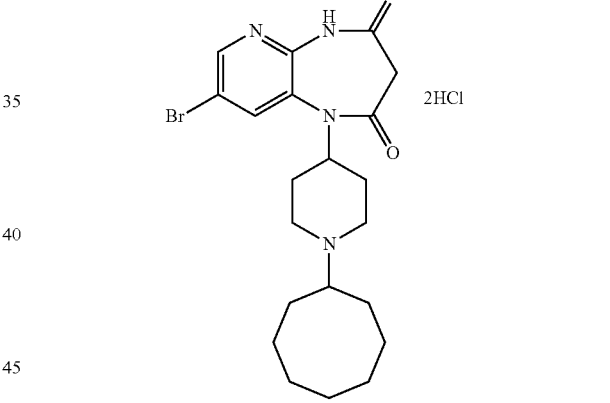

The dihydrochloride of Heterocyclic-Substituted Piperidine Compound 30 was prepared as described above except that 5-chloropyridine-2,3-diamine (BD) was used in place of o-phenylenediamine. The identity of Heterocyclic-Substituted Piperidine Compound 30, 8-chloro-1-(1-cyclooctylpiperidin-4-yl)-1H-pyrido[3,2-b][1,4]diazepine-2,4(3H,5H)-dione, was confirmed using $^1$H NMR and LC/MS.

Heterocyclic-Substituted Piperidine Compound 30: $^1$H NMR: $\delta_H$ (300 MHz, CD$_3$OD): 8.37 (1H, d, J=2.4 Hz), 8.02 (1H, d, J=2.4 Hz), 4.21 (1H, m), 3.56-3.41 (4H, m), 3.19-3.13 (3H, m), 2.88-2.65 (2H, m), 2.21-1.52 (16H, m), m/z=405 [M+H]$^+$ (Calc: 404.9).

The compound of formula BD was prepared as follows. A mixture of the compound of formula BC (5-chloro-3-nitropyridin-2-amine, 1736 mg, 10 mmol, Sigma-Aldrich) and 2% platinum on carbon (200 mg, Sigma-Aldrich) in methanol (20 mL) was stirred under a hydrogen atmosphere at a temperature of about 25° C. for 2 h. After filtering off the Pt/C and washing with EtOAc, the filtrate was concentrated under reduced pressure. The resulting solid was washed with 1:1 n-hexane:diethyl ether, filtered, washed with n-hexane, and dried under reduced pressure at a temperature of about 25° C. to provide the compound of formula BD as a pale brown solid (yield 88%).

The identity of the compound of formula BD was confirmed using $^1$H NMR.

Compound BD: $^1$H NMR: $\delta_H$ (300 MHz, DMSO): 7.21 (1H, d, J=1.2 Hz), 6.69 (1H, d, J=1.2 Hz), 5.57 (2H, m), 5.01 (2H, m).

The dihydrochloride of Heterocyclic-Substituted Piperidine Compound 31 was prepared as described above except that 5-bromopyridine-2,3-diamine was used in place of 5-chloropyridine-2,3-diamine. The identity of Heterocyclic-Substituted Piperidine Compound 31, 8-bromo-1-(1-cyclooctylpiperidin-4-yl)-1H-pyrido[3,2-b][1,4]diazepine-2,4(3H,5H)-dione, was confirmed using $^1$H NMR and LC/MS.

Heterocyclic-Substituted Piperidine Compound 31: $^1$H NMR: $\delta_H$ (300 MHz, CD$_3$OD): 8.45 (1H, d, J=2.1 Hz), 8.12 (1H, d, J=2.1 Hz), 4.19 (1H, m), 3.52-3.41 (4H, m), 3.19-3.13 (3H, m), 2.69 (2H, m), 2.20-1.48 (16H, m), m/z=450.9 [M+H]$^+$ (Calc: 449.4).

5.3 Example 3

In a manner similar to Example 2, the following Heterocyclic-Substituted Piperidine Compounds were prepared from the compound of formula BB:

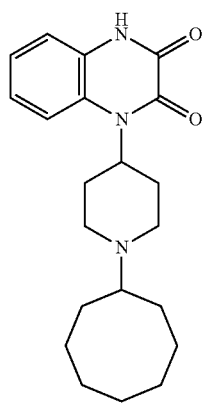

6

Heterocyclic-Substituted Piperidine Compound 6 was prepared by using oxalyl dichloride (8.37 g, 66.44 mmol, Sigma-Aldrich) in place of malonyl dichloride. The identity of Heterocyclic-Substituted Piperidine Compound 6, 1-(1-cyclooctylpiperidin-4-yl)quinoxaline-2,3(1H,4H)-dione, was confirmed using $^1$H NMR and LC/MS.

Heterocyclic-Substituted Piperidine Compound 6: $^1$H NMR: $\delta_H$ (400 MHz, MeOD): 7.81 (1H, m), 7.31 (3$\overline{H}$, m), 3.57 (3H, m), 3.43 (2H, m), 3.22 (2H, m), 2.17 (4H, m), 1.99 (4H, m), 1.78-1.46 (14H, m); LC/MS (100%, $t_r$=5.011 min), m/z=356.3 [M+H]$^+$ (Calc: 355.5).

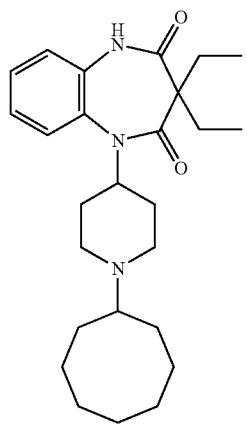

7

Heterocyclic-Substituted Piperidine Compound 7 was prepared by using 2,2-diethylmalonyl dichloride (Sigma-Aldrich) in place of malonyl dichloride. The identity of Heterocyclic-Substituted Piperidine Compound 7, 1-(1-cyclooctylpiperidin-4-yl)-3,3-diethyl-1H-benzo[b][1,4]diazepine-2,4(3H,5H)-dione, was confirmed using $^1$H NMR and LC/MS.

Heterocyclic-Substituted Piperidine Compound 7: $^1$H NMR: $\delta_H$ (400 MHz, MeOD): 7.30 (2H, m), 6.99 (1$\overline{H}$, m), 6.80 (1H, m), 3.72 (1H, m), 3.50 (3H, m), 2.41 (2H, m), 221 (1H, m), 2.10-1.41 (21H, m), 1.10 (6H, m); LC/MS (96.9%, $t_r$=8.655 min), m/z=426.3 [M+H]$^+$ (Calc: 425.6).

5.4 Example 4

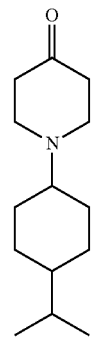

CA

The compound of formula CA, 1-(4-isopropylcyclohexyl)piperidin-4-one, was prepared according to the procedure in S. Kolczewski et al., *J. Med. Chem.* 46:255 (2003).

In a manner similar to Examples 2 and 3, the following Heterocyclic-Substituted Piperidine Compounds were prepared from the compound of formula CA:

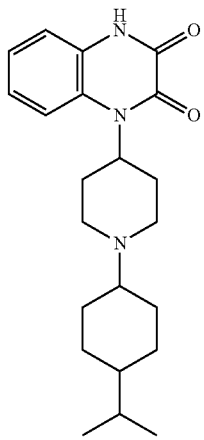

9

The identity of Heterocyclic-Substituted Piperidine Compound 9, 1-(1-(4-isopropylcyclohexyl)piperidin-4-yl)quinoxaline-2,3(1H,4H)-dione, was confirmed using $^1$H NMR and LC/MS.

Heterocyclic-Substituted Piperidine Compound 9: $^1$H NMR: $\delta_H$ (400 MHz, MeOD): 7.77 (1H, m), 7.29 (3$\overline{H}$, m), 3.70 (2H, m), 3.38 (2H, m), 3.26 (3H, m), 2.21 (1H, m), 2.13-1.90 (5H, m), 1.78 (2H, m), 1.55 (3H, m), 1.24 (2H, m), 0.98 (6H, m); LC/MS (100%, $t_r$=5.446 min), m/z=370.4 [M+H]$^+$ (Calc: 369.5).

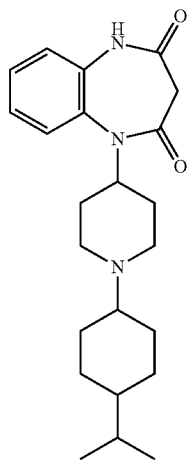

10

The identity of Heterocyclic-Substituted Piperidine Compound 10, 1-(1-(4-isopropylcyclohexyl)piperidin-4-yl)-1H-benzo[b][1,4]diazepine-2,4(3H,5H)-dione, was confirmed using $^1$H NMR and LC/MS.

Heterocyclic-Substituted Piperidine Compound 10: $^1$H NMR: $\delta_H$ (400 MHz, MeOD): 7.57 (1H, m), 7.39 (2H, m), 7.26 (1H, m), 4.29 (1H, m), 3.59 (2H, m), 3.48 (1H, m), 3.30-3.07 (4H, m), 2.89 (2H, m), 2.17 (3H, m), 1.91 (2H, m), 1.72 (1H, m), 1.51 (2H, m), 1.18 (2H, m), 0.95 (6H, m); LC/MS (100%, $t_r$=5.538 min), m/z=384.3 [M+H]$^+$ (Calc: 383.5).

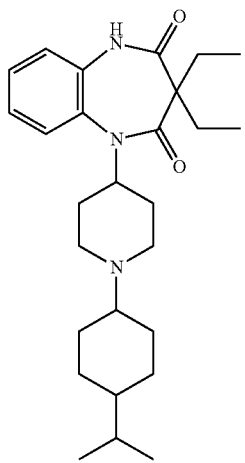

11

The identity of Heterocyclic-Substituted Piperidine Compound 11, 3,3-diethyl-1-(1-(4-isopropylcyclohexyl)piperidin-4-yl)-1H-benzo[b][1,4]diazepine-2,4(3H,5H)-dione, was confirmed using $^1$H NMR and LC/MS.

Heterocyclic-Substituted Piperidine Compound 11: $^1$H NMR: $\delta_H$ (400 MHz, MeOD): 7.31 (2H, m), 7.00 (1H, m), 6.81 (1H, m), 3.81-3.51 (2H, m), 3.45 (1H, m), 3.28 (2H, m), 2.41 (1H, m), 2.20 (2H, s), 2.93 (7H, m), 2.78 (3H, m), 2.59 (3H, m), 1.18 (8H, m), 0.99 (7H, m); LC/MS (100%, $t_r$=9.045 min), m/z=440.4 [M+H]$^+$ (Calc: 439.6).

5.5 Example 5

In a manner similar to Example 3, the following Heterocyclic-Substituted Piperidine Compound was prepared from the compound of formula AC:

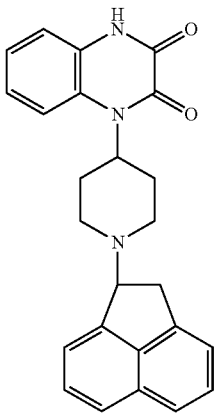

12

The identity of Heterocyclic-Substituted Piperidine Compound 12, 1-(1-(1,2-dihydroacenaphthylen-1-yl)piperidin-4-yl)quinoxaline-2,3(1H,4H)-dione, was confirmed using $^1$H NMR and LC/MS.

Heterocyclic-Substituted Piperidine Compound 12: $^1$H NMR: $\delta_H$ (400 MHz, MeOD): 7.83 (2H, m), 7.65 (3H, m), 7.49 (1H, m), 7.38 (1H, m), 7.16 (3H, m), 6.51 (1H, m), 3.79 (2H, m), 3.57-3.31 (2H, m), 3.28-3.03 (6H, m), 1.91 (2H, m); LC/MS (100%, $t_r$=5.009 min), m/z=356.3 [M+H]$^+$ (Calc: 355.5).

5.6 Example 6

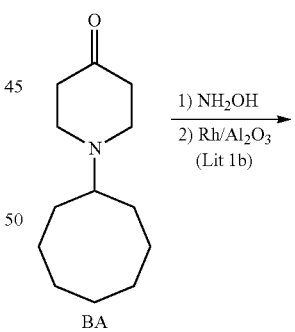

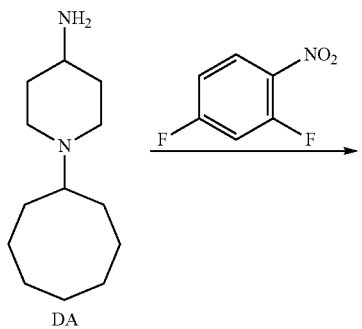

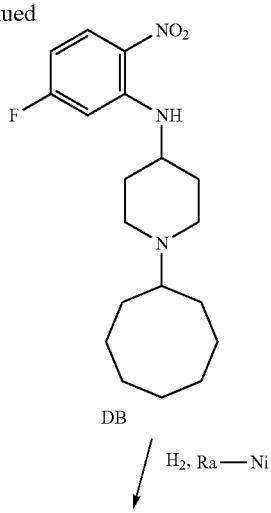

DB

| H₂, Ra—Ni

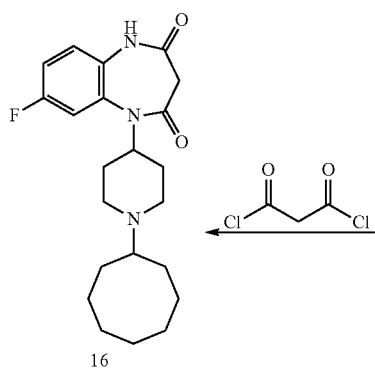

16

The compound of formula BA was converted to the compound of formula DA, 4-amino-N-cyclooctylpiperidine, by procedures known to those in the art, e.g., as described in International PCT Publication No. WO 2005/075459 A1 of Euro-Celtique S. A. published Aug. 18, 2005.

The compound of formula DA (2.00 g, 9.52 mmol) was dissolved in 25 mL of methanol and charged into a 100 mL high pressure microwave reaction vessel (MicroSYNTH Model HTR-300/6 S, Milestone Inc., Shelton, Conn.). To this was added 2,4-difluoro-1-nitrobenzene (1.43 g, 9.52 mmol). The vessel was sealed, placed into a microwave reactor (MicroSYNTH), warmed, with stirring, to 100° C., and maintained at that temperature for 1 h. The reaction mixture was cooled to a temperature of about 25° C., concentrated onto silica to provide residues that were chromatographed with a silica gel column eluted with a gradient of from 100%:0% EtOAc:MeOH to 50%:50% EtOAc:MeOH. The product fractions were combined and concentrated to dryness under reduced pressure to provide 1.57 g of the compound of formula DB as a bright orange solid.

The identity of the compound of formula DB, 1-cyclooctyl-N-(5-fluoro-2-nitrophenyl)piperidin-4-amine, was confirmed using $^1$H NMR and LC/MS.

Compound DB: $^1$H NMR: $\delta_H$ (400 MHz, CDCl$_3$): 8.21 (2H, m), 6.48 (1H, m), 6.32 (1H, m), 4.41 (1H, m), 2.80 (2H, m), 2.63 (1H, m), 2.40 (2H, m), 2.06 (2H, m), 2.38-2.82 (16H, m); LC/MS (100%, t$_r$=2.456 min), m/z=350.2 [M+H]$^+$ (Calc: 349.4).

The compound of formula DB was added to 100 mL of methanol and 1 g of Raney nickel (Alfa Aesar, Ward Hill, Mass.) was added. In a sealed vessel, the mixture was stirred under an atmosphere of hydrogen (5 atm) for 18 h. The Raney nickel was filtered off and the mixture concentrated to dryness to provide the compound of formula DC, N$^1$-(1-cyclooctylpiperidin-4-yl)-5-fluorobenzene-1,2-diamine, which LC/MS showed to be >99% pure material.

Thereafter, in a manner similar to Example 2, Heterocyclic-Substituted Piperidine Compound 16 was prepared from the compound of formula DC.

The identity of Heterocyclic-Substituted Piperidine Compound 16, 1-(1-cyclooctylpiperidin-4-yl)-8-fluoro-1H-benzo[b][1,4]diazepine-2,4(3H,5H)-dione, was confirmed using $^1$H NMR and LC/MS.

Heterocyclic-Substituted Piperidine Compound 16: $^1$H NMR: $\delta_H$ (400 MHz, CD$_3$OD) 7.35 (1 h, d, J=15 Hz), 7.23 (1H, m), 7.15 (1H, m), 4.30 (1H, m), 3.45 (4H, m), 3.30 (1H, d, J=15 Hz), 3.20 (2H, t, J=10 Hz), 3.10 (1H, d, J=15 Hz), 2.80 (2H, m), 2.10 (2H, m), 1.95 (2H, m), 1.90-1.50 (12H, m); LC/MS, m/z=388.2 [M+H]$^+$.

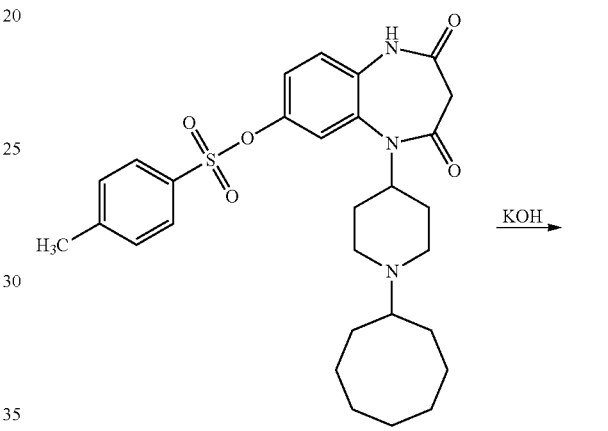

32

KOH

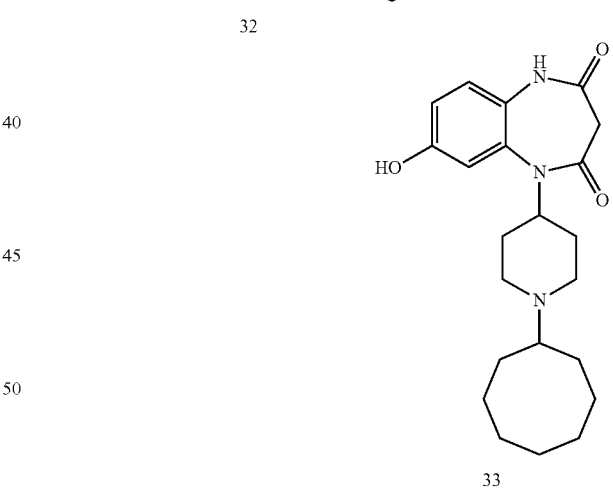

33

Heterocyclic-Substituted Piperidine Compound 32 was prepared from the compound of formula DA as described above except that 3-fluoro-4-nitrophenyl-4-methylbenzenesulfonate (DF) was used in place of 2,4-difluoro-1-nitrobenzene.

The identity of Heterocyclic-Substituted Piperidine Compound 32, 1-(1-cyclooctylpiperidin-4-yl)-8-tosyl-1H-benzo[b][1,4]diazepine-2,4(3H,5H)-dione, was confirmed using $^1$H NMR and LC/MS.

Heterocyclic-Substituted Piperidine Compound 32: $^1$H NMR: $\delta_H$ (400 MHz, MeOD): 7.08 (1H, m), 7.01 (2H, m), 4.43 (1H, m), 3.91 (3H, s), 3.45 (4H, m), 3.05-3.29 (3H, m), 2.71 (2H, m), 2.18 (1H, m), 2.00 (3H, m), 1.51-1.89 (12H, m); LC/MS (100%, t$_r$=5.139 min), m/z=400.4 [M+H]$^+$ (Calc: 399.5).

Heterocyclic-Substituted Piperidine Compound 33 was prepared as follows. Heterocyclic-Substituted Piperidine Compound 32 (280 mg, 0.7 mmol) was added to dry ethanol (10 mL). To this, potassium hydroxide (1.4 g, 25 mmol) in 10 mL of water was added. The reaction mixture was warmed to reflux for 18 h. Thereafter, the mixture was adsorbed onto silica gel to provide residues that were chromatographed with a silica gel column eluted with a gradient of from 100%:0% EtOAc:MeOH to 0%:100% EtOAc:MeOH(COMBI-FLASH). The product fractions were combined and concentrated to dryness under reduced pressure to provide Heterocyclic-Substituted Piperidine Compound 33.

The identity of Heterocyclic-Substituted Piperidine Compound 33, 1-(1-cyclooctylpiperidin-4-yl)-8-hydroxy-1H-benzo[b][1,4]diazepine-2,4(3H,5H)-dione, was confirmed using $^1$H NMR and LC/MS.

Heterocyclic-Substituted Piperidine Compound 33: $^1$H NMR: δ$_H$ (400 MHz, MeOD): 7.19 (1H, m), 6.89 (1H, m), 6.79 (1H, m), 4.25 (1H, m), 3.48 (1H, m), 3.27 (1H, m), 3.05 (3H, m), 2.60 (2H, m), 2.11 (1H, m), 1.90 (5H, m), 1.41-1.81 (11H, m); LC/MS (100%, t$_r$=4.809 min), m/z=386.2 [M+H]$^+$ (Calc: 385.5).

The compound of formula DF 3-fluoro-4-nitrophenyl-4-methylbenzenesulfonate, was prepared as follows.

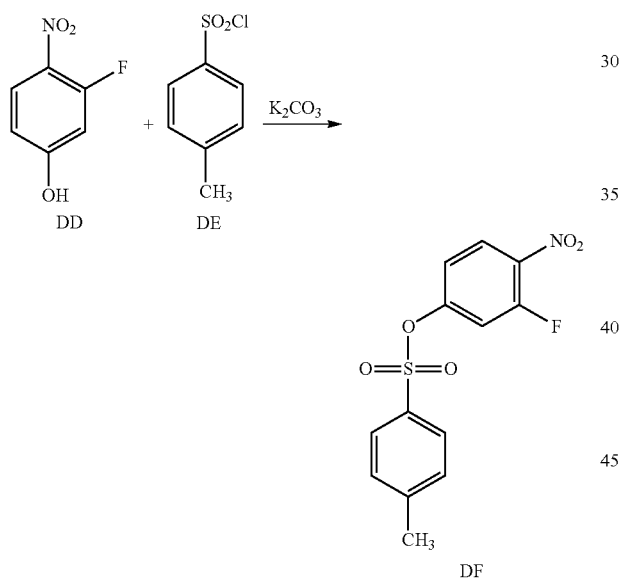

3-Fluoro-4-nitrophenol (DD, 5 g, 31.83 mmol, Sigma-Aldrich) was added to 100 mL dry acetone. To this, 4-methylbenzene-1-sulfonyl chloride (DE, 7.28 g, 38.19 mmol, Sigma-Aldrich) and potassium carbonate (11.0 g, 79.57 mmol) were added. In a sealed vessel, the reaction mixture was warmed to reflux for 2 h. The reaction mixture was cooled to a temperature of about 25° C. and concentrated to dryness under reduced pressure. The residue was partitioned between ethyl acetate (200 mL) and water (200 mL). The organic portion was separated, dried (MgSO$_4$), filtered, and concentrated to dryness under reduced pressure to provide the compound of formula DF.

5.7 Example 7

In a manner similar to Example 6, the following Heterocyclic-Substituted Piperidine Compound was prepared from the compound of formula DA except that 4-methyl-2-fluoro-1-nitrobenzene was used in place of 2,4-difluoro-1-nitrobenzene:

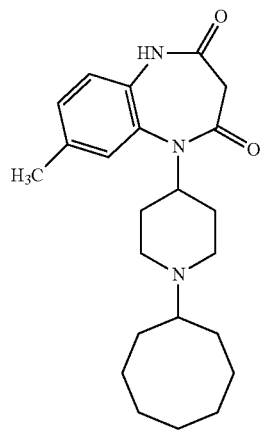

The identity of Heterocyclic-Substituted Piperidine Compound 34, 1-(1-cyclooctylpiperidin-4-yl)-8-methyl-1H-benzo[b][1,4]diazepine-2,4(3H,5H)-dione, was confirmed using $^1$H NMR and LC/MS.

Heterocyclic-Substituted Piperidine Compound 34: $^1$H NMR: δ$_H$ (400 MHz, MeOD): 7.23 (1H, m), 7.09 (1H, m), 7.01 (1H, m), 4.19 (1H, m), 4.38 (4H, m), 3.12 (2H, m), 2.98 (1H, m), 2.68 (2H, m), 2.33 (3H, s), 1.97 (4H, m), 1.72 (4H, m), 1.32-1.65 (10H, m); LC/MS (97.4%, t$_r$=5.258 min), m/z=384.3 [M+H]$^+$ (Calc: 383.5).

In a manner similar to Examples 3 and 6, the following Heterocyclic-Substituted Piperidine Compounds were prepared from the compound of formula DA:

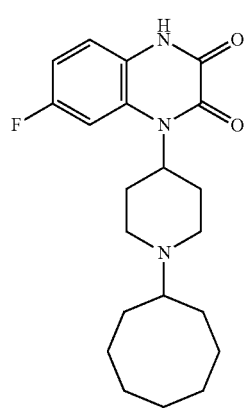

The identity of Heterocyclic-Substituted Piperidine Compound 17, 1-(1-cyclooctylpiperidin-4-yl)-7-fluoroquinoxaline-2,3(1H,4H)-dione, was confirmed using $^1$H NMR and LC/MS.

Heterocyclic-Substituted Piperidine Compound 17: $^1$H NMR: δ$_H$ (400 MHz, MeOD): 7.61 (1H, d), 7.22 (1H, t), 6.98 (1H, m), 4.74 (1H, m), 3.53 (3H, m), 3.38 (2H, m), 3.19 (2H, m), 2.09 (4H, m), 1.90 (4H, m), 1.80-1.49 (8H, m); LC/MS (97.3%, t$_r$=7.689 min), m/z=374.2 [M+H]$^+$ (Calc.: 373.5).

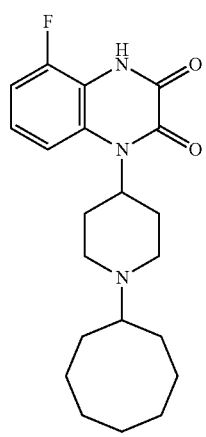

18

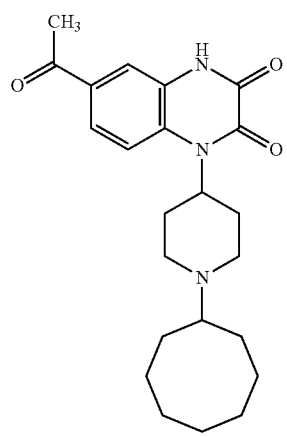

36

Heterocyclic-Substituted Piperidine Compound 18 was prepared from the compound of formula DA except that 2,6-difluoro-1-nitrobenzene was used in Example 6 in place of 2,4-difluoro-1-nitrobenzene.

The identity of Heterocyclic-Substituted Piperidine Compound 18, 1-(1-cyclooctylpiperidin-4-yl)-5-fluoroquinoxaline-2,3(1H,4H)-dione, was confirmed using $^1$H NMR and LC/MS.

Heterocyclic-Substituted Piperidine Compound 18: $\delta_H$ (400 MHz, MeOD): 7.57 (1H, m), 7.28 (1H, m), 7.11 (1H, m), 4.86 (1H, m), 3.58 (3H, m), 3.41 (2H, m), 3.20 (2H, m), 2.10 (4H, m), 1.90 (4H, m), 1.80-1.49 (8H, m); LC/MS (100%, $t_r$=4.862 min), m/z=374.2 [M+H]$^+$ (Calc.: 373.5).

Heterocyclic-Substituted Piperidine Compound 36 was prepared from the compound of formula DA except that oxalic acid was used in Example 3 in place of oxalyl dichloride and 1-(4-fluoro-3-nitrophenyl)ethanone was used in Example 6 in place of 2,4-difluoro-1-nitrobenzene.

The identity of Heterocyclic-Substituted Piperidine Compound 36, 6-acetyl-1-(1-cyclooctylpiperidin-4-yl)quinoxaline-2,3(1H,4H)-dione, was confirmed using $^1$H NMR and LC/MS.

Heterocyclic-Substituted Piperidine Compound 36: $\delta_H$ (400 MHz, MeOD): 7.91 (1H, m), 7.82 (2H, m), 4.22 (1H, q), 3.44 (2H, m), 3.17 (4H, m), 2.64 (3H, s), 2.02 (4H, m), 1.50-1.98 (14H, m), 1.32 (1H, t); LC/MS (97.1%, $t_r$=4.841 min), m/z=398.3 [M+H]$^+$ (Calc: 397.5).

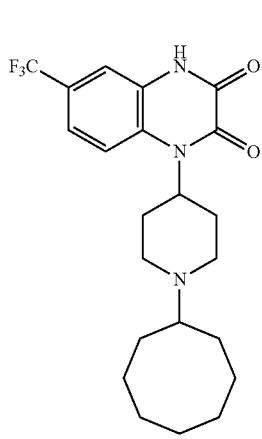

35

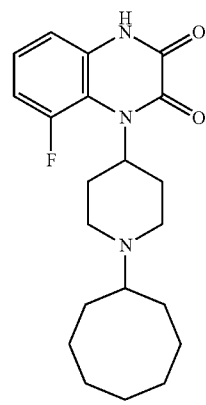

37

Heterocyclic-Substituted Piperidine Compound 35 was prepared from the compound of formula DA except that oxalic acid was used in Example 3 in place of oxalyl dichloride and 2-fluoro-5-(trifluoromethyl)-1-nitrobenzene was used in Example 6 in place of 2,4-difluoro-1-nitrobenzene.

The identity of Heterocyclic-Substituted Piperidine Compound 35, 1-(1-cyclooctylpiperidin-4-yl)-6-(trifluoromethyl)quinoxaline-2,3(1H,4H)-dione, was confirmed using $^1$H NMR and LC/MS.

Heterocyclic-Substituted Piperidine Compound 35: $\delta_H$ (400 MHz, MeOD): 7.91 (1H, m), 7.58 (1H, m), 7.51 (1H, s), 4.22 (3H, q), 3.55 (3H, m), 3.39 (2H, m), 3.18 (2H, m), 2.09 (4H, m), 1.87 (4H, m), 1.48-1.81 (8H, m), 1.32 (4H, t); LC/MS (100%, $t_r$=5.705 min), m/z=424.2 [M+H]$^+$ (Calc: 423.5).

Heterocyclic-Substituted Piperidine Compound 37 was prepared from the compound of formula DA except that oxalic acid was used in Example 3 in place of oxalyl dichloride and 2,3-difluoro-1-nitrobenzene was used in Example 6 in place of 2,4-difluoro-1-nitrobenzene.

The identity of Heterocyclic-Substituted Piperidine Compound 37, 1-(1-cyclooctylpiperidin-4-yl)-8-fluoroquinoxaline-2,3(1H,4H)-dione, was confirmed using $^1$H NMR and LC/MS.

Heterocyclic-Substituted Piperidine Compound 37: $\delta_H$ (400 MHz, MeOD): 7.23 (1H, m), 7.08 (2H, m), 4.66 (1H, m), 4.22 (2H, q), 3.57 (2H, m), 3.54 (1H, m), 3.28 (2H, m), 3.19 (2H, m), 2.20 (2H, m), 2.02 (2H, m), 1.89 (4H, m), 1.45-1.79 (8H, m), 1.32 (3H, t); LC/MS (100%, $t_r$=5.109 min), m/z=374.2 [M+H]$^+$ (Calc: 373.5).

38

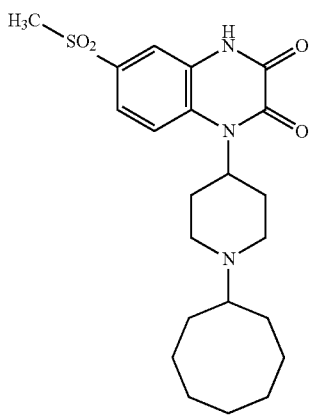

Heterocyclic-Substituted Piperidine Compound 38 was prepared from the compound of formula DA except that oxalic acid was used in Example 3 in place of oxalyl dichloride and 2-fluoro-5-(methylsulfonyl)-1-nitrobenzene was used in Example 6 in place of 2,4-difluoro-1-nitrobenzene.

The identity of Heterocyclic-Substituted Piperidine Compound 38, 1-(1-cyclooctylpiperidin-4-yl)-6-(methylsulfonyl)quinoxaline-2,3(1H,4H)-dione, was confirmed using $^1$H NMR and LC/MS.

Heterocyclic-Substituted Piperidine Compound 38: $\delta_H$ (400 MHz, DMSO-d$_6$): 7.92 (1H, m), 7.81 (2H, m), 4.22 (1H, q), 3.67 (2H, m), 3.51 (1H, m), 3.40 (2H, m), 3.18 (5H, m), 2.11 (4H, m), 1.91 (4H, m), 1.51-1.79 (8H, m), 1.32 (21-1, t); LC/MS (97.0%, t$_r$=4.730 min), m/z=434.2 [M+H]$^+$ (Calc: 433.6).

39

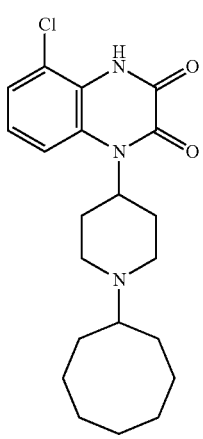

Heterocyclic-Substituted Piperidine Compound 39 was prepared from the compound of formula DA except that oxalic acid was used in Example 3 in place of oxalyl dichloride and 6-chloro-2-fluoro-1-nitrobenzene was used in Example 6 in place of 2,4-difluoro-1-nitrobenzene.

The identity of Heterocyclic-Substituted Piperidine Compound 39, 5-chloro-1-(1-cyclooctylpiperidin-4-yl)quinoxaline-2,3(1H,4H)-dione, was confirmed using $^1$H NMR and LC/MS.

Heterocyclic-Substituted Piperidine Compound 39: $\delta_H$ (400 MHz, MeOD): 7.70 (1H, m), 7.39 (1H, m), 7.30 (1H, m), 4.22 (4H, q), 3.78 (2H, m), 3.56 (3H, m), 3.21 (2H, m), 2.10 (4H, m), 1.90 (4H, m), 1.48-1.79 (8H, m), 1.34 (6H, t); LC/MS (100%, t$_r$=5.258 min), m/z=390.1 [M+H]$^+$ (Calc: 389.9).

40

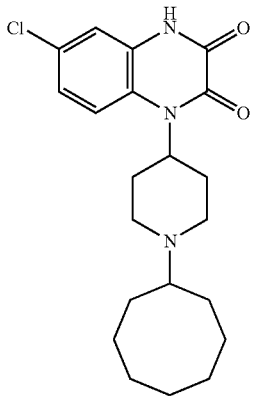

Heterocyclic-Substituted Piperidine Compound 40 was prepared from the compound of formula DA except that oxalic acid was used in Example 3 in place of oxalyl dichloride and 5-chloro-2-fluoro-1-nitrobenzene was used in Example 6 in place of 2,4-difluoro-1-nitrobenzene.

The identity of Heterocyclic-Substituted Piperidine Compound 40, 6-chloro-1-(1-cyclooctylpiperidin-4-yl)quinoxaline-2,3(1H,4H)-dione, was confirmed using $^1$H NMR and LC/MS.

Heterocyclic-Substituted Piperidine Compound 40: $\delta_H$ (400 MHz, MeOD): 7.68 (1H, m), 7.29 (2H, m), 4.78 (1H, m), 4.22 (2H, q), 3.58 (3H, m), 3.40 (2H, m), 3.18 (2H, m), 2.09 (4H, m), 1.90 (4H, m), 1.47-1.79 (8H, m), 1.34 (3H, t); LC/MS (97.1%, t$_r$=5.356 min), m/z=390.1 [M+H]$^+$ (Calc: 389.9).

41

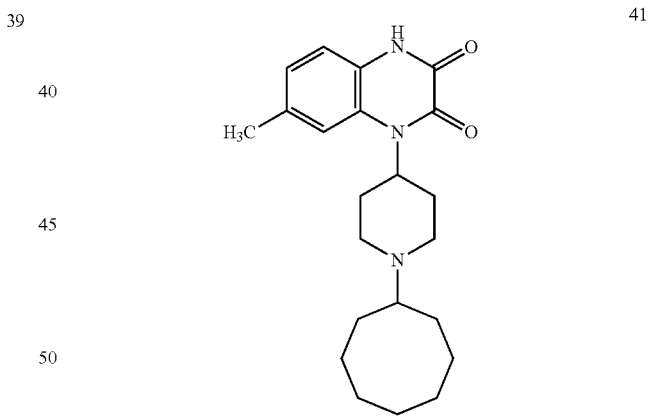

Heterocyclic-Substituted Piperidine Compound 41 was prepared from the compound of formula DA except that oxalic acid was used in Example 3 in place of oxalyl dichloride and 4-methyl-2-fluoro-1-nitrobenzene was used in Example 6 in place of 2,4-difluoro-1-nitrobenzene.

The identity of Heterocyclic-Substituted Piperidine Compound 41, 1-(1-cyclooctylpiperidin-4-yl)-7-methylquinoxaline-2,3(1H,4H)-dione, was confirmed using $^1$H NMR and LC/MS.

Heterocyclic-Substituted Piperidine Compound 41: $\delta_H$ (400 MHz, MeOD): 7.59 (1H, s), 7.14 (2H, m), 4.88 (1H, m), 3.59 (4H, m), 3.47 (2H, m), 3.23 (2H, m), 2.49 (3H, s), 2.09 (4H, m), 1.92 (4H, m), 1.47-1.82 (8H, m); LC/MS (100%, t$_r$=5.347 min), m/z=370.4 [M+H]$^+$ (Calc: 369.5).

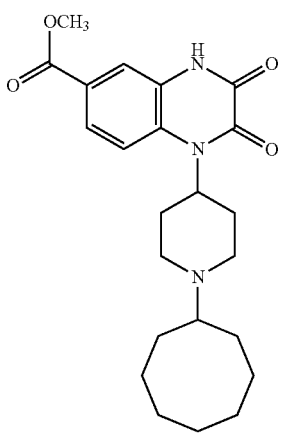

42

Heterocyclic-Substituted Piperidine Compound 42 was prepared from the compound of formula DA except that oxalic acid was used in Example 3 in place of oxalyl dichloride and methyl 4-fluoro-3-nitrobenzoate was used in Example 6 in place of 2,4-difluoro-1-nitrobenzene.

The identity of Heterocyclic-Substituted Piperidine Compound 42, methyl 1-(1-cyclooctylpiperidin-4-yl)-2,3-dioxo-1,2,3,4-tetrahydroquinoxaline-6-carboxylate, was confirmed using $^1$H NMR and LC/MS.

Heterocyclic-Substituted Piperidine Compound 42: $\delta_H$ (400 MHz, MeOD): 7.91 (2H, m), 7.82 (1H, m), 4.78 (1H, m), 4.22 (1H, q), 3.95 (3H, s), 3.50 (3H, m), 3.18 (2H, m), 2.09 (4H, m), 1.90 (4H, m), 1.48-1.81 (8H, m), 1.34 (1H, t); LC/MS (97.0%, $t_r$=5.085 min), m/z=414.3 [M+H]$^+$ (Calc: 413.5).

5.8 Example 8

In a manner similar to Examples 2 and 6, the following Heterocyclic-Substituted Piperidine Compounds were prepared from the compound of formula DA:

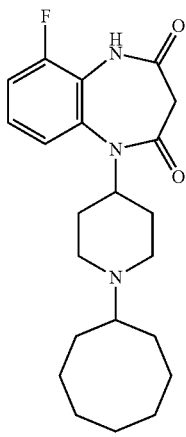

20

Heterocyclic-Substituted Piperidine Compound 20 was prepared from the compound of formula DA except that 2,6-difluoro-1-nitrobenzene was used in Example 6 in place of 2,4-difluoro-1-nitrobenzene.

The identity of Heterocyclic-Substituted Piperidine Compound 20, 1-(1-cyclooctylpiperidin-4-yl)-6-fluoro-1H-benzo[b][1,4]diazepine-2,4(3H,5H)-dione, was confirmed using $^1$H NMR and LC/MS.

Heterocyclic-Substituted Piperidine Compound 20: $^1$H NMR: $\delta_H$ (400 MHz, (CD$_3$)$_2$SO): 9.55 (1H, bs), 7.30 (1H, m), 7.25 (2H, m), 4.30 (1H, m), 3.50 (1H, d, J=20 Hz), 3.10 (2H, m), 2.90 (1H, d, J=20 Hz), 2.67 (1H, m), 2.54 (2H, m), 1.95 (4H, m), 1.80-1.40 (14H, m); LC/MS, m/z=388.4 [M+H]$^+$.

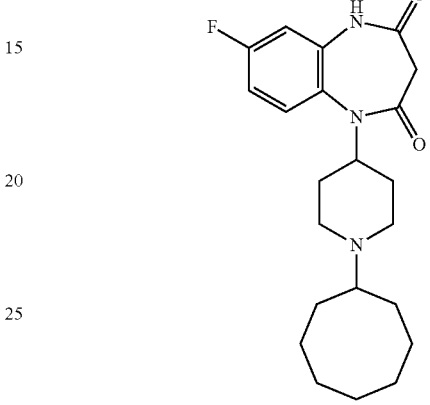

21

Heterocyclic-Substituted Piperidine Compound 21 was prepared from the compound of formula DA except that 2,5-difluoro-1-nitrobenzene was used in Example 6 in place of 2,4-difluoro-1-nitrobenzene.

The identity of Heterocyclic-Substituted Piperidine Compound 21, 1-(1-cyclooctylpiperidin-4-yl)-7-fluoro-1H-benzo[b][1,4]diazepine-2,4(3H,5H)-dione, was confirmed using $^1$H NMR and LC/MS.

Heterocyclic-Substituted Piperidine Compound 21: $^1$H NMR: $\delta_H$ (400 MHz, (CD$_3$)$_2$SO): 9.65 (1H, bs), 7.55 (1H, m), 7.10 (1H, m), 7.00 (1H, m), 4.27 (1H, m), 3.45 (1H, d, J=20 Hz), 3.10 (2H, m), 2.90 (1H, d, J=20 Hz), 2.55 (1H, m), 2.38 (2H, m), 2.0-1.80 (4H, m), 1.75-1.35 (14H, m); LC/MS, m/z=520.3 [M+H]$^+$.

5.9 Example 9

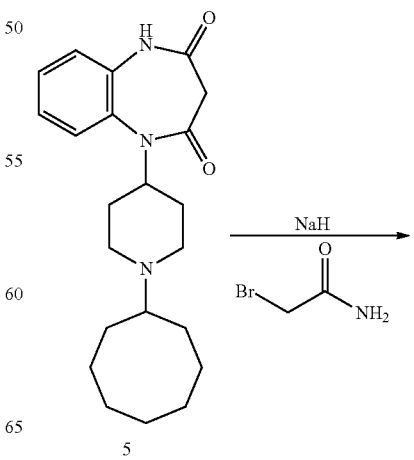

5

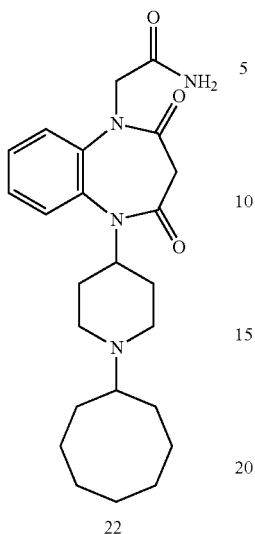

22

Heterocyclic-Substituted Piperidine Compound 5 where the 3-position nitrogen atom was optionally protected by a protecting group as described above, was added to dry DMF and to this mixture was added sodium hydride. The mixture was warmed under an argon atmosphere then allowed to cool whereupon 2-bromoacetamide in DMF was added in one portion. The resulting mixture was stirred until the desired product was obtained; thereafter, if an optional protecting group was used, it was removed. The solvent was removed under reduced pressure to provide residues that were chromatographed with a silica gel column eluted with a gradient of from 100%:0% EtOAc:MeOH to 0%:100% EtOAc:MeOH. The product fractions were combined and concentrated to dryness under reduced pressure to provide Heterocyclic-Substituted Piperidine Compound 22 as a solid.

The identity of Heterocyclic-Substituted Piperidine Compound 22, 2-(5-(1-cyclooctylpiperidin-4-yl)-2,4-dioxo-2,3,4,5-tetrahydro-1H-benzo[b][1,4]diazepin-1-yl)acetamide, was confirmed using $^1$H NMR and LC/MS.

Heterocyclic-Substituted Piperidine Compound 22: $^1$H NMR: $\delta_H$ (400 MHz, MeOD): 7.58 (1H, m), 7.50 (1H, m), 7.41 (2H, m), 4.85 (1H, m), 4.49 (1H, m), 4.29 (1H, m), 3.61-3.40 (4H, m), 3.31-3.10 (3H, m), 2.71 (2H, m), 2.41 (1H, m), 2.20 (1H, m), 2.01 (2H, m), 1.83 (4H, m), 1.71-1.42 (8H, m); LC/MS (96.1%, $t_r$=4.741 min), m/z=427.4 [M+H]$^+$ (Calc: 426.6).

5.10 Example 10

In a manner similar to Example 9, the following Heterocyclic-Substituted Piperidine Compounds were prepared from the Heterocyclic-Substituted Piperidine Compounds previously synthesized.

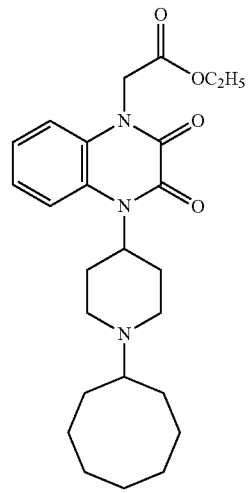

23

Heterocyclic-Substituted Piperidine Compound 23 was prepared by reacting Heterocyclic-Substituted Piperidine Compound 6 with ethyl bromoacetate.

The identity of Heterocyclic-Substituted Piperidine Compound 23, 1-(1-cyclooctylpiperidin-4-yl)-7-fluoro-1H-benzo[b][1,4]diazepine-2,4(3H,5H)-dione, was confirmed using $^1$H NMR and LC/MS.

Heterocyclic-Substituted Piperidine Compound 23: $^1$H NMR: $\delta_H$ (400 MHz, CDCl$_3$): 7.65 (1H, m), 7.20 (2H, m), 6.95 (1H, d, J=12 Hz), 4.92 (2H, s), 4.80 (1H, m), 4.24 (2H, q, J=10 Hz), 2.96 (2H, m), 2.85-2.60 (3H, m), 2.50 (2H, t, J=12 Hz), 1.85-1.40 (16H, m); LC/MS, m/z=441.0 [M+H]$^+$.

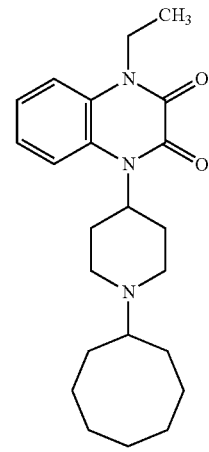

43

Heterocyclic-Substituted Piperidine Compound 43 was prepared by reacting Heterocyclic-Substituted Piperidine Compound 6 with ethyl iodide (Sigma-Aldrich).

The identity of Heterocyclic-Substituted Piperidine Compound 43, 1-(1-cyclooctylpiperidin-4-yl)-4-ethylquinoxaline-2,3(1H,4H)-dione, was confirmed using $^1$H NMR and LC/MS.

Heterocyclic-Substituted Piperidine Compound 43: $^1$H NMR: $\delta_H$ (400 MHz, CDCl$_3$): 7.78-7.81 (1H, m), 7.51-7.53 (1H, m), 7.31-7.36 (2H, m), 4.74 (1H, m), 4.29 (2H, q, J=7.1 Hz), 3.15 (2H, m), 2.88-3.10 (3H, m), 2.66-2.70 (2H, m), 1.84-1.92 (6H, m), 1.52-1.70 (10H, m), 1.36 (3H, t, J=7.1 Hz); LC/MS, m/z=384.3 [M+H]$^+$.

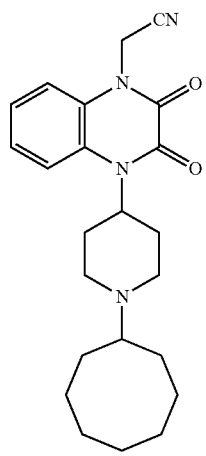

44

Heterocyclic-Substituted Piperidine Compound 44 was prepared by reacting Heterocyclic-Substituted Piperidine Compound 6 with bromoacetonitrile (Sigma-Aldrich).

The identity of Heterocyclic-Substituted Piperidine Compound 44, 2-(4-(1-cyclooctylpiperidin-4-yl)-2,3-dioxo-3,4-dihydroquinoxalin-1(2H)-yl)acetonitrile, was confirmed using $^1$H NMR and LC/MS.

Heterocyclic-Substituted Piperidine Compound 44: $^1$H NMR: $\delta_H$ (400 MHz, CDCl$_3$): 7.71-7.73 (1H, m), 7.41-7.43 (1H, m), 7.28-7.32 (2H, m), 5.21 (2H, s), 4.60 (1H, m), 2.96-3.05 (2H, m), 2.79-2.85 (3H, m), 2.53-2.76 (2H, m), 1.71-1.81 (6H, m), 1.43-1.59 (10H, m); LC/MS, m/z=395.2 [M+H]$^+$.

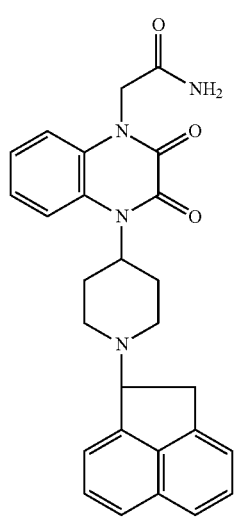

24

Heterocyclic-Substituted Piperidine Compound 24 was prepared by reacting Heterocyclic-Substituted Piperidine Compound 12 with bromo acetamide.

The identity of Heterocyclic-Substituted Piperidine Compound 24, 2-(4-(1-(1,2-dihydroacenaphthylen-1-yl)piperidin-4-yl)-2,3-dioxo-3,4-dihydroquinoxalin-1(2H)-yl)acetamide, was confirmed using $^1$H NMR and LC/MS.

Heterocyclic-Substituted Piperidine Compound 24: $^1$H NMR: $\delta_H$ (400 MHz, DMSO-d$_6$): 8.18-7.05 (12H, m), 5.63 (1H, m), 4.79 (2H, s), 3.98 (1H, m), 3.78 (1H, m), 3.56 (1H, s), 3.31 (4H, m), 3.05 (2H, m), 1.91 (2H, m); LC/MS (100%, t$_r$=4.936 min), m/z=455.3 [M+H]$^+$ (Calc 454.5).

5.11 Example 11

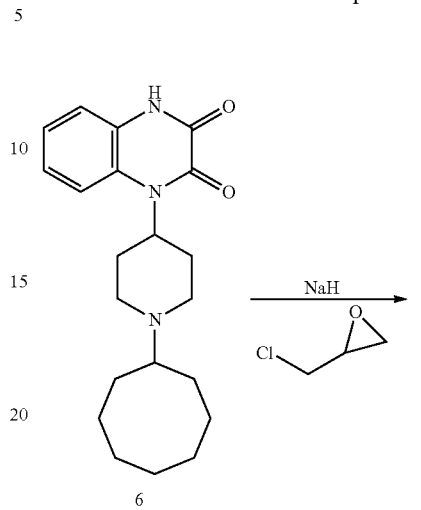

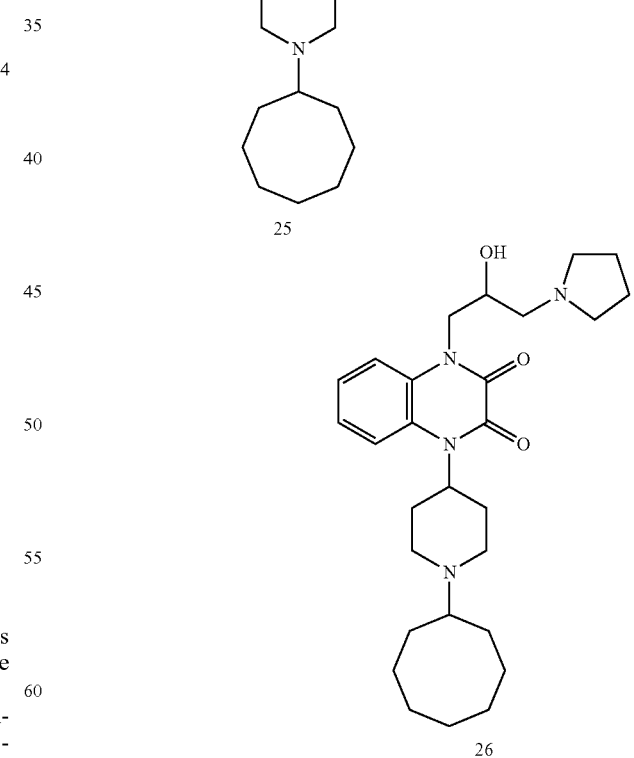

To a suspension of sodium hydride (0.56 g, 60% in oil, 14.07 mmole) in 15 mL of DMF was added a solution of Heterocyclic-Substituted Piperidine Compound 6 (4.0 g, 11.25 mmole) in 10 mL of DMF. The resulting solution was allowed to stir for 3 h at about 25° C. A solution of epibromohydrin (2.0 g, 14.63 mmole) in 5 mL of DMF was added dropwise, and the resulting mixture was heated with stirring for at 50° C. After cooling to about 25° C., the reaction mixture was poured into 250 mL of water and extracted three times with 100 mL of ethyl acetate each time. The combined organic layers were dried (MgSO$_4$) and concentrated under reduced pressure to provide Heterocyclic-Substituted Piperidine Compound 25, 1-(1-cyclooctylpiperidin-4-yl)-4-(oxiran-2-ylmethyl)quinoxaline-2,3(1H,4H)-dione, as an orange glass.

A solution of Heterocyclic-Substituted Piperidine Compound 25 (0.58 g, 1.41 mmole) and pyrrolidine (0.2 g, 2.8 mmole) in 15 mL of DMF was heated at 50° C. for 20 h. The reaction mixture was cooled to a temperature of about 25° C. and poured into 200 mL of water. The aqueous mixture was extracted three times with 100 mL of ethyl acetate each time, and the combined organic layers were dried (MgSO$_4$) and concentrated under reduced pressure to provide a viscous orange oil. The oil was chromatographed with a silica gel column eluted with 10:10:80 EtOH:TEA:EtOAc to provide a yellow solid which was recrystallized from ethyl acetate to provide 255 mg of Heterocyclic-Substituted Piperidine Compound 26 as an off-white colored solid.

The identity of Heterocyclic-Substituted Piperidine Compound 26, 1-(1-cyclooctylpiperidin-4-yl)-4-(2-hydroxy-3-(pyrrolidin-1-yl)propyl)quinoxaline-2,3(1H,4H)-dione, was confirmed using $^1$H NMR.

Heterocyclic-Substituted Piperidine Compound 26: $^1$H NMR: $\delta_H$ (400 MHz, DMSO-d$_6$): d 7.7 (m, 2H); 7.2 (m, 2H); 4.9 (m, 2H); 4.4 (bs, 1H); 4.25 (m, 1H); 4.1 (bs, 1H); 2.9-2.3 (bm, 13H); 1.8-1.3 (bm, 20H).

5.12 Example 12

In a manner similar to Example 11, the following Heterocyclic-Substituted Piperidine Compound was prepared from Heterocyclic-Substituted Piperidine Compound 25 except that morpholine was used in place of pyrrolidine:

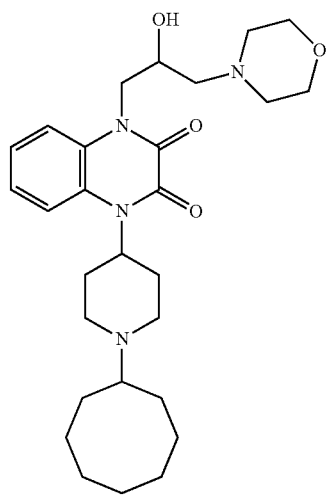

27

The identity of Heterocyclic-Substituted Piperidine Compound 27, 1-(1-cyclooctylpiperidin-4-yl)-4-(2-hydroxy-3-morpholinopropyl)quinoxaline-2,3(1H,4H)-dione, was confirmed using $^1$H NMR and LC/MS.

Heterocyclic-Substituted Piperidine Compound 27: $^1$H NMR: $\delta_H$ (400 MHz, (CD$_3$)$_2$SO): 10.75 (1H, bs), 7.95 (1H, bs), 7.68 (1H, dd), 7.27 (3H, m), 6.05 (1H, bs), 5.00 (1H, bs), 4.50 (1H, m), 4.17 (2H, m), 3.85 (2H, t), 3.80 (2H, m), 3.60-3.00 (15H, m), 2.10 (2H, m), 1.90 (2H, m), 1.80-1.40 (12H, m); LC/MS, m/z=499.2 [M+H]$^+$.

5.13 Example 13

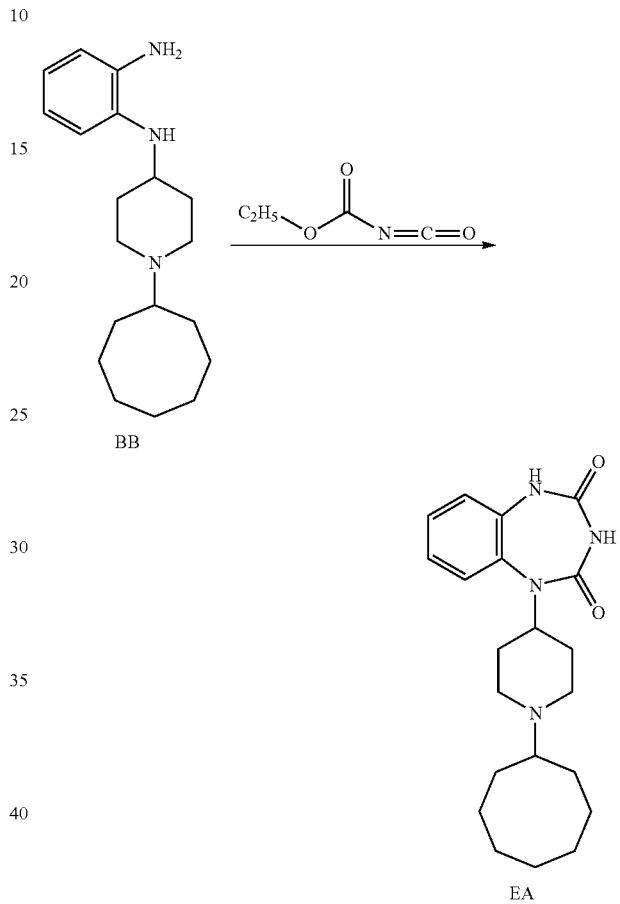

The compound of formula BB (1.00 g, 3.32 mmol) was added to 50 mL of DCE. To this was added O-ethyl carbonisocyanatidate (0.0735 mL; 6.64 mmol, Sigma-Aldrich). The mixture was sealed in a 100 mL high pressure microwave reaction vessel (MicroSYNTH Model HTR-300/6 S), placed into a microwave reactor (MicroSYNTH), warmed, with stirring, to 150° C., and maintained at that temperature for 30 min. The reaction mixture was cooled to a temperature of about 25° C., concentrated onto silica to provide residues that were chromatographed with a silica gel column eluted with a gradient of from 100%:0% EtOAc:MeOH to 0%:100% EtOAc:MeOH. The product fractions were combined and concentrated to dryness under reduced pressure to provide 120 mg of a compound of formula EA as a white solid (yield 10%).

The identity of the compound of formula EA, 1-(1-cyclooctylpiperidin-4-yl)-1H-benzo[f][1,3,5]triazepine-2,4(3H,5H)-dione, was confirmed using $^1$H NMR and LC/MS.

Compound EA: $\delta_H$ (400 MHz, DMSO-d$_6$): 10.92 (1H, s), 10.24 (1H, m), 7.83 (1H, s), 7.00 (3H, s), 4.62 (1H, m), 3.42 (3H, m), 3.29 (2H, m), 2.85 (2H, q), 1.99 (2H, m), 1.85 (2H, m), 1.70 (4H, m), 1.48 (8H, m); LC/MS (100.0%, t$_r$=4.958 min), m/z=371.2 [M+H]$^+$ (Calc: 370.5).

5.14 Example 14

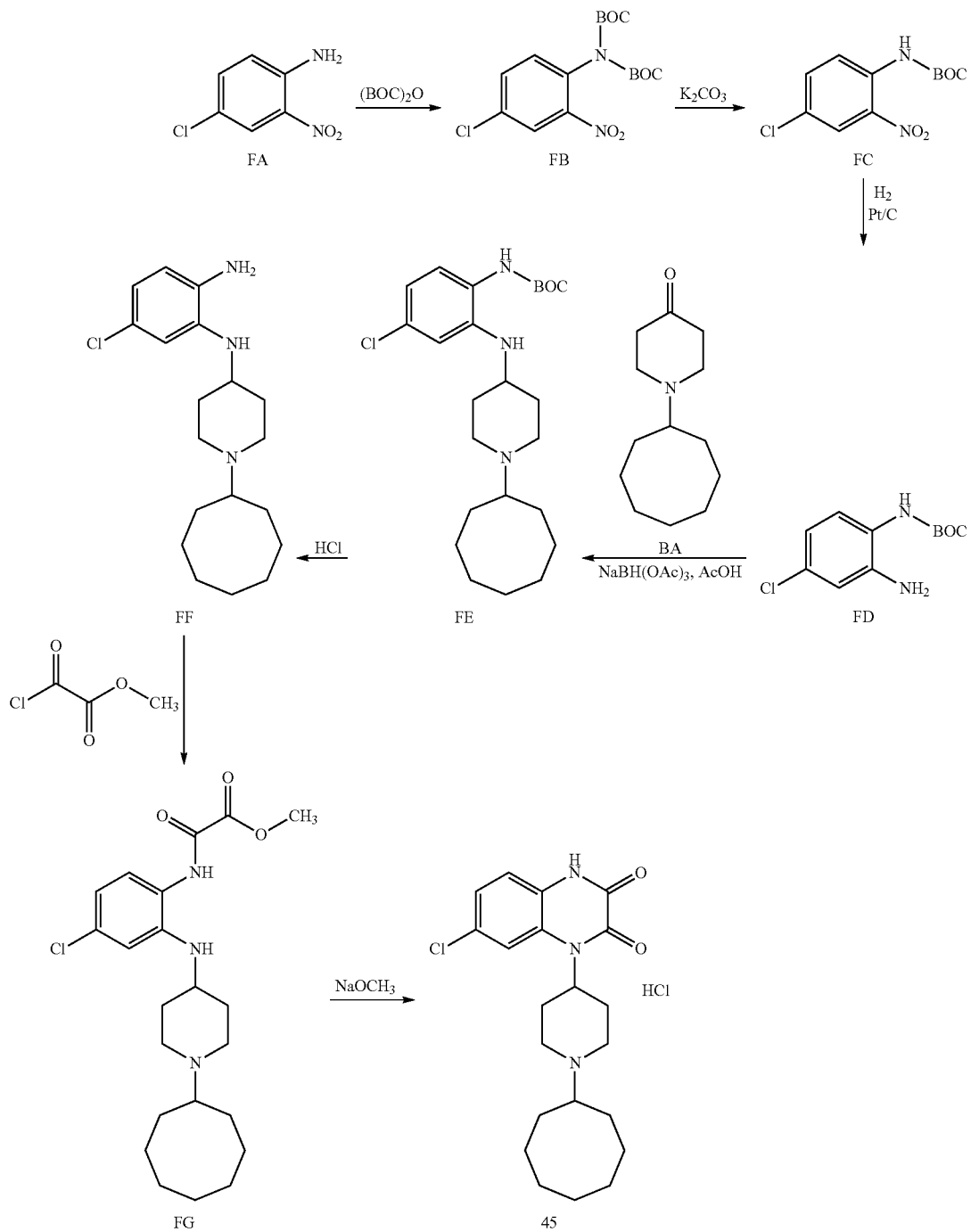

A mixture of 4-chloro-2-nitroaniline (FA, 1.726 g, 10 mmol, Sigma-Aldrich), di-tert-butyl dicarbonate ([BOC]$_2$O, 20 mmol, Sigma-Aldrich) and 4-dimethylaminopyridine (DMAP, catalytic amount, Sigma-Aldrich) in THF (34 mL) was stirred at 90° C. for 1 h. After cooling to a temperature of about 25° C., the reaction mixture was concentrated under reduced pressure. The residue was chromatographed with a silica gel column eluted with a gradient of from 1:9 EtOAc: n-hexane to 1:4 EtOAc:n-hexane to provide the compound of formula FB as a colorless solid (yield>99%).

The identity of the compound of formula FB was confirmed using $^1$H NMR.

Compound FB: $^1$H NMR: $\delta_H$ (400 MHz, CDCl$_3$): 8.06 (1H, d, J=4 Hz), 7.60 (1H, dd, J=8 Hz, J=4 Hz), 7.27 (1H, d, J=4 Hz), 1.41 (18H, s).

To a mixture of the compound of formula FB (3.70 g, 9.9 mmol) and methanol (40 mL) was added K$_2$CO$_3$ (29.7 mmol) and the reaction mixture was stirred for 3 h at a temperature of about 25° C. After quenching with water (20 mL), the reaction mixture was neutralized with 1N HCl, adjusted to a pH within the range of from about 7 to about 8, extracted with EtOAc, washed with brine, dried (MgSO$_4$), and concentrated under reduced pressure. The residue was chromatographed with a silica gel column eluted with a gradient of from 1:19 EtOAc: n-hexane to 3:17 EtOAc:n-hexane to provide the compound of formula FC as a yellow solid (yield 90%).

The identity of the compound of formula FC, tert-butyl 4-chloro-2-nitrophenylcarbamate, was confirmed using $^1$H NMR.

Compound FC: $^1$H NMR: δ$_H$ (400 MHz, CDCl$_3$): 9.59 (1H, s), 8.57 (1H, d, J=8 Hz), 8.18 (1H, d, J=4 Hz), 7.55 (1H, dd, J=8 Hz, J=4 Hz), 1.54 (9H, s).

A mixture of the compound of formula FC (1.00 g, 3.67 mmol), 2% platinum on carbon (200 mg), and methanol (20 mL) was stirred at a temperature of about 25° C. for 2 h in a hydrogen atmosphere. After filtration through CELITE and washing of the filter pad with EtOAc, the filtrate was concentrated under reduced pressure and chromatographed with an amino-silica gel column (Yamazen Corp. WO91-01) eluted with a gradient of from 1:4 EtOAc:n-hexane to 1:1 EtOAc:n-hexane to provide the compound of formula FD as a colorless solid (yield 94%).

The identity of the compound of formula FD, tert-butyl 2-amino-4-chlorophenylcarbamate, was confirmed using $^1$H NMR and LC/MS.

Compound FD: $^1$H NMR: δ$_H$ (400 MHz, CDCl$_3$): 7.18 (1H, d, J=8 Hz), 6.86 (1H, d, J=4 Hz), 6.80 (1H, dd, J=8 Hz, J=4 Hz), 6.25 (1H, s), 1.50 (9H, s); LC/MS, m/z=243.0 [M+H]$^+$ (Calc: 242.7).

A mixture of the compound of formula FD (840 mg, 3.46 mmol), the compound of formula BA (5.54 mmol), sodium triacetoxyborohydride (10.4 mmol), acetic acid (3.46 mmol), and chloroform (30 mL) was stirred for 16 h at a temperature of about 25° C. After quenching with saturated NaHCO$_3$ solution, the mixture was extracted with chloroform, dried (MgSO$_4$), and concentrated under reduced pressure. The residue was chromatographed with an amino-silica gel column (Yamazen Corp. W091-01) eluted with a gradient of from 3:17 EtOAc:n-hexane to 3:7 EtOAc:n-hexane to provide the compound of formula FE as a colorless solid (yield 56%).

The identity of the compound of formula FE, tert-butyl 4-chloro-2-(1-cyclooctylpiperidin-4-ylamino)phenylcarbamate, was confirmed using $^1$H NMR.

Compound FE: $^1$H NMR: δ$_H$ (400 MHz, CDCl$_3$): 7.15 (1H, d, J=8 Hz), 6.66 (1H, s), 6.65 (1H, s), 5.98 (1H, m), 3.84 (1H, m), 3.23 (1H, m), 2.84-2.70 (3H, m), 2.42 (2H, m), 2.04 (2H, m), 1.92-1.39 (24H, m).

To a suspension of the compound of formula FE (844 mg, 1.93 mmol) in 1,4-dioxane (8 mL) was added 4N HCl in 1,4-dioxane (19.3 mmol) and the reaction mixture was stirred for 2 h at a temperature of about 25° C. Thereafter, the reaction mixture was heated to 50° C. and stirred for 30 min. After concentration under reduced pressure, the mixture was neutralized with 28% aqueous ammonia to adjust the pH within the range from about 13 to about 14. After extraction with chloroform, the organic layer was dried (MgSO$_4$) and concentrated under reduced pressure to provide the compound of formula FF as a brown solid (yield>99%).

The identity of the compound of formula FF, 5-chloro-N$^1$-(1-cyclooctylpiperidin-4-yl)benzene-1,2-diamine, was confirmed using $^1$H NMR.

Compound FF: $^1$H NMR: δ$_H$ (400 MHz, CDCl$_3$): 6.63-6.58 (3H, m), 5.98 (1H, m), 3.37 (1H, m), 3.22 (2H, m), 2.85-2.83 (2H, m), 2.44 (1H, d, J=12 Hz), 2.41 (2H, t, J=12 Hz), 2.08 (2H, d, J=12 Hz), 1.83-1.45 (17H, m).

To a mixture of the compound of formula FF (168 mg, 0.5 mmol) and methylene chloride (3 mL) at a temperature of 0° C. was added dropwise over a 10 minute period a mixture of methyl 2-chloro-2-oxoacetate (0.55 mmol, Sigma-Aldrich) and methylene chloride (1.5 mL). The resulting reaction mixture was stirred at 0° C. for 30 min. After quenching with saturated NaHCO$_3$ solution, the mixture was extracted with chloroform, dried (MgSO$_4$), and concentrated under reduced pressure to provide an oil. The oil was chromatographed with a silica gel column eluted with a gradient of from 97%:3% CHCl$_3$:MeOH to 90%:10% CHCl$_3$:MeOH to provide 181 mg of the compound of formula FG as a yellow amorphous solid (yield 86%).

The identity of the compound of formula FG, methyl 2-(4-chloro-2-(1-cyclooctylpiperidin-4-ylamino)phenylamino)-2-oxoacetate, was confirmed using NMR and LC/MS.

Compound FG: $^1$H NMR: δ$_H$ (300 MHz, CDCl$_3$): 8.80 (1H, s), 7.43 (1H, d, J=8.7 Hz), 6.79 (1H, d, J=8.7 Hz), 6.69 (1H, d, J=2.4 Hz), 3.98 (3H, s), 3.40-2.83 (7H, m), 2.84-1.45 (17H, m); LC/MS, m/z=421.8 [M+H]$^+$ (Calc: 422.0).

To a mixture of the compound of formula FG (259 mg, 0.614 mmol) and ethanol (6 mL) was added sodium methoxide (133 mg, 2.46 mmol, Sigma-Aldrich) at a temperature of about 25° C. The reaction mixture was heated to 70° C. then stirred at that temperature for 3 h. After concentration under reduced pressure, 1N aqueous HCl was added to adjust the pH within the range of from about 2 to about 3; thereafter a white precipitate formed. The precipitate was filtered, washed with water, washed with methanol, and dried under reduced pressure at 50° C. to provide 171 mg of the hydrochloride of Heterocyclic-Substituted Piperidine Compound 45 as a colorless solid (yield 65%).

The identity of Heterocyclic-Substituted Piperidine Compound 45, 7-chloro-1-(1-cyclooctylpiperidin-4-yl)quinoxaline-2,3(1H,4H)-dione, was confirmed using $^1$H NMR and LC/MS.

Heterocyclic-Substituted Piperidine Compound 45: $^1$H NMR: δ$_H$ (300 MHz, MeOD): 7.78 (1H, d, J=1.8 Hz), 7.25 (1H, dd, J=2 Hz, J=8.7 Hz), 7.18 (1H, d, J=8.7 Hz), 4.77 (1H, m), 3.60-3.37 (6H, m), 3.32-3.10 (3H, m), 2.09-1.48 (15H, m); LC/MS (97%, t$_r$=2.09 min), m/z=390.0 [M+H]$^+$ (Calc: 389.9).

5.15 Example 15

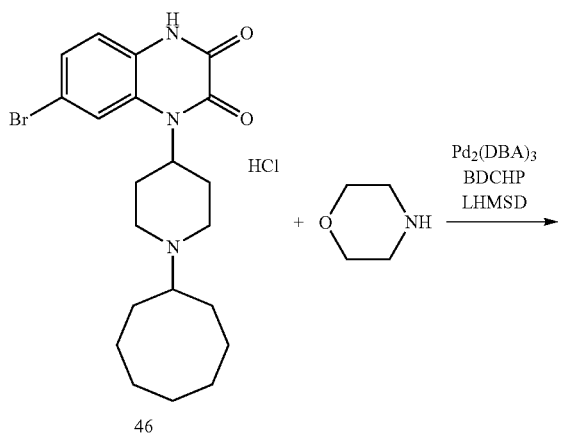

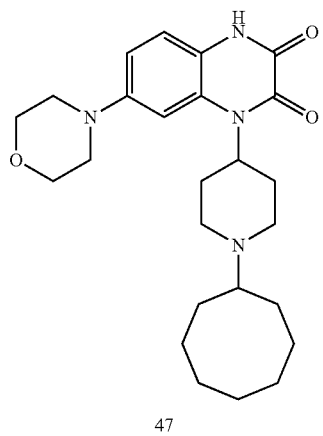

47

Heterocyclic-Substituted Piperidine Compound 46 was prepared in a manner similar to Heterocyclic-Substituted Piperidine Compound 45 in Example 14 except that 4-bromo-2-nitroaniline (Sigma-Aldrich) was used in place of 4-chloro-2-nitroaniline.

The identity of Heterocyclic-Substituted Piperidine Compound 46, 7-bromo-1-(1-cyclooctylpiperidin-4-yl)quinoxaline-2,3(1H,4H)-dione, was confirmed using $^1$H NMR and LC/MS.

Heterocyclic-Substituted Piperidine Compound 46: $^1$H NMR: $\delta_H$ (300 MHz, MeOD): 7.88 (1H, d, J=1.8 Hz), 7.38 (1H, dd, J=1.8 Hz, J=8.7 Hz), 7.13 (1H, d, J=8.7 Hz), 4.81 (1H, m), 3.60-3.34 (6H, m), 3.25-3.10 (3H, m), 1.48-2.12 (15H, m); LC/MS (97%, $t_r$=2.10 min), m/z=435.9 [M+H]$^+$ (Calc: 434.4).

To a mixture of the hydrochlorice of Heterocyclic-Substituted Piperidine Compound 46 (120 mg, 0.25 mmol, 1 eq.), morpholine (0.61 mmol, 2.4 eq., Wako Pure Chemical Industries, Ltd., Osaka, Japan), tris(dibenzylideneacetone) dipalladium (Pd$_2$(DBA)$_3$, 0.013 mmol, 0.05 eq., Sigma-Aldrich), (2-biphenyl)-dicyclohexylphosphine (BDCHP, 0.013 mmol, 0.05 eq., Sigma-Aldrich), and DMF (3 mL) in a tube at a temperature of about 25° C. was added a µmol/L THF solution of lithium hexamethyldisilazide (LHMDS, 1.15 mmol, 4.6 eq., Sigma-Aldrich) and the tube was sealed. Thereafter, under microwave irradiation, the reaction mixture was stirred for 30 min at 150° C. After cooling to a temperature of about 25° C., to the reaction mixture was added to 2N HCl (0.5 mL) and the mixture was stirred for 5 min. After concentration under reduced pressure, the resulting black oil was chromatographed with an amino-silica gel column (Yamazen Corp. WO91-01) eluted with a gradient of from 90%:10% EtOAc:MeOH to 70%:30% EtOAc:MeOH to provide a yellow solid. The solid was recrystallized with 4:1 MeOH:EtOAc to provide Heterocyclic-Substituted Piperidine Compound 47 as a pale yellow solid (yield 38%).

The identity of Heterocyclic-Substituted Piperidine Compound 47, 1-(1-cyclooctylpiperidin-4-yl)-7-morpholinoquinoxaline-2,3(1H,4H)-dione, was confirmed using $^1$H NMR and LC/MS.

Heterocyclic-Substituted Piperidine Compound 47: $^1$H NMR: $\delta_H$ (300 MHz, CD$_3$OD): 7.12-7.09 (2H, m), 6.88 (1H, dd, J=2.4 Hz, J=8.7 Hz), 4.88 (1H, m), 3.86 (4H, t, J=4.5 Hz), 3.17 (4H, t, J=4.5 Hz), 3.02-2.99 (2H, m), 2.84-2.74 (4H, m), 2.58-2.50 (2H, m), 1.89-1.54 (15H, m); LC/MS, m/z=441.0 [M+H]$^+$ (Calc: 440.6).

5.16 Example 16

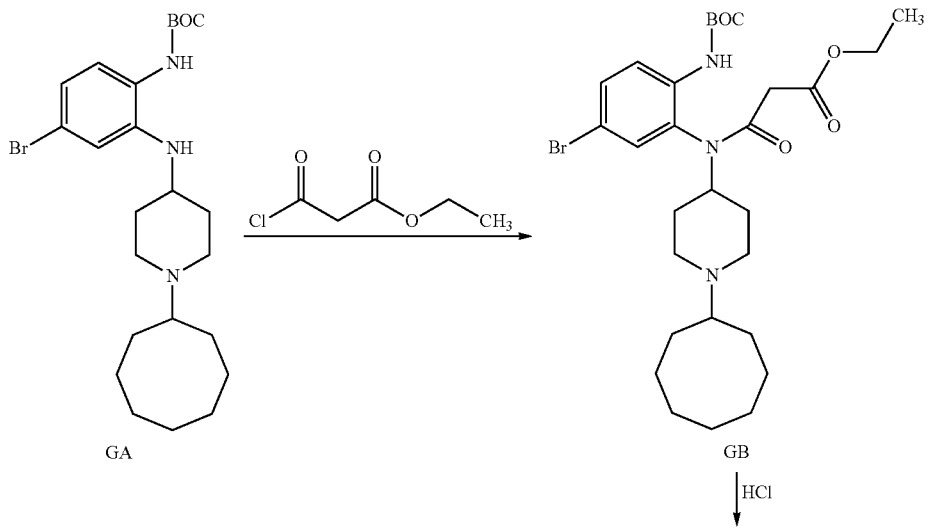

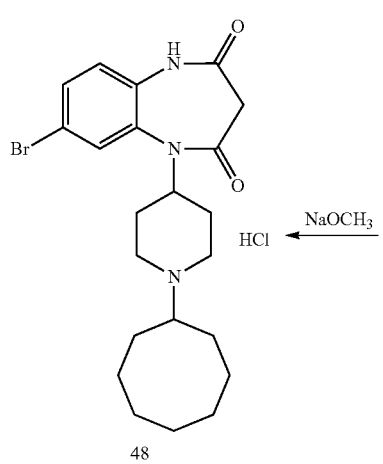 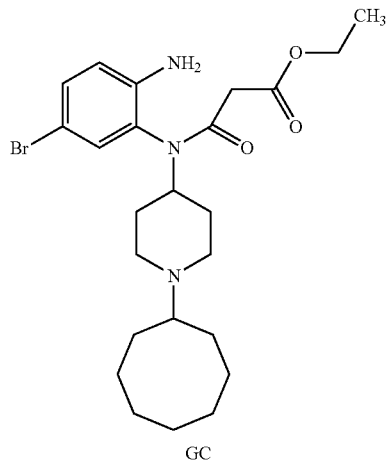

The compound of formula GA, tert-butyl 4-bromo-2-(1-cyclooctylpiperidin-4-ylamino)phenylcarbamate, was prepared in a manner similar to the compound of formula FE in Example 14 except that 4-bromo-2-nitroaniline was used in place of 4-chloro-2-nitroaniline.

To a mixture of the compound of formula GA (300 mg, 0.624 mmol), pyridine (1.25 mmol), and methylene chloride (8 mL) at a temperature of 0° C. was added dropwise over a 10 minute period a mixture of ethyl 3-chloro-3-oxopropanoate (0.66 mmol, Sigma-Aldrich) in methylene chloride (2 mL). The resulting reaction mixture was stirred at 0° C. for 1 h. After quenching with water and extraction with chloroform, the organic layer was dried (MgSO$_4$) and concentrated under reduced pressure. The resulting oil was chromatographed with an amino-silica gel column (Yamazen Corp. W091-01) eluted with a gradient of from 3:97 EtOAc:n-hexane to 1:4 EtOAc:n-hexane to provide 166 mg of the compound of formula GB as a colorless amorphous solid (yield 44%).

The identity of the compound of formula GB, ethyl 3-((5-bromo-2-(tert-butoxycarbonylamino)phenyl)(1-cyclooctylpiperidin-4-yl)amino)-3-oxopropanoate, was confirmed using $^1$H NMR.

Compound GB: $^1$H NMR: $\delta_H$ (400 MHz, DMSO): 8.84 (1H, s), 7.69 (1H, dd, J=8.4 Hz), 7.58 (1H, d, J=8.5 Hz), 7.26 (1H, d, J=4 Hz), 4.21 (1H, m), 3.99 (2H, q, J=8 Hz), 2.97 (2H, m), 2.64 (2H, m), 2.44 (1H, s), 2.15 (2H, m), 1.77-1.32 (14H, m), 1.14 (3H, t, J=8 Hz).

To a mixture of the compound of formula GB (160 mg, 0.27 mmol) and 1,4-dioxane (3 mL) at a temperature of about 25° C. was added 4N HCl in 1,4-dioxane (5.4 mmol). The resulting reaction mixture was cooled to 0° C. and stirred for 2 h. Thereafter, the reaction mixture was warmed to a temperature of about 25° C. and stirred for 1 h. After quenching with water, the mixture was neutralized with 28% aqueous ammonia to adjust the pH within the range of from about 13 to about 14. Thereafter, After chloroform was used in an extraction, the organic layer was dried (MgSO$_4$), and concentrated under reduced pressure. The resulting oil was chromatographed with a silica gel column eluted with a gradient of from 97%:3% CHCl$_3$:MeOH to 90%:10% CHCl$_3$:MeOH to provide 30 mg of the compound of formula GC as a colorless amorphous solid (yield 23%).

The identity of the compound of formula GC, ethyl 3-((2-amino-5-bromophenyl)(1-cyclooctylpiperidin-4-yl)amino)-3-oxopropanoate, was confirmed using $^1$H NMR and LC/MS.

Compound GC: $^1$H NMR: $\delta_H$ (400 MHz, CDCl$_3$): 7.25 (1H, d, J=8 Hz), 7.07 (1H, d, J=2 Hz), 6.65 (1H, d, J=8 Hz), 4.11 (2H, q, J=8 Hz), 3.99 (1H, s), 3.13 (2H, s), 2.95-2.23 (7H, m), 2.02-1.38 (14H, m), 1.22 (3H, t, J=8 Hz); LC/MS, m/z=496.0 [M+H]$^+$ (Calc: 494.5).

To a mixture of the compound of formula GC (65 mg, 0.13 mmol) in ethanol (4 mL) at a temperature of about 25° C. was added sodium methoxide (28 mg, 0.53 mmol). The reaction mixture was heated to 70° C. then stirred at that temperature for 1 h. After concentration under reduced pressure, the oil obtained was chromatographed by preparative thin layer chromatography (TLC, eluted with 10:1:0.1 CHCl$_3$:MeOH: aqueous ammonia) to provide a colorless amorphous solid. To the solid was added 4N HCl in 1,4-dioxane. The resulting mixture was concentrated under reduced pressure. The residue was dried under reduced pressure at 50° C. to provide 50 mg of the hydrochloride of Heterocyclic-Substituted Piperidine Compound 48 as a colorless solid (yield 79%).

The identity of Heterocyclic-Substituted Piperidine Compound 48, 8-bromo-1-(1-cyclooctylpiperidin-4-yl)-1H-benzo[b][1,4]diazepine-2,4(3H,5H)-dione, was confirmed using $^1$H NMR and LC/MS.

Heterocyclic-Substituted Piperidine Compound 48: $^1$H NMR: $\delta_H$ (300 MHz, MeOD): 7.67 (1H, d, J=2.4 Hz), 7.50 (1H, dd, J=2.4 Hz, J=8.4 Hz), 7.14 (1H, d, J=8.4 Hz), 4.22 (1H, m), 3.59-3.02 (8H, m), 2.65 (2H, m), 2.20-1.41 (15H, m); LC/MS (98%, t$_r$=2.05 min), m/z=449.9 [M+H]$^+$ (Calc: 448.4).

5.17 Example 17

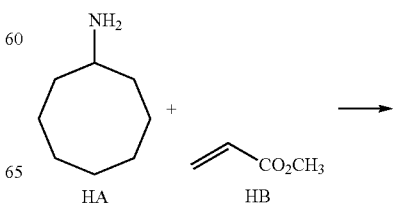

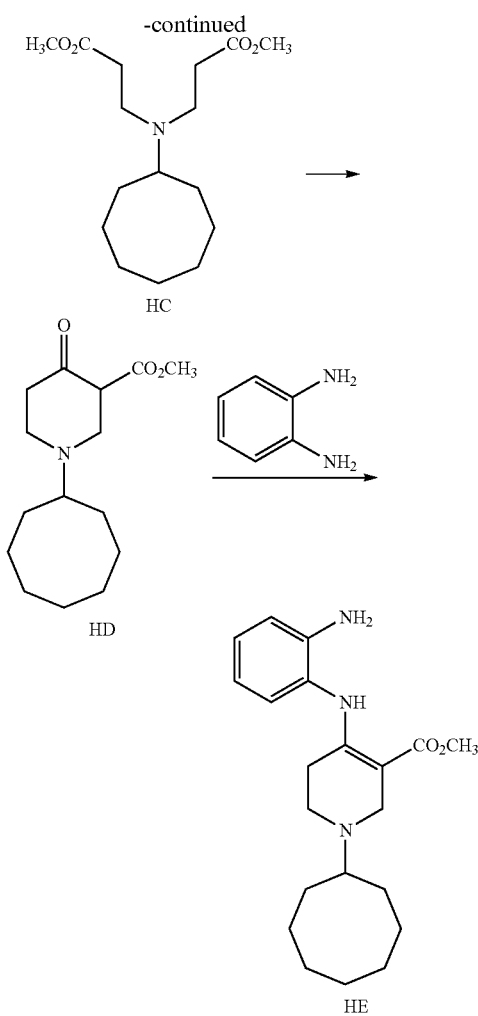

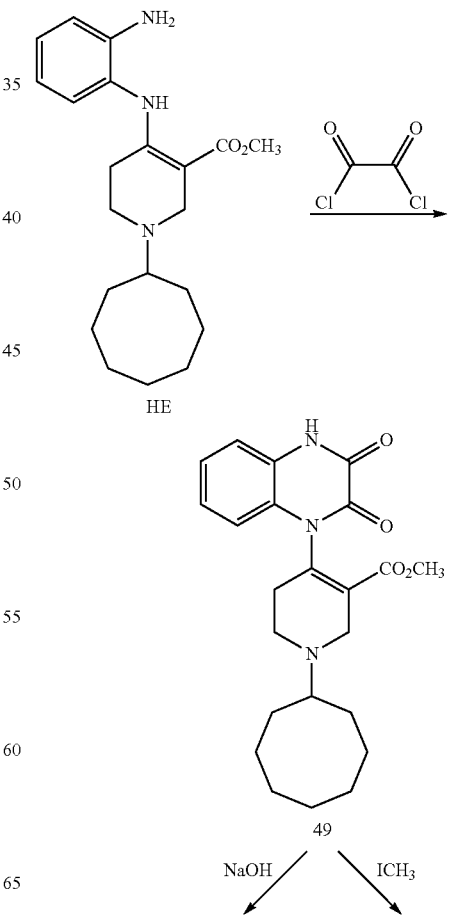

Cyclooctylamine (HA, 155 g, 1218.5 mmol, Sigma-Aldrich) was dissolved in acetonitrile (500 mL). Methyl acrylate (HB, 470 g, 5460 mmol, Sigma-Aldrich) was added, followed by the addition of bismuth triflate (15 g, Sigma-Aldrich), and the mixture heated under reflux for 18 h. The mixture was concentrated under reduced pressure and was chromatographed by flash silica eluted with hexanes, followed by eluting with 10:1 hexanes:EtOAc to provide 360 g of a compound of formula HC as a colorless oil (yield>99%).

The identity of the compound of formula HC, dimethyl 3,3'-(cyclooctylazanediyl)dipropanoate, was confirmed using $^1$H NMR.

Compound HC: $^1$H NMR: δ (400 MHz, CDCl$_3$): 3.68 (3H, s), 2.70 (2H, t, J=10 Hz), 2.65 (1H, m), 2.40 (2H, t, J=10 Hz), 1.75-1.35 (14H, m).

The compound of formula HC (100 g, 334 mmol) was dissolved in dry toluene (2 L) and cooled to 0° C. under a nitrogen atmosphere. Sodium tert-butoxide (41.7 g, 434.2 mmol, Sigma-Aldrich) was added and the mixture was stirred for 3 h at 0° C. When LC/MS showed about 10-20% of the compound of formula HC remained, a further portion of sodium tert-butoxide (10 g) was added and stirring was continued for an additional 1 h. The mixture was poured into water (2 L) and the organic phase was separated. The aqueous phase was extracted with ethyl acetate (1 L). The organic phases were combined, dried (MgSO$_4$), and concentrated under reduced pressure to provide a yellow oil which was chromatographed by flash silica eluted with 5:1 hexanes: EtOAc to provide 60 g of the compound of formula HD as a yellow oil (yield 68%) which slowly solidified upon standing.

The identity of the compound of formula HD, methyl 1-cyclooctyl-4-oxopiperidine-3-carboxylate, was confirmed using TLC.

Compound HD: TLC (SiO$_2$) 5:1 Hexanes:EtOAc: Rf=0.25 with UV detection, Dragendorffs reagent.

The compound of formula HD (20 g, 75.4 mmol) and o-phenylenediamine (16.29 g, 150.8 mmol) were dissolved in toluene (200 mL). Acetic acid (1 mL) was added and the mixture was heated under reflux with azeotropic removal of water for 1 h. The mixture was concentrated under reduced pressure and the residue was chromatographed by flash silica eluted with 100:2 EtOAc:AcOH, followed by eluting with 100:2:5 EtOAc:AcOH:MeOH to provide an orange gum. The gum was dissolved in ethyl acetate (400 mL) and treated with potassium carbonate/water until neutralized, i.e., had a pH greater than 7. The organic phase was separated, dried (MgSO$_4$) and concentrated under reduced pressure to provide and orange gum which crystallized upon standing. Trituration with 1:10 hexanes:diethyl ether (200 mL) provided 17 g of the compound of formula HE as a buff-colored solid (yield 63%).

The identity of the compound of formula HE, methyl 4-(2-aminophenylamino)-1-cyclooctyl-1,2,5,6-tetrahydropyridine-3-carboxylate, was confirmed using $^1$H NMR.

Compound HE: $^1$H NMR: δ (400 MHz, CDCl$_3$): 9.8 (1H, s), 7.05 (1H, t, J=10 Hz), 6.95 (1H, d, J=10 Hz), 6.75-6.65 (2H, m), 3.85 (2H, bs), 3.70 (3H, s), 3.32 (2H, s), 2.72 (1H, m), 2.50 (2H, t, J=10 Hz), 2.25 (2H, t, J=10 Hz), 1.80-1.40 (14H, m).

5.18 Example 18

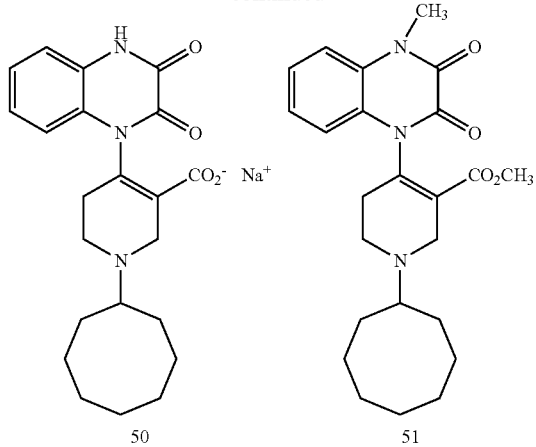

The compound of formula HE (11 g, 30.77 mmol), prepared in Example 17, was dissolved in dichloromethane (2 L) and added dropwise to a cold, -78° C., mixture of oxalyl dichloride (2.86 mL, 33.85 mmol, Sigma-Aldrich) in dichloromethane (6 L) over 3 h. Thereafter with stirring, over 18 h the resulting mixture was allowed to warm to a temperature of about 25° C. The mixture was concentrated under reduced pressure and the residue was chromatographed by flash silica eluted with 400:10:1 EtOAc:MeOH:ammonia to provide a yellow solid. This solid was triturated with diethyl ether (30 mL) to provide 4.0 g of Heterocyclic-Substituted Piperidine Compound 49 as a light yellow solid (yield 32%).

The identity of Heterocyclic-Substituted Piperidine Compound 49, methyl 1-cyclooctyl-4-(2,3-dioxo-3,4-dihydroquinoxalin-1(2H)-yl)-1,2,5,6-tetrahydropyridine-3-carboxylate, was confirmed using $^1$H NMR.

Heterocyclic-Substituted Piperidine Compound 49: $^1$H NMR: δ (400 MHz, CDCl$_3$): 10.7 (1H, bs), 7.28 (1H, m), 7.15 (2H, m), 7.05 (1H, m), 3.55 (2H, m), 3.50 (3H, m), 2.90 (3H, m), 2.50 (2H, m), 1.90-1.40 (14H, m).

Heterocyclic-Substituted Piperidine Compound 49 (100 mg, 0.24 mmol) was dissolved in methanol (1 mL). Crushed sodium hydroxide (50 mg, 1.21 mmol) was dissolved in water (0.3 mL), added to the methanol, and the resulting mixture stirred for 1 h. After this time a solid had precipitated. The mixture was filtered and the filter cake was washed with methanol (3 mL) and concentrated under reduced pressure to provide 105 mg of Heterocyclic-Substituted Piperidine Compound 50 as a buff-colored solid (yield>99%).

The identity of Heterocyclic-Substituted Piperidine Compound 50, methyl 1-cyclooctyl-4-(2,3-dioxo-3,4-dihydroquinoxalin-1(2H)-yl)-1,2,5,6-tetrahydropyridine-3-carboxylic acid sodium salt, was confirmed using $^1$H NMR.

Heterocyclic-Substituted Piperidine Compound 50: $^1$H NMR: δ (400 MHz, (CD$_3$)$_2$SO): 7.00 (1H, m), 6.90 (1H, m), 6.85 (1H, m), 6.77 (1H, m), 3.40 (1H, m), 2.65 (4H, m), 220 (1H, m), 2.00 (1H, m), 1.80-1.40 (14H, m).

The Heterocyclic-Substituted Piperidine Compound 49 (100 mg, 0.24 mmol) was dissolved in dry DMF (2 mL) under a nitrogen atmosphere. Sodium hydride (95%, Sigma-Aldrich) was added and the mixture was heated to 90° C. for 1 h then cooled to 50° C. with stirring. Iodomethane (18 μL, 0.292 mmol, Sigma-Aldrich) was added and the mixture stirred for 3 h. LC/MS showed greater than 75% conversion after this time. The mixture was partitioned between diethyl ether (100 mL) and 1M potassium carbonate (100 mL) and the organic phase separated, dried (MgSO$_4$), and concentrated under reduced pressure to provide a residue. The residue was chromatographed by flash silica eluted with 1:1 EtOAc:hexanes, followed by eluting with 100:100:10:1 EtOAc:hexanes:MeOH:ammonia to provide 35 mg of Heterocyclic-Substituted Piperidine Compound 51 as a yellow solid.

The identity of Heterocyclic-Substituted Piperidine Compound 51, methyl 1-cyclooctyl-4-(4-methyl-2,3-dioxo-3,4-dihydroquinoxalin-1(2H)-yl)-1,2,5,6-tetrahydropyridine-3-carboxylate, was confirmed using $^1$H NMR and TLC.

Heterocyclic-Substituted Piperidine Compound 51: $^1$H NMR: δ (400 MHz, CDCl$_3$): 7.25 (1H, m), 7.18 (2H, m), 7.12 (1H, m), 3.70 (3H, S), 3.56 (2H, m), 3.50 (3H, s), 2.85 (1H, m), 2.50 (2H, m), 1.80 (4H, m), 1.70-1.45 (10H, m); TLC (SiO$_2$) 100:100:10:1 EtOAc:hexanes:MeOH:ammonia: Rf=0.22 with UV detection, Dragendorff's reagent.

5.19 Example 19

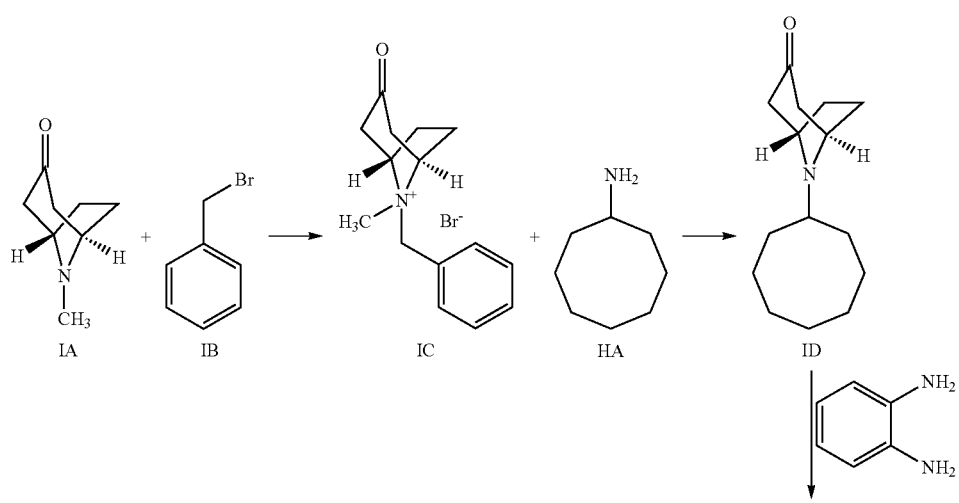

-continued

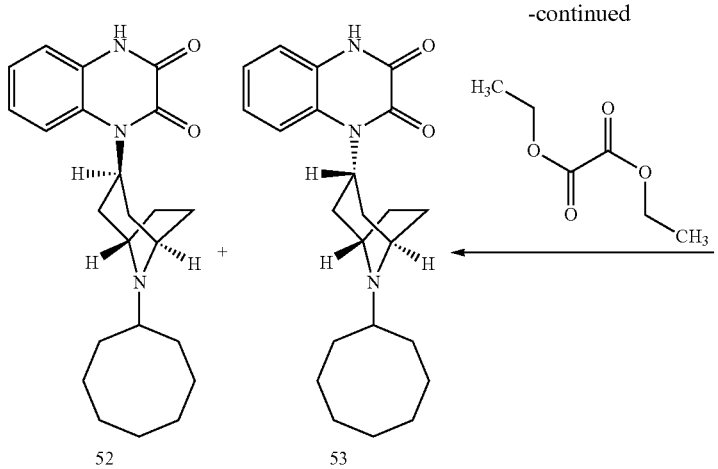

52    53

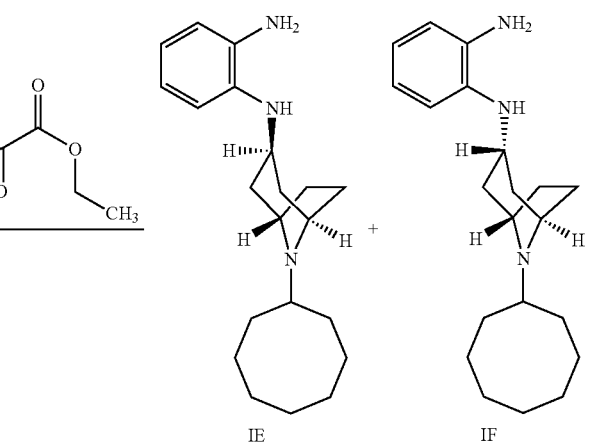

IE    IF

The compound of formula IB, (bromomethyl)benzene (6.5 g, 38 mmol, Sigma-Aldrich), was added to a mixture of the compound of formula IA, (1R,5S)-8-methyl-8-azabicyclo [3.2.1]octan-3-one (5 g, 36 mmol, Sigma-Aldrich), in acetone (100 mL) over 30 min at a temperature of about 25° C. The resulting mixture was stirred at a temperature of about 25° C. for 1 h then at 38° C. for 2 h. Thereafter, the mixture was cooled to a temperature of about 25° C., filtered, and washed twice with hexanes (10 mL for each wash) to provide 10 g of the compound of formula IC as white solid (yield 85%).

The compound of formula IC, (1R,5S)-8-benzyl-8-methyl-3-oxo-8-azoniabicyclo[3.2.1]octane bromide (5 g, 16.1 mmol), was mixed with 40 mL ethanol and 20 mL of water. This mixture was added to a mixture at 70° C. of the compound of formula HA (2.0 g, 16 mmol), and $K_2CO_3$ (0.2 g, 1.4 mmol) in ethanol (150 mL) over 30 min. After 3 h at 70° C., the reaction mixture was cooled to a temperature of about 25° C. and concentrated. The residue was treated with water (50 mL), and extracted three times with chloroform (100 mL for each extraction). The combined organic layers were washed with brine (50 mL), and concentrated to provide 3.5 g of the compound of formula ID (yield 92%).

Sodium triacetoxyborohydride (50 mmol) was added to a mixture of the compound of formula ID, (1R,5S)-8-cyclooctyl-8-azabicyclo[3.2.1]octan-3-one (3 g, 12.8 mmol), and o-phenylenediamine (3 g, 27.8 mmol) in 100 mL of methylene chloride at a temperature of about 25° C. Thereafter, 3 mL of acetic acid was added. The resulting mixture was stirred at a temperature of about 25° C. for about 16 h. Thereafter, methanol (2 mL) and water (25 mL) were added and the mixture was neutralized with 28% aqueous ammonia to adjust the pH to about 8. The organic layer was separated, washed with brine (10 mL), concentrated, and chromatographed with a silica gel column eluted with 10:1:1 EtOAc: MeOH:TEA to provide 2.8 g of a mixture of the compounds of formula IE and IF as brown oil (yield 68%).

The identity of the compound of formula IE, $N^1$-((1R,3r,5S)-8-cyclooctyl-8-azabicyclo[3.2.1]octan-3-yl)benzene-1,2-diamine, was confirmed using TLC.

Compound IE: TLC ($SiO_2$) 100:7:1 EtOAc:MeOH: $NH_4OH$: Rf=0.6 with UV detection, Dragendorff's reagent.

The identity of the compound of formula IF, $N^1$-((1R,3s,5S)-8-cyclooctyl-8-azabicyclo[3.2.1]octan-3-yl)benzene-1,2-diamine, was confirmed using TLC.

Compound IF: TLC ($SiO_2$) 100:7:1 EtOAc:MeOH: $NH_4OH$: Rf=0.4 with UV detection, Dragendorff's reagent.

A mixture of the above brown oil (0.3 g, containing the compounds of formula IE and IF) in 20 mL of diethyl oxalate (Sigma-Aldrich) was heated at 140° C. for 16 h. After cooling to a temperature of about 25° C., the reaction mixture was diluted with EtOAc, washed with 30 mL of 2N aqueous NaOH and brine (20 mL), concentrated, and chromatographed with a silica gel column eluted with 5:5:0.5:0.5 EtOAc:hexane:MeOH:TEA to provide 60 mg and 20 mg of the two Heterocyclic-Substituted Piperidine Compounds 52 and 53, respectively, each as a white solid (yield 18% and 6%, respectively).

The identity of Heterocyclic-Substituted Piperidine Compound 52, 1-(1R,3r,5S)-8-cyclooctyl-8-azabicyclo[3.2.1]octan-3-yl)quinoxaline-2,3(1H,4H)-dione, was confirmed using $^1H$ NMR, LC/MS and TLC.

Heterocyclic-Substituted Piperidine Compound 52: $^1H$ NMR: $\delta_H$ (400 MHz, ($CD_3OD+CDCl_3$)): 7.51 (1H, d, J=7.9 Hz), 7.11-7.21 (m, 3H), 5.16-5.24 (m, 1H), 4.08 (br, 2H), 2.9 (br, 1H), 2.56-2.64 (m, 2H), 2.06-2.26 (m, 6H), 1.72-1.96 (m, 6H), 1.32-1.62 (m, 8H); LC/MS (100%, $t_r$=4.988 min), m/z=382.4 [M+H]$^+$ (Calc: 381.5); TLC ($SiO_2$) 100:7:1 EtOAc:MeOH:$NH_4OH$: Rf=0.5 with UV detection, Dragendorff's reagent.

The identity of Heterocyclic-Substituted Piperidine Compound 53, 1-((1R,3s,5S)-8-cyclooctyl-8-azabicyclo[3.2.1] octan-3-yl)quinoxaline-2,3(1H,4H)-dione, was confirmed using $^1H$ NMR, LC/MS and TLC.

Heterocyclic-Substituted Piperidine Compound 53: $^1H$ NMR: $\delta_H$ (400 MHz, ($CD_3OD+CDCl_3$)): 7.62 (br, 1H), 7.21-7.24 (m, 3H), 4.95 (br, 1H), 3.75 (br, 2H), 3.36 (br, 1H), 2.91-2.98 (m, 2H), 2.06-2.16 (m, 2H), 1.42-1.96 (m, 18H); LC/MS (100%, $t_r$=4.718 min), m/z=382.2 [M+H]$^+$ (Calc: 381.5); TLC ($SiO_2$) 100:7:1 EtOAc:MeOH:$NH_4OH$: Rf=0.45 with UV detection, Dragendorff's reagent.

5.20 Example 20

In a manner similar to Example 19, the following Heterocyclic-Substituted Piperidine Compounds were prepared from compounds previously synthesized.

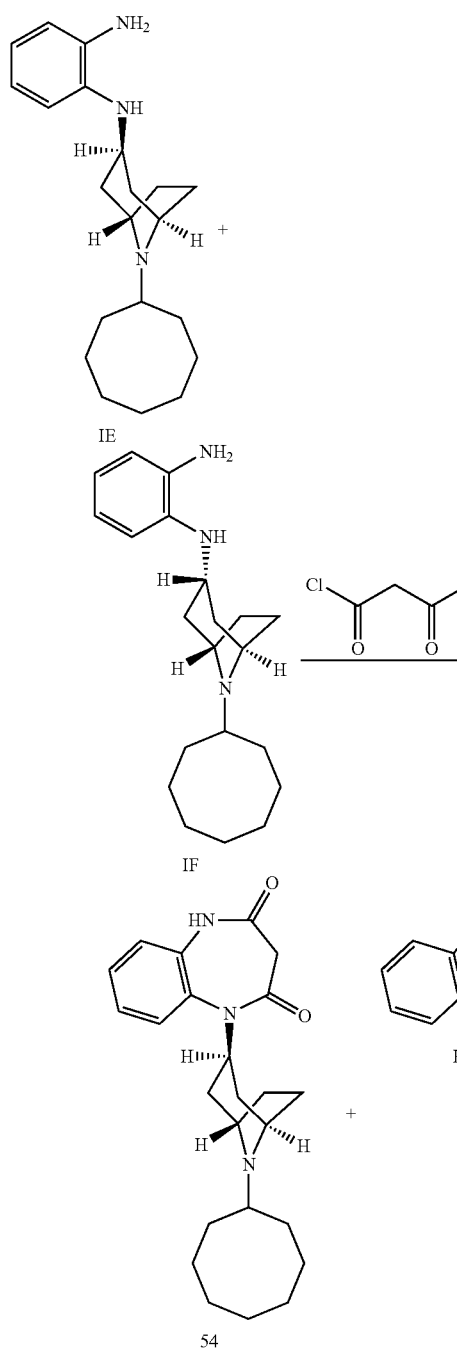

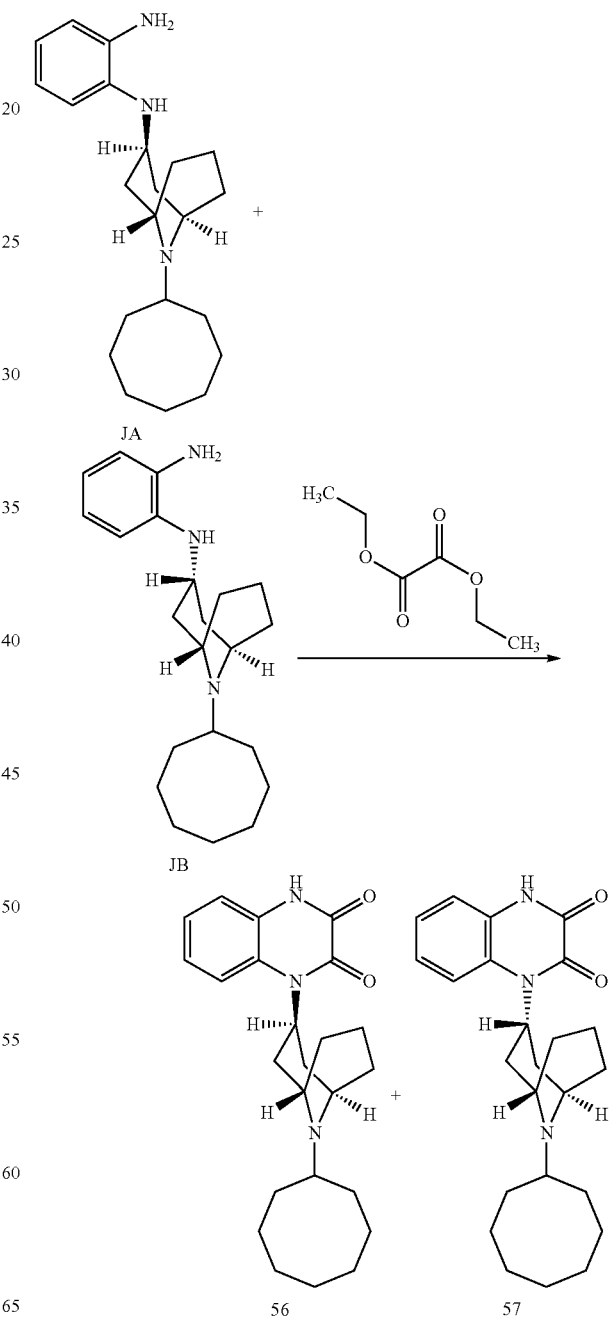

Heterocyclic-Substituted Piperidine Compounds 54 and 55 were prepared from the compounds of formula IE and IF, respectively, except that malonyl dichloride was used in Example 19 in place of diethyl oxalate.

The identity of Heterocyclic-Substituted Piperidine Compound 54, 1-(1R,3r,5S)-8-cyclooctyl-8-azabicyclo[3.2.1]octan-3-yl)-1H-benzo[b][1,4]diazepine-2,4(3H,5H)-dione, was confirmed using $^1$H NMR, LC/MS and TLC.

Heterocyclic-Substituted Piperidine Compound 54: $^1$H NMR: $\delta_H$ (400 MHz, (CD$_3$OD+CDCl$_3$)): 7.38-7.42 (m, 1H), 7.28-7.32 (m, 2H), 7.16-7.25 (m, 1H), 4.18-4.24 (m, 1H), 3.56-3.68 (m, 2H), 3.36 (1H, d, J=12.4 Hz), 3.07 (d, 1H, J=12.3 Hz), 2.52-2.61 (m, 1H), 2.2-2.4 (m, 3H), 1.96-2.02 (m, 3H), 1.44-1.82 (m, 16H); LC/MS (100%, t$_r$=5.054 min), m/z=396.3 [M+H]$^+$ (Calc: 395.5); TLC (SiO$_2$) 100:7:1 EtOAc:MeOH:NH$_4$OH: Rf=0.7 with UV detection, Dragendorffs reagent.

The identity of Heterocyclic-Substituted Piperidine Compound 55, 1-(1R,3s,5S)-8-cyclooctyl-8-azabicyclo[3.2.1]octan-3-yl)-1H-benzo[b][1,4]diazepine-2,4(3H,5H)-dione, was confirmed using $^1$H NMR, LC/MS and TLC.

Heterocyclic-Substituted Piperidine Compound 55: $^1$H NMR: $\delta_H$ (400 MHz, (CD$_3$OD+CDCl$_3$)): 7.38-7.42 (m, 1H), 7.28-7.32 (m, 2H), 7.16-7.25 (m, 1H), 4.42-4.46 (m, 1H), 3.56-3.68 (m, 2H), 3.36 (1H, d, J=12.4 Hz), 3.21-3.24 (m, 1H), 3.07 (d, 1H, J=12.3 Hz), 2.45-2.58 (m, 1H), 1.44-1.84 (m, 18H); LC/MS (98.6%, t$_r$=5.000 min), m/z=396.3 [M+H]$^+$ (Calc: 395.5); TLC (SiO$_2$) 100:7:1 EtOAc:MeOH:NH$_4$OH: Rf=0.5 with UV detection, Dragendorff's reagent.

Heterocyclic-Substituted Piperidine Compounds 56 and 57 were prepared according to the procedure in Example 19 except that 9-methyl-9-azabicyclo[3.3.1]nonan-3-one (Pseudo-Pelletierine, obtained from Oakwook Products, Inc., West Columbia, S.C.) was used in place of the compound of formula IA to prepare the compounds of formula JA and JB which were used to prepare Heterocyclic-Substituted Piperidine Compounds 56 and 57, respectively.

The identity of Heterocyclic-Substituted Piperidine Compound 56, 1-((1R,3r,5S)-9-cyclooctyl-9-azabicyclo[3.3.1]nonan-3-yl)quinoxaline-2,3(1H,4H)-dione, was confirmed using $^1$H NMR, LC/MS and TLC.

Heterocyclic-Substituted Piperidine Compound 56: $^1$H NMR: $\delta_H$ (400 MHz, (CD$_3$OD+CDCl$_3$): 7.5-7.55 (m, 1H), 7.2-7.26 (m, 3H), 5.08 (br, 1H), 3.52-3.6 (m, 2H), 3.08-3.16 (m, 1H), 2.64-2.76 (m, 2H), 2.44-2.52 (m, 1H), 2.08-2.16 (m, 2H), 1.48-1.82 (m, 17H), 1.12-1.2 (m, 2H); LC/MS (97.9%, t$_r$=4.450 min), m/z=396.3 [M+H]$^+$ (Calc: 395.5); TLC (SiO$_2$) 10:2:1 EtOAc:MeOH:NH$_4$OH: Rf=0.62 with UV detection, Dragendorff's reagent.

The identity of Heterocyclic-Substituted Piperidine Compound 57, 1-((1R,3s,5S)-9-cyclooctyl-9-azabicyclo[3.3.1]nonan-3-yl)quinoxaline-2,3(1H,4H)-dione, was confirmed using $^1$H NMR, LC/MS and TLC.

Heterocyclic-Substituted Piperidine Compound 57: $^1$H NMR: $\delta_H$ (400 MHz, (CD$_3$OD+CDCl$_3$): 7.72 (br, 1H), 7.21-7.26 (m, 3H), 5.8 (br, 1H), 4.53 (br, 2H), 3.49-3.54 (m, 2H), 3.37-3.41 (m, 1H), 2.97-3.06 (m, 2H), 2.04-2.12 (m, 3H), 1.52-1.86 (m, 19H), 1.12-1.2 (m, 2H); LC/MS (97%, t$_r$=4.936 min), m/z=396.3 [M+H]$^+$ (Calc: 395.5); TLC (SiO$_2$) 10:2:1 EtOAc:MeOH:NH$_4$OH: Rf=0.3 with UV detection, Dragendorff's reagent.

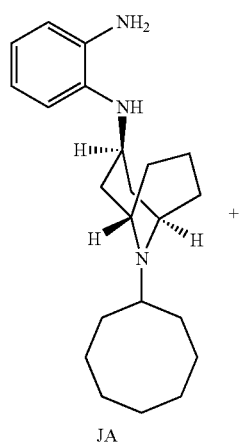

JA

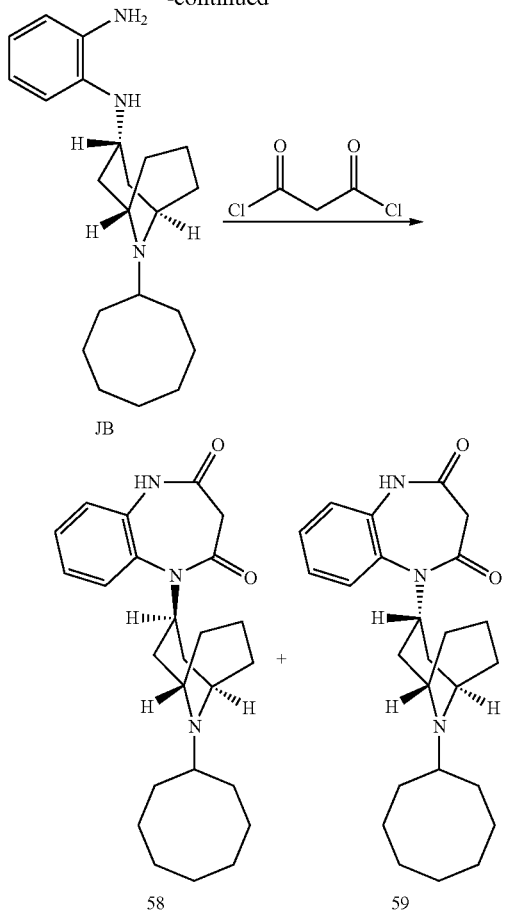

Heterocyclic-Substituted Piperidine Compounds 58 and 59 were prepared according to the procedure in Example 19 except that 9-methyl-9-azabicyclo[3.3.1]nonan-3-one was used in place of the compound of formula IA to prepare the compounds of formula JA and JB. Thereafter, in a manner similar to Example 2, Heterocyclic-Substituted Piperidine Compounds 58 and 59 were prepared from malonyl dichloride and the compounds of formula JA and JB, respectively.

The identity of Heterocyclic-Substituted Piperidine Compound 58, 1-((1R,3r,5S)-9-cyclooctyl-9-azabicyclo[3.3.1]nonan-3-yl)-1H-benzo[b][1,4]diazepine-2,4(3H,5H)-dione, was confirmed using $^1$H NMR, LC/MS and TLC.

Heterocyclic-Substituted Piperidine Compound 58: $^1$H NMR: $\delta_H$ (400 MHz, (CD$_3$OD+CDCl$_3$)): 7.46-7.50 (m, 1H), 7.27-7.31 (m, 2H), 7.13-7.17 (m, 1H), 4.42-4.48 (m, 1H), 3.44-3.64 (m, 2H), 3.3-3.33 (m, 1H), 3.16-3.21 (m, 1H), 2.92-2.98 (m, 1H), 2.12-2.22 (m, 4H), 1.35-1.75 (m, 20H); LC/MS (100%, t$_r$=5.299 min), m/z=410.2 [M+H]$^+$ (Calc: 409.6); TLC (SiO$_2$) 10:2:1 EtOAc:MeOH:NH$_4$OH: Rf=0.71 with UV detection, Dragendorff's reagent.

The identity of Heterocyclic-Substituted Piperidine Compound 59, 1-((1R,3s,5S)-9-cyclooctyl-9-azabicyclo[3.3.1]nonan-3-yl)-1H-benzo[b][1,4]diazepine-2,4(3H,5H)-dione, was confirmed using LC/MS and TLC.

Heterocyclic-Substituted Piperidine Compound 59: LC/MS (184%, t$_r$=5.116 min), m/z=410.2 [M+1-1]$^+$ (Calc: 409.6); TLC (SiO$_2$) 10:2:1 EtOAc:MeOH:NH$_4$OH: Rf=0.18 with UV detection, Dragendorff's reagent.

5.21 Example 21

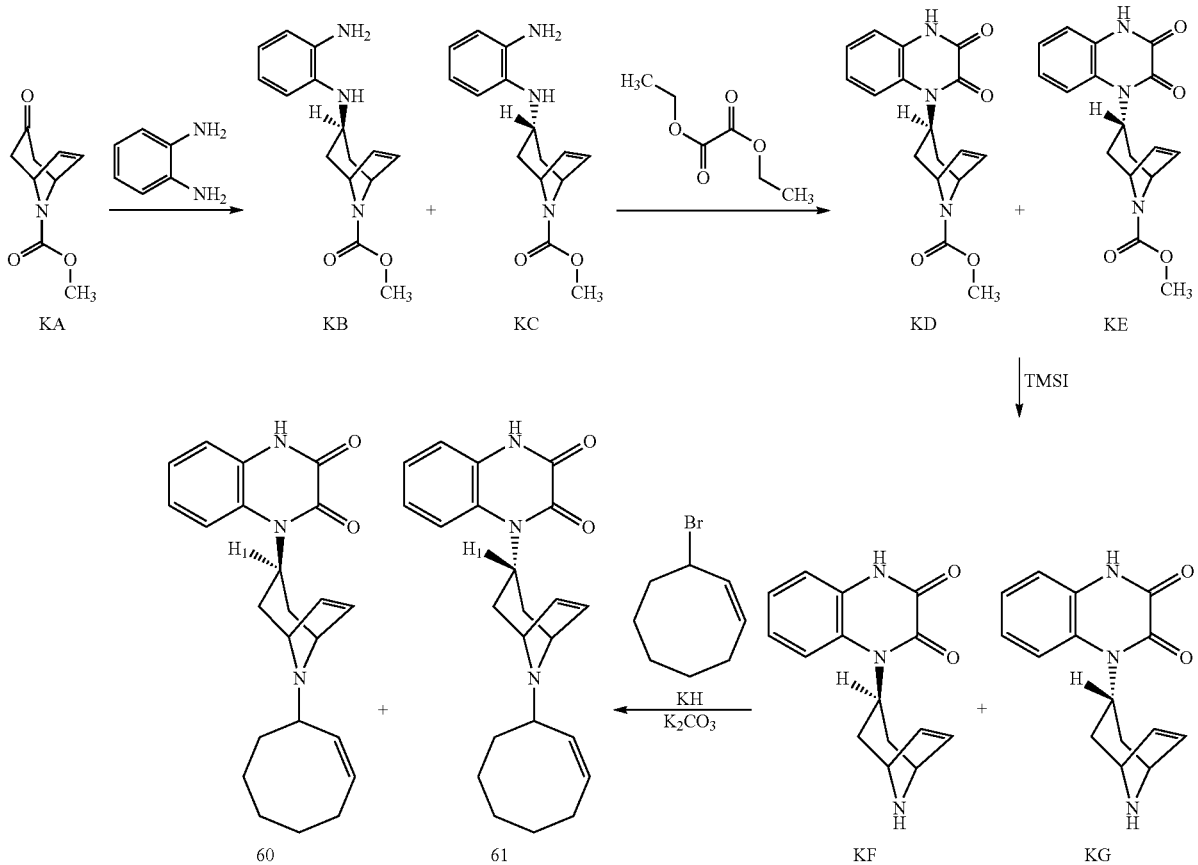

The compound of formula KA, methyl 3-oxo-8-azabicyclo[3.2.1]oct-6-ene-8-carboxylate, was prepared by the procedure provided in N. Ctamer, S. Laschat, A. Baro and W. Frey, Synlett 2175-2177 (2003).

A mixture of the compound of formula KA (1.0 g, 5.5 mmol), o-phenylenediamine (1.2 g, 11 mmol), NaB(OAc)$_3$H (2.5 g, 12.5 mmol) and acetic acid (0.7 g, 11 mmol) in 40 mL of DCE was stirred under nitrogen at a temperature of about 25° C. for 36 h. Methanol (1 mL) was added slowly such that the temperature of the reaction mixture did not exceed 25° C. The reaction mixture was washed with water (20 mL), extracted three times with DCM (20 mL for each extraction), concentrated under reduced pressure, and chromatographed with a silica gel column eluted with 10:3 EtOAc:MeOH to provide a mixture of the compounds of formulas KB and KC.

The mixture of the compounds of formulas KB and KC in 40 mL of diethyl oxalate was heated at 150° C. for 16 h. After cooling to a temperature of about 25° C., the solid was filtered off and the mixture concentrated under reduced pressure. The residue was chromatographed with a silica gel column eluted with 10:3 EtOAc:MeOH to provide a mixture of the compounds of formulas KD and KE.

Iodotrimethylsilane (TMSI, 0.2 mL, Sigma-Aldrich) was added to a mixture of the compounds of formulas KD and KE (110 mg, 0.4 mmol) in 10 mL of dry DCM at a temperature of about 25° C. Thereafter, the reaction mixture was heated and shaken at 50° C. for 2 h. After cooling to a temperature of about 25° C., acetic acid (0.2 mL) was added to the reaction mixture and it was concentrated under reduced pressure to provide a mixture of the compounds of formulas KF and KG as a brown solid.

The mixture of the compounds of formulas KF and KG was added to acetonitrile (4 mL). 3-Bromo-cyclooctene (KH, 100 mg, 0.5 mmol, prepared according to the method in M. Sellen et al., J. Org. Chem. 56: 835 (1991)), TEA (0.1 mL), potassium iodide (20 mg), and potassium carbonate (0.4 g) were then added to the acetonitrile. The resulting reaction mixture was shaken at 60° C. for 16 h. After cooling to a temperature of about 25° C., water (10 mL) was added to the reaction mixture and it was extracted three times with DCM (10 mL for each extraction), concentrated under reduced pressure, and chromatographed with a silica gel column eluted with 10:1:0.1 EtOAc:MeOH:TEA to provide 20 mg and 14 mg of the two Heterocyclic-Substituted Piperidine Compounds 60 and 61, respectively, each as a white solid (yield 15% and 11%, respectively).

The identity of Heterocyclic-Substituted Piperidine Compound 60, (Z)-1-(8-(cyclooct-2-enyl)-8-azabicyclo[3.2.1]oct-6-en-3-yl)quinoxaline-2,3(1H,4H)-dione, was confirmed using $^1$H NMR, LC/MS and TLC.

Heterocyclic-Substituted Piperidine Compound 60: $^1$H NMR: $\delta_H$ (400 MHz, (CD$_3$OD+CDCl$_3$)): 7.83 (1H, d, J=8.3 Hz), 7.21-7.28 (m, 3H), 6.32-6.41 (m, 2H), 6.02-6.08 (m, 2H), 5.72-5.8 (m, 1H), 4.44-4.64 (m, 3H), 2.42-2.54 (m, 3H), 2.02-2.14 (m, 3H), 1.54-1.78 (m, 5H), 1.28-1.36 (m, 3H); LC/MS (100%, t$_r$=4.977 min), m/z=378.1 [M+H]$^+$ (Calc: 377.5); TLC (SiO$_2$) 10:2:1 EtOAc:MeOH:NH$_4$OH: Rf=0.51 with UV detection, Dragendorff's reagent.

The relative structure of Heterocyclic-Substituted Piperidine Compound 60, trans-H1 to bridge, was assigned based on 2D NMR spectrometry.

The identity of Heterocyclic-Substituted Piperidine Compound 61, (Z)-1-(8-(cyclooct-2-enyl)-8-azabicyclo[3.2.1]oct-6-en-3-yl)quinoxaline-2,3(1H,4H)-dione, was confirmed using $^1$H NMR, LC/MS and TLC.

Heterocyclic-Substituted Piperidine Compound 61: $^1$H NMR: $\delta_H$ (400 MHz, (CD$_3$OD+CDCl$_3$)): 7.52-7.56 (m, 1H), 7.18-7.25 (m, 3H), 6.28-6.34 (m, 2H), 5.84-5.92 (m, 1H), 5.32-5.43 (m, 1H), 4.54-4.58 (m, 1H), 4.1-4.14 (m, 1H), 2.62-2.68 (m, 1H), 2.08-2.14 (m, 1H), 1.94-1.96 (m, 1H), 1.72-1.82 (m, 3H), 1.52-1.62 (m, 4H), 1.22-1.35 (m, 5H); LC/MS (100%, $t_r$=4.777 min), m/z=378.1 [M+H]$^+$ (Calc: 377.5); TLC (SiO$_2$) 10:2:1 EtOAc:MeOH:NH$_4$OH: Rf=0.23 with UV detection, Dragendorff's reagent.

The relative structure of Heterocyclic-Substituted Piperidine Compound 61, cis-H1 to bridge, was assigned based on 2D NMR spectrometry.

5.22 Example 22

0%:100% EtOAc:hexanes to 50%:50% EtOAc:hexanes to provide, after concentration under reduced pressure, 8.10 g of the compound of formula LB as a pale yellow solid (yield 76.8%).

The identity of the compound of formula LB, 1-tert-butyl 4-ethyl 4-methylpiperidine-1,4-dicarboxylate, was confirmed using $^1$H NMR.

Compound LB: $^1$H NMR: $\delta_H$ (400 MHz, CDCl$_3$): 4.16 (2H, q, J=7.1 Hz), 3.76 (2H, br), 2.95-3.01 (2H, m), 2.05-2.08 (2H, m), 1.45 (9H, s), 1.32-1.43 (2H, m), 1.26 (3H, t, J=7.1 Hz), 1.20 (3H, s).

A mixture of the compound of formula LB (4.10 g, 15.1 mmol) and lithium hydroxide (2.17 g, 90.6 mmol) in methanol (30 mL)/H$_2$O (20 mL) was stirred at a temperature of about 25° C. for 16 h. After evaporation to dryness, the residue was partitioned between DCM and brine. The organic layer was separated, dried (MgSO$_4$), filtered, and concentrated under reduced pressure to provide 3.38 g of the compound of formula LC as a white solid (yield 92.0%).

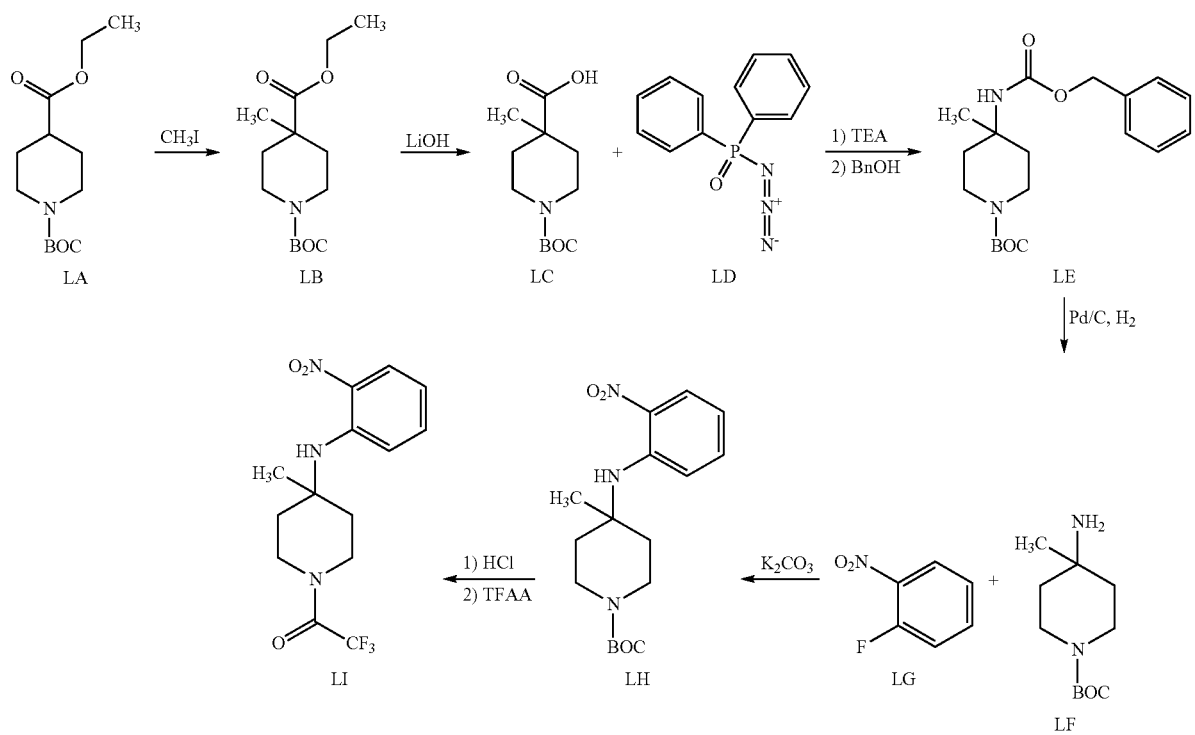

To a mixture of N,N-diisopropylamine (6.81 mL, 48.6 mmol) in THF (100 mL) at a temperature of 0° C. was added dropwise a mixture of 1.6N n-butyl lithium (Sigma-Aldrich) in THF (30.4 mL, 48.6 mmol). The resulting mixture was stirred at 0° C. for 15 min. After cooling to a temperature of -78° C., a mixture of the compound of formula LA (1-tert-butyl 4-ethyl piperidine-1,4-dicarboxylate, 10.0 g, 38.9 mmol, Sigma-Aldrich) in THF (50 mL) was added dropwise over a 30 min period. After being stirred at -78° C. for 2 h, a mixture of methyl iodide (4.84 mL, 77.7 mmol) in THF (30 mL) was added dropwise at -78° C. The mixture was allowed to warm to a temperature of about 25° C. for 16 h. After quenching with saturated aqueous NH$_4$Cl, the mixture was partitioned between THF and saturated aqueous NH$_4$Cl. The organic layer was separated, dried (Na$_2$SO$_4$), filtered, and concentrated under reduced pressure. The product was chromatographed (COMBIFLASH) with a gradient of from The identity of the compound of formula LC, 1-(tert-butoxycarbonyl)-4-methylpiperidine-4-carboxylic acid, was confirmed using $^1$H NMR and LC/MS.

Compound LC: $^1$H NMR: $\delta_H$ (400 MHz, CDCl$_3$): 3.60-3.70 (2H, m), 3.03-3.09 (2H, m) 2.05-2.08 (2H, m), 1.45 (9H, s), 1.36-1.45 (2H, m), 1.27 (3H, m); LC/MS (100%, $t_r$=2.500 min), m/z=266.1 [M+H]$^+$ (Calc: 243).

To a mixture of the compound of formula LC (2.00 g, 8.22 mmol) and TEA (1.72 mL, 12.3 mmol) in toluene (20 mL) at a temperature of about 25° C. was added the compound of formula LD (diphenylphosphoryl azide ("DPPA"), 2.42 mL, 11.2 mmol, Sigma-Aldrich). The mixture was stirred at a temperature of about 25° C. for 18 h. After evaporation to dryness, the residue was partitioned between EtOAc and 1N aqueous NaOH. The organic layer was separated, dried (Na$_2$SO$_4$), filtered, and concentrated to dryness under reduced pressure. The residue was chromatographed (COM- BIFLASH) with a gradient of from 0%:100% EtOAc:hexanes to 50%:50% EtOAc:hexanes to provide, after concentration under reduced pressure, 2.00 g of the compound of formula LE as colorless oil (yield 70.1%).

The identity of the compound of formula LE, tert-butyl 4-(benzyloxycarbonylamino)-4-methylpiperidine-1-carboxylate, was confirmed using $^1$H NMR and LC/MS.

Compound LE: $^1$H NMR: $\delta_H$ (400 MHz, CDCl$_3$): 7.30-7.39 (5H, m), 5.06 (2H, s), 4.61 (1H, brs), 3.66 (2H, m), 3.12-3.17 (2H, m), 1.97 (2H, br), 1.50-1.60 (2H, m), 1.45 (9H, s), 1.38 (3H, s); LC/MS (100%, t$_r$=2.500 min), m/z=355 [M+Na]$^+$ (Calc: 328).

A mixture of the compound of formula LE (2.48 g, 7.11 mmol) and 10% palladium on carbon (200 mg, Sigma-Aldrich) in methanol (20 mL) was stirred under a hydrogen atmosphere at a temperature of about 25° C. for 16 h. The Pd/C was filtered off and the filtrate was concentrated under reduced pressure to provide 1.37 g of the compound of formula LF as a silverery-colored viscous oil (yield 90.2%).

The identity of the compound of formula LF, tert-butyl 4-amino-4-methylpiperidine-1-carboxylate, was confirmed using $^1$H NMR.

Compound LF: $^1$H NMR: $\delta_H$ (400 MHz, CDCl$_3$): 3.47-3.49 (4H, m), 1.47-1.61 (4H, m), 1.46 (9H, s), 1.31-1.42 (2H, m), 1.15 (3H, s).

A mixture of the compound of formula LF (1.37 g, 6.4 mmol), the compound of formula LG (2-fluoro-1-nitrobenzene, 2.71 mL, 25.6 mmol, Sigma-Aldrich) and potassium carbonate (4.43 g, 32.1 mmol) in DMSO (10 mL) was stirred at a temperature of 80° C. for 24 h. The mixture was partitioned between EtOAc and water. The organic layer was separated, washed with brine, dried (Na$_2$SO$_4$), filtered, and concentrated to dryness under reduced pressure. The residue was chromatographed (COMBIFLASH) with a gradient of from 0%:100% EtOAc:hexanes to 50%:50% EtOAc:hexanes to provide, after concentration under reduced pressure, 2.03 g of the compound of formula LH as pale yellow oil (yield 94.4%).

The identity of the compound of formula LH, tert-butyl 4-methyl-4-(2-nitrophenylamino)piperidine-1-carboxylate, was confirmed using $^1$H NMR and LC/MS.

Compound LH: $^1$H NMR: $\delta_H$ (400 MHz, CDCl$_3$): 8.41 (1H, br), 8.20 (1H, dd, J=8.6 Hz, 1.7 Hz), 7.36-7.40 (1H, m), 7.03 (1H, dd, J=8.8 Hz, 0.9 Hz), 6.62-6.66 (1H, m), 3.77-3.79 (2H, m), 3.16-3.18 (2H, m), 2.10-2.13 (2H, m), 1.67-1.74 (2H, m), 1.53 (3H, s), 1.46 (9H, s); LC/MS (100%, t$_r$=3.410 min), m/z=358.1 [M+Na]$^+$ (Calc: 335).

To a mixture of the compound of formula LH (3.02 g, 9.00 mmol) in DCM (10 mL) at a temperature of 0° C. was added 1N HCl in diethyl ether (30 mL, 30 mmol). The mixture was allowed to warm to a temperature of about 25° C. for 20 h. The mixture was concentrated under reduced pressure to provide a pale yellow solid. To a mixture of the solid and TEA (4.39 mL, 31.5 mmol) in DCM (25 mL) at a temperature of 0° C. was added trifluoroacetic anhydride (TFFA, 1.40 mL, 9.90 mmol, Sigma-Aldrich). After being stirred at 0° C. for 45 min, 0.70 mL of additional TFFA was added to the mixture. The mixture was further stirred at 0° C. for 5 min after which it was partitioned between DCM and water. The organic layer was separated, washed with brine, dried (MgSO$_4$), filtered, and concentrated under reduced pressure to provide 2.80 g of the compound of formula LI as an orange solid (yield 93.9%).

The identity of the compound of formula LI, 2,2,2-trifluoro-1-(4-methyl-4-(2-nitrophenylamino)piperidin-1-yl)ethanone, was confirmed using LC/MS.

Compound LI: LC/MS (100%, t$_r$=2.933 min), m/z=354.1 [M+Na]$^+$ (Calc: 331).

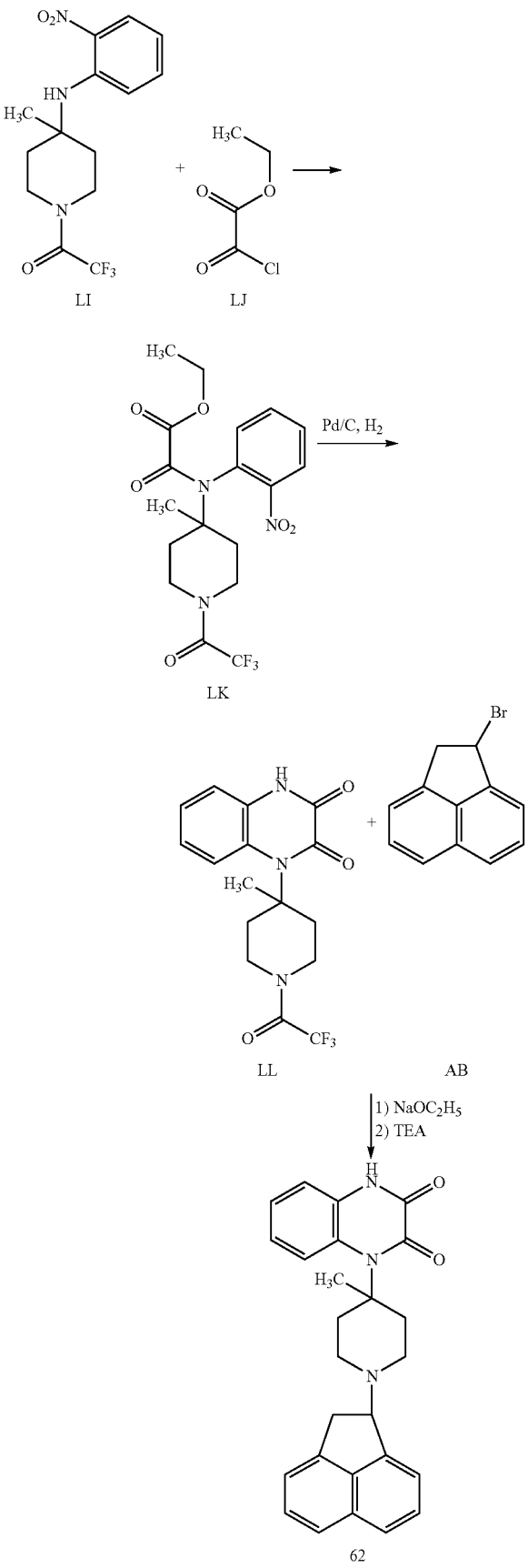

A mixture of the compound of formula LI (1.50 g, 4.53 mmol) in neat compound of formula LJ (ethyl 2-chloro-2-oxoacetate, 10.1 mL, 90.6 mmol, Sigma-Aldrich) was stirred at a temperature of 65° C. for 3 h. After cooling to a temperature of about 25° C., the mixture was partitioned between EtOAc and water. The organic layer was separated, washed with brine, dried (Na$_2$SO$_4$), filtered, and concentrated to dryness under reduced pressure. The residue was chromatographed (COMBIFLASH) with a gradient of from 0%:100% EtOAc:hexanes to 50%:50% EtOAc:hexanes to provide, after concentration under reduced pressure, 2.80 g of the compound of formula LK as a yellow oil (yield 93.9%).

The identity of the compound of formula LK, ethyl 2-((4-methyl-1-(2,2,2-trifluoroacetyl)piperidin-4-yl)(2-nitrophenyl)amino)-2-oxoacetate, was confirmed using $^1$H NMR and LC/MS.

Compound LK: $^1$H NMR: $\delta_H$ (400 MHz, CDCl$_3$): 8.04 (1H, ddd, J=7.8 Hz, 3.2 Hz, 1.8 Hz), 7.61-7.70 (2H, m), 7.39-7.43 (1H, m), 4.39 (2H, q, J=7.1 Hz), 3.87-3.96 (2H, m), 3.26-3.35 (1H, m), 2.88-2.98 (1H, m), 2.49-2.53 (0.5H, m), 2.28-2.31 (0.5H, m), 1.95-2.19 (2H, m), 1.90-1.93 (1H, m), 1.82 (1.5H, s), 1.77 (1.5H, m), 1.39 (3H, t, J=7.1 Hz); LC/MS (100%, t$_r$=2.833 min), m/z=454.1 [M+Na]$^+$ (Calc: 431).

A mixture of the compound of formula LK (1.48 g, 3.43 mmol) and 10% palladium on carbon (150 mg) in EtOH (10 mL) was stirred under a hydrogen atmosphere at a temperature of about 25° C. for 4 h. The Pd/C was filtered off and the filtrate was concentrated to dryness under reduced pressure. The residue was chromatographed with a silica gel column eluted with 0%-50% EtOAc:hexanes to provide, after concentration under reduced pressure, 723 mg of the compound of formula LL as a white solid (yield 52.5%).

The identity of the compound of formula LL, 1-(4-methyl-1-(2,2,2-trifluoroacetyl)piperidin-4-yl)quinoxaline-2,3(1H, 4H)-dione, was confirmed using $^1$H NMR and LC/MS.

Compound LL: $^1$H NMR: $\delta_H$ (400 MHz, DMSO-d$_6$): 11.54 (1H, br), 7.64 (1H, d, J=8.1 Hz), 7.52 (1H, dd, J=8.1 Hz, 1.5 Hz), 7.27-7.30 (1H, m), 7.16-7.20 (1H, m), 3.74-3.78 (1H, m), 3.56-3.59 (1H, m), 2.88-2.94 (1H, m), 2.71-2.81 (3H, m), 2.04-2.12 (2H, m), 1.80 (3H, s); LC/MS (100%, t$_r$=2.250 min), m/z=378.1 [M+H]$^+$ (Calc: 355).

To a mixture of the compound of formula LL (331 mg, 0.93 mmol) in EtOH (2 mL)/H$_2$O (0.5 mL) at a temperature of about 25° C. was added 21 wt. % sodium ethoxide in EtOH (0.38 mL, 1.03 mmol). The mixture was stirred at a temperature of about 25° C. for 16 h. The mixture was concentrated to dryness under reduced pressure. The residue was washed with DCM to provide a tan solid.

To a suspension of the solid in DMSO (3 mL) at a temperature of about 25° C. was added the compound of formula AB (260 mg, 1.12 mmol). After being stirred at a temperature of about 25° C. for 1 h, TEA (0.16 mL, 1.12 mmol) was added. The mixture was stirred an additional 3 h at a temperature of about 25° C. The mixture was partitioned between EtOAc and water. The organic layer was separated, washed with brine, dried (Na$_2$SO$_4$), filtered, and concentrated to dryness under reduced pressure. The residue was chromatographed with a silica gel column eluted with a gradient of from 100%:0% MeOH:DCM to 20%:80% MeOH:DCM. Further chromatography was conducted with preparative TLC (eluted with a gradient of from 0%:100% MeOH:DCM to 20%:80% MeOH:DCM) to provide 26.6 mg of Heterocyclic-Substituted Piperidine Compound 62 as a white solid (yield 6.9%).

The identity of Heterocyclic-Substituted Piperidine Compound 62, 1-(1-(1,2-dihydroacenaphthylen-1-yl)-4-methylpiperidin-4-yl)quinoxaline-2,3(1H,4H)-dione, was confirmed using $^1$H NMR and LC/MS.

Heterocyclic-Substituted Piperidine Compound 62: $^1$H NMR: $\delta_H$ (400 MHz, CD$_3$OD): 7.56 (1H, d, J=8.2 Hz), 7.45 (1H, d, J=8.2 Hz), 7.39 (1H, d, J=6.8 Hz), 7.37 (1H, d, J=6.8 Hz), 7.27-7.30 (1H, m), 7.18 (1H, d, J=6.8 Hz), 7.11 (1H, d, J=6.8 Hz), 6.82-7.03 (3H, m), 4.66-4.67 (1H, m), 3.31 (1H, dd, J=17.7 Hz, 8.0 Hz), 3.04-3.09 (1H, m), 2.83-2.92 (2H, m), 2.31-2.34 (2H, m), 2.11 (1H, m), 1.69-1.77 (2H, m), 1.67 (3H, s), 1.42 (1H, m); LC/MS (100%, t$_r$=4.64 min), m/z=412.2 [M+H]$^+$ (Calc: 411).

5.23 Example 23

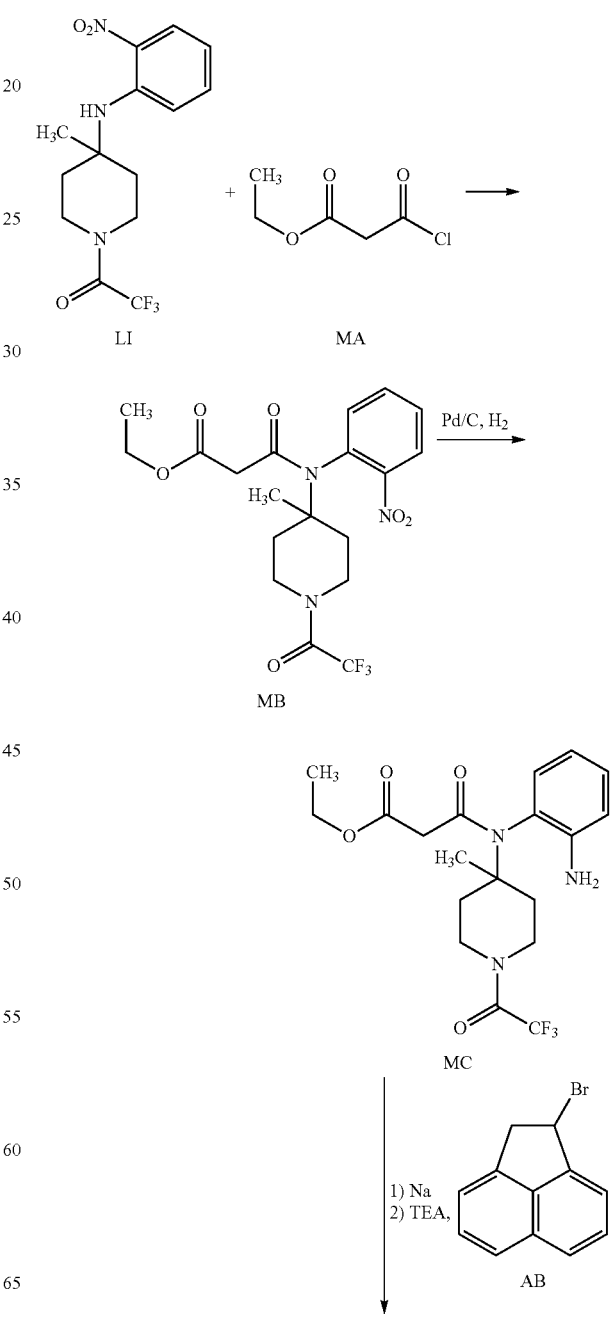

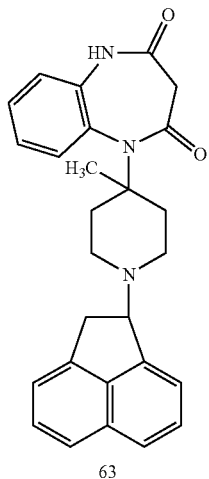

63

A mixture of the compound of formula LI (797 mg, 2.41 mmol) and the compound of formula MA (ethyl 3-chloro-3-oxopropanoate, 1.51 mL, 12.0 mmol), in DCE (15 mL) was stirred at a temperature of 70° C. for 55 h. After cooling to a temperature of about 25° C., the mixture was partitioned between DCM and water. The organic layer was separated, washed with brine, dried (MgSO$_4$), filtered, and concentrated to dryness under reduced pressure. The residue was chromatographed with a silica gel column eluted with a gradient of from 0%:100% EtOAc:hexanes to 50%:50% EtOAc:hexanes to provide, after concentration under reduced pressure, 659 mg of the compound of formula MB as a pale yellow oil (yield 61.5%).

The identity of the compound of formula MB, ethyl 3-((4-methyl-1-(2,2,2-trifluoroacetyl)piperidin-4-yl)(2-nitrophenyl)amino)-3-oxopropanoate, was confirmed using $^1$H NMR and LC/MS.

Compound MB: $^1$H NMR: $\delta_H$ (400 MHz, CDCl$_3$): 7.85-7.89 (1H, m), 7.60-7.68 (2H, m), 7.39-7.42 (1H, m), 4.31-4.38 (1H, m), 4.12 (2H, q, J=7.1 Hz), 4.07-4.16 (1H, m), 3.18-3.27 (2H, m), 3.02 (1H, dd, J=16.0 Hz, 5.4 Hz), 2.85-2.88 (1H, m), 2.24-2.37 (1H, m), 2.05 (3H, s), 1.64-1.95 (3H, m 1.23 (3H, t, J=7.1 Hz); LC/MS (100%, t$_r$=2.787 min), m/z=468.1 [M+H]$^+$ (Calc: 445).

A mixture of the compound of formula MB (659 mg, 1.59 mmol) and 10% palladium on carbon (60 mg) in EtOH (5 mL) was stirred under a hydrogen atmosphere at a temperature of about 25° C. for 3 h. The Pd/C was filtered off and the filtrate was concentrated under reduced pressure to provide 572 mg of the compound of formula MC as a colorless oil (yield 93.1%).

The identity of the compound of formula MC, ethyl 3-((2-aminophenyl)(4-methyl-1-(2,2,2-trifluoroacetyl)piperidin-4-yl)amino)-3-oxopropanoate, was confirmed using LC/MS.

Compound MC: LC/MS (100%, t$_r$=2.898 min), m/z=438.1 [M+Na]$^+$ (Calc: 415).

To a mixture of the compound of formula MC (106 mg, 0.254 mmol) in EtOH (2 mL) at a temperature of about 25° C. was added pieces of sodium (20.4 mg, 0.889 mmol). The mixture was stirred at a temperature of about 25° C. for 1 h, then stirred at a temperature of 70° C. for 1 h. After cooling to a temperature of about 25° C., the mixture was concentrated under reduced pressure to provide an orange solid. A mixture of the solid, the compound of formula AB (88.8 mg, 0.381 mmol), and TEA (0.078 mL, 0.559 mmol) in DCE (2 mL) was stirred at a temperature of about 25° C. for 16 h. The mixture was partitioned between DCM and water. The organic layer was separated, washed with brine, dried (MgSO$_4$), filtered, and concentrated to dryness under reduced pressure. The residue was chromatographed by preparative TLC (eluted with a gradient of from 0%:100% MeOH:DCM to 20%:80% MeOH:DCM) to provide 14.5 mg of Heterocyclic-Substituted Piperidine Compound 63 as an off white solid (yield 13.4%).

The identity of Heterocyclic-Substituted Piperidine Compound 63, 1-(1-(1,2-dihydroacenaphthylen-1-yl)-4-methylpiperidin-4-yl)-1H-benzo[b][1,4]diazepine-2,4(3H,5H)-dione, was confirmed using $^1$H NMR and LC/MS.

Heterocyclic-Substituted Piperidine Compound 63: $^1$H NMR: $\delta_H$ (400 MHz, CD$_3$OD): 7.65-7.69 (1H, m), 7.57-7.60 (1H, m), 7.37-7.52 (4H, m), 7.15-7.36 (4H, m), 4.74-4.80 (1H, m), 3.39-3.49 (2H, m), 2.74-3.00 (2H, m), 2.43-2.47 (1H, m), 2.13-2.31 (1H, m), 1.57-1.96 (4H, m), 1.751 (1.5H, s), 1.747 (1.5H, s); LC/MS (100%, t$_r$=2.064 min), m/z=426.1 [M+H]$^+$ (Calc: 425).

5.24 Example 24

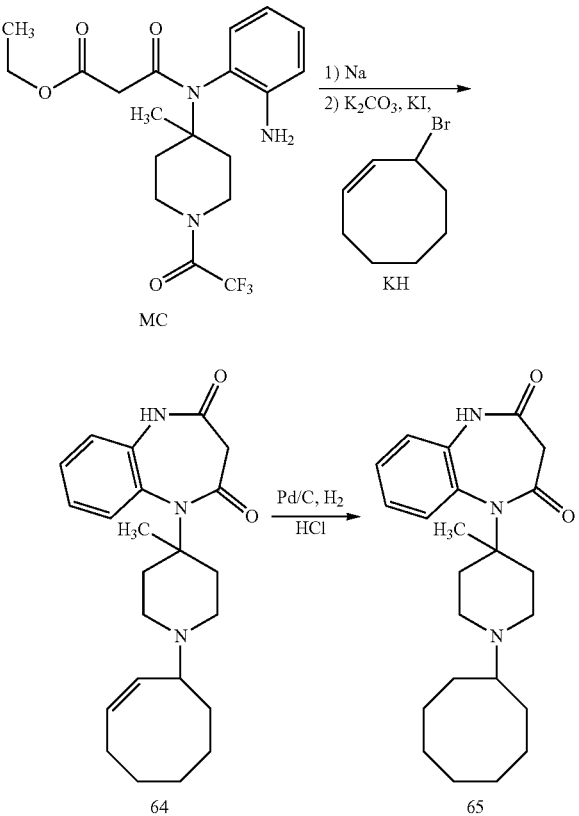

To a mixture of the compound of formula MC (572 mg, 1.38 mmol) in EtOH (2 mL) at a temperature of about 25° C. was added pieces of sodium (111 mg, 4.82 mmol). The mixture was stirred at a temperature of 70° C. for 3 h. After cooling to a temperature of about 25° C., the mixture was concentrated under reduced pressure to provide a white solid.

A mixture of that solid, the compound of formula KH (252 mg, 1.33 mmol), potassium carbonate (368 mg, 2.66 mmol) and potassium iodide (23.8 mg, 0.11 mmol) in acetonitrile (5 mL) was stirred at a temperature of 80° C. for 3 h. The mixture was partitioned between EtOAc and water. The organic layer was separated, washed with brine, dried ($Na_2SO_4$), filtered, and concentrated to dryness under reduced pressure. The residue was chromatographed with a silica gel column eluted with a gradient of from 0%:100% MeOH:DCM to 20%:80% MeOH:DCM to provide, after concentration under reduced pressure, 136 mg of Heterocyclic-Substituted Piperidine Compound 64 as a white solid (yield 32.0%).

The identity of Heterocyclic-Substituted Piperidine Compound 64, (Z)-1-(1-(cyclooct-2-enyl)-4-methylpiperidin-4-yl)-1H-benzo[b][1,4]diazepine-2,4(3H,5H)-dione, was confirmed using $^1$H NMR and LC/MS.

Heterocyclic-Substituted Piperidine Compound 64: $^1$H NMR: $\delta_H$ (400 MHz, $CD_3OD$): 7.49-7.51 (1H, m), 7.36-7.41 (1H, m), 7.24-7.30 (2H, m), 5.76-5.87 (1H, m), 5.30-5.39 (1H, m) 3.22-3.27 (1H, m), 2.81-2.99 (2H, brs), 2.68-2.69 (1H, m), 2.05-2.38 (5H, m), 1.59-1.95 (8H, m), 1.78 (3H, s), 1.21-1.51 (4H, m); LC/MS (100%, $t_r$=1.952 min), m/z=382.2 [M H]$^+$ (Calc: 381).

Heterocyclic-Substituted Piperidine Compound 64 (76.7 mg, 0.20 mmol), 10% palladium on carbon (20 mg) and concentrated HCl (0.05 mL) in methanol (2 mL) was stirred under a hydrogen atmosphere at a temperature of about 25° C. for 3 h. The Pd/C was filtered off and the filtrate was concentrated to dryness under reduced pressure. The residue was partitioned between EtOAc and 1N aqueous NaOH. The organic layer was washed with brine, dried ($Na_2SO_4$), filtered, and concentrated to dryness under reduced pressure. The residue was triturated with hexanes to provide 572 mg of Heterocyclic-Substituted Piperidine Compound 65 as a white solid (yield 93.1%).

The identity of Heterocyclic-Substituted Piperidine Compound 65, 1-(1-cyclooctyl-4-methylpiperidin-4-yl)-1H-benzo[b][1,4]diazepine-2,4(3H,5H)-dione, was confirmed using $^1$H NMR and LC/MS.

Heterocyclic-Substituted Piperidine Compound 65: $^1$H NMR: $\delta_H$ (400 MHz, $CDCl_3$): 7.49 (1H, d, J=7.0 Hz), 7.38 (1H, td, J=7.7 Hz, 1.3 Hz), 7.23-7.29 (2H, m), 2.79-3.14 (2H, brs), 2.50 (2H, m), 2.31-2.36 (1H, m), 2.19-2.22 (1H, m), 1.44-1.91 (19H, m), 1.77 (3H, s); LC/MS (100%, $t_r$=1.972 min), m/z=384.2 [M+Na]$^+$ (Calc: 383).

5.25 Example 25

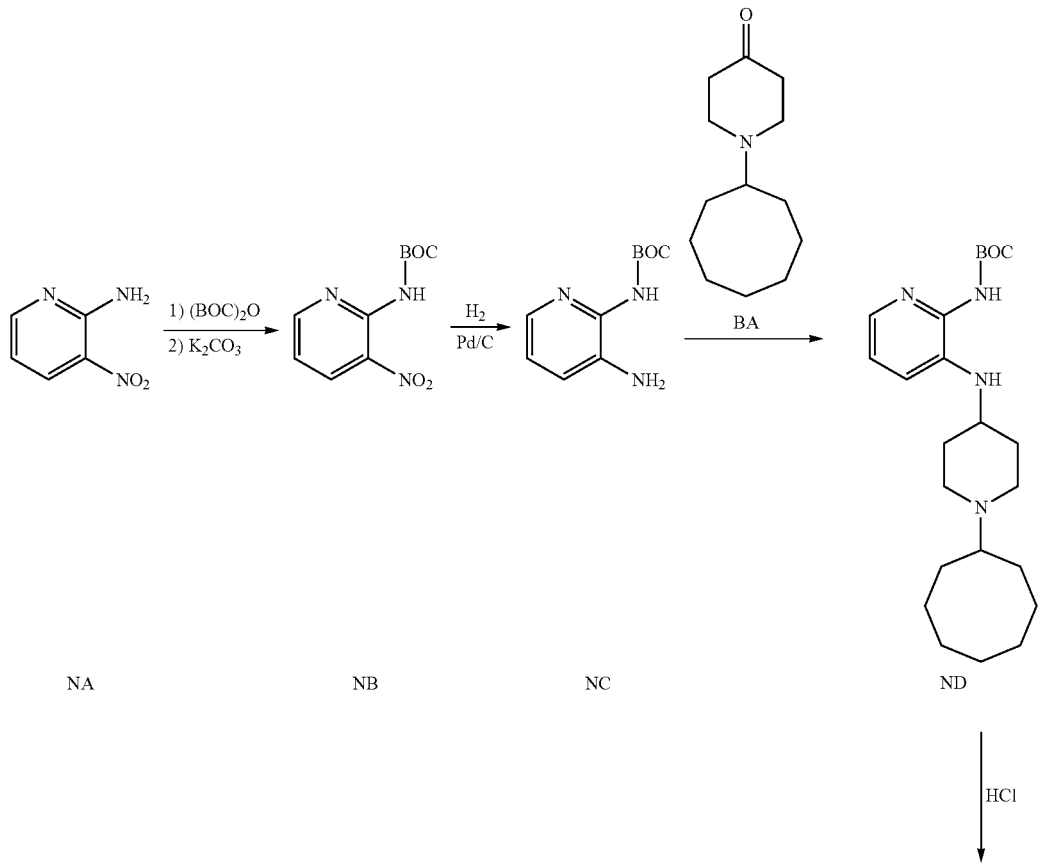

-continued

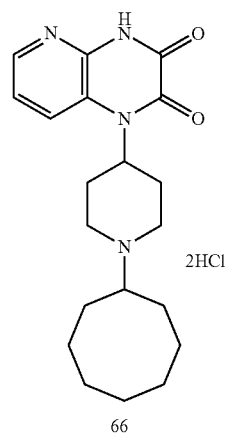

66 · 2HCl

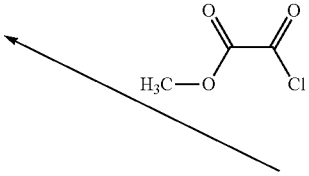

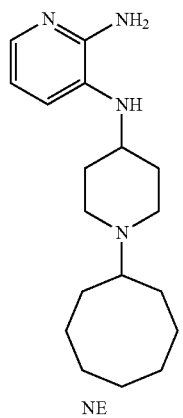

NE

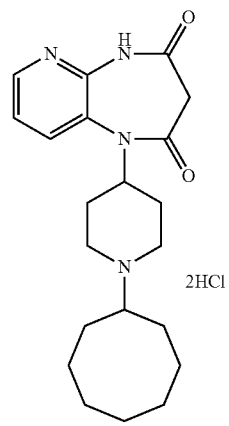

67 · 2HCl

A mixture of the compound of formula NA (3-nitropyridin-2-amine, 1.39 g, 10 mmol), (BOC)$_2$O (20 mmol), and DMAP (catalytic amount) in THF (28 mL) was stirred at 90° C. for 1 h. After cooling to a temperature of about 25° C. and quenching with water (10 mL), the mixture was extracted three times with EtOAc, dried (MgSO$_4$), and concentrated under reduced pressure. At a temperature of about 25° C., the resulting yellow oil was mixed with methanol (33 mL) then added to K$_2$CO$_3$ (30 mmol). The reaction mixture was stirred at 60° C. for 1 h. After cooling to a temperature of about 25° C., 2N HCl (10 mL) was added and the pH was adjusted within the range of from about 7 to about 8. Thereafter, the mixture was extracted three times with EtOAc, dried (MgSO$_4$), and concentrated under reduced pressure. The resulting oil was chromatographed with a silica gel column eluted with a gradient of from 10%:90% EtOAc:n-hexane to 50%:50% EtOAc:n-hexane to provide the compound of formula NB as a yellow solid (yield 91%).

The identity of the compound of formula NB, tert-butyl 3-nitropyridin-2-ylcarbamate, was confirmed using $^1$H NMR.

Compound NB: $^1$H NMR: $\delta_H$ (300 MHz, CDCl$_3$): 9.59 (1H, s), 8.72 (1H, dd, J=4.5 Hz, J=1.5 Hz), 8.5 (1H, dd, J=8.4 Hz, J=1.5 Hz), 7.14 (1H, dd, J=8.4 Hz, J=4.8 Hz), 1.56 (9H, s).

A mixture of the compound of formula NB (2.11 g, 9.07 mmol) and 5% palladium on carbon (210 mg, Sigma-Aldrich) in methanol (35 mL) was stirred at a temperature of about 25° C. for 16 h in a hydrogen atmosphere. After the Pd/C was filtered off, the mixture was washed with EtOAc and methanol, and the filtrate was concentrated under reduced pressure. The resulting solid was suspended with 3:2 n-hexane:diethyl ether which was filtered and washed with n-hexane to provide the compound of formula NC as a pale yellow solid (yield 87%).

The identity of the compound of formula NC, tert-butyl 3-aminopyridin-2-ylcarbamate, was confirmed using $^1$H NMR.

Compound NC: $^1$H NMR: $\delta_H$ (400 MHz, CDCl$_3$): 7.76 (1H, d, J=1.5 Hz), 7.10 (1H, dd, J=8.4 Hz, J=1.5 Hz), 6.99 (1H, dd, J=8.4 Hz, J=4.8 Hz), 1.52 (9H, s).

A mixture of the compound of formula NC (710 mg, 3.4 mmol), the compound of formula BA (5.1 mmol), NaBH(OAc)$_3$ (10.2 mmol) and AcOH (5.1 mmol) in chloroform (18 mL) was stirred at a temperature of about 25° C. for 16 h. After quenching with saturated NaHCO$_3$ solution, the mixture was extracted with chloroform, dried (MgSO$_4$), and concentrated under reduced pressure. The residue was chromatographed with an amino-silica gel column (Yamazen Corp. W091-01) eluted with a gradient of from 5%:95% EtOAc:n- hexane to 20%:80% EtOAc:n-hexane to 50%:50% EtOAc:n-hexane to provide the compound of formula ND as a colorless solid (yield 63%).

The identity of the compound of formula ND, tert-butyl 3-(1-cyclooctylpiperidin-4-ylamino)pyridin-2-ylcarbamate, was confirmed using $^1$H NMR.

Compound ND: $^1$H NMR: $\delta_H$ (400 MHz, DMSO-$d_6$): 8.59 (1H, s), 7.60 (1H, t, J=4 Hz), 7.01 (2H, d), 4.67 (1H, d, J=8 Hz), 3.25 (1H, m), 2.67 (2H, m), 2.35-2.30 (2H, m), 1.88-1.85 (2H, m), 1.69-1.60 (2H, m), 1.56-1.32 (25H, m).

To a suspension of the compound of formula ND (317 mg, 0.79 mmol) in EtOAc (5 mL) at a temperature of about 25° C. was added 4N HCl in EtOAc (7.9 mmol) which was stirred at about 25° C. for 1 h and then for 3 h more at 50° C. After neutralization with 28% aqueous ammonia, the pH was adjusted within the range of from about 13 to about 14. Thereafter, the mixture was extracted three times with EtOAc, the organic layer was dried (MgSO$_4$), and concentrated under reduced pressure to provide 237 mg of the compound of formula NE as a brown solid (yield>99%).

The identity of the compound of formula NE, N$^3$-(1-cyclooctylpiperidin-4-yl)pyridine-2,3-diamine, was confirmed using $^1$H NMR.

Compound NE: $^1$H NMR: $\delta_H$ (400 MHz, CDCl$_3$): 7.80 (1H, d, J=4 Hz), 7.66 (1H, s), 6.39 (1H, d, J=4 Hz), 4.12 (1H, m), 2.79 (1H, m), 2.68-2.61 (6H, m), 2.43 (2H, m), 1.92-1.48 (24H, m).

To a mixture of the compound of formula NE (168 mg, 0.79 mmol) in methylene chloride (10 mL) at 0° C. was added dropwise over 10 min methyl 2-chloro-2-oxoacetate (0.79 mmol) in methylene chloride (3 mL). The resulting reaction mixture was stirred at 0° C. for 30 min. After quenching with saturated NaHCO$_3$ solution, the mixture was extracted three times with chloroform. Thereafter, the organic layer was dried (MgSO$_4$) and concentrated under reduced pressure. At a temperature of about 25° C., the resulting oil was mixed with EtOH (4 mL) and the mixture was then added to sodium methoxide (1.09 mmol). The reaction mixture was stirred at 70° C. for 1 h. After concentration under reduced pressure, to the resulting oil was added water (0.5 mL) and 2N HCl (1 mL). The resulting precipitate was filtered, washed with 90%:10% water:MeOH, and dried under reduced pressure at 60° C. for 12 h to provide the dihydrochloride of Heterocyclic-Substituted Piperidine Compound 66 as a colorless solid.

The identity of Heterocyclic-Substituted Piperidine Compound 66, 1-(1-cyclooctylpiperidin-4-yl)pyrido[3,2-b]pyrazine-2,3(1H,4H)-dione, was confirmed using $^1$H NMR and LC/MS.

Heterocyclic-Substituted Piperidine Compound 66: $^1$H NMR: $\delta_H$ (300 MHz, DMSO-$d_6$): 12.39 (1H, s), 9.8 (1H, br), 8.27 (1H, m), 8.14 (1H, d, J=4.5 Hz), 7.21 (1H, dd, J=4.5 Hz, J=8.1 Hz), 4.91 (1H, m), 3.45-3.3 (6H, m), 2.99 (2H, m), 2.02 (2H, m), 1.99 (2H, m), 1.58-1.46 (11H, m); LC/MS, m/z=357 [M+H]$^+$ (Calc: 356.5).

To a mixture of the compound of formula NE (302 mg, 1 mmol) in methylene chloride (30 mL) at 0° C. was added dropwise over 2 h malonyl dichloride (1.5 mmol) in methylene chloride (30 mL). Thereafter, the resulting reaction mixture was stirred at a temperature of about 25° C. for 3 days. After concentration under reduced pressure, the resulting oil was chromatographed with a silica gel column eluted with a gradient of from 97%:3%:0.3% chloroform:MeOH:28% aqueous ammonia to 90%:10%:0.1% chloroform:MeOH:

28% aqueous ammonia to provide a yellow amorphous solid. The solid was mixed with 1:1 EtOAc:MeOH (2 mL) and added to 4N HCl in EtOAc (0.5 mL) at a temperature of about 25° C. to provide a white precipitate. The precipitate was filtered and washed with 9:1 diethyl ether:MeOH. The resulting colorless solid was dried under reduced pressure at 60° C. for 12 h to provide 60 mg of the dihydrochloride of Heterocyclic-Substituted Piperidine Compound 67 (yield 14%).

The identity of Heterocyclic-Substituted Piperidine Compound 67, 1-(1-cyclooctylpiperidin-4-yl)-1H-pyrido[3,2-b][1,4]diazepine-2,4(3H,5H)-dione, was confirmed using $^1$H NMR and LC/MS.

Heterocyclic-Substituted Piperidine Compound 67: $^1$H NMR: $\delta_H$ (300 MHz, CD$_3$OD): 8.36 (1H, dd, J=1.5 Hz, J=4.8 Hz), 7.97 (1H, dd, J=8.1 Hz, J=1.5 Hz), 7.37 (1H, dd, J=8.1 Hz, J=4.8 Hz), 4.23 (1H, m), 3.53-3.42 (4H, m), 3.27-3.13 (3H, m), 2.78 (2H, m), 2.14-1.54 (16H, m); LC/MS, m/z=371.0 [M+H]$^+$ (Calc: 370.4).

5.26 Example 26

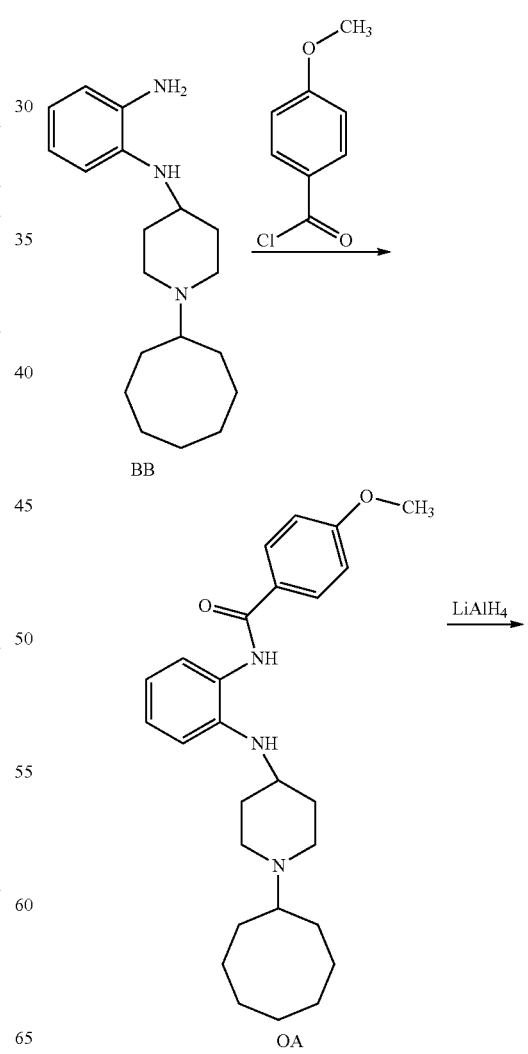

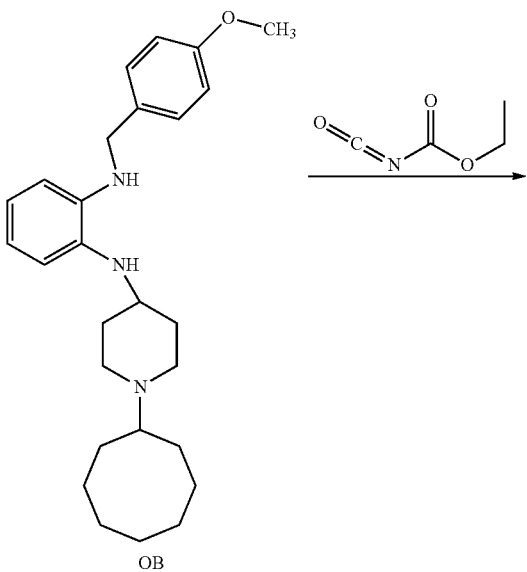

OB

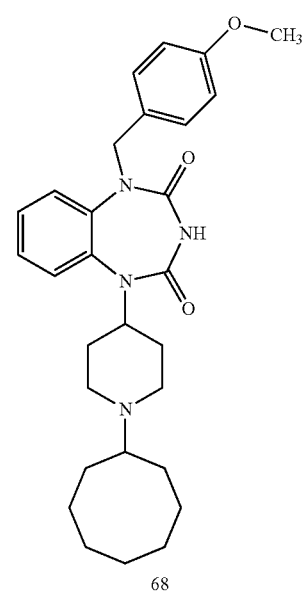

68

At 0° C., 4-methoxybenzoyl chloride (3.03 g, 17.8 mmol, Sigma-Aldrich) in 10 mL of dry methylene chloride was added dropwise to a mixture of the compound of formula BB (5.37 g, 17.8 mmol), TEA (2.48 mL, 17.8 mmol), and 53 mL of dry methylene chloride. The reaction mixture was stirred at 0° C. for 1 h. After concentration under reduced pressure, the resulting solid was filtered and washed with methylene chloride. After drying under reduced pressure, 8 g of the compound of formula OA was obtained.

The identity of the compound of formula OA, N-(2-(1-cyclooctylpiperidin-4-ylamino)phenyl)-4-methoxybenzamide, was confirmed using $^1$H NMR.

Compound OA: $^1$H NMR: $\delta_H$ (400 MHz, DMSO-$d_6$): 9.61 (1H, s), 7.97 (2H, d, J=8.8 Hz), 7.18 (1H, m), 7.11 (1H, m), 7.04 (2H, d, J=8.0 Hz), 6.80 (1H, m), 6.66 (1H, m), 4.88 (1H, m), 3.83 (3H, s), 3.57 (1H, m), 3.10-3.33 (4H, cm), 1.89-2.20 (5H, cm), 1.46-1.87 (14H, cm).

A slurry of the compound of formula OA in 100 mL of dry THF was added to a stirred solution of lithium aluminum hydride (LiAlH$_4$, 1.43 g, 37.6 mmol, Sigma-Aldrich) in 50 mL of dry THF at 0° C., then heated to reflux for 3 h. Thereafter, the reaction mixture was cooled to a temperature of about 25° C. and water (1.43 mL), 2N aqueous NaOH (1.43 mL), water (4.29 mL), and chloroform were added in that order. After filtering the resulting mixture through a pad of CELLITE, the filtrate was extracted with chloroform. The organic layer was dried (Na$_2$SO$_4$), filtered, and concentrated to dryness under reduced pressure to provide 7.2 g of the compound of formula OB.

The identity of the compound of formula OB, $N^1$-(1-cyclooctylpiperidin-4-yl)-$N^2$-(4-methoxybenzyl)benzene-1,2-diamine, was confirmed using $^1$H NMR.

Compound OB: $^1$H NMR: $\delta_H$ (400 MHz, DMSO-$d_6$): 7.27 (2H, d, J=8.4 Hz), 6.87 (2H, d, J=8.4 Hz), 6.48 (2H, m), 6.42 (1H, m), 6.39 (1H, m), 5.15 (1H, t, J=5.2 Hz), 4.28 (1H, d, J=6.8 Hz), 4.19 (2H, d, J=5.2 Hz), 3.72 (3H, s), 3.13 (1H, m), 2.73 (2H, m), 2.55 (1H, m), 2.27 (2H, m), 1.93 (2H, m), 1.31-1.70 (16H, cm).

To a mixture of the compound of formula OB (3.4 g, 8.08 mmol) and 60 mL of THF was added ethyl isocyanatidocarbonate (1.48 mL, 12.11 mmol, Sigma-Aldrich). The mixture was sealed in a microwave reaction vessel and warmed to 150° C. with microwave irradiation and stirring for 45 min. Thereafter, the reaction mixture was concentrated to dryness under reduced pressure. The resulting solid was filtered then washed with ethyl acetate. After drying under reduced pressure, 2.9 g of Heterocyclic-Substituted Piperidine Compound 68 was obtained (yield 73%).

The identity of Heterocyclic-Substituted Piperidine Compound 68, 1-(1-cyclooctylpiperidin-4-yl)-5-(4-methoxybenzyl)-1H-benzo[f][1,3,5]triazepine-2,4(3H,5H)-dione, was confirmed using $^1$H NMR and LC/MS.

Heterocyclic-Substituted Piperidine Compound 68: $^1$H NMR: $\delta_H$ (400 MHz, DMSO-$d_6$): 8.79 (1H, s), 7.49 (1H, m), 7.31 (1H, m), 7.25 (2H, m), 7.11 (2H, d, J=8.4 Hz), 6.79 (2H, d, J=8.4 Hz), 5.20 (1H, d, J=20 Hz), 4.73 (1H, d, J=20 Hz), 3.66 (3H, s), 3.53 (1H, m), 2.75 (1H, m), 2.64 (1H, m), 2.17 (2H, m), 2.05-1.70 (3H, cm), 1.31-1.70 (16H, cm); LC/MS (100%, $t_r$=2.79 min), m/z=490.9 [M+H]$^+$ (Calc: 490.0).

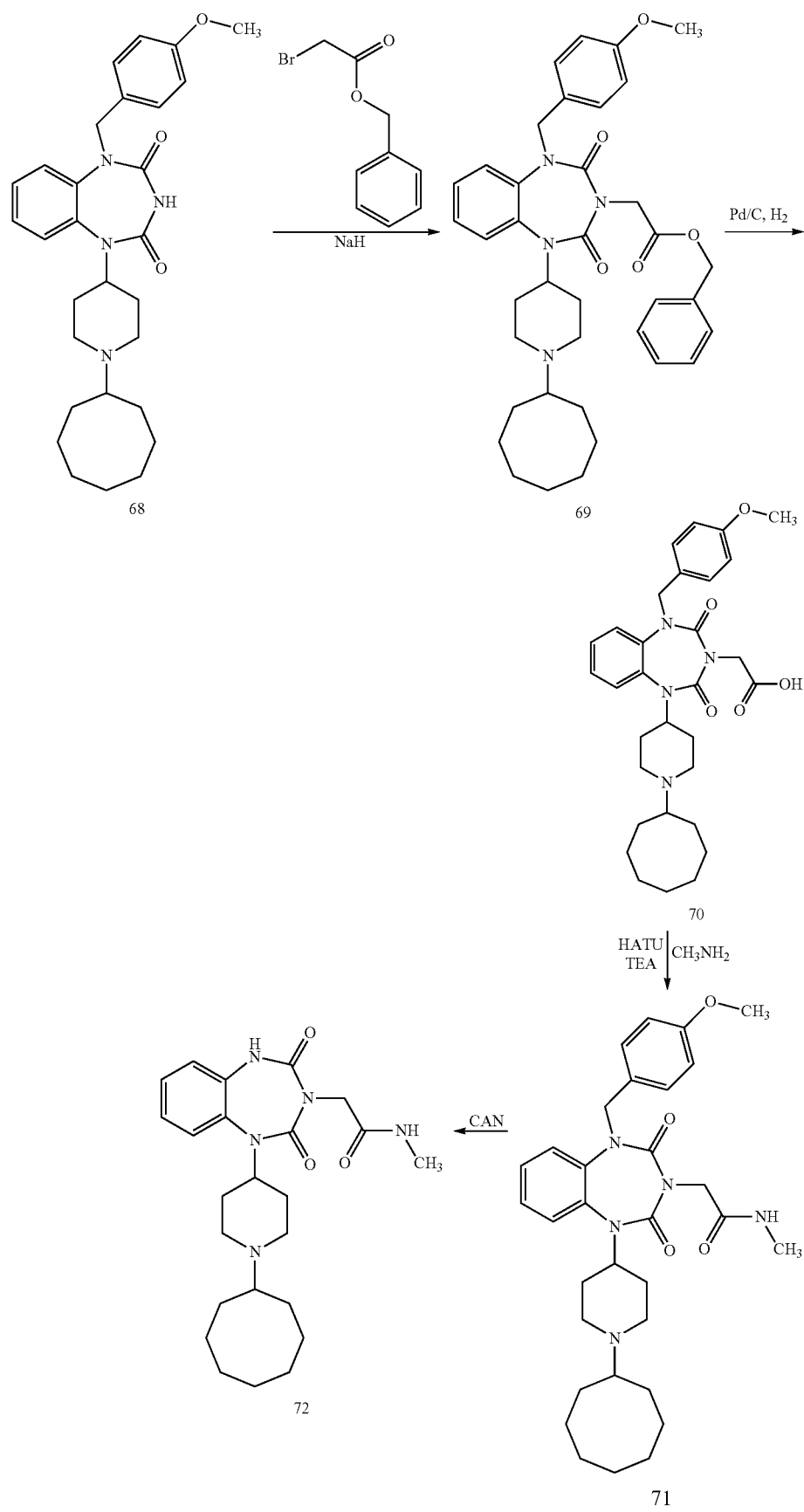

Heterocyclic-Substituted Piperidine Compound 68 (500 mg, 1.02 mol) in 5 mL of DMF was added dropwise to a suspension of NaH (61 mg, 1.53 mmol, Sigma-Aldrich) in 2 mL of DMF at 0° C. Thereafter, the reaction mixture was stirred at a temperature of about 25° C. for 1 h. Then, benzyl 2-bromoacetate (193 μL, 1.22 mmol, TCI America) was added to the reaction mixture at 0° C. followed by stirring at a temperature of about 25° C. for 3 h. Water was then added to the reaction mixture followed by extraction with EtOAc. The organic layer was washed with water, dried ($Na_2SO_4$), filtered, and concentrated to dryness under reduced pressure to provide 844 mg of Heterocyclic-Substituted Piperidine Compound 69 benzyl 2-(1-(1-cyclooctylpiperidin-4-yl)-5-(4-methoxybenzyl)-2,4-dioxo-4,5-dihydro-1H-benzo[f][1,3,5]triazepin-3(2H)-yl)acetate.

A mixture of Heterocyclic-Substituted Piperidine Compound 69 (844 mg), 10% palladium on carbon (254 mg, N.E. Chemcat, Tokyo, Japan), and methanol (20 mL) was stirred under a hydrogen atmosphere at a temperature of about 25° C. for 2 h. After the Pd/C was filtered off, the remaining material was washed with methanol and DMF and the filtrate was concentrated under reduced pressure to provide a solid. The resulting solid was washed with EtOAc to provide 500 mg of Heterocyclic-Substituted Piperidine Compound 70 as a gray solid (yield 89% for two steps).

The identity of Heterocyclic-Substituted Piperidine Compound 70, 2-(1-(1-cyclooctylpiperidin-acid, was confirmed using MS.

Heterocyclic-Substituted Piperidine Compound 70: MS, m/z=549.1 $[M+H]^+$ (Calc: 548).

To a mixture of Heterocyclic-Substituted Piperidine Compound 70 (100 mg, 0.182 mmol), HATU (2-(3H-[1,2,3]-triazolo[4,5-b]pyridin-3-yl)-1,1,3,3-tetramethyluronium hexafluorophosphate(V), 83.3 mg, 0.219 mmol, Peptide Institute/Peptides International, Louisville, Ky.), triethylamine (50.7 μL, 0.364 mmol) and DMF (10 mL) was added methanamine (as a 2M THF solution, 109 μL, 0.219 mmol, Sigma-Aldrich). The reaction mixture was stirred at a temperature of about 25° C. for 2 h. Water was then added to the reaction mixture followed by extraction with EtOAc. The organic layer was washed with water, dried ($Na_2SO_4$), filtered, and concentrated to dryness under reduced pressure to provide the Heterocyclic-Substituted Piperidine Compound 71, 2-(1-(1-cyclooctylpiperidin-4-yl)-5-(4-methoxybenzyl)-2,4-dioxo-4,5-dihydro-1H-benzo[f][1,3 ,5]triazepin-3(2H)-yl)-N-methylacetamide.

At a temperature of about 25° C., ceric ammonium nitrate (CAN, 559 mg, 1.02 mmol, Nacalai Tesque, Koyoto, Japan) was added portionwise over a 10 min period to a stirred mixture of the quantity of Heterocyclic-Substituted Piperidine Compound 71 prepared above and acetonitrile:water (4.5 mL:0.5 mL). Then, the reaction mixture was stirred at 50° C. for 5 h. Thereafter, the mixture was cooled to a temperature of about 25° C., saturated aqueous $NaHCO_3$ was added, and the mixture was extracted with chloroform. The organic layer was dried ($Na_2SO_4$), filtered, and concentrated under reduced pressure. The residue was chromatographed with a silica gel column eluted with a gradient of from 0%:100% $CHCl_3$:MeOH to 80%:20% $CHCl_3$:MeOH. The product fractions were combined and concentrated to dryness under reduced pressure to provide 21.7 mg of Heterocyclic-Substituted Piperidine Compound 72 (yield 27% for two steps).

The identity of Heterocyclic-Substituted Piperidine Compound 72, 2-(1-(1-cyclooctylpiperidin-4-yl)-2,4-dioxo-4,5-dihydro-1H-benzo[f][1,3,5]triazepin-3(2H)-yl)-N-methylacetamide, was confirmed using $^1H$ NMR and LC/MS.

Heterocyclic-Substituted Piperidine Compound 72: $^1H$ NMR: $\delta_H$ (400 MHz, DMSO-$d_6$): 9.80 (1H, s), 7.77 (1H, m), 7.36 (1H, m), 7.24 (2H, m), 7.11 (1H, m), 3.93 (2H, s), 3.68 (1H, m), 2.73 (2H, m), 2.51 (3H, s), 2.20 (2H, m), 2.05 (1H, m), 1.97 (2H, m), 1.31-1.70 (16H, cm); LC/MS (100%, $t_r$=1.87 min), m/z=456.1 $[M+H]^+$ (Calc: 455).

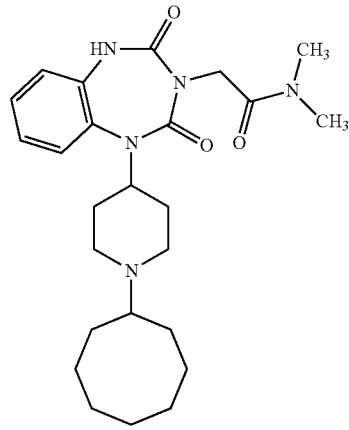

73

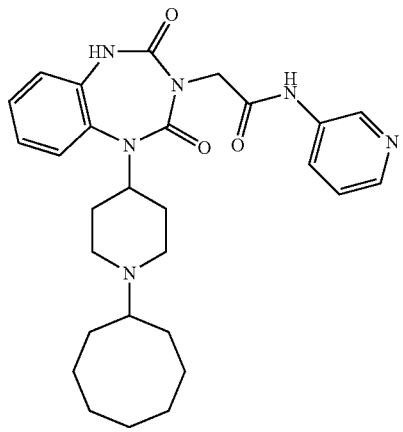

74

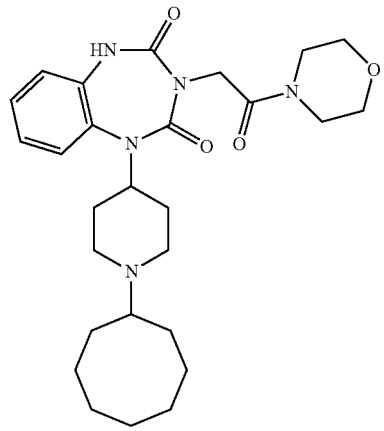

75

Heterocyclic-Substituted Piperidine Compounds 73, 74 and 75 were prepared from the compound of formula L2 as described above except that dimethylamine, pyridin-3-amine, or morpholine, respectively, was used in place of methanamine The identity of Heterocyclic-Substituted Piperidine Compound 73, 2-(1-(1-cyclooctylpiperidin-4-yl)-2,4-dioxo-4,5-dihydro-1H-benzo[f][1,3,5]triazepin-3(2H)-yl)-N,N-dimethylacetamide, was confirmed using $^1$H NMR and LC/MS.

Heterocyclic-Substituted Piperidine Compound 73: $^1$H NMR: $\delta_H$ (400 MHz, DMSO-d$_6$): 9.80 (1H, s), 7.36 (1H, m), 7.21 (2H, m), 7.13 (1H, m), 4.21 (2H, s), 3.74 (1H, m), 2.93 (3H, s), 2.80 (2H, m), 2.73 (3H, s), 2.31 (1H, m), 2.11 (1H, m), 1.99 (2H, m), 1.31-1.70 (16H, cm); LC/MS (100%, $t_r$=1.66 min), m/z=442.08 [M+H]$^+$ (Calc: 441).

The identity of Heterocyclic-Substituted Piperidine Compound 74, 2-(1-(1-cyclooctylpiperidin-4-yl)-2,4-dioxo-4,5-dihydro-1H-benzo[f][1,3,5]triazepin-3(2H)-yl)-N-(pyridin-3-yl)acetamide, was confirmed using $^1$H NMR and LC/MS.

Heterocyclic-Substituted Piperidine Compound 74: $^1$H NMR: $\delta_H$ (400 MHz, DMSO-d$_6$): 10.34 (1H, brs), 9.96 (1H, s), 8.66 (1H, m), 8.24 (1H, m), 7.95 (1H, m), 7.42 (1H, m), 7.26 (3H, m), 7.16 (1H, m), 4.22 (2H, s), 3.75 (1H, m), 2.74 (2H, m), 1.99 (1H, m), 1.31-1.88 (20H, cm); LC/MS (100%, $t_r$=1.27 min), m/z=505.0 [M+H]$^+$ (Calc: 504).

The identity of Heterocyclic-Substituted Piperidine Compound 75, 1-(1-cyclooctylpiperidin-4-yl)-3-(2-morpholino-2-oxoethyl)-1H-benzo[f][1,3,5]triazepine-2,4(3H,5H)-dione, was confirmed using $^1$H NMR and LC/MS.

Heterocyclic-Substituted Piperidine Compound 75: $^1$H NMR: $\delta_H$ (400 MHz, DMSO-d$_6$): 10.25 (1H, brs), 9.89 (1H, s), 7.47 (1H, m), 7.21 (3H, m), 4.26 (2H, s), 4.14 (1H, m), 3.50 (4H, m), 3.36 (4H, m), 3.14 (2H, m), 2.66 (1H, m), 2.17 (1H, m), 1.99 (2H, m), 1.31-1.70 (16H, cm); LC/MS (100%, tr=1.77 min), m/z=497.8 [M+H]+ (Calc: 497).

5.27 Example 27

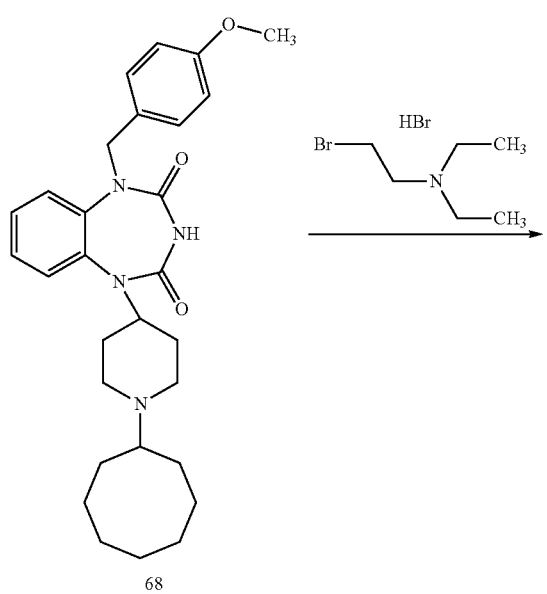

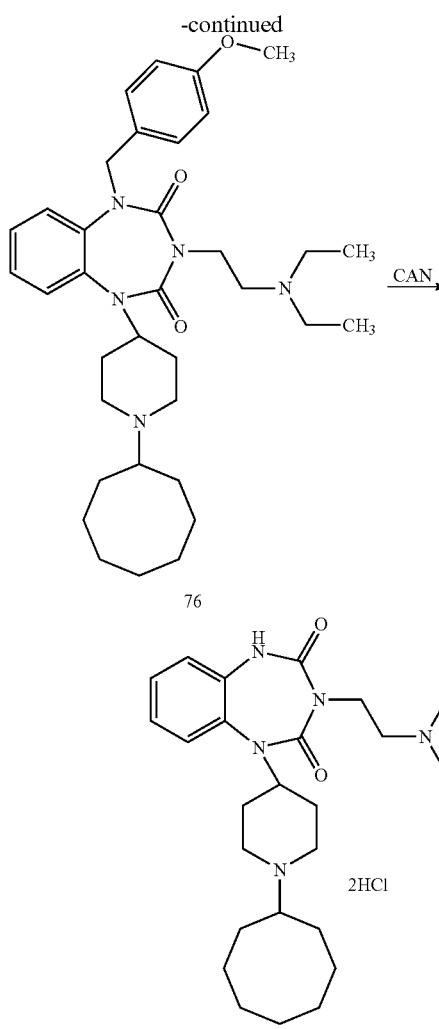

Heterocyclic-Substituted Piperidine Compound 68 (200 mg, 0.408 mol) in 3 mL of DMF was added dropwise to a suspension of NaH (48 mg, 1.224 mmol) in 1 mL of DMF at 0° C., and the mixture was stirred at a temperature of about 25° C. for 1 h. After cooling the reaction mixture to 0° C., 2-(diethylamino)ethyl bromide hydrobromide (256 mg, 0.980 mmol, Sigma-Aldrich) and TEA (136 µL, 0.980 mmol) were added. The resulting mixture was heated to 50° C. and remained at that temperature for 3 h. The reaction mixture was cooled to a temperature of about 25° C., water was added, and the mixture was extracted with ethyl acetate. The organic layer was washed with water, dried (Na$_2$SO$_4$), filtered, and concentrated to dryness under reduced pressure to provide 275 mg of Heterocyclic-Substituted Piperidine Compound 76, 1-(1-cyclooctylpiperidin-4-yl)-3-(2-(diethylamino)ethyl)-5-(4-methoxybenzyl)-1H-benzo[f][1,3,5]triazepine-2,4(3H,5H)-dione.

Using ceric ammonium nitrate, Heterocyclic-Substituted Piperidine Compound 77 was prepared as described in Example 26 except that Heterocyclic-Substituted Piperidine Compound 76 was used in place of Heterocyclic-Substituted Piperidine Compound 71. After concentrating to dryness under reduced pressure, the residue was mixed with 2 mL of ethyl acetate. To this was added 1 mL of 4M HCl in ethyl acetate. After again concentrating to dryness under reduced pressure, the resulting residue was triturated with methanol, filtered, and dried under reduced pressure to provide 79 mg of the dihydrochloride of Heterocyclic-Substituted Piperidine Compound 77 (yield 36% for two steps).

The identity of Heterocyclic-Substituted Piperidine Compound 77, 1-(1-cyclooctylpiperidin-4-yl)-3-(2-(diethylamino)ethyl)-1H-benzo[f][1,3,5]triazepine-2,4(3H,5H)-dione, was confirmed using $^1$H NMR and LC/MS.

Heterocyclic-Substituted Piperidine Compound 77: $^1$H NMR: $\delta_H$(400 MHz, DMSO-d$_6$): 10.63 (1H, brs), 10.48 (1H, brs), 10.16 (1H, s), 7.49 (1H, m), 7.31 (1H, m), 7.20 (2H, m), 4.19 (1H, m), 3.73 (2H, m), 3.35 (2H, m), 3.14 (4H, m), 2.97 (4H, m), 2.70 (1H, m), 2.26 (1H, m), 1.98 (2H, m), 1.31-1.70 (15H, cm), 0.97-1.16 (6H, m); LC/MS (100%, t$_r$=2.08 min), m/z=470.0 [M+H]$^+$ (Calc: 469.0).

5.28 Example 28

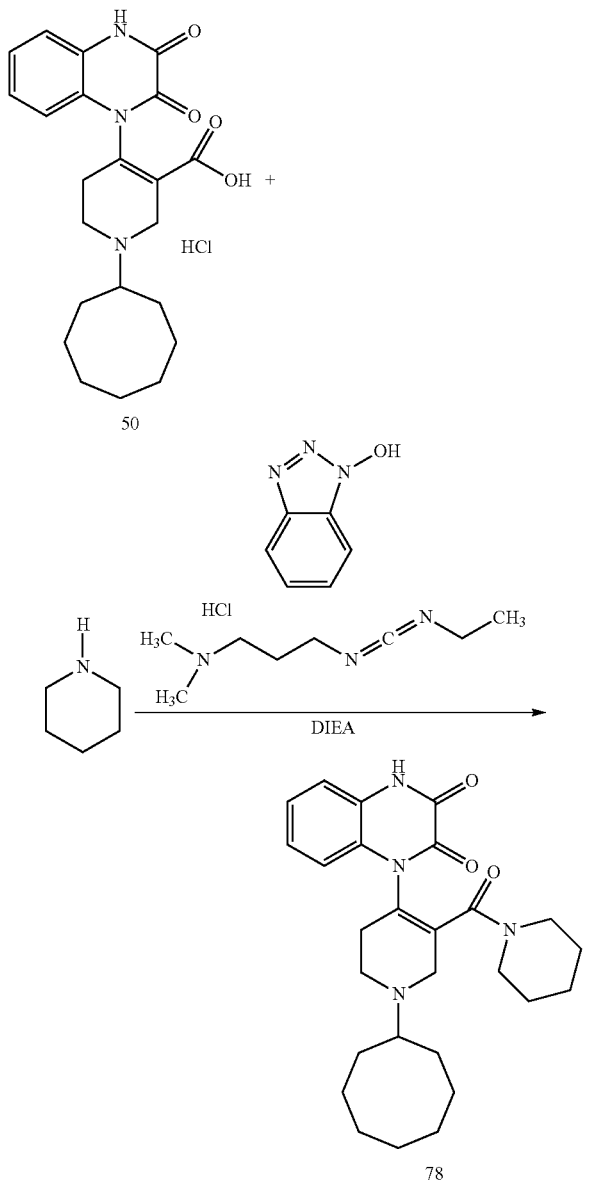

From the sodium salt of Heterocyclic-Substituted Piperidine Compound 50, the synthesis of which is described in Example 18, the carboxylic acid hydrochloride was prepared. To a mixture of the hydrochloride of Heterocyclic-Substituted Piperidine Compound 50 (200 mg, 0.46 mmol) and dry DMF (5 mL) was added 1-hydroxybenzotriazole (94.6 mg, 0.70 mmol, Sigma-Aldrich) and N-ethyl-dimethylaminopropyl carbodiimide hydrochloride (108.6 mg, 0.70 mmol, Sigma-Aldrich). Thereafter, piperidine (0.069 mL, 0.70 mmmol) and DIEA (0.244 mL, 1.38 mmol) were added and the reaction mixture was stirred at a temperature of about 25° C. for 18 h. The mixture was partitioned between an aqueous potassium carbonate solution (100 mL) and ethyl acetate (100 mL). The organic phase was separated, dried (MgSO$_4$), and concentrated to dryness under reduced pressure to provide a yellow gum that was chromatographed by flash silica eluted with 200:10:1 EtOAc:MeOH:ammonia to provide 28 mg of Heterocyclic-Substituted Piperidine Compound 78 as a as a white solid.

The identity of Heterocyclic-Substituted Piperidine Compound 78, 1-(1-cyclooctyl-5-(piperidine-1-carbonyl)-1,2,3,6-tetrahydropyridin-4-yl)quinoxaline-2,3(1H,4H)-dione, was confirmed using $^1$H NMR and TLC.

Heterocyclic-Substituted Piperidine Compound 78: $^1$H NMR: $\delta_H$(400 MHz, CDCl$_3$): 11.9 (1H, s), 6.95 (3H, m), 6.85 (1H, m), 3.10-2.85 (5H, m), 2.6 (3H, m), 2.20 (1H, m), 1.90 (1H, m), 1.65-1.10 (21H, m); TLC (SiO$_2$) 200:10:1 EtOAc:MeOH:ammonia: Rf=0.38 with UV detection, Dragendorff's reagent.

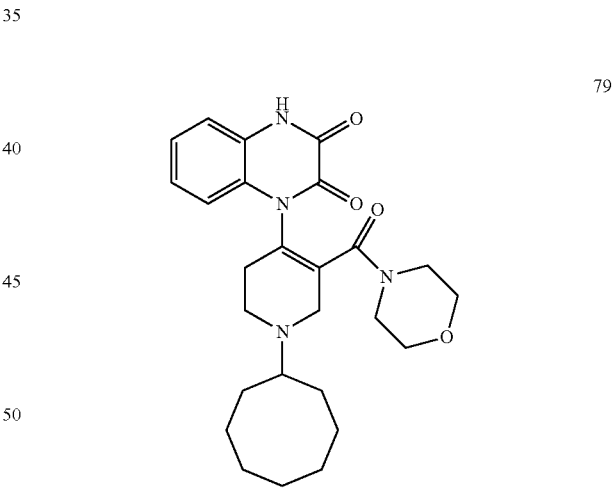

Heterocyclic-Substituted Piperidine Compound 79 was prepared in a manner similar to that described above except that morpholine was used in place of piperidine.

The identity of Heterocyclic-Substituted Piperidine Compound 79, 1-(1-cyclooctyl-5-(morpholine-4-carbonyl)-1,2,3,6-tetrahydropyridin-4-yl)quinoxaline-2,3(1H,4H)-dione, was confirmed using $^1$H NMR.

Heterocyclic-Substituted Piperidine Compound 79: $^1$H NMR: $\delta_H$(400 MHz, CDCl$_3$): 12.1 (1H, s), 7.15 (3H, m), 7.00 (1H, m), 3.60-3.35 (4H, m), 3.15 (1H, m), 3.00 (1H, m), 2.78 (3H, m), 2.30 (1H, m), 2.10 (1H, m), 1.80-1.39 (14H, m).

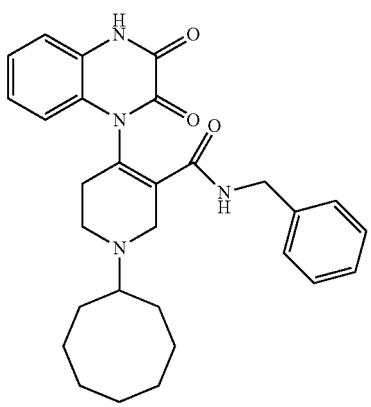

Heterocyclic-Substituted Piperidine Compound 80 was prepared in a manner similar to that described above except that benzylamine (Sigma-Aldrich) was used in place of piperidine.

The identity of Heterocyclic-Substituted Piperidine Compound 80, N-benzyl-1-cyclooctyl-4-(2,3-dioxo-3,4-dihydroquinoxalin-1(2H)-yl)-1,2,5,6-tetrahydropyridine-3-carboxamide, was confirmed using $^1$H NMR and TLC.

Heterocyclic-Substituted Piperidine Compound 80: $^1$H NMR: $\delta_H$ (400 MHz, CDCl$_3$): 8.08 (1H, t, J=6.1 Hz), 7.20-7.06 (6H, m), 7.01 (1H, d, J=8.9 Hz), 6.81 (1H, d, J=8.9 Hz), 4.10 (2H, ddd, 16.7, 6.1 Hz), 2.77 (3H, m), 2.37 (1H, m), 2.15 (1H, m), 1.84-1.46 (14H, m); TLC (SiO$_2$) 40:10:1 EtOAc:MeOH:ammonia: Rf=0.14 with UV detection, Dragendorff's reagent.

5.29 Example 29

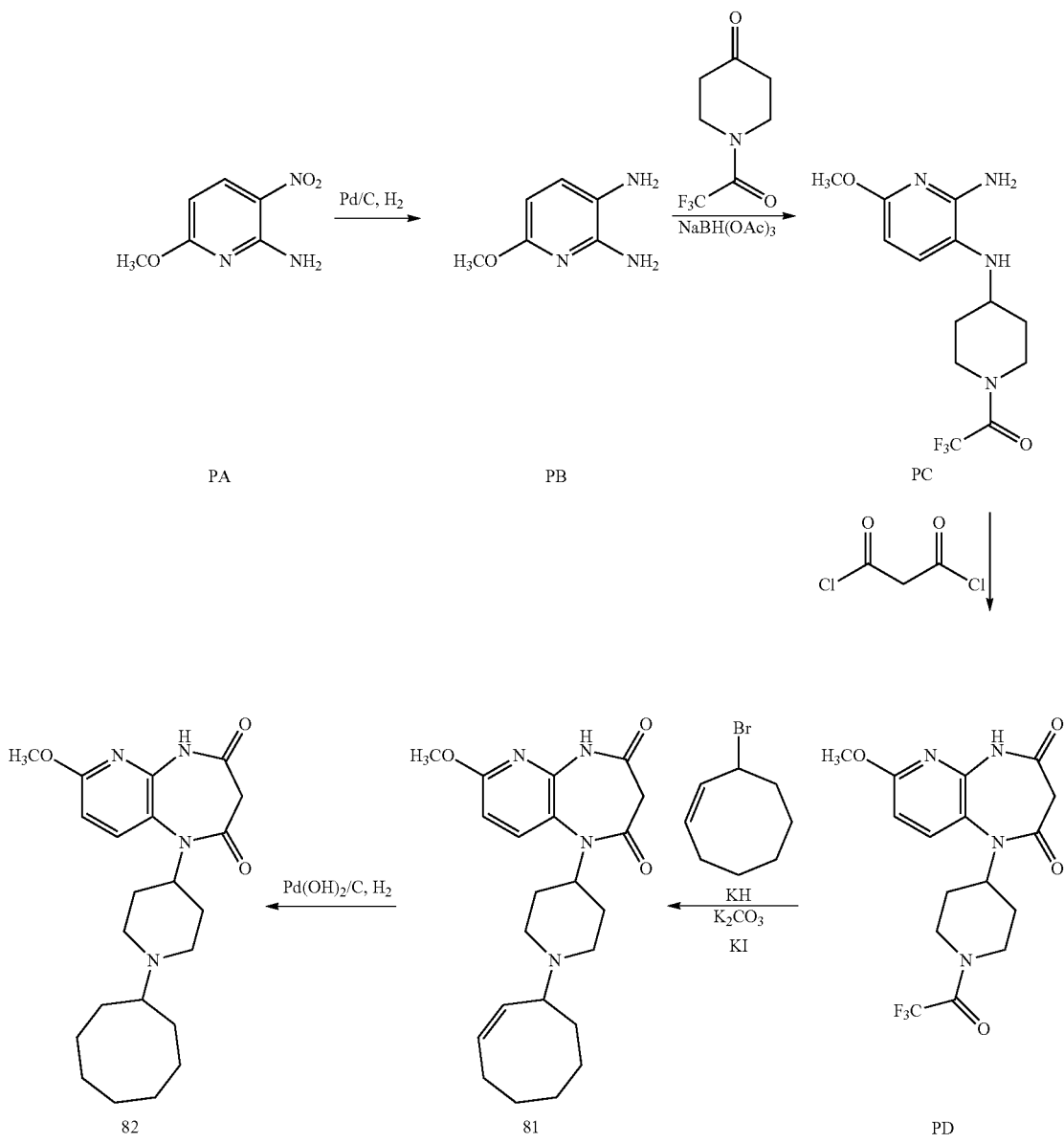

In 200 mL of methanol, the compound of formula PA, 6-methoxy-3-nitropyridin-2-amine (3.45 g, 20.0 mmol, Sigma-Aldrich) was suspended. To this, 10% palladium on carbon (350 mg) was added and the reaction mixture was stirred for 6 h under a hydrogen atmosphere at a temperature of about 25° C. The mixture was filtered through CELITE and concentrated to dryness under reduced pressure to provide 2.78 g of the compound of formula PB as a violet solid (yield>99%).

The identity of the compound of formula PB, 6-methoxy-pyridine-2,3-diamine, was confirmed using $^1$H NMR.

Compound PB: $^1$H NMR: $\delta_H$ (CDCl$_3$): 6.93 (1H, d, 0.1=8.1 Hz), 6.04 (1H, d, J=8.1 Hz), 3.80 (3H, s).

The compound of formula PB (417 mg, 3.0 mmol) and 1-(2,2,2-trifluoroacetyl)piperidin-4-one (702 mg, 3.6 mmol, Sigma-Aldrich) were suspended in 30 mL of dry chloroform. To this, sodium triacetoxyborohydride (1.27 g, 6.0 mmol) was added and the reaction mixture was stirred for 3 h at a temperature of about 25° C. Then, the mixture was poured into aqueous NaHCO$_3$ (20 mL) and extracted twice with chloroform (30 mL for each extraction). The extracts were combined, dried (MgSO$_4$), and concentrated to dryness under reduced pressure. The residue was chromatographed with a silica gel column eluted with a gradient of from 20%:80% EtOAc:n-hexane to 60%:40% EtOAc:n-hexane to provide 668 mg of the compound of formula PC as a violet solid (yield 70%).

The identity of the compound of formula PC, 1-(4-(2-amino-6-methoxypyridin-3-ylamino)piperidin-1-yl)-2,2,2-trifluoroethanone, was confirmed using $^1$H NMR.

Compound PC: $^1$H NMR: $\delta_H$ (CDCl$_3$): 7.01 (1H, d, J=8.1 Hz), 6.06 (1H, d, J=8.1 Hz), 4.50 (1H, brs), 4.35-4.40 (1H, m), 3.94-3.99 (1H, m), 3.82 (3H, s), 3.19-3.36 (2H, m), 3.00-3.10 (1H, m), 2.04 (2H, m), 1.39-1.53 (2H, m).

A mixture of the compound of formula PC (646 mg, 2.0 mmol) and 200 mL of dry dichloromethane was added dropwise to a mixture of malonyl dichloride (571 mg, 4.0 mmol) and 200 mL of dry dichloromethane. The resulting reaction mixture was stirred for 3 h under a nitrogen atmosphere at 0° C. The mixture was allowed to warm to a temperature of about 25° C. for 20 h. Then, the reaction mixture was poured into aqueous NaHCO$_3$ (300 mL) and extracted twice with chloroform (200 mL for each extraction). The extracts were combined, dried (MgSO$_4$), and concentrated to dryness under reduced pressure. The residue was chromatographed with a silica gel column eluted with a gradient of from 70%:30% EtOAc:n-hexane to 100%:0% EtOAc:n-hexane to provide 548 mg of the compound of formula PD as a colorless solid (yield 70%).

The identity of the compound of formula PD, 7-methoxy-1-(1-(2,2,2-trifluoroacetyl)piperidin-4-yl)-1H-pyrido[3,2-b][1,4]diazepine-2,4(3H,5H)-dione, was confirmed using $^1$H NMR.

Compound PD: $^1$H NMR: $\delta_H$ (CDCl$_3$): 7.73 (1H, s), 7.50 (1H, dd, J=10.4, 9.1 Hz), 6.66 (1H, d, J=9.1 Hz), 4.71-4.44 (2H, m), 4.15-4.01 (1H, m), 3.92 (3H, s), 3.43 (1H, d, J=12.7 Hz), 3.32 (1H, d, J=12.7 Hz), 3.22-3.16 (1H, m), 2.84-2.78 (1H, m), 2.29-2.26 (1H, m), 2.02-1.97 (1H, m), 1.69-1.62 (2H, m).

Potassium carbonate (1.00 g, 7.24 mmol) was added to a mixture of the compound of formula PD (700 mg, 1.8 mmol) and 20 mL of methanol and the reaction mixture was stirred for 5 h at a temperature of about 25° C. Thereafter, the mixture was concentrated to dryness under reduced pressure and the resulting solid was suspended in 20 mL of acetonitrile. To this, the compound of formula KH (855 mg, 4.52 mmol) and potassium iodide (30 mg, 0.181 mmol) were added and the reaction mixture was refluxed for 6 h. Then, the reaction mixture was poured into water (30 mL) and extracted twice with chloroform (50 mL for each extraction). The extracts were combined, dried (MgSO$_4$), and concentrated to dryness under reduced pressure. The residue was chromatographed with an amino-silica gel column eluted with a gradient of from 70%:30% EtOAc:n-hexane to 100%:0% EtOAc:n-hexane to provide 548 mg of Heterocyclic-Substituted Piperidine Compound 81 as a pale yellow solid (yield 70%).

The identity of Heterocyclic-Substituted Piperidine Compound 81 (Z)-1-(1-(cyclooct-2-enyl)piperidin-4-yl)-7-methoxy-1H-pyrido[3,2-b][1,4]diazepine-2,4(3H,5H)-dione, was confirmed using $^1$H NMR and LC/MS.

Heterocyclic-Substituted Piperidine Compound 81: $^1$H NMR: $\delta_H$ (DMSO-d$_6$): 10.59 (1H, s), 7.81 (1H, dd, J=8.6, 1.8 Hz), 6.72 (1H, d, J=8.6 Hz), 5.67-5.65 (1H, m), 5.46-5.43 (1H, m), 3.98-3.95 (1H, m), 3.86 (3H, s), 3.49 (1H, d, J=12.2 Hz), 3.27-3.24 (1H, m), 2.94-2.89 (3H, m), 2.20-1.21 (16H, m); LC/MS (100%, t$_r$=1.72 min), m/z=399.0 [M+H]$^+$ (Calc: 398.2).

A mixture of Heterocyclic-Substituted Piperidine Compound 81 (434 mg, 1.09 mmol), 20% Pd(OH)$_2$ on carbon (90 mg, Sigma-Aldrich), and methanol (25 mL) was stirred at a temperature of about 25° C. for 14 h in a hydrogen atmosphere. After filtration through CELITE, the filtrate was concentrated under reduced pressure to provide 425 mg of Heterocyclic-Substituted Piperidine Compound 82 as a pale yellow solid (yield 97%).

The identity of Heterocyclic-Substituted Piperidine Compound 82, 1-(1-cyclooctylpiperidin-4-yl)-7-methoxy-1H-pyrido[3,2-b][1,4]diazepine-2,4(3H,5H)-dione, was confirmed using $^1$H NMR and LC/MS.

Heterocyclic-Substituted Piperidine Compound 82: $^1$H NMR: $\delta_H$ (DMSO-d$_6$): 10.59 (1H, s), 7.80 (1H, d, J=8.6 Hz), 6.72 (1H, d, J=8.6 Hz), 3.94 (1H, m), 3.86 (3H, s), 3.49 (1H, d, J=12.7 Hz), 2.93 (1H, d, J=12.7 Hz), 2.73 (2H, m), 2.21 (2H, m), 2.01-1.85 (2H, m), 1.64-1.29 (17H, m); LC/MS (100%, t$_r$=1.66 min), m/z=401.1 [M+H]$^+$ (Calc: 400.3).

5.30 Example 30
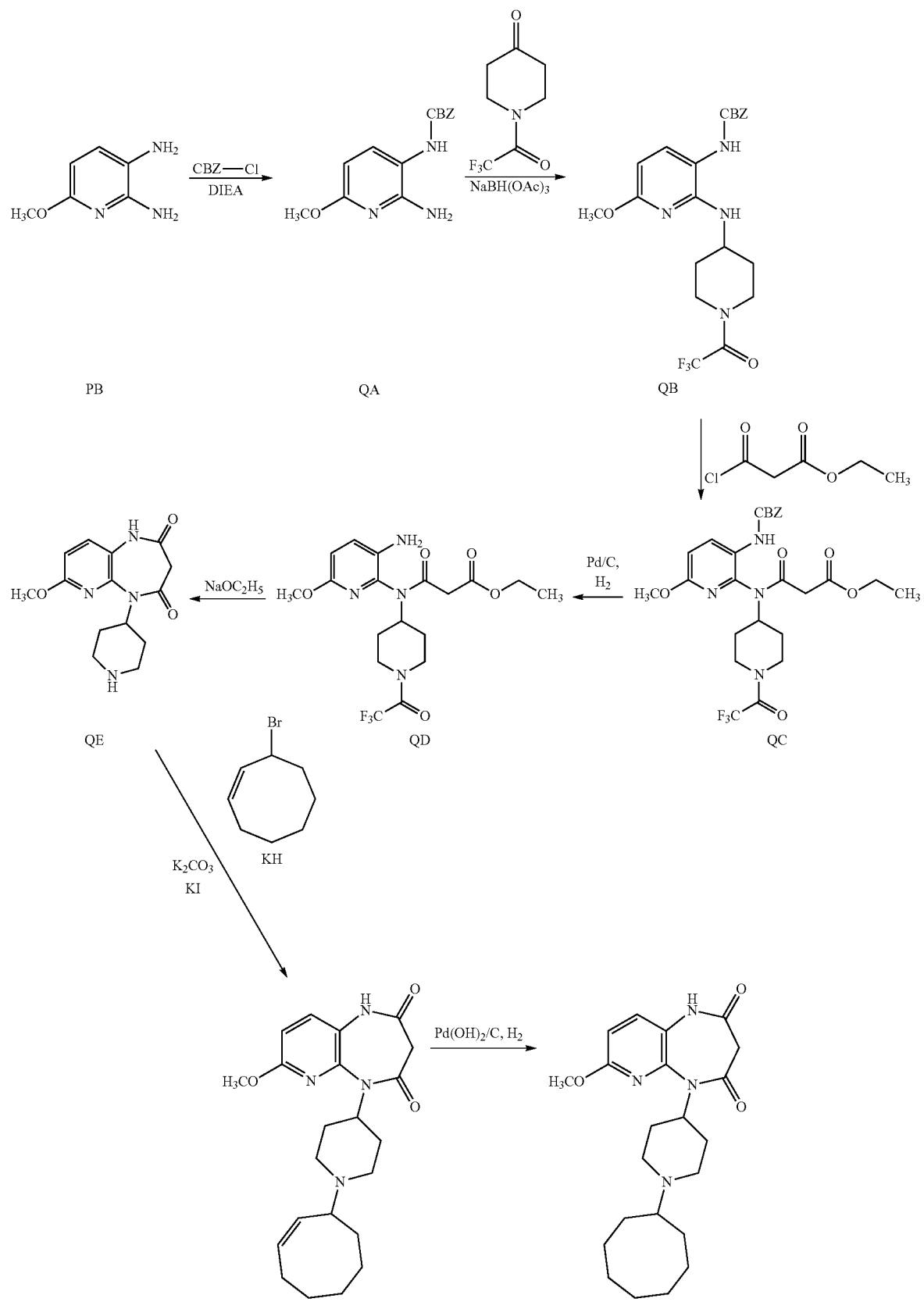

A mixture of the compound of formula PB (2.00 g, 14.3 mmol), DIEA (2.96 mL, 17.2 mmol), and 70 mL of dry dichloromethane was cooled to 0° C. under a nitrogen atmosphere. To this, a mixture of benzyl carbonochloridate (2.70 g, 15.8 mL, Sigma-Aldrich) and 70 mL of dry dichloromethane was added and the reaction mixture was stirred for 1 h at 0° C. Then, the mixture was poured into aqueous NaHCO$_3$ (100 mL) and extracted twice with chloroform (100 mL for each extraction). The extracts were combined, dried (MgSO$_4$), and concentrated to dryness under reduced pressure. The residue was chromatographed with a silica gel column eluted with a gradient of from 35%:65% EtOAc:n-hexane to 55%:45% EtOAc:n-hexane to provide 3.26 g of the compound of formula QA as a violet solid (yield 83%).

The identity of the compound of formula QA, benzyl 2-amino-6-methoxypyridin-3-ylcarbamate, was confirmed using $^1$H NMR.

Compound QA: $^1$H NMR: $\delta_H$(CDCl$_3$): 7.38 (6H, s), 6.10-6.06 (2H, m), 5.18 (2H, s), 4.52 (2H, bs), 3.83 (3H, s).

The compound of formula QB was prepared from 1-(2,2,2-trifluoroacetyl)piperidin-4-one in a manner similar to Example 29 except that the compound of formula QA was used in place of the compound of formula PB.

The identity of the compound of formula QB, benzyl 6-methoxy-2-(1-(2,2,2-trifluoroacetyl)piperidin-4-ylamino)pyridin-3-ylcarbamate, was confirmed using $^1$H NMR.

Compound QB: $^1$H NMR: $\delta_H$ (CDCl$_3$): 7.37 (5H, s), 7.24 (1H, d, J=8.1 Hz), 6.03 (1H, d, J=8.1 Hz), 5.92 (1H, s), 5.17 (2H, s), 4.54 (1H, s), 4.32-4.29 (1H, m), 4.19-4.11 (1H, m), 3.93-3.90 (1H, m), 3.85 (3H, s), 3.32-3.29 (1H, m), 3.09-3.06 (1H, m), 2.17-2.09 (2H, m), 1.46-1.43 (2H, m).

The compound of formula QC was prepared from ethyl 3-chloro-3-oxopropanoate in a manner similar to Example 16 except that the compound of formula QB was used in place of the compound of formula GA.

The identity of the compound of formula QC, ethyl 3-((3-(benzyloxycarbonylamino)-6-methoxypyridin-2-yl)(1-(2,2,2-trifluoroacetyl)piperidin-4-yl)amino)-3-oxopropanoate, was confirmed using $^1$H NMR.

Compound QC: $^1$H NMR: $\delta_H$(CDCl$_3$): 8.26-8.24 (1H, m), 7.38-7.30 (6H, m), 6.85 (1H, d, J=8.6 Hz), 5.24-5.15 (2H, m), 4.65-4.43 (2H, m), 4.15-3.97 (3H, m), 3.83-3.82 (3H, m), 3.17-3.03 (3H, m), 2.78-2.66 (1H, m), 2.18-2.12 (1H, m), 1.79-1.70 (2H, m), 1.26-1.19 (4H, m).

The compound of formula QC (188 mg, 0.332 mmol), 10% palladium on carbon (20 mg), and 10 mL of methanol were stirred for 1 h under a hydrogen atmosphere at a temperature of about 25° C. The reaction mixture was filtered through CELITE and concentrated to dryness under reduced pressure to provide 143 mg of the compound of formula QD as a colorless amorphous solid (yield>99%).

The identity of the compound of formula QD, ethyl 3-((3-amino-6-methoxypyridin-2-yl)(1-(2,2,2-trifluoroacetyl)piperidin-4-yl)amino)-3-oxopropanoate, was confirmed using $^1$H NMR.

Compound QD: $^1$H NMR: $\delta_H$ (CDCl$_3$): 7.12 (1H, d, J=8.6 Hz), 6.69 (1H, d, J=8.6 Hz), 4.76-4.69 (1H, m), 4.61-4.52 (1H, m), 4.13 (2H, q, J=7.1 Hz), 4.01 (1H, m), 3.78 (3H, d, J=8.1 Hz), 3.62 (2H, bs), 3.22-3.16 (3H, m), 2.84-2.77 (1H, m), 2.28-2.18 (1H, m), 2.07-1.80 (2H, m), 1.41-1.29 (1H, m), 1.23 (3H, t, J=7.1 Hz).

The compound of formula QE was prepared in a manner similar to Example 14 except that the compound of formula QD was used in place of the compound of formula FG and sodium ethoxide (Sigma-Aldrich) was used in place of sodium methoxide.

The identity of the compound of formula QE, 7-methoxy-5-(piperidin-4-yl)-1H-pyrido[2,3-b][1,4]diazepine-2,4(3H,5H)-dione, was confirmed using $^1$H NMR.

Compound QE: $^1$H NMR: $\delta_H$ (CDCl$_3$): 7.40 (1H, d, J=8.6 Hz), 6.69 (1H, d, J=8.6 Hz), 4.54 (1H, m), 3.97 (3H, s), 3.33 (2H, m), 3.15 (2H, m), 2.73-2.58 (3H, m), 1.99 (2H, m), 1.53-1.44 (2H, m).

Heterocyclic-Substituted Piperidine Compound 83 was prepared from the compound of formula KH in a manner similar to Example 29 except that the compound of formula QE was used in place of the compound of formula PD.

The identity of Heterocyclic-Substituted Piperidine Compound 83, (Z)-5-(1-(cyclooct-2-enyl)piperidin-4-yl)-7-methoxy-1H-pyrido[2,3-b][1,4]diazepine-2,4(3H,5H)-dione, was confirmed using $^1$H NMR and LC/MS.

Heterocyclic-Substituted Piperidine Compound 83: $^1$H NMR: $\delta_H$ (DMSO-d$_6$): 10.22 (1H, s), 7.51 (1H, d, J=8.6 Hz), 6.80 (1H, d, J=8.6 Hz), 5.66 (1H, m), 5.49 (1H, m), 4.25 (1H, m), 3.86 (3H, s), 3.47 (1H, d, J=12.2 Hz), 2.96 (3H, m), 2.65 (1H, d, J=12.2 Hz), 2.22-1.25 (16H, m); LC/MS (98%, t$_r$=1.77 min), m/z=399.0 [M+H]$^+$ (Calc: 398.2).

Heterocyclic-Substituted Piperidine Compound 84 was prepared in a manner similar to Example 29 except that Heterocyclic-Substituted Piperidine Compound 83 was used in place of Heterocyclic-Substituted Piperidine Compound 81.

The identity of Heterocyclic-Substituted Piperidine Compound 84, 5-(1-cyclooctylpiperidin-4-yl)-7-methoxy-1H-pyrido[2,3-b][1,4]diazepine-2,4(3H,5H)-dione, was confirmed using $^1$H NMR and LC/MS.

Heterocyclic-Substituted Piperidine Compound 84: $^1$H NMR: $\delta_H$ (DMSO-d$_6$): 10.22 (1H, s), 7.51 (1H, d, J=8.6 Hz), 6.79 (1H, d, J=8.6 Hz), 4.22 (1H, m), 3.86 (3H, s), 3.46 (1H, d, J=11.7 Hz), 2.97 (1H, d, J=11.7 Hz), 2.76-2.53 (3H, m), 2.20 (2H, m), 1.99-1.23 (18H, m); LC/MS (100%, t$_r$=1.81 min), m/z=401.2 [M+H]$^+$ (Calc: 400.3).

5.31 Example 31

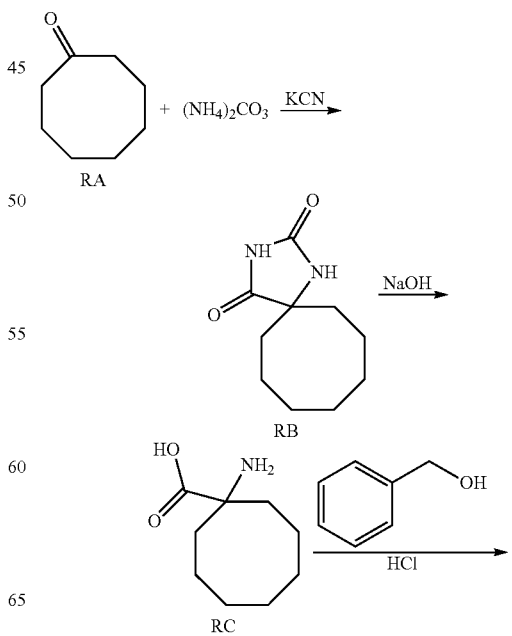

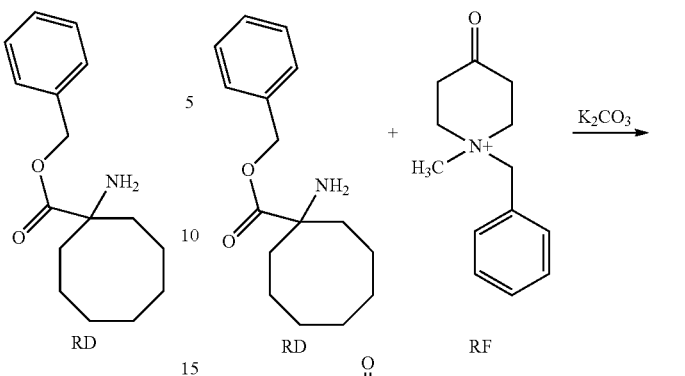

To a mixture of cyclooctanone (RA 17 g, 135 mmol, Sigma-Aldrich) in ethanol (200 mL) and water (200 mL) were added KCN (17.5 g, 269 mmol, Sigma-Aldrich) followed by ammonium carbonate ($[NH_4]_2CO_3$, 51.8 g, 539 mmol, Sigma-Aldrich). The resulting reaction mixture was stirred at 80° C. for 6 h. The reaction mixture was evaporated to dryness under reduced pressure to provide a white solid precipitate which was filtered, collected, and dried for 16 h to provide 15.9 g of the compound of formula RB, 1,3-diaza-spiro[4.7]dodecane-2,4-dione (yield 73%).

A mixture of the compound of formula RB (15.9 g, 81 mmol) in 2N NaOH was refluxed for 96 h. The reaction mixture was neutralized by the addition of 2N HCl to provide a white solid precipitate which was filtered and collected to provide the compound of formula RC, 1-aminocyclooctanecarboxylic acid. The compound of formula RC was dissolved with hot phenylmethanol (i.e., benzyl alcohol, Sigma-Aldrich) then concentrated HCl was added. The resulting reaction mixture was refluxed for 16 h. After neutralizing the reaction mixture with 2N NaOH, the resulting mixture was extracted three times with 4:1 $CHCl_3$:MeOH. The organic portions were combined, washed with water, washed with brine, dried ($MgSO_4$), filtered, and concentrated under reduced pressure to provide 920 mg of the compound of formula RD, benzyl 1-aminocyclooctanecarboxylate (yield 6% for two steps).

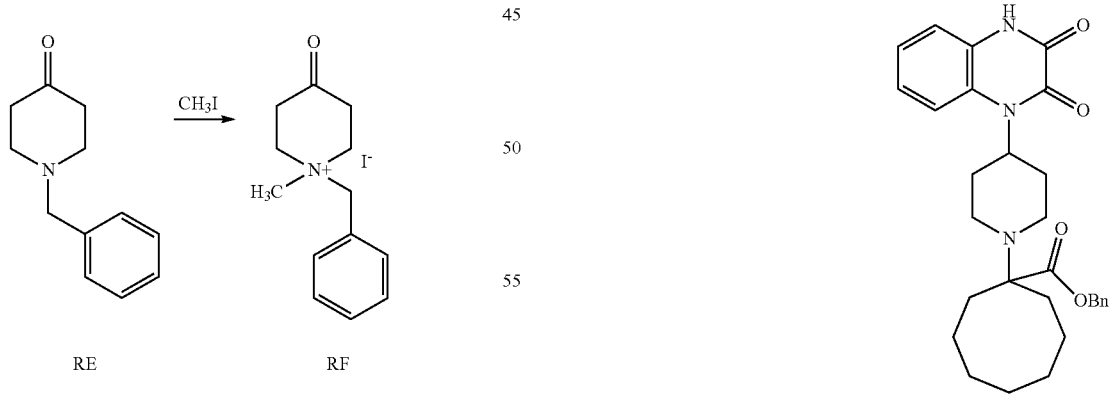

A mixture of the compound of formula RE (1-benzylpiperidin-4-one, 1.49 mol, Sigma-Aldrich) and acetone (1 L) was cooled to 0° C. Methyl iodide (94.4 mL, 1.51 mol) was added dropwise over 30 min and the resulting reaction mixture was stirred for 3 h, then filtered. The filter cake was dried under reduced pressure for 18 h to provide the compound of formula RF as a solid.

At a temperature of 90° C., a mixture of the compound of formula RF (10 mmol), MeOH (6 mL) and water (20 mL) was added dropwise to a mixture of the compound of formula RD (10 mmol), $K_2CO_3$ (1 mmol), MeOH (10 mL) and water (4 mL) over 20 min. The resulting reaction mixture was stirred at 90° C. for 48 h. After concentration under reduced pressure, the mixture was extracted three times with a mixture of EtOAc and water. The organic layers were combined, dried (MgSO$_4$), and concentrated under reduced pressure to provide a yellow oil. The resulting oil was chromatographed with a silica gel column eluted with a gradient of from 10%:90% EtOAc:n-hexane to 50%:50% EtOAc:n-hexane to provide the compound of formula RG, benzyl 1-(4-oxopiperidin-1-yl)cyclooctanecarboxylate.

Sodium triacetoxyborohydride (50 mmol) was added to a mixture of the compound of formula RG (12.8 mmol), and o-phenylenediamine (3 g, 27.8 mmol) in 100 mL of CH$_2$Cl$_2$ at a temperature of about 25° C. Thereafter, 3 mL of acetic acid was added. The resulting mixture was stirred at a temperature of about 25° C. for about 16 h. MeOH (2 mL) and water (25 mL) were added and the mixture was neutralized with 28% aqueous ammonia to adjust the pH to about 8. The organic layer was separated, washed with brine (10 mL), concentrated under reduced pressure, and chromatographed with a silica gel column eluted with 10:1:1 EtOAc:MeOH:TEA to provide the compound of formula RH, benzyl 1-(4-(2-aminophenylamino)piperidin-1-yl)cyclooctanecarboxylate.

A mixture of the compound of formula RH in 20 mL of diethyl oxalate was heated at 140° C. for 16 h. After cooling to a temperature of about 25° C., the reaction mixture was diluted with EtOAc, washed with 2N aqueous NaOH (30 mL), washed with brine (20 mL), concentrated under reduced pressure, and chromatographed with a silica gel column eluted with 5:5:0.5:0.5 EtOAc:hexane:MeOH:TEA to provide Heterocyclic-Substituted Piperidine Compound 88.

The identity of Heterocyclic-Substituted Piperidine Compound 88, benzyl 1-(4-(2,3-dioxo-3,4-dihydroquinoxalin-1(2H)-yl)piperidin-1-yl)cyclooctanecarboxylate, was confirmed using $^1$H NMR and LC/MS.

Heterocyclic-Substituted Piperidine Compound 88: $^1$H NMR: $\delta_H$ (300 MHz, DMSO-d$_6$): 11.51 (1H, s), 7.47 (1H, d, J=8.1 Hz), 7.41-7.33 (5H, m), 7.24-7.17 (3H, m), 5.17 (2H, s), 4.58 (1H, br), 3.24 (2H, d, J=11.1 Hz), 2.76 (2H, d, J=9.3 Hz), 2.33 (2H, t, J=10.8 Hz), 2.01-1.47 (16H, m); LC/MS (100%, t$_r$=1.87 min), m/z=490.2 [M+H]$^+$ (Calc: 489.3).

Alternatively, the compound of formula RD was prepared by the following route.

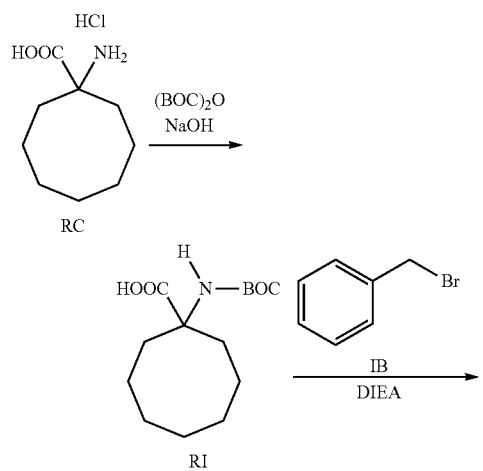

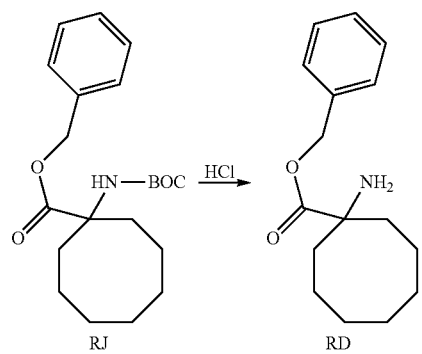

To a mixture of the hydrochloride of the compound of formula RC (414 mg, 2.00 mmol), aqueous 1N NaOH (4 mL, 4.00 mmol), and dioxane (4 mL) at a temperature of about 25° C. was added (BOC)$_2$O (0.51 mL, 2.2 mmol). After the addition, the reaction mixture was stirred for 18 h at a temperature of about 25° C. The mixture was quenched by pouring it into aqueous 1N HCl and extracted with CHCl$_3$. The organic portion was dried (Na$_2$SO$_4$) and concentrated under reduced pressure to provide a white solid. The solid was triturated with iso-propyl ether and collected to provide 221 mg of the compound of formula RI as a colorless solid (yield 41%).

The identity of the compound of formula RI, 1-(tert-butoxycarbonylamino)cyclooctanecarboxylic acid, was confirmed using $^1$H NMR.

Compound RI: $^1$H NMR: $\delta_H$ (400 MHz, DMSO-d$_6$): 12.01 (1H, s), 6.90 (1H, s), 1.89-1.45 (14H, m), 1.35 (9H, s).

To a mixture of the compound of formula RI (215 mg, 0.792 mmol) in DMF (1 mL) at a temperature of about 25° C. was added the compound of formula IB (0.103 mmol, 0.871 mmol) and DIEA (0.166 mL, 0.950 mmol). After the addition, the reaction mixture was stirred for 20 h at a temperature of about 25° C. The mixture was quenched by pouring it into water. A white precipitate formed. The precipitate was collected, washed with dilute aqueous NaHCO$_3$, and washed with water to provide 240 mg of the compound of formula RJ as a white solid (yield 84%).

The identity of the compound of formula RJ, benzyl 1-(tert-butoxycarbonylamino)cyclooctanecarboxylate, was confirmed using $^1$H NMR.

Compound RJ: $^1$H NMR: $\delta_H$ (400 MHz, CDCl$_3$): 7.37-7.34 (5H, m), 5.16 (2H, s), 4.69 (1H, s), 2.08-2.04 (4H, m), 1.57 (10H, d, J=8.06 Hz), 1.43 (9H, s).

To a suspension of the compound of formula RJ in 1,4-dioxane (4 mL) and MeOH (1 mL) was added 4N HCl in 1,4-dioxane (2 mL) at a temperature of about 25° C. The reaction mixture was stirred at 25° C. for 1 h. The resulting precipitate was filtered, washed with diethyl ether (3 mL), and dried under reduced pressure at 70° C. to provide the compound of formula RD as a solid (yield>98%).

The identity of the compound of formula RD was confirmed using $^1$H NMR.

Compound RD: $^1$H NMR: $\delta_H$ (400 MHz, CDCl$_3$): 7.40-7.34 (5H, m), 5.21 (2H, s), 2.06-1.71 (14H, m).

Alternatively, Heterocyclic-Substituted Piperidine Compound 88 was prepared by the following route.

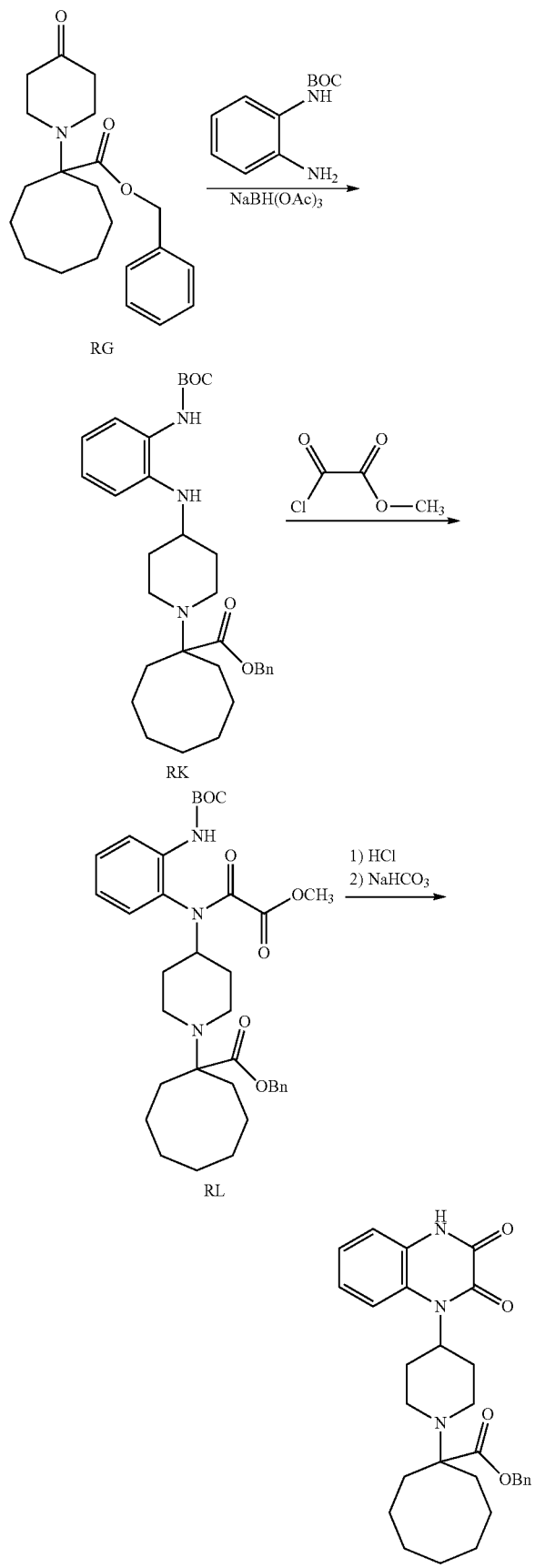

The compound of formula RG was prepared from the compounds of formula RD and RF in a manner similar to that described above (yield 38%).

The identity of the compound of formula RG was confirmed using $^1$H NMR.

Compound RG: $^1$H NMR: $\delta_H$ (400 MHz, CDCl$_3$): 7.38-7.36 (5H, m), 5.14 (2H, s), 2.92 (4H, t, J=5.62 Hz), 2.39 (4H, t, J=5.79 Hz), 2.00-1.59 (14H, m).

The compound of formula RG (48.0 mmol) and tert-butyl 2-aminophenylcarbamate (96.0 mmol, Sigma-Aldrich) were suspended in 200 mL of CH$_2$Cl$_2$. To this mixture, sodium triacetoxyborohydride (30.42 g, 144.0 mmol, Sigma-Aldrich) and acetic acid (10 mL) were added. These ingredients were stirred at a temperature of about 25° C. for 24 h after which the reaction mixture was extracted 10 times with about 200 mL of water each time. The organic layer was dried (MgSO$_4$), filtered, and concentrated to dryness under reduced pressure to provide the compound of formula RK as a solid (yield 95%).

The identity of the compound of formula RK, benzyl 1-(4-(2-(tert-butoxycarbonylamino)phenylamino)piperidin-1-yl) cyclooctanecarboxylate, was confirmed using $^1$H NMR.

Compound RK: $^1$H NMR: $\delta_H$ (400 MHz, CDCl$_3$): 7.46-7.37 (5H, m), 7.07 (2H, dd, J=12.51 Hz, 6.13 Hz), 6.78-6.71 (2H, m), 6.10 (1H, s), 5.16 (3H, s), 3.58 (1H, dd, J=9.65 Hz, 4.95 Hz), 3.19-2.90 (4H, m), 2.41-1.34 (18H, m), 2.41 (9H, s).

To a mixture of the compound of formula RK (0.79 mmol) in CH$_2$Cl$_2$ (10 mL) at 0° C. was added dropwise over 10 min methyl 2-chloro-2-oxoacetate (0.79 mmol) in CH$_2$Cl$_2$ (3 mL). The resulting reaction mixture was stirred at 0° C. for 30 min. After quenching with saturated NaHCO$_3$ solution, the mixture was extracted three times with CHCl$_3$. Thereafter, the organic layer was dried (MgSO$_4$) and concentrated under reduced pressure. At a temperature of about 25° C., the resulting residue was mixed with ethanol (4 mL) and the mixture was then added to sodium methoxide (1.09 mmol). The reaction mixture was stirred at 70° C. for 1 h. After concentration under reduced pressure, to the resulting residue was added water (0.5 mL) and 2N HCl (1 mL). The resulting precipitate was filtered, washed with 90%:10% water:MeOH, and dried under reduced pressure at 60° C. for 12 h to provide the compound of formula RL as a solid (yield>98%).

The identity of the compound of formula RL, benzyl 1-(4-(N-(2-(tert-butoxycarbonylamino)phenyl)-2-methoxy-2-oxoacetamido)piperidin-1-yl)cyclooctanecarboxylate, was confirmed using $^1$H NMR.

Compound RL: $^1$H NMR: $\delta_H$ (400 MHz, CDCl$_3$): 7.98 (1H, d, J=5.1 Hz), 7.42-7.32 (5H, m), 7.06-7.04 (2H, m), 6.68 (1H, s), 5.10 (2H, s), 4.35 (1H, m), 3.49 (3H, s), 3.02 (2H, t, J=10.8 Hz), 2.90 (1H, t, J=6.0 Hz), 2.35 (1H, t, J=6.0 Hz), 2.24 (2H, t, J=12.0 Hz), 1.87-1.78 (6H, m), 1.51-1.27 (19H, m).

To the compound of formula RL (553 mg, 0.89 mmol) was added 4N HCl in EtOAc (5.5 mL) at 0° C. Thereafter, the reaction mixture was stirred for 30 min at a temperature of about 25° C. A white precipitate formed. Saturated aqueous NaHCO$_3$ (pH>8) was added and the reaction mixture was stirred for 30 min at a temperature of about 25° C. Thereafter, the mixture was extracted twice with CHCl$_3$ (50 mL for each extraction). The organic layers were combined, washed with water, dried (MgSO$_4$), and concentrated under reduced pressure to provide a colorless amorphous solid. The solid was recrystallized from a mixture of diethyl ether and iso-propyl ether to provide 333 mg of Heterocyclic-Substituted Piperidine Compound 88 as a white powder (yield 76%).

5.32 Example 32

In Vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) were prepared by lysing cells in ice-cold hypotonic buffer (2.5 mM $MgCl_2$, 50 mM HEPES, pH 7.4) (10mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3mg/mL. Protein concentrations were determined using the BioRad protein assay reagent with bovine serum albumen as standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 μg membrane protein in a final volume of 500 μL binding buffer (10 mM $MgCl_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma). Harvesting was performed using a 96-well tissue harvester (Packard) followed by three filtration washes with 500 μL ice-cold binding buffer. Filter plates were subsequently dried at 50° C. for 2-3 hours. Fifty μL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data: Typically, the Heterocyclic-Substituted Piperidine Compounds will have a $K_i$, (nM) of about 300 or less for binding to ORL-1 receptors. In one embodiment, the Heterocyclic-Substituted Piperidine Compounds will have a $K_i$, (nM) of about 100 or less. In another embodiment, the Heterocyclic-Substituted Piperidine Compounds of the invention will have a $K_i$, (nM) of about 35 or less. In another embodiment, the Heterocyclic-Substituted Piperidine Compounds of the invention will have a $K_i$, (nM) of about 20 or less. In another embodiment, the Heterocyclic-Substituted Piperidine Compounds of the invention will have a $K_i$, (nM) of about 15 or less. In another embodiment, the Heterocyclic-Substituted Piperidine Compounds of the invention will have a $K_i$, (nM) of about 10 or less. In another embodiment, the Heterocyclic-Substituted Piperidine Compounds of the invention will have a $K_i$, (nM) of about 4 or less. In another embodiment, the Heterocyclic-Substituted Piperidine Compounds of the invention will have a $K_i$, (nM) of about 1 or less. In another embodiment, the Heterocyclic-Substituted Piperidine Compounds of the invention will have a $K_i$, (nM) of about 0.4 or less. In another embodiment, the Heterocyclic-Substituted Piperidine Compounds of the invention will have a $K_i$, (nM) of about 0.1 or less.

5.33 Example 33

In Vitro ORL-1 Receptor Functional Assay

ORL-1 Receptor [$^{35}$S]GTPγS Binding Assay Procedures: Membranes from recombinant HEK-293 cells expressing the human opioid receptor-like (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 μg/μL ORL-1 membrane protein, 10 μg/mL saponin, 3 μM GDP and 0.20 nM [35S] GTPγS to binding buffer (100 mM NaCl, 10 mM $MgCl_2$, 20 mM HEPES, pH 7.4) on ice. The prepared membrane solution (190 μL/well) was transferred to 96-shallow well polypropylene plates containing 10 μL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 2-3 hours. Fifty μL/well scintillation cocktail (BetaScint;Wallac) was added and plates were counted in Packard Top-Count for 1 min/well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. Heterocyclic-Substituted Piperidine Compounds typically will have an ORL-1 GTP $EC_{50}$ (nM) of about 5000 or less to stimulate ORL-1 receptor function. In one embodiment, the Heterocyclic-Substituted Piperidine Compounds of the invention will have an ORL-1 GTP $EC_{50}$ (nM) of about 1000 or less. In another embodiment, the Heterocyclic-Substituted Piperidine Compounds of the invention will have an ORL-1 GTP $EC_{50}$ (nM) of about 100 or less. In another embodiment, the Heterocyclic-Substituted Piperidine Compounds of the invention will have an ORL-1 GTP $EC_{50}$ (nM) of about 80 or less. In another embodiment, the Heterocyclic-Substituted Piperidine Compounds of the invention will have an ORL-1 GTP $EC_{50}$ (nM) of about 50 or less. In another embodiment, the Heterocyclic-Substituted Piperidine Compounds of the invention will have an ORL-1 GTP $EC_{50}$ (nM) of about 35 or less. In another embodiment, the Heterocyclic-Substituted Piperidine Compounds of the invention will have an ORL-1 GTP $EC_{50}$ (nM) of about 15 or less. In another embodiment, the Heterocyclic-Substituted Piperidine Compounds of the invention will have an ORL-1 GTP $EC_{50}$ (nM) of about 10 or less. In another embodiment, the Heterocyclic-Substituted Piperidine Compounds will have an ORL-1 GTP $EC_{50}$ (nM) of about 4 or less. In another embodiment, the Heterocyclic-Substituted Piperidine Compounds will have an ORL-1 GTP $EC_{50}$ (nM) of about 1 or less. In another embodiment, the Heterocyclic-Substituted Piperidine Compounds will have an ORL-1 GTP $EC_{50}$ (nM) of about 0.4 or less. In another embodiment, the Heterocyclic-Substituted Piperidine Compounds will have an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. Typically, the Heterocyclic-Substituted Piperidine Compounds of the invention will have an ORL-1 GTP Emax (%) of greater than about 50%. In one embodiment, the Heterocyclic-Substituted Piperidine Compounds will have an ORL-1 GTP Emax (%) of greater than about 75%. In another embodiment, the Heterocyclic-Substituted Piperidine Compounds will have an ORL-1 GTP Emax (%) of greater than about 85%. In another embodiment, the Heterocyclic-Substituted Piperidine Compounds will have an ORL-1 GTP Emax (%) of greater than about 95%. In another embodiment, the Heterocyclic-Substituted Piperidine Compounds will have an ORL-1 GTP Emax (%) of about 100% or greater. In another embodiment, the Heterocyclic-Substituted Piperidine Compounds will have an ORL-1 GTP Emax (%) of about 110% or greater.

5.34 Example 34

In Vitro μ-Opioid Receptor Binding Assays

μ-Opioid Receptor Binding Assay Procedures: Radioligand dose-displacement binding assays for μ-opioid receptors used 0.2 nM[$^3$H]-diprenorphine (NEN, Boston, Mass.), with 5-20mg membrane protein/well in a final volume of 500 μL binding buffer (10 mM MgCl$_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 h at about 25° C. Binding reactions were terminated by rapid filtration onto 96-well Unifilter GF/C filter plates (Packard, Meriden, Conn.) presoaked in 0.5% polyethylemimine using a 96-well tissue harvester (Brandel, Gaithersburg, Md.) followed by performing three filtration washes with 500 μl of ice-cold binding buffer. Filter plates were subsequently dried at 50° C. for 2-3 hours. BetaScint scintillation cocktail (Wallac, Turku, Finland) was added (50 μL/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

μ-Opioid Receptor Binding Data: Generally, the lower the $K_i$, value, the more effective the Heterocyclic-Substituted Piperidine Compounds will be at treating pain or diarrhea. Typically, the Heterocyclic-Substituted Piperidine Compounds will have a $K_i$ (nM) of about 3000 or less for binding to μ-opioid receptors. In one embodiment, the Heterocyclic-Substituted Piperidine Compounds will have a $K_i$ (nM) of about 1000 or less. In another embodiment, the Heterocyclic-Substituted Piperidine Compounds of the invention will have a $K_i$ (nM) of about 650 or less. In another embodiment, the Heterocyclic-Substituted Piperidine Compounds of the invention will have a $K_i$ (nM) of about 525 or less. In another embodiment, the Heterocyclic-Substituted Piperidine Compounds of the invention will have a $K_i$ (nM) of about 250 or less. In another embodiment, the Heterocyclic-Substituted Piperidine Compounds of the invention will have a (nM) of about 100 or less. In another embodiment, the Heterocyclic-Substituted Piperidine Compounds of the invention will have a $K_i$ (nM) of about 10 or less. In another embodiment, the Heterocyclic-Substituted Piperidine Compounds of the invention will have a $K_i$(nM) of about 1 or less. In another embodiment, the Heterocyclic-Substituted Piperidine Compounds of the invention will have a $K_i$ (nM) of about 0.1 or less.

5.35 Example 35

In Vitro μ-Opioid Receptor Functional Assays

μ-Opioid Receptor Functional Assay Procedures: [$^{35}$S]GTPγS functional assays were conducted using freshly thawed μ-receptor membranes. Assay reactions were prepared by sequentially adding the following reagents to binding buffer (100 mM NaCl, 10mM MgCl$_2$, 20 mM HEPES, pH 7.4) on ice (final condentrations indicated): membrane protein (0.026 mg/mL), saponin (10 mg/mL), GDP (3 mM) and [$^{35}$S]GTPγS (0.20 nM; NEN). The prepared membrane solution (190 μL/well) was transferred to 96-shallow well polypropylene plates containing 10 μL of 20× concentrated stock solutions of the agonist DAMGO ([D-Ala2, N-methyl-Phe4 Gly-o15]-enkephalin) prepared in dimethyl sulfoxide (DMSO). Plates were incubated for 30 min at about 25° C. with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 μL of ice-cold wash buffer (10 mM NaH$_2$PO$_4$, 10 mM Na$_2$HPO$_4$, pH 7.4). Filter plates were subsequently dried at 50° C. for 2-3 h. BetaScint scintillation cocktail (Wallac, Turku, Finland) was added (50 μL/ well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data: μ GTP EC$_{50}$ is the concentration of a compound providing 50% of the maximal response for the compound at a μ-opioid receptor. Heterocyclic-Substituted Piperidine Compounds typically will have a μ GTP EC$_{50}$ (nM) of about 5000 or less to stimulate μ-opioid receptor function. In one embodiment, the Heterocyclic-Substituted Piperidine Compounds of the invention will have a μ GTP EC$_{50}$ (nM) of about 4100 or less. In another embodiment, the Heterocyclic-Substituted Piperidine Compounds of the invention will have a μ GTP EC$_{50}$ (nM) of about 3100 or less. In another embodiment, the Heterocyclic-Substituted Piperidine Compounds of the invention will have a μ GTP EC$_{50}$ (nM) of about 2000 or less. In another embodiment, the Heterocyclic-Substituted Piperidine Compounds of the invention will have a μ GTP EC$_{50}$ (nM) of about 1000 or less. In another embodiment, the Heterocyclic-Substituted Piperidine Compounds of the invention will have a μ GTP EC$_{50}$ (nM) of about 100 or less. In another embodiment, the Heterocyclic-Substituted Piperidine Compounds of the invention will have a μ GTP EC$_{50}$ (nM) of about 10 or less. In another embodiment, the Heterocyclic-Substituted Piperidine Compounds will have a μ GTP EC$_{50}$ (nM) of about 1 or less. In another embodiment, the Heterocyclic-Substituted Piperidine Compounds will have a μ GTP EC$_{50}$ (nM) of about 0.4 or less. In another embodiment, the Heterocyclic-Substituted Piperidine Compounds will have a μ GTP EC$_{50}$ (nM) of about 0.1 or less.

μ GTP Emax (%) is the maximal effect elicited by a compound relative to the effect elicited by DAMGO, a standard μ agonist. Generally, the μ GTP Emax (%) value measures the efficacy of a compound to treat or prevent a Condition such as pain or diarrhea. Typically, the Heterocyclic-Substituted Piperidine Compounds of the invention will have a μ GTP Emax (%) of greater than about 10%. In one embodiment, the Heterocyclic-Substituted Piperidine Compounds will have a μ GTP Emax (%) of greater than about 20%. In another embodiment, the Heterocyclic-Substituted Piperidine Compounds will have a μ GTP Emax (%) of greater than about 50%. In another embodiment, the Heterocyclic-Substituted Piperidine Compounds will have a μ GTP Emax (%) of greater than about 65%. In another embodiment, the Heterocyclic-Substituted Piperidine Compounds will have a μ GTP Emax (%) of greater than about 75%. In another embodiment, the Heterocyclic-Substituted Piperidine Compounds will have a μ GTP Emax (%) of greater than about 88%. In another embodiment, the Heterocyclic-Substituted Piperidine Compounds will have a μ GTP Emax (%) of about 100% or greater.

5.36 Example 36

In Vitro κ-Opioid Receptor Binding Assays

κ-Opioid Receptor Binding Assay Procedures: Membranes from recombinant HEK-293 cells expressing the human kappa opioid receptor (kappa) (cloned in house) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/mL. Protein concentrations were determined using the BioRad protein assay reagent with bovine serum albumen as a standard. Aliquots of kappa receptor membranes were stored at −80 °C.

Radioligand dose displacement assays used 0.4-0.8 nM [$^3$H]-U69,593 (NEN; 40 Ci/mmole) with 10-20 μg membrane protein (recombinant kappa opioid receptor expressed in HEK 293 cells; in-house prep) in a final volume of 200 μL binding buffer (5% DMSO, 50 mM Trizma base, pH 7.4). Non-specific binding was determined in the presence of 10 μM unlabeled naloxone or U69,593. All reactions were performed in 96-well polypropylene plates for 1 h at a temperature of about 25° C. Binding reactions were determined by rapid filtration onto 96-well Unifilter GF/C filter plates (Packard) presoaked in 0.5% polyethylenimine (Sigma). Harvesting was performed using a 96-well tissue harvester (Packard) followed by five filtration washes with 200 4, ice-cold binding buffer. Filter plates were subsequently dried at 50° C. for 1-2 hours. Fifty μL/well scintillation cocktail (MicroScint20, Packard) was added and plates were counted in a Packard Top-Count for 1 min/well.

κ-Opioid Receptor Binding Data: Typically, the Heterocyclic-Substituted Piperidine Compounds will have a Ki (nM) of about 10,000 or less for κ receptors. In one embodiment, the Heterocyclic-Substituted Piperidine Compounds will have a Ki (nM) of about 5000 or less. In another embodiment, the Heterocyclic-Substituted Piperidine Compounds will have a Ki (nM) of about 1000 or less. In another embodiment, the Heterocyclic-Substituted Piperidine Compounds will have a Ki (nM) of about 500 or less. In another embodiment, the Heterocyclic-Substituted Piperidine Compounds will have a Ki (nM) of about 300 or less. In another embodiment, the Heterocyclic-Substituted Piperidine Compounds will have a Ki (nM) of about 200 or less. In another embodiment, the Heterocyclic-Substituted Piperidine Compounds will have a Ki (nM) of about 100 or less. In another embodiment, the Heterocyclic-Substituted Piperidine Compounds will have a Ki (nM) of about 50 or less. In another embodiment, the Heterocyclic-Substituted Piperidine Compounds will have a Ki (nM) of about 20 or less. In another embodiment, the Heterocyclic-Substituted Piperidine Compounds will have a Ki (nM) of about 15 or less. In another embodiment, the Heterocyclic-Substituted Piperidine Compounds will have a Ki (nM) of about 10 or less.

5.37 Example 37

In Vitro κ-Opioid Receptor Functional Assays

κ-Opioid Receptor Functional Assay Procedures: Functional [$^{35}$S]GTPγS binding assays were conducted as follows. Kappa opioid receptor membrane solution was prepared by sequentially adding final concentrations of 0.026 μg/μL kappa membrane protein (in-house), 10 μg/mL saponin, 3 μM GDP and 0.20 nM [$^{35}$S]GTPγS to binding buffer (100mM NaCl, 10mM $MgCl_2$, 20mM HEPES, pH 7.4) on ice. The prepared membrane solution (190μL/well) was transferred to 96-shallow well polypropylene plates containing 10 μL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 2-3 hours. Fifty μL/well scintillation cocktail (MicroScint20, Packard) was added and plates were counted in a Packard Top-Count for 1 min/well.

κ-Opioid Receptor Functional Data: κ GTP $EC_{50}$ is the concentration of a compound providing 50% of the maximal response for the compound at a κ receptor. Heterocyclic-Substituted Piperidine Compounds typically will have a κ GTP $EC_{50}$ (nM) of about 10,000 or less to stimulate κ opioid receptor function. In one embodiment, the Heterocyclic-Substituted Piperidine Compounds will have a κ GTP $EC_{50}$ (nM) of about 5000 or less. In another embodiment, the Heterocyclic-Substituted Piperidine Compounds will have a κ GTP $EC_{50}$ (nM) of about 2000 or less. In another embodiment, the Heterocyclic-Substituted Piperidine Compounds will have a κ GTP $EC_{50}$ (nM) of about 1500 or less. In another embodiment, the Heterocyclic-Substituted Piperidine Compounds will have a κ GTP $EC_{50}$ (nM) of about 800 or less. In another embodiment, the Heterocyclic-Substituted Piperidine Compounds will have a κ GTP $EC_{50}$ (nM) of about 500 or less. In another embodiment, the Heterocyclic-Substituted Piperidine Compounds will have a κ GTP $EC_{50}$ (nM) of about 300 or less. In another embodiment, the Heterocyclic-Substituted Piperidine Compounds will have a κ GTP $EC_{50}$ (nM) of about 100 or less. In another embodiment, the Heterocyclic-Substituted Piperidine Compounds will have a κ GTP $EC_{50}$ (nM) of about 50 or less. In another embodiment, the Heterocyclic-Substituted Piperidine Compounds will have a κ GTP $EC_{50}$ (nM) of about 25 or less. In another embodiment, the Heterocyclic-Substituted Piperidine Compounds will have a κ GTP $EC_{50}$ (nM) of about 10 or less.

κ GTP Emax (%) is the maximal effect elicited by a compound relative to the effect elicited by U69,593. Typically, the Heterocyclic-Substituted Piperidine Compounds of the invention have a κ GTP Emax (%) of greater than about 15%. In one embodiment, the Heterocyclic-Substituted Piperidine Compounds have a κ GTP Emax (%) of greater than about 30%. In another embodiment, the Heterocyclic-Substituted Piperidine Compounds have a κ GTP Emax (%) of greater than about 40%. In another embodiment, the Heterocyclic-Substituted Piperidine Compounds have a κ GTP Emax (%) of greater than about 45%. In another embodiment, the Heterocyclic-Substituted Piperidine Compounds have a κ GTP Emax (%) of greater than about 55%. In another embodiment, the Heterocyclic-Substituted Piperidine Compounds have a κ

GIP Emax (%) of greater than about 75%. In another embodiment, the Heterocyclic-Substituted Piperidine Compounds have a κ GTP Emax (%) of greater than about 90%. In another embodiment, the Heterocyclic-Substituted Piperidine Compounds have a κ GTP Emax (%) of about 100% or greater.

5.38 Example 38

In Vitro δ-Opioid Receptor Binding Assays

δ-Receptor Binding Assay Procedures: Radioligand dose-displacement assays used 0.2 nM [$^3$H]-Naltrindole (NEN; 33.0 Ci/mmole) with 10-20 μg membrane protein (recombinant delta opioid receptor expressend in CHO-K1 cells; Perkin Elmer) in a final volume of 5004 binding buffer (5 mM MgCl$_2$, 5% DMSO, 50 mM Trizma base, pH 7.4). Non-specific binding was determined in the presence of 25μm M unlabeled naloxone. All reactions were performed in 96-deep well polypropylene plates for 1 h at a temperature of about 25° C. Binding reactions were determined by rapid filtration onto 96-well Unifilter GF/C filter plates (Packard) presoaked in 0.5% polyethylenimine (Sigma). Harvesting was performed using a 96-well tissue harvester (Packard) followed by five filtration washes with 500 μL ice-cold binding buffer. Filter plates were subsequently dried at 50° C. for 1-2 hours. Fifty μL/well scintillation cocktail (MicroScint20, Packard) was added and plates were counted in a Packard Top-Count for 1 min/well.

δ-Opioid Receptor Binding Data: Typically, the Heterocyclic-Substituted Piperidine Compounds will have a Ki (nM) of about 10,000 or less for δreceptors. In one embodiment, the Heterocyclic-Substituted Piperidine Compounds will have a Ki (nM) of about 9000 or less. In another embodiment, the Heterocyclic-Substituted Piperidine Compounds will have a Ki (nM) of about 7500 or less. In another embodiment, the Heterocyclic-Substituted Piperidine Compounds will have a Ki (nM) of about 6500 or less. In another embodiment, the Heterocyclic-Substituted Piperidine Compounds will have a Ki (nM) of about 5000 or less. In another embodiment, the Heterocyclic-Substituted Piperidine Compounds will have a Ki (nM) of about 3000 or less. In another embodiment, the Heterocyclic-Substituted Piperidine Compounds will have a Ki (nM) of about 2500 or less. In another embodiment, the Heterocyclic-Substituted Piperidine Compounds will have a Ki (nM) of about 1000 or less. In another embodiment, the Heterocyclic-Substituted Piperidine Compounds will have a Ki (nM) of about 500 or less. In another embodiment, the Heterocyclic-Substituted Piperidine Compounds will have a Ki (nM) of about 350 or less. In another embodiment, the Heterocyclic-Substituted Piperidine Compounds will have a Ki (nM) of about 250 or less. In another embodiment, the Heterocyclic-Substituted Piperidine Compounds will have a Ki (nM) of about 100 or less. In another embodiment, the Heterocyclic-Substituted Piperidine Compounds will have a Ki (nM) of about 10 or less.

5.39 Example 39

In Vitro δ-Opioid Receptor Functional Assays

δ-Opioid Receptor Functional Assay Procedures: Functional [$^{35}$S]GTPγS binding assays were conducted as follows. Delta opioid receptor membrane solution was prepared by sequentially adding final concentrations of 0.026 μg/μL delta membrane protein (Perkin Elmer), 10 μg/mL saponin, 3 μM GDP and 0.20 nM [$^{35}$S]GTPγS to binding buffer (100 mM NaCl, 10 mM MgCl$_2$, 20mM HEPES, pH 7.4) on ice. The prepared membrane solution (19 μL/well) was transferred to 96-shallow well polypropylene plates containing 10 μL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM NaH$_2$PO$_4$, 10 mM Na$_2$HPO$_4$, pH 7.4). Filter plates were subsequently dried at 50° C. for 1-2 hours. Fifty μL/well scintillation cocktail (MicroScint20, Packard) was added and plates were counted in a Packard Top-count for 1 min/well.

δ-Opioid Receptor Functional Data: δ GTP EC$_{50}$ is the concentration of a compound providing 50% of the maximal response for the compound at a δ receptor. Heterocyclic-Substituted Piperidine Compounds typically will have a δ GTP EC$_{50}$ (nM) of about 10,000 or less to stimulate δ opioid receptor function. In one embodiment, the Heterocyclic-Substituted Piperidine Compounds will have a δ GTP EC$_{50}$ (nM) of about 3500 or less. In another embodiment, the Heterocyclic-Substituted Piperidine Compounds will have a μ GTP EC$_{50}$ (nM) of about 1000 or less. In another embodiment, the Heterocyclic-Substituted Piperidine Compounds will have a μ GTP EC$_{50}$ (nM) of about 500 or less. In another embodiment, the Heterocyclic-Substituted Piperidine Compounds will have a μ GTP EC$_{50}$ (nM) of about 100 or less. In another embodiment, the Heterocyclic-Substituted Piperidine Compounds will have a μ GTP EC$_{50}$ (nM) of about 90 or less. In another embodiment, the Heterocyclic-Substituted Piperidine Compounds will have a μ GTP EC$_{50}$ (nM) of about 50 or less. In another embodiment, the Heterocyclic-Substituted Piperidine Compounds will have a μ GTP EC$_{50}$ (nM) of about 25 or less. In another embodiment, the Heterocyclic-Substituted Piperidine Compounds will have a μ GTP EC$_{50}$ (nM) of about 10 or less.

δ GTP Emax (%) is the maximal effect elicited by a compound relative to the effect elicited by met-enkephalin. Typically, the Heterocyclic-Substituted Piperidine Compounds of the invention will have a δ GTP Emax (%) of greater than about 10%. In one embodiment, the Heterocyclic-Substituted Piperidine Compounds will have a δ GTP Emax (%) of greater than about 30%. In another embodiment, the Heterocyclic-Substituted Piperidine Compounds will have a δ GTP Emax (%) of greater than about 50%. In another embodiment, the Heterocyclic-Substituted Piperidine Compounds will have a δ GTP Emax (%) of greater than about 75%. In another embodiment, the Heterocyclic-Substituted Piperidine Compounds will have a δ GTP Emax (%) of greater than about 90%. In another embodiment, the Heterocyclic-Substituted Piperidine Compounds will have a δ GTP Emax (%) of about 100% or greater. In another embodiment, the Heterocyclic-Substituted Piperidine Compounds will have a δ GTP Emax (%) of about 110% or greater.

5.40 Example 40

Efficacy of Receptor Binding and Activity Response

The following Tables provide results on the efficacy of binding and activity response of several Heterocyclic-Substituted Piperidine Compounds to the ORL-1 receptor and, for certain Heterocyclic-Substituted Piperidine Compounds, the μ opioid receptor, the κ opioid receptor and/or the δ opioid receptor.

In Table 1, binding efficacy to the ORL-1 receptor was determined by the procedure in Example 32. Binding efficacy to the μ opioid receptor was determined by the procedure in Example 34. Binding efficacy to the κ opioid receptor was determined by the procedure in Example 36. Binding efficacy to the δ opioid receptor was determined by the procedure in Example 38.

In Table 2, activity response to the ORL-1 receptor was determined by the procedure in Example 33. Activity response to the μ opioid receptor was determined by the procedure in Example 35. Activity response to the κ opioid receptor was determined by the procedure in Example 37. Activity response to the δ opioid receptor can be determined by the procedure in Example 39.

TABLE 1

Efficacy of Receptor Binding of Heterocyclic-Substituted Piperidine Compounds

| Ref. No. | Compound | $K_i$ [Average ± Std Deviation] (nM) ORL-1 | Opioid Receptor μ | κ | Δ |
|---|---|---|---|---|---|
| 6 | | 65 ± 26 | 2200 ± 300 | 167 ± 6 | 2900 ± 235 |
| 18 | | 63.2 ± 2.5 | | | |
| 17 | | 11.5 ± 1.0 | 2500 ± 525 | | |

TABLE 1-continued

Efficacy of Receptor Binding of Heterocyclic-Substituted Piperidine Compounds

| Ref. No. | Compound | $K_i$ [Average ± Std Deviation] (nM) ORL-1 | μ | κ | Δ |
|---|---|---|---|---|---|
| 9 | | 22.8 ± 8.5 | 825 ± 30 | 880 ± 80 | 9600 ± 2600 |
| 12 | | 8.9 ± 0.2 | 1300 ± 2200 | 439 ± 6 | 4050 ± 400 |
| 24 | | 453 ± 32 | 3300 ± 715 | 6950 ± 1350 | 5450 ± 1400 |

TABLE 1-continued

Efficacy of Receptor Binding of Heterocyclic-Substituted Piperidine Compounds

| Ref. No. | Compound | $K_i$ [Average ± Std Deviation] (nM) | | | |
| --- | --- | --- | --- | --- | --- |
| | | ORL-1 | Opioid Receptor | | |
| | | | μ | κ | Δ |
| 5 | | 35.5 ± 7.5 | 13,700 ± 3800 | 355 ± 30 | 16,200 ± 3250 |
| 20 | | 229 ± 12 | | | |
| 16 | | 32.6 ± 1.6 | 3800 ± 1150 | | |

TABLE 1-continued
Efficacy of Receptor Binding of Heterocyclic-Substituted Piperidine Compounds
| Ref. No. | Compound | K$_i$ [Average ± Std Deviation] (nM) ORL-1 | μ | κ | Δ |
|---|---|---|---|---|---|
| 7 | 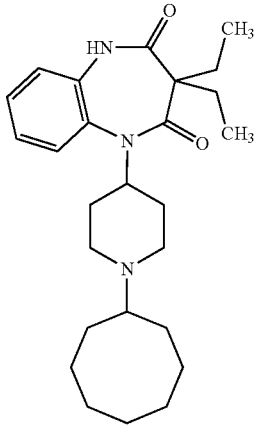 [SMILES: CCC1(CC)C(=O)Nc2ccccc2N(C2CCN(C3CCCCCCC3)CC2)C1=O] | 620 ± 56 | 6200 ± 1300 | | |
| 10 | 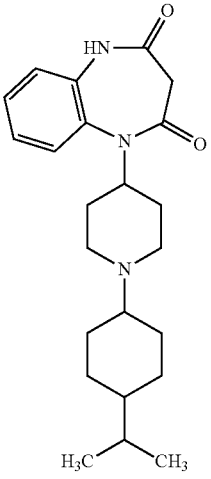 [SMILES: CC(C)C1CCC(N2CCC(N3C(=O)CC(=O)Nc4ccccc43)CC2)CC1] | 610 ± 65 | 2950 ± 325 | | |
| 11 | 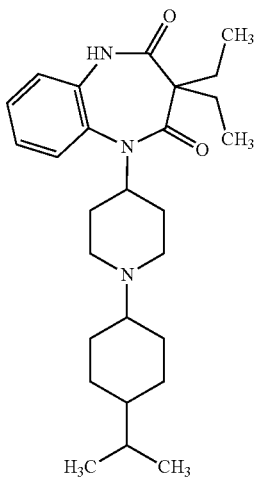 [SMILES: CCC1(CC)C(=O)Nc2ccccc2N(C2CCN(C3CCC(C(C)C)CC3)CC2)C1=O] | 1550 ± 285 | 5000 ± 375 | | |

TABLE 1-continued

Efficacy of Receptor Binding of Heterocyclic-Substituted Piperidine Compounds

| Ref. No. | Compound | $K_i$ [Average ± Std Deviation] (nM) | | | |
|---|---|---|---|---|---|
| | | ORL-1 | Opioid Receptor | | |
| | | | μ | κ | Δ |
| 85 | | 39930 | | | |
| 43 | | 291 ± 20 | >10$^6$ | | |
| 44 | | 52 ± 8 | 9540 ± 2122 | 4232 ± 739 | 65660 |

TABLE 1-continued

Efficacy of Receptor Binding of Heterocyclic-Substituted Piperidine Compounds

| Ref. No. | Compound | K_i [Average ± Std Deviation] (nM) | | | |
|---|---|---|---|---|---|
| | | ORL-1 | μ | κ | Δ |
| | | | Opioid Receptor | | |
| 29 | (structure) | 1526 ± 219 | | | |
| 66 | (structure) | 89 ± 22 | 17385 ± 2235 | 1317 ± 148 | 54760 |
| 47 | (structure) | 584 ± 104 | 28200 | 559 ± 75 | 52100 |

TABLE 1-continued
Efficacy of Receptor Binding of Heterocyclic-Substituted Piperidine Compounds
| Ref. No. | Compound | K$_i$ [Average ± Std Deviation] (nM) | | | |
|---|---|---|---|---|---|
| | | ORL-1 | Opioid Receptor | | |
| | | | μ | κ | Δ |
| 78 | 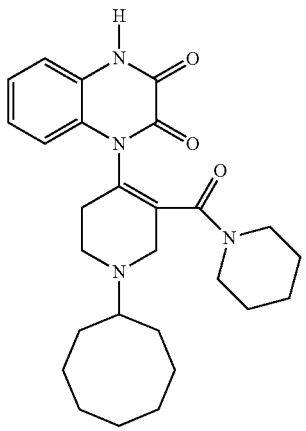 [SMILES: O=C(C1=C(n2c(=O)c(=O)[nH]c3ccccc32)CCN(C2CCCCCCC2)C1)N1CCCCC1] | 1762 ± 226 | | | |
| 79 | 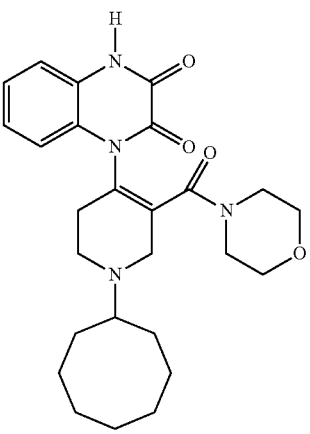 [SMILES: O=C(C1=C(n2c(=O)c(=O)[nH]c3ccccc32)CCN(C2CCCCCCC2)C1)N1CCOCC1] | 1965 ± 750 | | | |
| 56 | 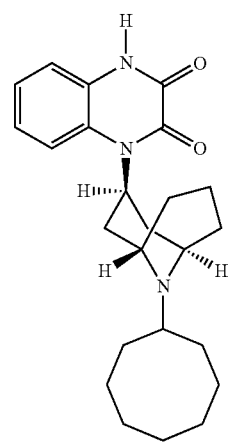 [SMILES: O=c1[nH]c2ccccc2n([C@H]2C[C@H]3CCC[C@@H](C2)N3C2CCCCCCC2)c1=O] | 4 ± 0.1 | 529 ± 127 | | 20800 |

TABLE 1-continued

Efficacy of Receptor Binding of Heterocyclic-Substituted Piperidine Compounds

| Ref. No. | Compound | $K_i$ [Average ± Std Deviation] (nM) | | | |
|---|---|---|---|---|---|
| | | ORL-1 | Opioid Receptor | | |
| | | | μ | κ | Δ |
| 57 | | 13 ± 4 | 769 ± 6 | 170 ± 21 | 21900 |
| 67 | | 51 ± 6 | 12380 | | 72400 |
| 86 | | >10$^6$ | | | |

TABLE 1-continued

Efficacy of Receptor Binding of Heterocyclic-Substituted Piperidine Compounds

| Ref. No. | Compound | K$_i$ [Average ± Std Deviation] (nM) | | | |
| --- | --- | --- | --- | --- | --- |
| | | ORL-1 | Opioid Receptor | | |
| | | | μ | κ | Δ |
| 60 | | 5.6 ± 0.4 | 1380 ± 515 | 119 ± 4 | 23400 |
| 61 | | 56 ± 6 | 15750 ± 1550 | 682 ± 106 | 22800 |
| 58 | | 173 ± 49 | 11930 ± 2620 | | |

TABLE 1-continued
Efficacy of Receptor Binding of Heterocyclic-Substituted Piperidine Compounds
| Ref. No. | Compound | $K_i$ [Average ± Std Deviation] (nM) | | | |
|---|---|---|---|---|---|
| | | ORL-1 | μ | κ | Δ |
| | | | Opioid Receptor | | |
| 81 | 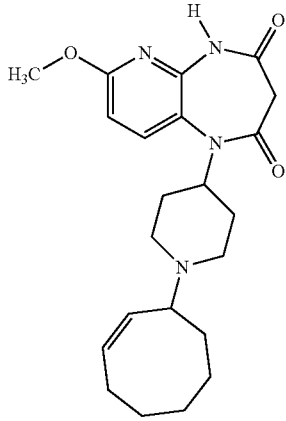 [SMILES: COc1ccc2c(n1)NC(=O)CC(=O)N2C1CCN(C2/C=C\CCCCC2)CC1] | 16500 ± 1550 | | | |
| 83 | 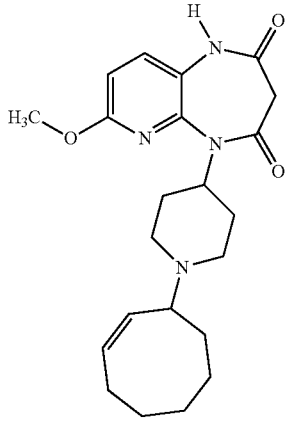 [SMILES: COc1ccc2c(n1)N(C1CCN(C3/C=C\CCCCC3)CC1)C(=O)CC(=O)N2] | 6010 ± 686 | | | |
| 87 | 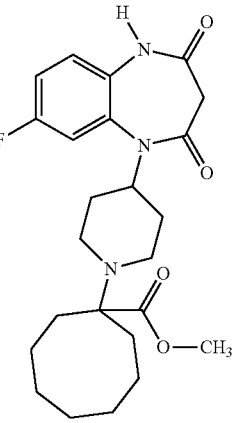 | 68 ± 6 | 11670 ± 1200 | | |

TABLE 1-continued

Efficacy of Receptor Binding of Heterocyclic-Substituted Piperidine Compounds

| Ref. No. | Compound | $K_i$ [Average ± Std Deviation] (nM) | | | |
|---|---|---|---|---|---|
| | | Opioid Receptor | | | |
| | | ORL-1 | μ | κ | Δ |
| 80 | | | 1777 ± 50 | | |

TABLE 2

Activity Response of Heterocyclic-Substituted Piperidine Compounds

| Ref. No. | Compound | GTP $EC_{50}$ (nM) | | | GTP Emax (%) | | |
|---|---|---|---|---|---|---|---|
| | | Opioid Receptor | | | Opioid Receptor | | |
| | | ORL-1 | μ | κ | ORL-1 | μ | κ |
| 6 | | 240 ± 115 | | 590 ± 180 | 87.3 ± 5.3 | | 13.7 ± 0.9 |

TABLE 2-continued

Activity Response of Heterocyclic-Substituted Piperidine Compounds

| Ref. No. | Compound | GTP EC$_{50}$ (nM) | | | GTP Emax (%) | | |
| --- | --- | --- | --- | --- | --- | --- | --- |
| | | | Opioid Receptor | | | Opioid Receptor | |
| | | ORL-1 | μ | κ | ORL-1 | μ | κ |
| 18 | (structure) | 183 ± 14.5 | | | 60.3 ± 4.6 | | |
| 17 | (structure) | 11.5 ± 1.0 | 2500 ± 525 | | 74 ± 16 | | |
| 9 | (structure) | 208 ± 8.6 | 3924 ± 13 | 4050 ± 670 | 68 ± 1.0 | 28.5 ± 2.6 | 22.5 ± 2.6 |

TABLE 2-continued

Activity Response of Heterocyclic-Substituted Piperidine Compounds

| Ref. No. | Compound | GTP EC$_{50}$ (nM) | | | GTP Emax (%) | | |
| --- | --- | --- | --- | --- | --- | --- | --- |
| | | | Opioid Receptor | | | Opioid Receptor | |
| | | ORL-1 | μ | κ | ORL-1 | μ | κ |
| 12 | | 31.9 ± 3.5 | 1640 ± 440 | 7000 ± 345 | 132 ± 8.5 | 66.0 ± 0.7 | 57.7 ± 4.3 |
| 24 | | 5250 ± 465 | | | 152 ± 18 | | |
| 5 | | 166 ± 34 | 1290 ± 220 | | 55.8 ± 3.8 | 114 ± 8.7 | |

TABLE 2-continued

Activity Response of Heterocyclic-Substituted Piperidine Compounds

| Ref. No. | Compound | GTP EC$_{50}$ (nM) | | | GTP Emax (%) | | |
|---|---|---|---|---|---|---|---|
| | | | Opioid Receptor | | | Opioid Receptor | |
| | | ORL-1 | μ | κ | ORL-1 | μ | κ |
| 20 | | 770 ± 43 | | | 39.3 ± 0.9 | | |
| 16 | | 153 ± 22 | | | 55.0 ± 4.2 | | |
| 7 | | 1300 ± 175 | | | 41.3 ± 9.8 | | |

TABLE 2-continued
Activity Response of Heterocyclic-Substituted Piperidine Compounds
| Ref. No. | Compound | GTP $EC_{50}$ (nM) | | | GTP Emax (%) | | |
|---|---|---|---|---|---|---|---|
| | | ORL-1 | μ (Opioid Receptor) | κ | ORL-1 | μ (Opioid Receptor) | κ |
| 10 | 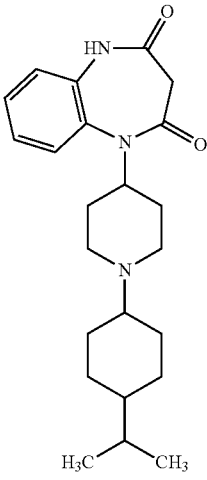 [SMILES: CC(C)C1CCC(N2CCC(N3C(=O)CC(=O)Nc4ccccc43)CC2)CC1] | 1400 ± 125 | | | 45.3 ± 1.8 | | |
| 43 | 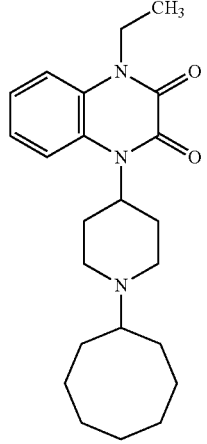 [SMILES: CCn1c(=O)c(=O)n(C2CCN(C3CCCCCCC3)CC2)c2ccccc21] | 450 ± 47 | | | 27 | | |
| 44 | 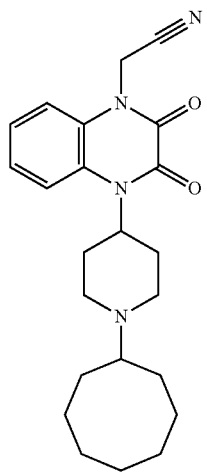 [SMILES: N#CCn1c(=O)c(=O)n(C2CCN(C3CCCCCCC3)CC2)c2ccccc21] | 141 ± 27 | | | 46 | | |

TABLE 2-continued

Activity Response of Heterocyclic-Substituted Piperidine Compounds

| Ref. No. | Compound | GTP EC$_{50}$ (nM) | | | GTP Emax (%) | | |
|---|---|---|---|---|---|---|---|
| | | | Opioid Receptor | | | Opioid Receptor | |
| | | ORL-1 | μ | κ | ORL-1 | μ | κ |
| 66 | | 202 ± 37 | | | 38 | | |
| 47 | | 7800 ± 1600 | 13992 ± 2370 | | 90 | 25 | |
| 56 | | 25 ± 7 | | | 44 | | |

TABLE 2-continued

Activity Response of Heterocyclic-Substituted Piperidine Compounds

| Ref. No. | Compound | GTP EC$_{50}$ (nM) | | | GTP Emax (%) | | |
|---|---|---|---|---|---|---|---|
| | | ORL-1 | μ (Opioid Receptor) | κ | ORL-1 | μ (Opioid Receptor) | κ |
| 57 | | 96 ± 23 | | 4800 ± 700 | 53 | | 28 |
| 67 | | 574 ± 39 | | | 40 | | |
| 60 | | 36 ± 19 | | 460 ± 70 | 62 | | 17 |

TABLE 2-continued

Activity Response of Heterocyclic-Substituted Piperidine Compounds

| Ref. No. | Compound | GTP EC$_{50}$ (nM) | | | GTP Emax (%) | | |
|---|---|---|---|---|---|---|---|
| | | | Opioid Receptor | | | Opioid Receptor | |
| | | ORL-1 | μ | κ | ORL-1 | μ | κ |
| 61 | | 830 ± 125 | | 6460 ± 500 | 82 | | 22 |
| 58 | | 168 ± 12 | | | 22 | | |
| 87 | | 1550 ± 140 | | | 135 | | |

5.41 Example 41

In Vivo Assays for Prevention or Treatment of Pain

Test Animals: Each experiment uses rats weighing between 200-260 g at the start of the experiment. The rats are group-housed and have free access to food and water at all times, except prior to oral administration of a Heterocyclic-Substituted Piperidine Compound when food is removed for 16 hours before dosing. A control group acts as a comparison to rats treated with a Heterocyclic-Substituted Piperidine Compound. The control group is administered the carrier for the Heterocyclic-Substituted Piperidine Compound. The volume of carrier administered to the control group is the same as the volume of carrier and Heterocyclic-Substituted Piperidine Compound administered to the test group.

Acute Pain: To assess the actions of a Heterocyclic-Substituted Piperidine Compound for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Heterocyclic-Substituted Piperidine Compound. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20 \text{ s pre-administration latency})} \times 100$$

The rat tail flick test is described in F.E. D'Amour et al., "A Method for Determining Loss of Pain Sensation," *J. Pharmacal. Exp. Ther.* 72:74-79 (1941).

Acute pain can also be assessed by measuring the animal's response to noxious mechanical stimuli by determining the paw withdrawal threshold ("PWT"), as described below.

Inflammatory Pain: To assess the actions of a Heterocyclic-Substituted Piperidine Compound for the treatment or prevention of inflammatory pain, the Freund's complete adjuvant ("FCA") model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10 or 30mg/kg of either a Heterocyclic-Substituted Piperidine Compound; 30 mg/kg of a control selected from Celebrex, indomethacin or naproxen; or carrier. Responses to noxious mechanical stimuli are then determined 1, 3, 5 and 24 hours post administration. Percentage reversal of hyperalgesia for each animal is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Heterocyclic-Substituted Piperidine Compound for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a 3/8 curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Heterocyclic-Substituted Piperidine Compound for the left rear paw of the animal. The animal can also be assessed for response to noxious thermal stimuli or for tactile allodynia, as described below. The Chung model for neuropathic pain is described in S.H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and either only the affected (ipsilateral) paw is tested, or both the ipsilateral and contralateral (non-injured) paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference for all purposes.

What is claimed is:

1. A compound of formula (III):

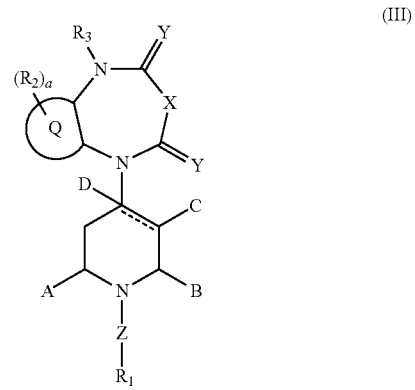

or a pharmaceutically acceptable salt thereof wherein:
Q is benzo;
each $R_2$ is independently:
(a) -halo, —CN, —NO$_2$, —OT$_3$, —C(O)T$_3$, —C(O)OT$_3$, —C(O)N(T$_1$)(T$_2$), —S(O)$_2$OH, —S(O)T$_3$, —S(O)$_2$T$_3$, —S(O)$_2$N(T$_1$)(T$_2$), —N(T$_1$)(T$_2$), —N(T$_3$)C(O)T$_3$, —N(T$_3$)C(O)N(T$_1$)(T$_2$), —N(T$_3$)S(O)$_2$T$_3$, or —N(T$_3$)S(O)$_2$N(T$_1$)(T$_2$); or
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2, or 3 independently selected R$_8$ groups; or
(c) -phenyl, -naphthalenyl, —(C$_{14}$)aryl, or -(5- or 6-membered)heteroaryl, each of which is unsubstituted or substituted with 1, 2, or 3 independently selected R$_7$ groups;
a is an integer selected from 0, 1, and 2;
R$_3$ is:
(a) —H; or
(b) —(C$_1$-C$_6$)alkyl, —(C$_2$-C$_6$)alkenyl, —(C$_2$-C$_6$)alkynyl, —O(C$_1$-C$_6$)alkyl, —O(C$_2$-C$_6$)alkenyl, —O(C$_2$-C$_6$)alkynyl, —(C$_3$-C$_7$)cycloalkyl, —(C$_3$-C$_7$)cycloalkenyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, or -(7- to 10-membered)bicycloheterocycle, each of which is unsubstituted or substituted with 1, 2, or 3 independently selected R$_8$ groups; or
(c) -phenyl, -naphthalenyl, —(C$_{14}$)aryl, or -(5- to 10-membered)heteroaryl, each of which is unsubstituted or substituted with 1, 2, or 3 independently selected R$_7$ groups; or
(d) —(C$_1$-C$_6$)alkyl(=O)W$_1$, —(C$_1$-C$_6$)alkyl(=NH)W$_1$, —C(O)OV$_1$, —C(O)N(V$_1$)$_2$, —S(O)$_2$N(V$_1$)$_2$, or —S(O)$_2$(C$_1$-C$_6$)alkyl; or
(e) —(C$_1$-C$_4$)alkyl substituted with 1, 2, or 3 substituents independently selected from —(C$_3$-C$_7$)cycloalkyl, —(C$_3$-C$_7$)cycloalkenyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, -(7- to 10-membered)bicycloheterocycle, -phenyl, -naphthalenyl, —($C_{14}$)aryl, or -(5- to 10-membered)heteroaryl; or (f) —($C_1$-$C_3$)alkyl substituted with a substituent selected from —N($R_6$)$_2$, —S(O)$_2$N($V_1$)$_2$, —N($R_9$)C(O)$W_1$, —N($R_9$)S(O)$_2$$W_1$, and —C(O)N($V_1$)$_2$;

each Y is independently selected from O and S;

X is —C($R_4$)($R_5$)—;

$R_4$ is selected from —H, —O$R_6$, —($C_1$-$C_6$)alkyl, and —($C_3$-$C_7$)cycloalkyl; or, independently, $R_4$ and $R_5$ together can form an oxo group;

$R_5$ is selected from —H, —($C_1$-$C_6$)alkyl, and —($C_3$-$C_7$)cycloalkyl;

A and B are independently selected from:

(a) —H, —CN, —C(O)O$T_3$, —C(O)N($T_1$)($T_2$), —($C_3$-$C_{12}$)cycloalkyl, —($C_3$-$C_{12}$)cycloalkoxy, —($C_1$-$C_6$)alkyl, —($C_2$-$C_6$)alkenyl, —($C_2$-$C_6$)alkynyl, and —($C_1$-$C_6$)alkoxy, each of which —($C_3$-$C_{12}$)cycloalkyl, —($C_3$-$C_{12}$)cycloalkoxy, —($C_1$-$C_6$)alkyl, —($C_2$-$C_6$)alkenyl, and —($C_2$-$C_6$)alkynyl is unsubstituted or substituted with 1 or 2 substituents independently selected from —OH, —S(O)$_2$NH$_2$, —N($R_6$)$_2$, =N$R_6$, —C(O)O$T_3$, —C(O)N($R_6$)$_2$, —N($R_6$)C(O)$R_9$, and -(5- or 6-membered)heterocycle or 1, 2, or 3 independently selected -halo; or (b) A-B together form a ($C_2$-$C_6$)bridge, which is unsubstituted or substituted with 1, 2, or 3 independently selected $R_8$ groups, and which bridge optionally contains —HC=CH— within the ($C_2$-$C_6$)bridge; wherein the heterocyclic ring that is fused to the Q group can be in the endo- or exo-conformation with respect to the A-B bridge; or (c) A-B together form a —CH$_2$—N($R_a$)—CH$_2$— bridge, a

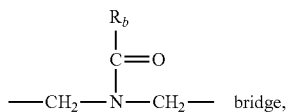

or a

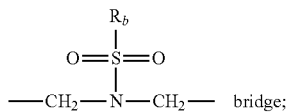

wherein the heterocyclic ring that is fused to the Q group can be in the endo- or exo-conformation with respect to the A-B bridge;

$R_a$ is selected from —H, —($C_1$-$C_6$)alkyl, —($C_3$-$C_7$)cycloalkyl, —CH$_2$—C(O)—$R_c$, —(CH$_2$)—C(O)—O$R_c$, —(CH$_2$)—C(O)—N($R_c$)$_2$, —(CH$_2$)$_2$—O—$R_c$, —(CH$_2$)$_2$—S(O)$_2$—N($R_c$)$_2$, $R_c$, and —(CH$_2$)$_2$—N($R_c$)S(O)$_2$—$R_c$;

$R_b$ is selected from:

(a) —H, —($C_1$-$C_6$)alkyl, —($C_3$-$C_7$)cycloalkyl, -(3- to 7-membered)heterocycle, —N($R_c$)$_2$, —N($R_c$)—($C_3$-$C_7$)cycloalkyl, and —N($R_c$) -(3- to 7-membered)heterocycle; and (b) -phenyl, -naphthalenyl, and -(5- or 6-membered)heteroaryl, each of which is unsubstituted or substituted with 1, 2, or 3 independently selected $R_7$ groups; and (c) —N($R_c$)-phenyl, —N($R_c$)-naphthalenyl, —N($R_c$)—($C_{14}$)aryl, and —N($R_c$) -(5- to 10-membered)heteroaryl, each of which is unsubstituted or substituted with 1, 2, or 3 independently selected $R_7$ groups;

each $R_c$ is independently selected from —H and —($C_1$-$C_4$)alkyl;

C is selected from —H, -halo, —CN, —O$T_3$, —C(O)O$T_3$, —C(O)N($T_1$) ($T_2$), —($C_3$-$C_{12}$)cycloalkyl, —($C_3$-$C_{12}$)cycloalkoxy, —N($R_6$)$_2$, —N($R_6$)C(O)$R_9$, —N$R_6$SO$_2$N($R_6$)$_2$, —N$R_6$—C(=N$R_6$)N($R_6$)$_2$, —($C_1$-$C_6$)alkyl, —($C_2$-$C_6$)alkenyl, and —($C_2$-$C_6$)alkynyl, each of which —($C_1$-$C_6$)alkyl, —($C_2$-$C_6$)alkenyl, and —($C_2$-$C_6$)alkynyl is unsubstituted or substituted with 1 or 2 substituents independently selected from —OH, —S(O)$_2$NH$_2$, —N($R_6$)$_2$, =N$R_6$, —C(O)O$T_3$, —C(O)N($R_6$)$_2$, —N($R_6$)C(O)$R_9$, and -(5- or 6-membered)heterocycle or from 1, 2, or 3 independently selected -halo;

the dashed line in the piperidine or bridged piperidine central ring denotes the presence or absence of a bond, and when the dashed line denotes the presence of a bond then D is absent, otherwise D is:

(a) —H, —CN, —C(O)O$T_3$, or —C(O)N($T_1$)($T_2$); or (b) —($C_1$-$C_{10}$)alkyl which is unsubstituted or substituted with 1, 2, or 3 independently selected $R_8$ groups and, optionally, in which any D group carbon atom except the carbon atom bonded directly to the piperidine or bridged piperidine central ring, is independently replaced by O or S; or (c) -phenyl, -naphthalenyl, or -(5- or 6-membered)heteroaryl, each of which is unsubstituted or substituted with 1, 2, or 3 independently selected $R_7$ groups;

Z is —[($C_1$-$C_{10}$)alkyl optionally substituted by $R_1$]$_h$—, wherein h is 0 or 1; or —($C_1$-$C_{10}$)alkyl-N$R_6$C(=Y)—;

$R_1$ is:

(a) —H, -halo, —CN, —OH, —CH$_2$OH, —CH$_2$CH$_2$OH, —NO$_2$, —N($R_6$)$_2$, —S(O)NH$_2$, —S(O)$_2$NH$_2$, —C(O)O$V_1$, or —C(O)CN; or (b) —($C_1$-$C_6$)alkyl, —($C_2$-$C_6$)alkenyl, —($C_2$-$C_6$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyk —($C_8$-$C_{20}$)tricycloalkenyl, -(3- to 7-membered)heterocycle, or -(7- to 10-membered)bicycloheterocycle, each of which is unsubstituted or substituted with an $R_8$ group; or (c)

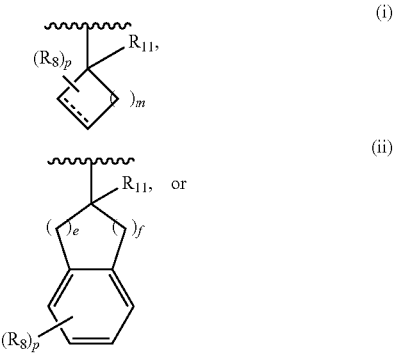

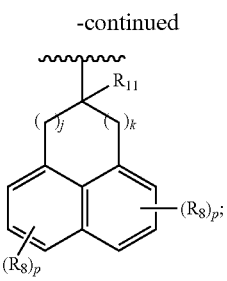

or (d) -phenyl, -naphthalenyl, —($C_{14}$)aryl, or -(5- to 10-membered)heteroaryl, each of which is unsubstituted or substituted with an $R_7$ group; or —Z—$R_1$ is 3,3-diphenylpropyl- optionally substituted at the 3 carbon of the propyl with —CN, —C(O)N($R_6$)$_2$, —C(O)O$V_1$, or -tetrazolyl; or —Z—$R_1$ is —($C_1$-$C_4$)alkyl substituted with tetrazolyl;

each $R_6$ is independently selected from —H, —($C_1$-$C_6$) alkyl, and —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_7$ is independently selected from —($C_1$-$C_4$)alkyl, —($C_2$-$C_6$)alkenyl, —($C_2$-$C_6$)alkynyl, —O$R_9$, —S$R_9$, —C(halo)$_3$, —CH(halo)$_2$, —CH$_2$(halo), —CN, -halo, —N$_3$, —NO$_2$, —CH=N$R_9$, —N$R_9$OH, —C(O)O$R_9$, —OC(O)$R_9$, —OC(O)O$R_9$, —S(O)$R_9$, and —S(O)$_2$$R_9$;

each $R_8$ is independently selected from —($C_1$-$C_4$)alkyl, —($C_2$-$C_6$)alkenyl, —($C_2$-$C_6$)alkynyl, —O$R_9$, —S$R_9$, —C(halo)$_3$, —CH(halo)$_2$, —CH$_2$(halo), —CN, oxo, =S, -phenyl, -halo, —N$_3$, —NO$_2$, —CH=N$R_9$, —N$R_9$OH, —C(O)O$R_9$, —OC(O)$R_9$, —OC(O)O$R_9$, —S(O)$R_9$, and —S(O)$_2$$R_9$;

each $R_9$ is independently selected from —H, —($C_1$-$C_6$) alkyl, —($C_2$-$C_6$)alkenyl, —($C_2$-$C_6$)alkynyl, —($C_3$-$C_8$) cycloalkyl, —($C_5$-$C_8$)cycloalkenyl, -phenyl, -benzyl, -(3- to 7-membered)heterocycle, —C(halo)$_3$, —CH(halo)$_2$, and —CH$_2$(halo);

if h is 0, $R_{11}$ is selected from —H, —C(O)O$R_9$, —C(O)N ($R_6$)$_2$, and —($C_1$-$C_4$)alkyl which is unsubstituted or substituted with —OH, —($C_1$-$C_4$)alkoxy, —N($R_6$)$_2$, —C(O)O$R_9$, or —C(O)N($R_6$)$_2$;

if h is 1, $R_{11}$ is selected from —H, —OH, -halo, —C(O) O$R_9$, —C(O)N($R_6$)$_2$, and —($C_1$-$C_4$)alkyl which is unsubstituted or substituted with —OH, —($C_1$-$C_4$) alkoxy, —N($R_6$)$_2$, —C(O)O$R_9$, or —C(O)N($R_6$)$_2$;

m is an integer selected from 0, 1, 2, 3, 4, 5, 6, and 7;

e and f are each an integer independently selected from 0, 1, 2, 3, 4, and 5 provided that $2 \leq (e+f) \leq 5$;

j and k are each an integer independently selected from 0, 1, 2, 3, and 4 provided that $1 \leq (j+k) \leq 4$;

each p is an integer independently selected from 0 and 1;

each $T_1$, $T_2$, and $T_3$ is independently —H or —($C_1$-$C_{10}$) alkyl which is unsubstituted or substituted with 1, 2, or 3 independently selected $R_8$ groups and, optionally, in which any carbon atom is independently replaced by O or S, or $T_1$ and $T_2$ together can form a 5- to 8-membered ring where the number of atoms in the ring includes the nitrogen atom to which $T_1$ and $T_2$ are bonded, said 5- to 8-membered ring is unsubstituted or substituted with 1, 2, or 3 independently selected $R_8$ groups and, optionally, any carbon atom in said 5- to 8-membered ring is independently replaced by O or S;

each $V_1$ is independently selected from —H, —($C_1$-$C_6$) alkyl, —($C_3$-$C_7$)cycloalkyl, -phenyl, and -benzyl;

each $W_1$ is independently:
(a) —H, —($C_1$-$C_6$)alkyl, —($C_3$-$C_7$)cycloalkyl, —O($C_1$-$C_6$)alkyl, —($C_3$-$C_7$)cycloalkoxy, —CH$_2$CH$_2$OH, or —N($R_6$)$_2$; or
(b) -(5- or 6-membered)heteroaryl optionally substituted with 1, 2, or 3 independently selected —($C_1$-$C_6$) alkyl; and each halo is independently selected from —F, —Cl, —Br, and —I;

provided that when h is 0, then $R_1$ is not -halo or —NO$_2$;

provided that $R_3$ is not —($C_1$-$C_2$)alkyl substituted with —C(O)N($V_1$)$_2$; and provided that $R_3$ does not include an imidazolyl group.

2. The compound of claim 1 or a pharmaceutically acceptable salt thereof, wherein $R_4$ and $R_5$ are independently selected from —H and —($C_1$-$C_6$)alkyl.

3. The compound of claim 2 or a pharmaceutically acceptable salt thereof, wherein each Y is O.

4. The compound of claim 2 or a pharmaceutically acceptable salt thereof, wherein $R_4$ and $R_5$ are each —H.

5. The compound of claim 3 or a pharmaceutically acceptable salt thereof, wherein A is H.

6. The compound of claim 3 or a pharmaceutically acceptable salt thereof, wherein B is H.

7. The compound of claim 6 or a pharmaceutically acceptable salt thereof, wherein A is H.

8. The compound of claim 3 or a pharmaceutically acceptable salt thereof, wherein C is H.

9. The compound of claim 3 or a pharmaceutically acceptable salt thereof, wherein D is H.

10. The compound of claim 9 or a pharmaceutically acceptable salt thereof, wherein C is H.

11. The compound of claim 3 or a pharmaceutically acceptable salt thereof, wherein D is —CH$_3$.

12. The compound of claim 3 or a pharmaceutically acceptable salt thereof, wherein A, B, C and D are each H, $R_3$ is —H or methyl substituted by —CN, and a is 0 or 1.

13. The compound of claim 3 or a pharmaceutically acceptable salt thereof, wherein A-B together form a ($C_2$-$C_6$)bridge, which is unsubstituted or substituted with 1, 2, or 3 independently selected $R_8$ groups, and which bridge optionally contains —HC=CH— within the ($C_2$-$C_6$)bridge.

14. The compound of claim 13 or a pharmaceutically acceptable salt thereof, wherein A-B together form a ($C_2$) bridge, a —HC=CH— bridge, or a ($C_3$)bridge.

15. The compound of claim 14 or a pharmaceutically acceptable salt thereof, wherein the bridge is unsubstituted.

16. The compound of claim 14 or a pharmaceutically acceptable salt thereof, wherein $R_3$ is —H, —($C_1$-$C_6$)alkyl, —($C_1$-$C_6$)alkyl substituted by an $R_8$ group, —($C_3$-$C_7$)cycloalkyl, or —($C_3$-$C_7$)cycloalkyl substituted by an $R_8$ group.

17. The compound of claim 16 or a pharmaceutically acceptable salt thereof, wherein $R_3$ is —($C_1$-$C_6$)alkyl.

18. The compound of claim 17 or a pharmaceutically acceptable salt thereof, wherein $R_3$ is methyl, ethyl, n-propyl or iso-propyl.

19. The compound of claim 16 or a pharmaceutically acceptable salt thereof, wherein $R_3$ is —($C_1$-$C_6$)alkyl substituted by an $R_8$ group.

20. The compound of claim 19 or a pharmaceutically acceptable salt thereof, wherein $R_3$ is methyl, ethyl, n-propyl or iso-propyl, each of which is substituted by an $R_8$ group.

21. The compound of claim 3 or a pharmaceutically acceptable salt thereof, wherein a is 0.

22. The compound of claim 3 or a pharmaceutically acceptable salt thereof, wherein each $R_2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl, or -(5- or 6-membered)heteroaryl.

23. The compound of claim 22 or a pharmaceutically acceptable salt thereof, wherein a is 1 and $R_2$ is -halo, —OH, —NH$_2$, —CN, methyl, ethyl, n-propyl, iso-propyl, cyclopentyl, cyclohexyl, cycloheptyl, or phenyl.

24. The compound of claim 23 or a pharmaceutically acceptable salt thereof, wherein $R_2$ is -halo.

25. The compound of claim 3 or a pharmaceutically acceptable salt thereof, wherein a is 1 and $R_2$ is -halo, —OH, —NH$_2$, —CN, methyl, ethyl, n-propyl, iso-propyl, cyclopentyl, cyclohexyl, cycloheptyl, phenyl, —OT$_3$, or —C(O)OT$_3$.

26. The compound of claim 25 or a pharmaceutically acceptable salt thereof, wherein $T_3$ is —H or —CH$_3$.

27. The compound of claim 25 or a pharmaceutically acceptable salt thereof, wherein a is 1 and $R_2$ is —F, —Cl, —Br, or —OCH$_3$.

28. The compound of claim 27 or a pharmaceutically acceptable salt thereof, wherein $R_2$ is —F.

29. The compound of claim 22 or a pharmaceutically acceptable salt thereof, wherein a is 2 and each $R_2$ is independently -halo, —OH, —NH$_2$, —CN, methyl, ethyl, n-propyl, iso-propyl, cyclopentyl, cyclohexyl, cycloheptyl, or phenyl.

30. The compound of claim 29 or a pharmaceutically acceptable salt thereof, wherein each $R_2$ is independently -halo.

31. The compound of claim 1 or a pharmaceutically acceptable salt thereof, wherein $R_3$ is:
(a) —C(O)OV$_1$; or
(b) —C(O)N(V$_1$)$_2$; or
(c) —(C$_1$-C$_2$)alkyl which is unsubstituted or substituted with a substituent selected from —NHS(O)$_2$W$_1$, —C(O)OR$_9$, and —C(O)N(V$_1$)$_2$; or
(d) —H.

32. The compound of claim 31 or a pharmaceutically acceptable salt thereof, wherein $R_3$ is —H.

33. The compound of claim 3 or a pharmaceutically acceptable salt thereof, wherein Z is a single bond and $R_1$ is selected from:

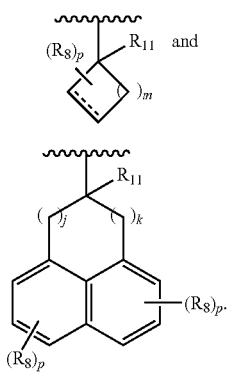

34. The compound of claim 33 or a pharmaceutically acceptable salt thereof, wherein $R_1$ is selected from formula (i), $R_{11}$ is —H, m is 5, and p is 0.

35. The compound of claim 33 or a pharmaceutically acceptable salt thereof, wherein $R_1$ is selected from formula (i), $R_{11}$ is —H, m is 3, p is 1, and $R_8$ is —(C$_1$-C$_4$)alkyl.

36. The compound of claim 35 or a pharmaceutically acceptable salt thereof, wherein $R_8$ is iso-propyl.

37. The compound of claim 33 or a pharmaceutically acceptable salt thereof, wherein $R_1$ is selected from formula (iii), $R_{11}$ is —H, p is 0, and j+k=1.

38. The compound of claim 3, wherein the pharmaceutically acceptable salt is a hydrochloride-salt, a sodium-salt, a potassium-salt, or a p-toluenesulfonic acid-salt.

39. The compound of claim 3 or a pharmaceutically acceptable salt thereof, which is a stereoisomer or a tautomer thereof.

40. The compound of claim 3, which is:

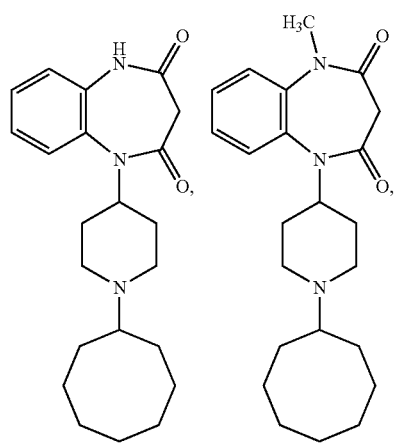

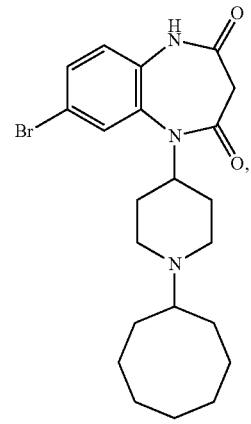

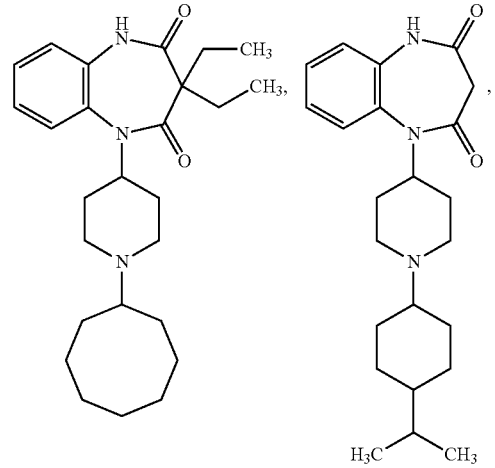

287
-continued
288
-continued
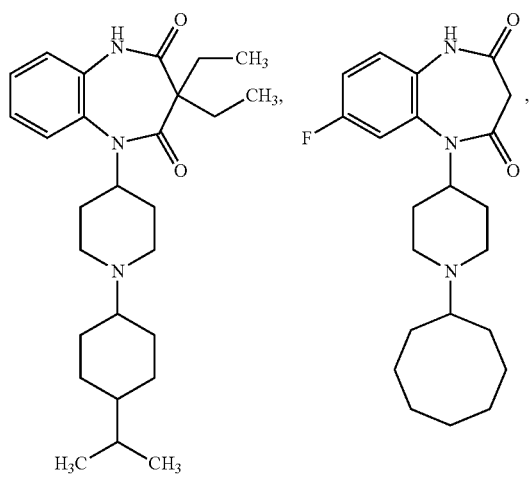
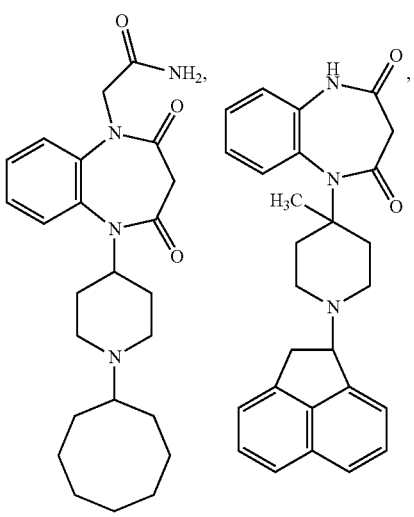
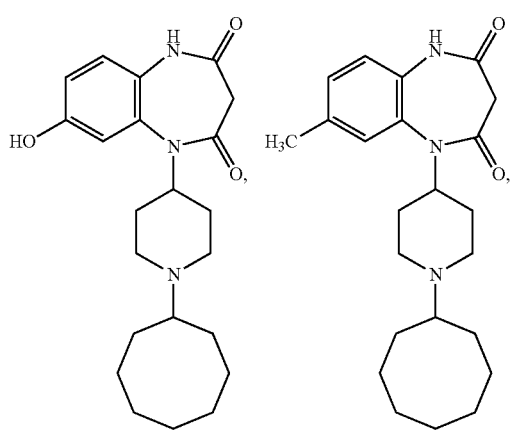
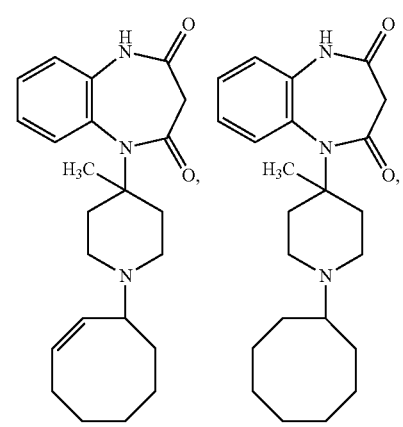
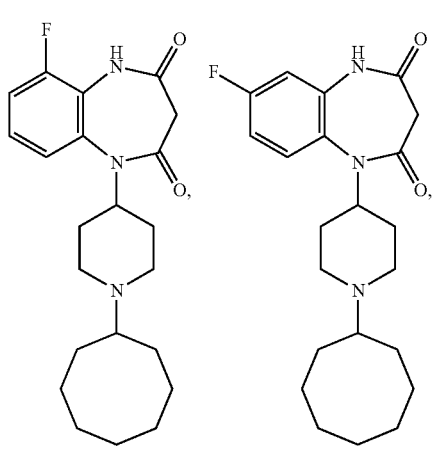
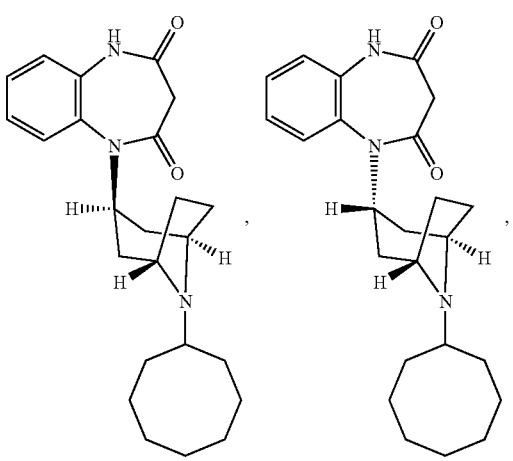

-continued

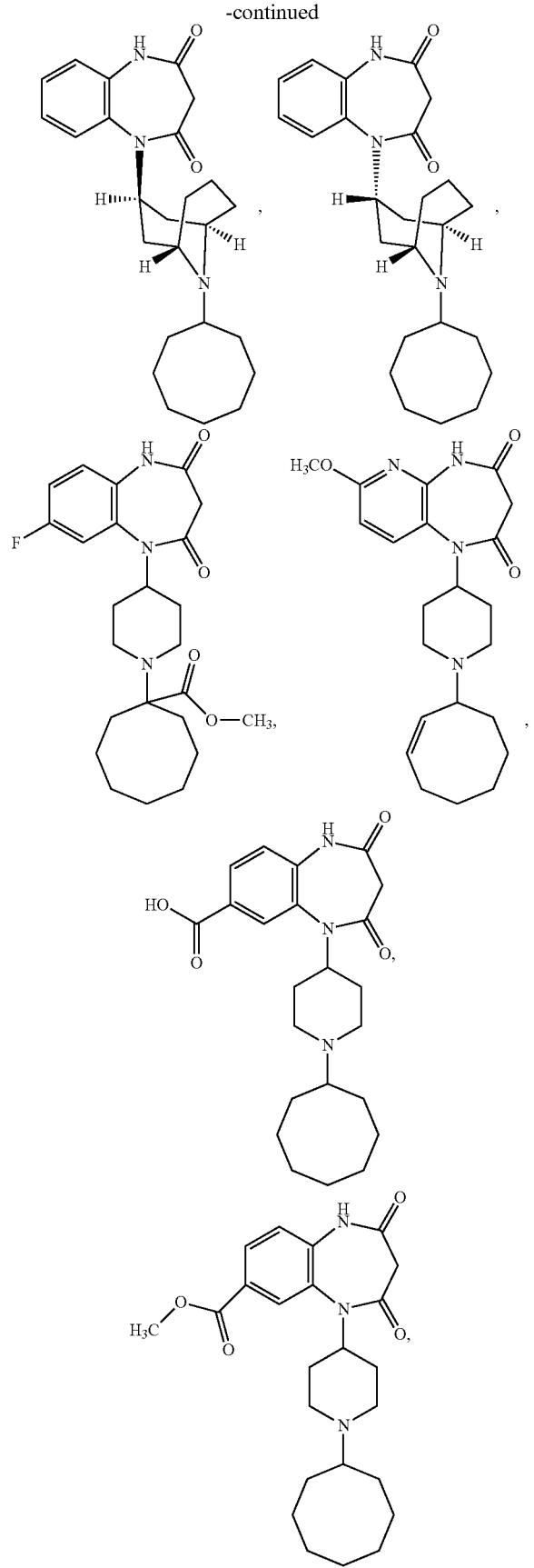

or a pharmaceutically acceptable salt thereof.

41. The compound of claim 40, which is:

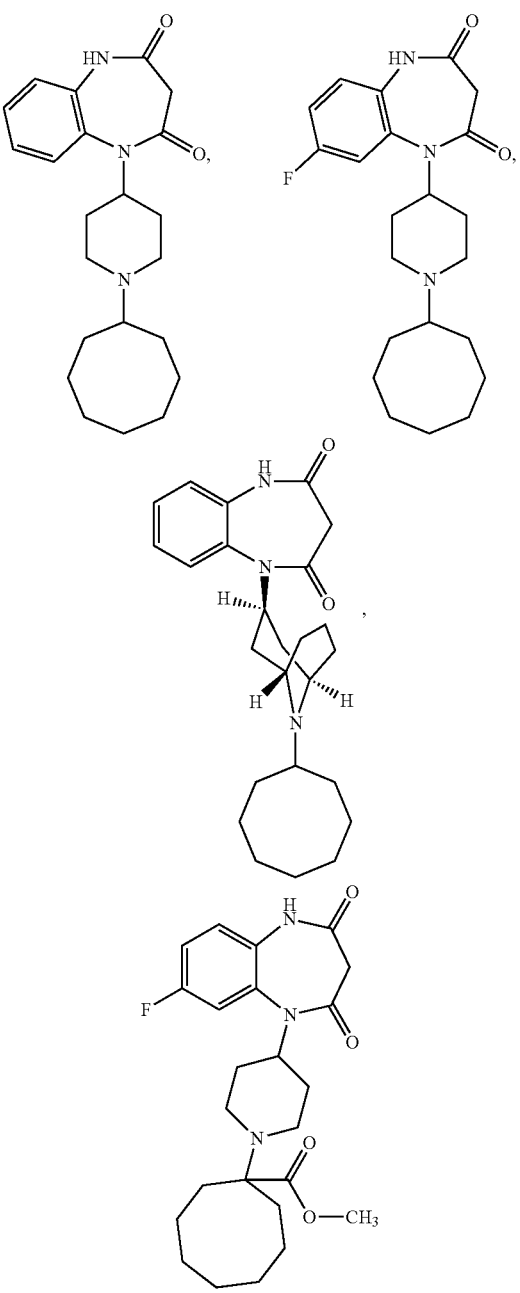

or a pharmaceutically acceptable salt thereof.

42. The compound of claim 40, wherein the pharmaceutically acceptable salt is a hydrochloride-salt, a sodium-salt, a potassium-salt, or a p-toluenesulfonic acid-salt.

43. A pharmaceutical composition comprising an effective amount of the compound or a pharmaceutically acceptable salt of the compound of claim 1 and a pharmaceutically acceptable carrier or excipient.

44. A method for modulating ORL-1 receptor function in a cell, comprising contacting a cell capable of expressing the ORL-1 receptor with an effective amount of the compound or a pharmaceutically acceptable salt of the compound of claim 1.

45. The method of claim 44, wherein the compound or the pharmaceutically acceptable salt of the compound acts as an agonist at the ORL-1 receptor or as an antagonist at the ORL-1 receptor.
46. A compound of formula:
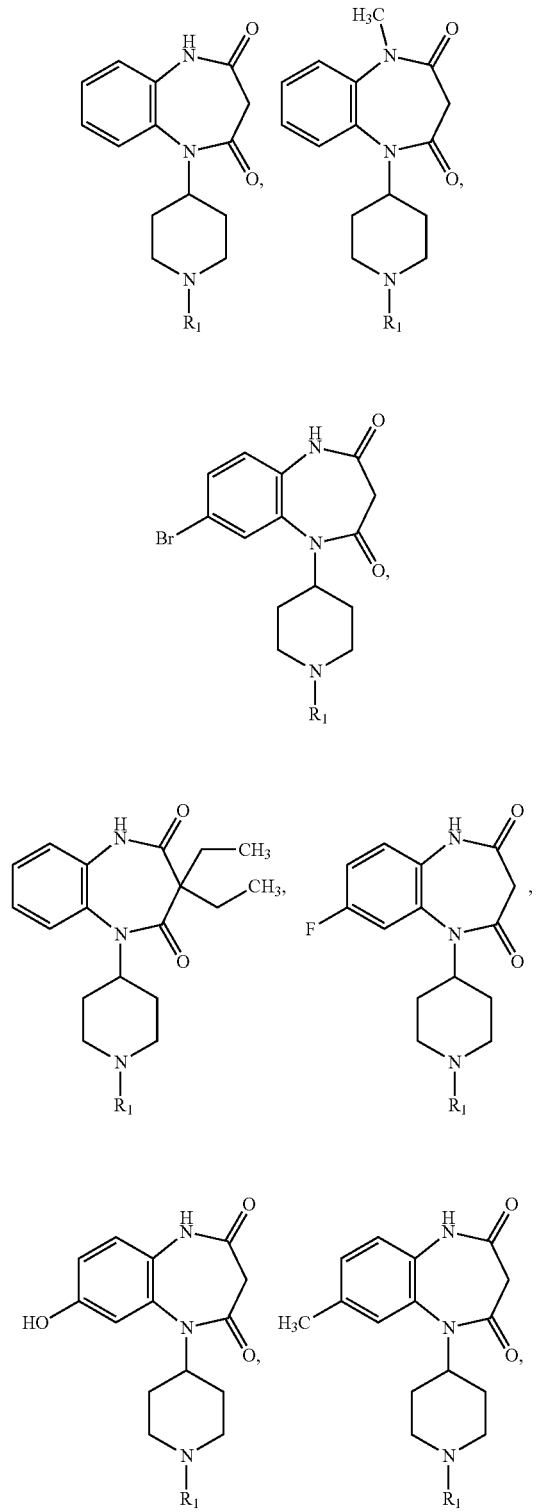
-continued
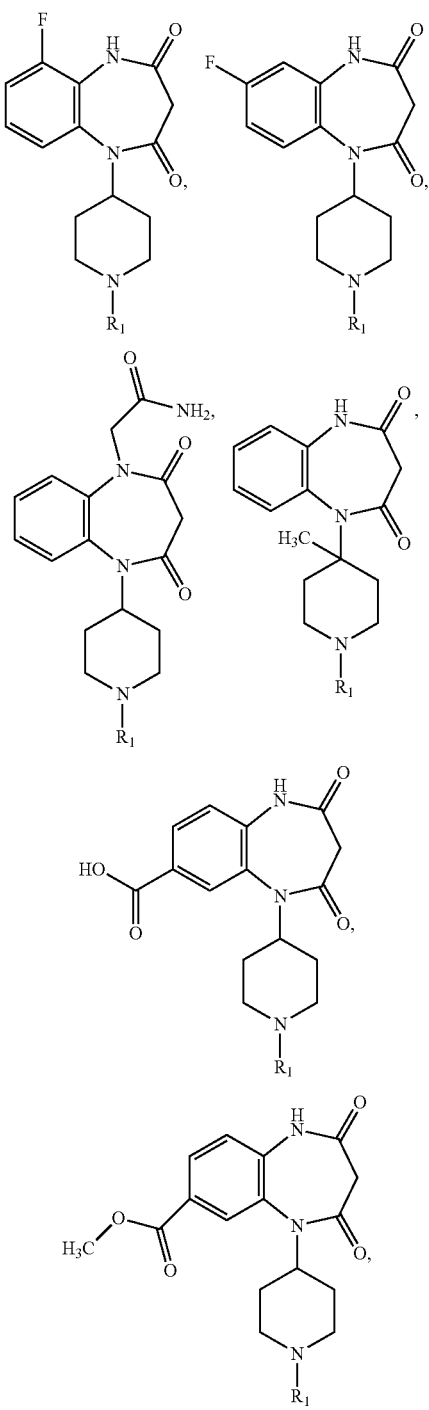
or a pharmaceutically acceptable salt thereof wherein:
R₁ is:
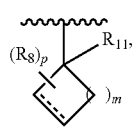
(i)

293

-continued

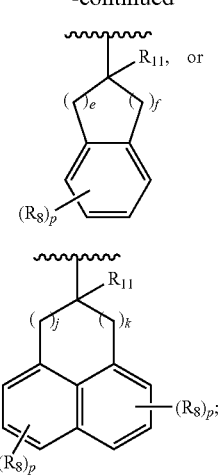

m is an integer selected from 0, 1, 2, 3, 4, 5, 6, and 7;
e and f are each an integer independently selected from 0, 1, 2, 3, 4, and 5 provided that 2≤(e+f)≤5;
j and k are each an integer independently selected from 0, 1, 2, 3, and 4 provided that 1≤(j+k)≤4;
each $R_6$ is independently selected from —H, —($C_1$-$C_6$)alkyl, and —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;
each $R_8$ is independently selected from —($C_1$-$C_4$)alkyl, —($C_2$-$C_6$)alkenyl, —($C_2$-$C_6$)alkynyl, —$OR_9$, —$SR_9$, —C(halo)$_3$, —CH(halo)$_2$, —CH$_2$(halo), —CN, oxo, =S, -phenyl, -halo, —$N_3$, —$NO_2$, —CH=$NR_9$, —$NR_9$OH, —C(O)$OR_9$, —OC(O)$R_9$, —OC(O)$OR_9$, —S(O)$R_9$, and —S(O)$_2$$R_9$;
each $R_9$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 7-membered)heterocycle, —C(halo)$_3$, —CH(halo)$_2$, and —CH$_2$(halo);
each p is an integer independently selected from 0 and 1;
$R_{11}$ is selected from —H, —C(O)$OR_9$, —C(O)N($R_6$)$_2$, and —($C_1$-$C_4$)alkyl which is unsubstituted or substituted with —OH, —($C_1$-$C_4$)alkoxy, —N($R_6$)$_2$, —C(O)$OR_9$, or —C(O)N($R_6$)$_2$; and
each halo is independently selected from —F, —Cl, —Br, and —I.

47. The compound of claim 46, wherein the pharmaceutically acceptable salt is a hydrochloride-salt, a sodium-salt, a potassium-salt, or a p-toluenesulfonic acid-salt.

48. The compound of claim 46 or a pharmaceutically acceptable salt thereof, which is a stereoisomer or a tautomer thereof.

49. A pharmaceutical composition comprising an effective amount of the compound or a pharmaceutically acceptable salt of the compound of claim 46 and a pharmaceutically acceptable carrier or excipient.

50. A method for modulating ORL-1 receptor function in a cell, comprising contacting a cell capable of expressing the ORL-1 receptor with an effective amount of the compound or a pharmaceutically acceptable salt of the compound of claim 46.

51. The method of claim 50, wherein the compound or the pharmaceutically acceptable salt of the compound acts as an agonist at the ORL-1 receptor or as an antagonist at the ORL-1 receptor.

294

52. A compound of formula:

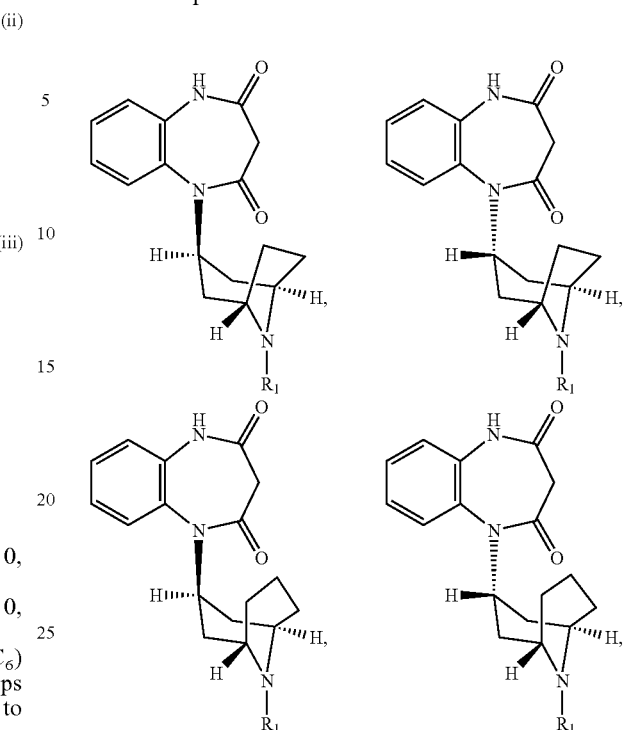

or a pharmaceutically acceptable salt thereof wherein:
$R_1$ is:

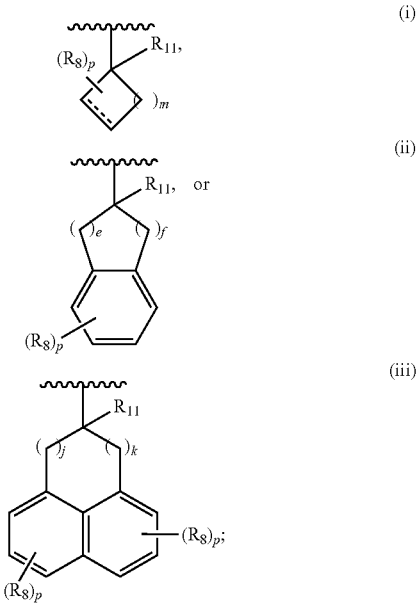

m is an integer selected from 0, 1, 2, 3, 4, 5, 6, and 7;
e and f are each an integer independently selected from 0, 1, 2, 3, 4, and 5 provided that 2≤(e+f)≤5;
j and k are each an integer independently selected from 0, 1, 2, 3, and 4 provided that 1≤(j+k)≤4;
each $R_6$ is independently selected from —H, —($C_1$-$C_6$)alkyl, and —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_8$ is independently selected from —$(C_1$-$C_4)$alkyl, —$(C_2$-$C_6)$alkenyl, —$(C_2$-$C_6)$alkynyl, —$OR_9$, —$SR_9$, —C(halo)$_3$, —CH(halo)$_2$, —CH$_2$(halo), —CN, oxo, =S, -phenyl, -halo, —$N_3$, —$NO_2$, —CH=$NR_9$, —$NR_9$OH, —C(O)$OR_9$, —OC(O)$R_9$, —OC(O)$OR_9$, —S(O)$R_9$, and —S(O)$_2R_9$;

each $R_9$ is independently selected from —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, -(3- to 7-membered)heterocycle, —C(halo)$_3$, —CH(halo)$_2$, and —CH$_2$(halo);

each p is an integer independently selected from 0 and 1;

$R_{11}$ is selected from —H, —C(O)$OR_9$, —C(O)N($R_6)_2$, and —$(C_1$-$C_4)$alkyl which is unsubstituted or substituted with —OH, —$(C_1$-$C_4)$alkoxy, —N($R_6)_2$, —C(O)$OR_9$, or —C(O)N($R_6)_2$; and each halo is independently selected from —F, —Cl, —Br, and —I.

53. The compound of claim 52, wherein the pharmaceutically acceptable salt is a hydrochloride-salt, a sodium-salt, a potassium-salt, or a p-toluenesulfonic acid-salt.

54. The compound of claim 52 or a pharmaceutically acceptable salt thereof, which is a stereoisomer or a tautomer thereof.

55. A pharmaceutical composition comprising an effective amount of the compound or a pharmaceutically acceptable salt of the compound of claim 52 and a pharmaceutically acceptable carrier or excipient.

56. A method for modulating ORL-1 receptor function in a cell, comprising contacting a cell capable of expressing the ORL-1 receptor with an effective amount of the compound or a pharmaceutically acceptable salt of the compound of claim 52.

57. The method of claim 56, wherein the compound or the pharmaceutically acceptable salt of the compound acts as an agonist at the ORL-1 receptor or as an antagonist at the ORL-1 receptor.

58. A compound of formula (IIIa):

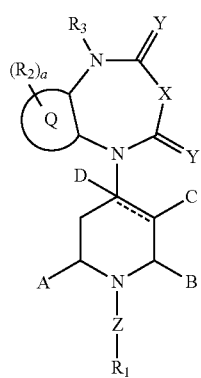

(IIIa)

or a pharmaceutically acceptable salt thereof wherein:

Q is benzo;

each $R_2$ is independently:
(a) -halo, —OH, —NH$_2$, —CN, or —NO$_2$; or
(b) —$(C_1$-$C_6)$alkyl, —$(C_2$-$C_6)$alkenyl, —$(C_2$-$C_6)$alkynyl, —$(C_3$-$C_7)$cycloalkyl, -(5- or 6-membered)heterocycle, -phenyl, -naphthyl, or -(5- or 6-membered) heteroaryl, each of which is unsubstituted or substituted with 1, 2 or 3 $R_8$ groups;

a is an integer selected from 0, 1, and 2;

$R_3$ is:
(a) —H; or
(b) —$(C_1$-$C_6)$alkyl, —$(C_2$-$C_6)$alkenyl, —$(C_2$-$C_6)$alkynyl, —O$(C_1$-$C_6)$alkyl, —O$(C_2$-$C_6)$alkenyl, —O$(C_2$-$C_6)$alkynyl, —$(C_3$-$C_7)$cycloalkyl, —$(C_5$-$C_7)$cycloalkenyl, —$(C_3$-$C_7)$cycloalkoxy, -(3- to 7-membered)heterocycle, -phenyl, -naphthyl, or -(5- to 10-membered)heteroaryl, each of which is unsubstituted or substituted with 1, 2 or 3 $R_8$ groups; or
(c) —CH$_2$CH$_2$OH, —$(C_1$-$C_6)$alkyl(=O)$W_1$, —C(O)$OV_1$, —C(O)N($V_1)_2$, or —S(O)$_2(C_1$-$C_6)$alkyl; or
(d) —$(C_1$-$C_4)$alkyl substituted with 1, 2 or 3 substituents independently selected from —$(C_3$-$C_7)$cycloalkyl, —$(C_3$-$C_7)$cycloalkoxy, -(3- to 7-membered)heterocycle, -phenyl, -naphthyl, and -(5- to 10-membered) heteroaryl; or
(e) —$(C_1$-$C_3)$alkyl substituted with a substituent selected from —N($R_6)_2$, —S(O)$_2$NH$_2$, —NHC(O)$W_1$, —NHS(O)$_2W_1$, —C(O)$OV_1$, and —C(O)N($V_1)_2$;

each Y is independently selected from O or S;

X is —C($R_4$)($R_5$)—;

$R_4$ is selected from —H, —$OR_6$, —$(C_1$-$C_6)$alkyl, and —$(C_3$-$C_7)$cycloalkyl; or, independently, $R_4$ and $R_5$ together can form an oxo group;

$R_5$ is selected from —H, —$(C_1$-$C_6)$alkyl, and —$(C_3$-$C_7)$cycloalkyl;

A and B are independently selected from —H, —N($R_6)_2$, —$(C_3$-$C_{12})$cycloalkyl, and —$(C_1$-$C_6)$alkyl each of which —$(C_1$-$C_6)$alkyl is unsubstituted or substituted with —OH, —S(O)$_2$NH$_2$, or from 1 to 3 independently selected -halo, or A-B together form a $(C_2$-$C_6)$bridge;

C is —H;

D is —H;

the dashed line in the piperidine or bridged piperidine central ring is absent;

Z is —[$(C_1$-$C_{10})$alkyl]$_h$-, wherein h is 0 or 1; or —$(C_1$-$C_{10})$alkyl-$NR_6$C(=Y)—;

$R_1$ is:
(a) —H, -halo, —CN, —OH, —CH$_2$OH, —CH$_2$CH$_2$OH, —NO$_2$, —N($R_6)_2$, —S(O)NH$_2$, —S(O)$_2$NH$_2$, —C(O)$OV_1$, or —C(O)CN; or
(b) —$(C_1$-$C_6)$alkyl, —$(C_2$-$C_6)$alkenyl, —$(C_2$-$C_6)$alkynyl, —O$(C_1$-$C_6)$alkyl, —$(C_3$-$C_7)$cycloalkoxy, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(3- to 7-membered)heterocycle, or -(7- to 10-membered)bicycloheterocycle, each of which is unsubstituted or substituted with an $R_8$ group; or

(i)

297

-continued

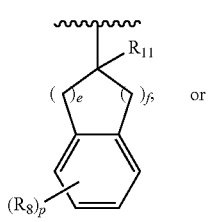

(ii)

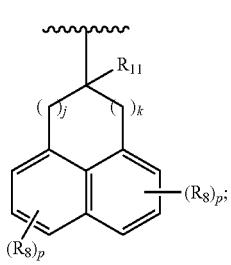

(iii)

or (c) -phenyl, -naphthyl, —($C_{14}$)aryl, or -(5- to 10-membered)heteroaryl, each of which is unsubstituted or substituted with an $R_8$ group; or —Z—$R_1$ is 3,3-diphenylpropyl- optionally substituted at the 3 carbon of the propyl with —CN, —C(O)N($R_6$)$_2$, —C(O)O$V_1$, or -tetrazolyl; or —Z—$R_1$ is —($C_1$-$C_4$)alkyl substituted with tetrazolyl;

each $R_6$ is independently selected from —H, —($C_1$-$C_6$) alkyl, and —($C_3$-$C_7$)cycloalkyl, or two $R_6$ groups attached to the same nitrogen atom can form a 5- to 8-membered ring, the number of atoms in the ring including the nitrogen atom, in which one of the ring carbon atoms is optionally replaced by O or S;

each $R_8$ is independently selected from —($C_1$-$C_4$)alkyl, —O($C_1$-$C_4$)alkyl, —C(halo)$_3$, —CH(halo)$_2$, —CH$_2$(halo), —CN, —OH, -halo, and —C(O)O$R_9$;

each $R_9$ is independently selected from —H, —($C_1$-$C_6$) alkyl, -phenyl, and -benzyl;

$R_{11}$ is selected from —H, —($C_1$-$C_4$)alkyl, and -halo;

m is an integer selected from 1, 2, 3, 4, 5, 6, and 7;

e and f are each an integer independently selected from 0, 1, 2, 3, 4, and 5 provided that 2≤(e+f)≤5;

j and k are each an integer independently selected from 0, 1, 2, 3, and 4 provided that 1≤(j+k)≤4;

each p is an integer independently selected from 0 and 1;

each $V_1$ is independently selected from —H, —($C_1$-$C_6$) alkyl, —($C_3$-$C_7$)cycloalkyl, -phenyl, and -benzyl;

each $W_1$ is independently:

(a) —H, —($C_1$-$C_6$)alkyl, —($C_3$-$C_7$)cycloalkyl, —O($C_1$-$C_6$)alkyl, —($C_3$-$C_7$)cycloalkoxy, —CH$_2$CH$_2$OH, or —N($R_6$)$_2$; or (b) -(5- or 6-membered)heteroaryl optionally substituted with 1, 2 or 3 independently selected —($C_1$-$C_6$) alkyl; and each halo is independently selected from —F, —Cl, —Br, and —I;

provided that when h is 0, then $R_1$ is not -halo or —NO$_2$;

provided that $R_3$ is not —($C_1$-$C_2$)alkyl substituted with —C(O)N($V_1$)$_2$; and

298 provided that $R_3$ does not include an imidazolyl group.

59. The compound of claim 58, wherein the pharmaceutically acceptable salt is a hydrochloride-salt, a sodium-salt, a potassium-salt, or a p-toluenesulfonic acid-salt.

60. The compound of claim 58 or a pharmaceutically acceptable salt thereof, which is a stereoisomer or a tautomer thereof.

61. A pharmaceutical composition comprising an effective amount of the compound or a pharmaceutically acceptable salt of the compound of claim 58 and a pharmaceutically acceptable carrier or excipient.

62. A method for modulating ORL-1 receptor function in a cell, comprising contacting a cell capable of expressing the ORL-1 receptor with an effective amount of the compound or a pharmaceutically acceptable salt of the compound of claim 58.

63. The method of claim 62, wherein the compound or the pharmaceutically acceptable salt of the compound acts as an agonist at the ORL-1 receptor or as an antagonist at the ORL-1 receptor.

64. The compound of claim 58, which is:

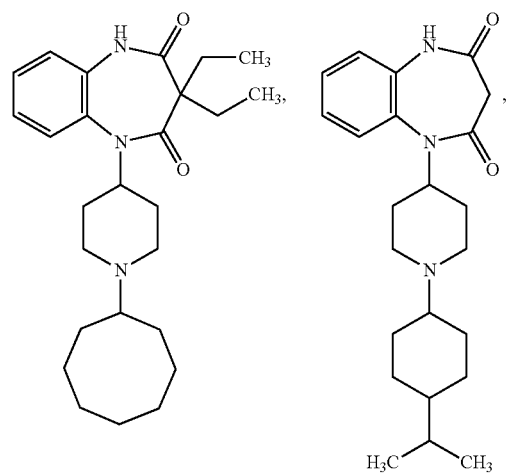

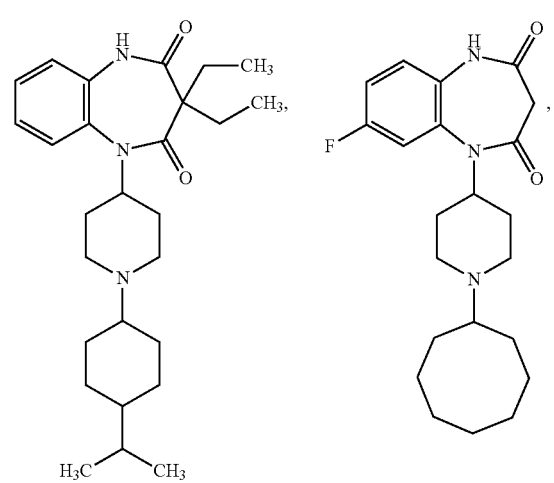

-continued

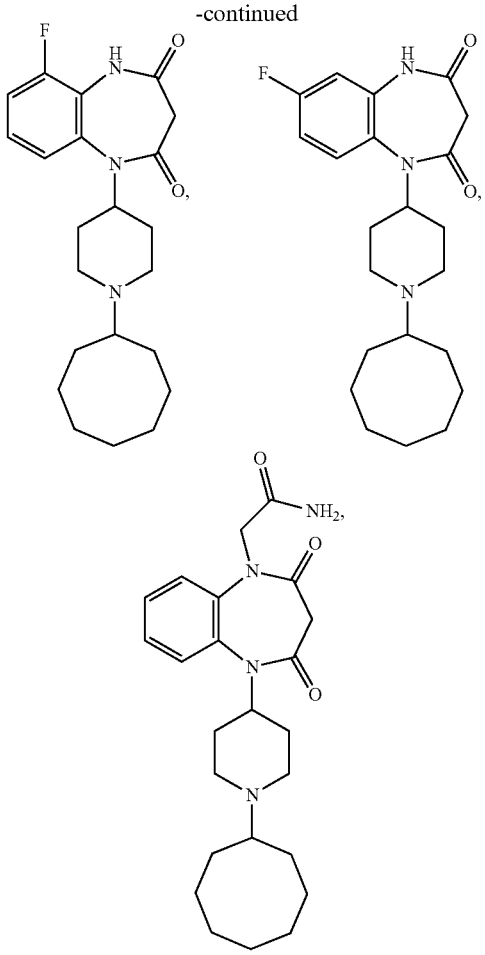

or a pharmaceutically acceptable salt thereof.

65. The compound of claim 64, wherein the pharmaceutically acceptable salt is a hydrochloride-salt, a sodium-salt, a potassium-salt, or a p-toluenesulfonic acid-salt.

66. The compound of claim 12 or a pharmaceutically acceptable salt thereof, wherein Z is a single bond and $R_1$ is selected from:

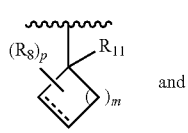 and

-continued

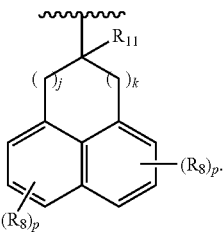

67. The compound of claim 66 or a pharmaceutically acceptable salt thereof, wherein $R_1$ is selected from formula (i), $R_{11}$ is —H, m is 5, and p is 0.

68. The compound of claim 67 or a pharmaceutically acceptable salt thereof, wherein a is 0.

69. The compound of claim 66 or a pharmaceutically acceptable salt thereof, wherein $R_1$ is selected from formula (i), $R_{11}$ is —H, m is 3, p is 1, and $R_8$ is —$(C_1$-$C_4)$alkyl.

70. The compound of claim 69 or a pharmaceutically acceptable salt thereof, wherein $R_8$ is iso-propyl.

71. The compound of claim 66 or a pharmaceutically acceptable salt thereof, wherein $R_1$ is selected from formula (iii), $R_{11}$ is —H, p is 0, and j+k=1.

72. The compound of claim 46, which is:

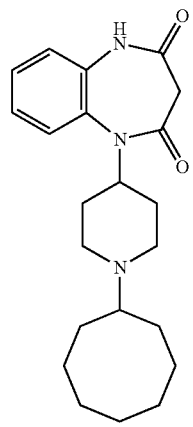 [SMILES: O=C1CC(=O)N(C2CCN(C3CCCCCCC3)CC2)c2ccccc2N1]

or a pharmaceutically acceptable salt thereof.

73. The compound of claim 72, wherein the pharmaceutically acceptable salt is a hydrochloride-salt, a sodium-salt, a potassium-salt, or a p-toluenesulfonic acid-salt.

* * * * *